US012286466B2

(12) United States Patent
Pecker et al.

(10) Patent No.: US 12,286,466 B2
(45) Date of Patent: Apr. 29, 2025

(54) PD1-4-1BBL VARIANT FUSION PROTEIN AND METHODS OF USE THEREOF

(71) Applicant: KAHR Medical Ltd., Jerusalem (IL)

(72) Inventors: Iris Pecker, Rishon LeZion (IL); Itai Bloch, Moshav Ramot Naftali (IL)

(73) Assignee: KAHR Medical Ltd., Modiln Makabim-ReUt (IL)

( * ) Notice: Subject to any disclaimer, the term of this patent is extended or adjusted under 35 U.S.C. 154(b) by 673 days.

(21) Appl. No.: 17/258,220

(22) PCT Filed: Jul. 11, 2019

(86) PCT No.: PCT/IL2019/050782
§ 371 (c)(1),
(2) Date: Jan. 6, 2021

(87) PCT Pub. No.: WO2020/012485
PCT Pub. Date: Jan. 16, 2020

(65) Prior Publication Data
US 2021/0284711 A1  Sep. 16, 2021

Related U.S. Application Data

(60) Provisional application No. 62/786,599, filed on Dec. 31, 2018, provisional application No. 62/696,365, filed on Jul. 11, 2018.

(51) Int. Cl.
C07K 14/70 (2006.01)
A61K 38/00 (2006.01)
C07K 14/705 (2006.01)

(52) U.S. Cl.
CPC .. C07K 14/70521 (2013.01); C07K 14/70578 (2013.01); *A61K 38/00* (2013.01); *C07K 2319/33* (2013.01)

(58) Field of Classification Search
CPC ........ C07K 14/70521; C07K 14/70578; C07K 2319/33; A61K 38/00
See application file for complete search history.

(56) References Cited

U.S. PATENT DOCUMENTS

| 5,287,386 | A | 2/1994 | Wade et al. |
| 5,674,704 | A | 10/1997 | Goodwin et al. |
| 6,046,048 | A | 4/2000 | Ashkenazi et al. |
| 6,740,739 | B1 | 5/2004 | Ashkenazi et al. |
| 7,142,018 | B2 | 11/2006 | Masleid et al. |
| 7,279,925 | B1 | 10/2007 | Richmond et al. |
| 7,569,663 | B2 | 8/2009 | Tykocinski et al. |
| 8,039,437 | B2 | 10/2011 | Tykocinski et al. |
| 8,216,805 | B2 | 7/2012 | Carter et al. |
| 9,562,087 | B2 | 2/2017 | Ring et al. |
| 10,040,841 | B2 | 8/2018 | Dranitzki Elhalel et al. |
| 10,183,060 | B2 | 1/2019 | Schreiber et al. |
| 10,392,445 | B2* | 8/2019 | Amann ............... C07K 16/2896 |
| 10,464,981 | B2 | 11/2019 | Amann et al. |
| 11,130,796 | B2 | 9/2021 | Shani et al. |
| 2003/0216546 | A1 | 11/2003 | Tykocinski et al. |
| 2007/0036783 | A1 | 2/2007 | Humeau et al. |
| 2007/0110746 | A1 | 5/2007 | Chung |
| 2012/0189625 | A1 | 7/2012 | Wang et al. |
| 2013/0039911 | A1* | 2/2013 | Bedi ................. C07K 16/2866 530/391.1 |
| 2013/0094307 | A1 | 4/2013 | Cheng |
| 2013/0287802 | A1 | 10/2013 | Govindappa et al. |
| 2015/0183881 | A1 | 7/2015 | Bedi et al. |
| 2015/0353642 | A1 | 12/2015 | Tykocinski |
| 2015/0376260 | A1 | 12/2015 | Elhalel et al. |
| 2016/0039903 | A1 | 2/2016 | Ring et al. |
| 2016/0200833 | A1* | 7/2016 | Amann ............... C07K 16/2896 |
| 2017/0095531 | A1 | 4/2017 | Schreiber et al. |
| 2017/0107270 | A1 | 4/2017 | Pons et al. |
| 2017/0327588 | A1 | 11/2017 | Baca et al. |
| 2019/0016782 | A1 | 1/2019 | Dranitzki Elhalel et al. |
| 2019/0151413 | A1 | 5/2019 | Schreiber et al. |
| 2019/0315834 | A1 | 10/2019 | Shani et al. |
| 2019/0330304 | A1 | 10/2019 | Shani et al. |
| 2019/0352371 | A1 | 11/2019 | Tykocinski et al. |
| 2019/0352372 | A1 | 11/2019 | Shani et al. |
| 2020/0087377 | A1 | 3/2020 | Yue et al. |
| 2020/0317773 | A1 | 10/2020 | Clark et al. |
| 2021/0214417 | A1 | 7/2021 | Pecker et al. |
| 2021/0301020 | A1 | 9/2021 | Yu et al. |
| 2021/0371500 | A1 | 12/2021 | Shani et al. |

(Continued)

FOREIGN PATENT DOCUMENTS

| CN | 104968364 | 10/2015 |
| CN | 107001485 | 8/2017 |

(Continued)

OTHER PUBLICATIONS

Chichili et al., 2012, Linkers in the structural biology of protein-protein interactions, Protein Science, 22: 153-167.*
Official Action Dated Sep. 7, 2022 from US Patent and Trademark Office Re. U.S. Appl. No. 16/475,705. (34 pages).
Notice of Reason(s) for Rejection Dated May 23, 2023 From the Japan Patent Office Re. Application No. 2021-500829. (3 pages).
Won et al. "The Structure of the Trimer of Human 4-1BB Ligand Is Unique Among Members of the Tumor Necrosis Factor Superfamily", The Journal of Biological Chemistry, 285(12): 9202-9210, Mar. 19, 2010.
Grounds of Reason of Rejection Dated Mar. 7, 2023 From the Korean Intellectual Property Office Re. Application No. 10-2019-7022848 (6 Pages).

(Continued)

*Primary Examiner* — Amber D Steele

(57) ABSTRACT

PD1-4-1BBL variant fusion proteins are provided. Also provided are isolated polypeptides comprising a PD1 variant or a 4-1BBL variant. Also provided are polynucleotides and nucleic acid constructs encoding the PD1-4-1BBL fusion protein or the isolated polypeptide, host-cells expressing the same and methods of use thereof.

13 Claims, 14 Drawing Sheets
(6 of 14 Drawing Sheet(s) Filed in Color)
Specification includes a Sequence Listing.

(56) References Cited

U.S. PATENT DOCUMENTS

| | | | |
|---|---|---|---|
| 2022/0204586 | A1 | 6/2022 | Shani et al. |
| 2022/0267409 | A1 | 8/2022 | Tykocinski et al. |
| 2023/0022040 | A1 | 1/2023 | Johansson et al. |
| 2023/0220040 | A1 | 7/2023 | Shani et al. |

FOREIGN PATENT DOCUMENTS

| | | | | |
|---|---|---|---|---|
| CN | 107857819 | | 3/2018 | |
| CN | 108350055 | | 7/2018 | |
| CN | 110128550 | | 8/2019 | |
| JP | 2013-521311 | | 6/2013 | |
| JP | 2017-060462 | | 3/2017 | |
| JP | 2017-525354 | | 9/2017 | |
| JP | 2021-531265 | | 11/2021 | |
| JP | 7491495 | | 5/2024 | |
| RU | 2636342 | | 11/2017 | |
| WO | WO 01/049318 | | 7/2001 | |
| WO | WO 01/75067 | | 10/2001 | |
| WO | WO 01/86003 | | 11/2001 | |
| WO | WO 03/046581 | | 6/2003 | |
| WO | WO 2005/087797 | | 9/2005 | |
| WO | WO 2010/027828 | | 3/2010 | |
| WO | WO 2010/070047 | | 6/2010 | |
| WO | WO 2011/109789 | | 9/2011 | |
| WO | WO 2012/042480 | | 4/2012 | |
| WO | WO 2013/064700 | | 5/2013 | |
| WO | WO 2013/109752 | | 7/2013 | |
| WO | WO 2013/112986 | | 8/2013 | |
| WO | WO 2013/144704 | | 10/2013 | |
| WO | WO 2014/072534 | | 5/2014 | |
| WO | WO 2014/106839 | | 7/2014 | |
| WO | WO 2014/121093 | | 8/2014 | |
| WO | WO 2014/180288 | | 11/2014 | |
| WO | WO 2015/148416 | | 10/2015 | |
| WO | WO 2016/022994 | | 2/2016 | |
| WO | WO 2016/023001 | | 2/2016 | |
| WO | WO 2016/024021 | | 2/2016 | |
| WO | WO 2016/063233 | | 4/2016 | |
| WO | WO-2016075278 | A1 * | 5/2016 | ............ A61K 38/00 |
| WO | WO 2016/090312 | | 6/2016 | |
| WO | WO 2017/194641 | | 6/2016 | |
| WO | WO 2016/139668 | | 9/2016 | |
| WO | WO 2016/169261 | | 10/2016 | |
| WO | WO 2016/187226 | | 11/2016 | |
| WO | WO 2017/012770 | | 1/2017 | |
| WO | WO 2017/019846 | | 2/2017 | |
| WO | WO 2017/027422 | | 2/2017 | |
| WO | WO 2017/059168 | | 4/2017 | |
| WO | WO 2017/068192 | | 4/2017 | |
| WO | WO 2017/152132 | | 9/2017 | |
| WO | WO 2017181119 | * | 10/2017 | ........... C07K 14/725 |
| WO | WO 2017/207775 | | 12/2017 | |
| WO | WO 2018/006881 | | 1/2018 | |
| WO | WO 2018/032793 | | 2/2018 | |
| WO | WO 2018/053885 | | 3/2018 | |
| WO | WO 2018/085358 | | 5/2018 | |
| WO | WO 2018/091580 | | 5/2018 | |
| WO | WO 2018/114754 | | 6/2018 | |
| WO | WO 2018/127916 | | 7/2018 | |
| WO | WO 2018/127916 | A9 | 7/2018 | |
| WO | WO 2018/127917 | | 7/2018 | |
| WO | WO 2018/127918 | | 7/2018 | |
| WO | WO 2018/127918 | A9 | 7/2018 | |
| WO | WO 2018/127919 | | 7/2018 | |
| WO | WO 2018/127919 | A9 | 7/2018 | |
| WO | WO 2019/086499 | | 5/2019 | |
| WO | WO 2020/012485 | | 1/2020 | |
| WO | WO 2020/012486 | | 1/2020 | |
| WO | WO 2020/012485 | A9 | 5/2020 | |
| WO | WO 2020/146423 | | 7/2020 | |
| WO | WO 2020/242919 | | 12/2020 | |
| WO | WO 2021/005599 | | 1/2021 | |
| WO | WO 2022/153307 | | 7/2022 | |
| WO | WO 2023/119295 | | 6/2023 | |

OTHER PUBLICATIONS

Request for Examination and Search Report Dated Jan. 12, 2023 From the (ROSPATENT), Federal Government Institution of Industrial Property of the Federal Service of Intellectual Property, Patents and Trademark of the Russian Federation Re. Application No. 2021101091. (13 Pages).

Office Action Dated Aug. 7, 2023 From the Israel Patent Office Re. Application No. 267862. (3 Pages).

Final Official Action Dated Dec. 14, 2022 from the US Patent and Trademark Office Re. U.S. Appl. No. 17/258,170. (55 pages).

Notice of Reason(s) for Rejection Dated Nov. 25, 2022 From the Japan Patent Office Re. Application No. 2019-536286 and Its Translation Into English. (7 pages).

Official Action Dated Dec. 14, 2022 from the US Patent and Trademark Office Re. U.S. Appl. No. 16/475,705. (7 pages).

Request for Examination Dated Dec. 5, 2022 From the (ROSPATENT), Federal Government Institution of Industrial Property of the Federal Service of Intellectual Property, Patents and Trademark of the Russian Federation Re. Application No. 2021101108 and English Summary. (16 pages).

Edgar "T cell immunodeficiency", Journal of Clinical Pathology, 61(9): 988-993, Aug. 28, 2008. Abstract.

Itoh et al. "Optimization of the Inter-Domain Structure of Galectin-9 for Recombinant Production", Glycobiology, 23(8): 920-925, Mar. 18, 2013.

Notification of Office Action and Search Report Dated Sep. 28, 2022 From the State Intellectual Property Office of the People's Republic of China Re. Application No. 201880015833.1. (9 Pages).

Office Action Dated Sep. 28, 2022 From the Israel Patent Office Re. Application No. 267861. (3 Pages).

Office Action Dated Sep. 29, 2022 From the Israel Patent Office Re. Application No. 267862. (3 Pages).

Official Action Dated Sep. 29, 2022 from US Patent and Trademark Office Re. U.S. Appl. No. 17/400,179. (104 pages).

Aaron "Overview of Fungal Skin Infections", Merck Manual, 1-2, accessed Feb. 19, 2019.

Bowie et al. "Deciphering the Message in Protein Sequences: Tolerance to Amino Acid Substitutions", Science 247(4948):1306-1310, Mar. 16, 1990.

Burgess et al. "Possible Dissociation of the Heparin-binding and Mitogenic Activities of Heparin-binding (acidic fibroblast) Growth Factor-1 from its Receptor-binding Activities by Site-directed Mutagenesis of a Single Lysine Residue", Jurnal of Cell Biology (1990) 111 (5): 2129-2138, Nov. 1, 1990.

CDC "Types of Fungal Diseases", Center for Disease Control and Prevention, 1-2, accessed May 21, 2021.

Doron "Bacterial Infections: Overview", International Encyclopedia of Public Healthy, 2008 : 273-282, PMC7149789, Aug. 26, 2008.

Gregory "Neuroblastoma", Merck Manual, 1-4, accessed Dec. 3, 2017.

Hershman "Thyroid cancers", 1-4, Dec. 3, 2017.

Kleinsmith et al. "Understanding Cancer and Related Topics—Understanding Cancer", National Cancer Institute, 1-63, 2007, accessed Aug. 21, 2014.

Kramer "Overview of Viruses", Merck Manual, 1-6, accessed Feb. 19, 2019.

Lazar et al. "Transforming Growth Factor: Mutation of Aspartic Acid 47 and Leucine 48 Results in Different Boiological Activities", Molecular and Cellular Biology, 8(3): 1247-1252, Mar. 1998.

Master "Renal Cell Carcinoma", Merck Manual, 1-6, accessed Dec. 3, 2017.

merckmanuals.com "Bladder Cancer", Merck Manual, 1-2, accessed Aug. 21, 2014.

merckmanuals.com "Colorectal Cancer", Merck Manual, 1-5, accessed on-line Aug. 21, 2014.

merckmanuals.com "Overview of Fungal Infections", Merck Manual, 1-3, accessed Oct. 21, 2020.

merckmanuals.com "Overview of Leukemia", Merck Manual, 1-2, accessed Aug. 21, 2014.

merckmanuals.com "Overview of Lymphoma", Merck Manual, 1, accessed Aug. 21, 2014.

(56) References Cited

OTHER PUBLICATIONS merckmanuals.com "Prostate Cancer", Merck Manual, 1-8, accessed Aug. 21, 2014.
NIH "Antimicrobial Resistance Threats", Natinal Institute of Allergy and Infectious Diseases, 1-3, 2020.
Pearson "Approach to Parasitic Infections", Merck Manual, 1-10, accessed Oct. 22, 2020.
Shanks et al. "Are animal models predictive for humans?", Philosophy, Ethics, and Humanities in Medicine, 4(2):1-20, Jan. 15, 2009.
Tsao Lung Carcinoma (Lung Cancer), Merck Manual, 1-18, accessed Dec. 3, 2017.
English summary dated Jul. 3, 2023 of Request for Examination Dated Jun. 7, 2023 From the Federal Government Institution, Federal Institute of Industrial Property of the Federal Service of Intellectual Property, Patents and Trademarks of the Russian Federation, FIPS Re. Application No. 2021101091.
Notice of Reason(s) for Rejection Dated Jun. 27, 2023 From the Japan Patent Office Re. Application No. 2021-500820. (3 pages).
Notice of Allowance Dated Aug. 22, 2023 From the US Patent and Trademark Office Re. U.S. Appl. No. 17/400,179. (32 Pages).
Search Report and Written Opinion Dated Feb. 24, 2023 From the Intellectual Property Office of Singapore, IPOS Re. Application No. 11202200041R. (15 Pages).
International Preliminary Report on Patentability Dated Jan. 20, 2022 From the International Bureau of WIPO Re. Application No. PCT/IL2020/050762. (8 Pages).
Summary Dated Nov. 4, 2022 of Notification of Office Action Dated Oct. 9, 2022 From the State Intellectual Property Office of the People's Republic of China Re. Application No. 201880016069.X. (5 Pages).
English Summary Dated May 11, 2023 of Notification of Office Action Dated Apr. 27, 2023 From the State Intellectual Property Office of the People's Republic of China Re. Application No. 201880016069.X (3 pages).
Notification of Office Action Dated Apr. 27, 2023 From the State Intellectual Property Office of the People's Republic of China Re. Application No. 201880016069.X (7 pages).
Official Action Dated May 8, 2023 from the US Patent and Trademark Office Re. U.S. Appl. No. 17/400,179. (48 pages).
Request for Examination Dated Apr. 14, 2023 From the Federal Government Institution, Federal Institute of Industrial Property of the Federal Service of Intellectual Property, Patents and Trademarks of the Russian Federation, FIPS Re. Application No. 2021101108. (7 Pages).
Barclay et al. "The Interaction Between Signal Regulatory Protein Alpha (SIRPα) and CD47: Structure, Function, and Therapeutic Target", Annual Review of Immunology, 32: 25-50, Nov. 6, 2013.
Willingham et al. "The CD47-Signal Regulatory Protein Alpha (SIRPα) Interaction is a Therapeutic Target for Human Solid Tumors", PNAS, 109(17): 6662-6667, Mar. 26, 2012.
Grounds of Reason of Rejection Dated Apr. 5, 2023 From the Korean Intellectual Property Office Re. Application No. 10-2019-7022855. (4 Pages).
Official Action Dated Apr. 13, 2023 from the US Patent and Trademark Office Re. U.S. Appl. No. 17/258,170. (27 pages).
Notification of Office Action and Search Report Dated Jun. 1, 2023 From the State Intellectual Property Office of the People's Republic of China Re. Application No. 201980052864.9. (7 Pages).
Notification of Office Action and Search Report Dated Jun. 2, 2023 From the State Intellectual Property Office of the People's Republic of China Re. Application No. 201980052845.6. (7 Pages).
Notification of Office Action and Search Report Dated Jun. 7, 2023 From the State Intellectual Property Office of the People's Republic of China Re. Application No. 202080063464.0. (8 Pages).
Ha et al. "Immunoglobulin Fc Heterodimer Platform Technology: From Design to Applications in Therapeutic Antibodies and Proteins", Frontiers in Immunology, 7(394): 1-16, Oct. 2016.
Restriction Official Action Dated Jan. 5, 2022 from US Patent and Trademark Office Re. U.S. Appl. No. 16/475,705. (8 pages).

Amiot et al. "Biology of HLA-G in Cancer: A Candidate Molecule for Therapeutic Intervention?", Cellular and Molecular Life Sciences, 68(3): 417-431, Published Online Nov. 10, 2010.
Anna et al. "First Immunotherapeutic CAR-T Cells Against the Immune Checkpoint Protein HLA-G", Journal for Immuno Therapy of Cancer, 9(3): e001998-1-e001998-14, Mar. 2021.
Blaschitz et al. "Reaction Patterns of Monoclonal Antibodies to HLA-G in Human Tissues and on Cell Lines: A Comparative Study", Human Immunology, 61(11): 1074-1085, Nov. 2000.
Carosella et al. "Beyond the Increasing Complexity of the Immunomodulatory HLA-G Molecule", Blood, 111(10): 4862-4870, Published Online Mar. 11, 2008.
Carosella et al. "HLA-G: An Immune Checkpoint Molecule", Advances in Immunology, 127: 33-144, Published Online May 27, 2015.
Carosella et al. "HLA-G: From Biology to Clinical Benefits", Trends in Immunology, 29(3): 125-132, Available Online Feb. 4, 2008.
Clements et al. "Crystal Structure of HLA-G: A Nonclassical MHC Class I Molecule Expressed at the Fetal-Maternal Interface", Proc. Natl. Acad. Sci. USA, PNAS, 102(9): 3360-3365, Mar. 1, 2005.
Kang et al. "Inhibitory Leukocyte Immunoglobulin-Like Receptors: Immune Checkpoint Proteins and Tumor Sustaining Factors", Cell Cycle, 15(1): 25-40, Jan. 2, 2016.
Katz "Inhibition of Inflammatory Responses by Leukocyte Ig-Like Receptors", Advances in Immunology, 91: 251-272, Jan. 2006.
Lin et al. "Human Leukocyte Antigen-G (HLA-G) Expression in Cancers: Roles in Immune Evasion, Metastasis and Target for Therapy", Molecular Medicine, 21(1): 782-791, Published Online Aug. 24, 2015.
Menier et al. "Characterization of Monoclonal Antibodies Recognizing HLA-G or HLA-E: New Tools to Analyze the Expression of Nonclassical HLA Class I Molecules", Human Immunology, 64(3): 315-326, Mar. 2003.
Shiroishi et al. "Efficient Leukocyte Ig-Like Receptor Signalling and Crystal Structure of Disulfide-Linked HLA-G Dimer", The Journal of Biological Chemistry, 281(15): 10439-10447, Published Online Feb. 2, 2006.
Shiroishi et al. "Human Inhibitory Receptors Ig-Like Transcript 2 (ILT2) and ILT4 Compete With CD8 for MHC Class I Binding and Bind Preferentially to HLA-G", Proc. Natl. Acad. Sci. USA, PNAS, 100(15): 8856-8861, Jul. 22, 2003.
Shiroishi ct al. "Structural Basis for Recognition of the Nonclassical MHC Molecule HLA-G by the Leukocyte Ig-Like Receptor B2 (LILRB2 / LIR2 / ILT4 / CD85d)", Proc. Natl. Acad. Sci. USA, PNAS, 103(44): 16412-16417, Oct. 31, 2006.
Yan "HLA-G Expression in Cancers: Potential Role in Diagnosis, Prognosis and Therapy", Endocrine, Metabolic & Immune Disorders—Drug Targets, 11(1): 76-89, Mar. 2011.
Request for Examination Dated Jun. 7, 2023 From the Federal Government Institution, Federal Institute of Industrial Property of the Federal Service of Intellectual Property, Patents and Trademarks of the Russian Federation, FIPS Re. Application No. 2021101091. (19 Pages).
Notification of Office Action Dated Apr. 21, 2023 From the State Intellectual Property Office of the People's Republic of China Re. Application No. 201880015833.1 (5 pages).
Translation Dated Mar. 22, 2023 of Grounds of Reason of Rejection Dated Mar. 7, 2023 From the Korean Intellectual Property Office Re. Application No. 10- 2019-7022848. (5 Pages).
Translation Dated Apr. 27, 2023 of Grounds of Reason of Rejection Dated Apr. 5, 2023 From the Korean Intellectual Property Office Re. Application No. 10- 2019-7022855. (3 Pages).
International Search Report and the Written Opinion Dated Feb. 16, 2023 From the International Searching Authority Re. Application No. PCT/IL2022/051378 (11 Pages).
Jones et al. "Leukocyte Immunoglobulin-like Receptor Subfamily B Member 2 Soluble Isoform [*Homo Sapiens*]", Database NCBI [Online], GenBank: ACK56072.1, Database Accession No. ACK56072, 3 pages, Feb. 18, 2010.
Notice of Reasons for Rejection Dated Apr. 26, 2022 From the Japan Patent Office Re. Application No. 2019-5363308. (3 Pages).

(56) References Cited

OTHER PUBLICATIONS

Translation Dated Jul. 14, 2023 of Notice of Reason(s) for Rejection Dated Jun. 27, 2023 From the Japan Patent Office Re. Application No. 2021-500820. (4 pages).
International Preliminary Report on Patentability Dated Jul. 27, 2023 From the International Bureau of WIPO Re. Application No. PCT/IL2022/050055 (10 Pages).
Translation Dated May 12, 2023 of Notification of Office Action Dated Apr. 21, 2023 From the State Intellectual Property Office of the People's Republic of China Re. Application No. 201880015833.1 (6 pages).
Communication Pursuant to Article 94(3) EPC Dated May 9, 2022 From the European Patent Office Re. Application No. 18736642.2. (8 Pages).
English Translation Dated May 9, 2022 of Notice of Reasons for Rejection Dated Apr. 26, 2022 From the Japan Patent Office Re. Application No. 2019-5363308. (4 Pages).
Request for Examination Dated Sep. 8, 2021 From the (ROSPATENT), Federal Government Institution of Industrial Property of the Federal Service of Intellectual Property, Patents and Trademark of the Russian Federation Re. Application No. 2019124676. (14 Pages).
Request for Examination Dated Sep. 8, 2021 From the (ROSPATENT), Federal Government Institution of Industrial Property of the Federal Service of Intellectual Property, Patents and Trademark of the Russian Federation Re. Application No. 2019124678. (12 Pages).
Tokuriki et al. "Stability Effects of Mutations and Protein Evolvability", Current Opinion in Structural Biology, 19(5):596-604, Oct. 2009.
Official Action Dated Mar. 2, 2022 from US Patent and Trademark Office Re. U.S. Appl. No. 16/475,705. (79 pages).
Uni Prot "Programmed Cell Death Protein 1", Uni Prot/NCBI Accession Q15116, Sequence Updated Apr. 17, 2017, 9 P., Accessed on Line Feb. 23, 2022.
UniProt "Tumor Necrosis Factor Ligand Superfamily Member 9", UniProt/NCBI Accession P41273, 4 P., Accessed Online Feb. 23, 2022, Sequence Updated Feb. 1, 1995.
Examination Report Dated Feb. 25, 2022 From the Intellectual Property Office of Singapore, IPOS Re. Application No. 11201905679S. (6 pages).
Invitation to Pay Additional Fees, Communication Relating to the Results of the Partial International Search Dated Mar. 10, 2022 From the International Searching Authority Re. Application No. PCT/IL2022/050055. (7 Pages).
Notice of Eligibility for Grant Dated Feb. 28, 2022 From the Intellectual Property Office of Singapore, IPOS Re. Application No. 11201905679S. (1 page).
Restriction Official Action Dated Mar. 28, 2022 from US Patent and Trademark Office Re. U.S. Appl. No. 16/475,139. (10 pages).
Supplementary European Search Report and the European Search Opinion Dated Mar. 7, 2022 From the European Patent Office Re. Application No. 19833103.5.(10 Pages).
Official Action Dated Jan. 21, 2022 from US Patent and Trademark Office Re. U.S. Appl. No. 16/027,382. (21 pages).
Translation Dated May 15, 2023 of Request for Examination Dated Apr. 14, 2023 From the Federal Government Institution, Federal Institute of Industrial Property of the Federal Service of Intellectual Property, Patents and Trademarks of the Russian Federation, FIPS Re. Application No. 2021101108. (4 Pages).
International Search Report and the Written Opinion Dated May 9, 2022 From the International Searching Authority Re. Application No. PCT/IL2022/050055. (19 Pages).
Notice of Reasons for Rejection Dated Apr. 26, 2022 From the Japan Patent Office Re. Application No. 2019-536286 and Its Translation Into English.(12 pages).
Chajut et al. "790 DSP502—A Novel Approach for Targeting TIGIT and PD1 Pathways for Cancer Immunotherapy", Journal for Immunotherapy of Cancer, 9(2): A825-A825, Nov. 30, 2021.
Hung et al. "TIGIT and PD-1 Dual Checkpoint Blockade Enhances Antitumor Immunity and Survival in GBM", OncoImmunology, 7(8): e1466769-1-e1466769-14, May 24, 2018.

Nguyen "Blocking 'Don't Eat Me' Signals CD47 and LILRB2 to Enhance Macrophage-and Granulocyte-Mediated Phagocytosis of Cancer Cells", Thesis, 1-31 P., Jul. 31, 2019.
Zak et al. "Structure of the Complex of Human Programmed Death 1, PD-1, and Its Ligand PD-L1", Structure, 23(12): 2341-2348,Dec. 1, 2015.
Notice of Allowance Dated Sep. 30, 2022 from US Patent and Trademark Office Re. U.S. Appl. No. 16/475,139. (11 pages).
Examination Report Under Sections 12 & 13 of the Patents Act, 1970 and the Patents Rules, 2003 Dated Jul. 18, 2022 From the Government of India, Intellectual Property India, Patents Designs, Trade Marks, Geographical Indications The Patent Office Re. Application No. 202127002771. (6 Pages).
English Summary Dated Jul. 4, 2023 of Notification of Office Action Dated Jun. 7, 2023 From the State Intellectual Property Office of the People's Republic of China Re. Application No. 202080063464.0. (4 pages).
Office Action Dated Jul. 6, 2023 From the Israel Patent Office Re. Application No. 267861. (3 Pages).
Search Report and Written Opinion Dated Mar. 23, 2022 From the Intellectual Property Office of Singapore Re. Application No. 11202013167U. (10 Pages).
Search Report and Written Opinion Dated Mar. 23, 2022 From the Intellectual Property Office of Singapore, IPOS Re. Application No. 11202013170R. (10 Pages).
Supplementary European Search Report and the European Search Opinion Dated Mar. 23, 2022 From the European Patent Office Re. Application No. 19833260.3. (7 Pages).
Cendrowicz et al. "DSP107 Combines Inhibition of CD47/SIRP Alpha Axis With Activation of 4-1BB to Trigger Anticancer Immunity", Journal of Experimental & Clinical Cancer Research, 41(1): 97-1-97-16, Mar. 14, 2022.
Official Action Dated Jul. 7, 2021 from the US Patent and Trademark Office Re. U.S. Appl. No. 16/475,683. (46 pages).
Interview Summary Dated Feb. 17, 2023 from the US Patent and Trademark Office Re. U.S. Appl. No. 16/027,382. (2 pages).
Notice of Allowance Dated Feb. 24, 2023 from the US Patent and Trademark Office Re. U.S. Appl. No. 16/475,705. (21 pages).
Official Action Dated Aug. 5, 2022 from US Patent and Trademark Office Re. U.S. Appl. No. 16/027,382. (37 pages).
Notice of Reason(s) for Rejection Dated Sep. 28, 2021 From the Japan Patent Office Re. Application No. 2019-536286 and Its Translation Into English. (11 Pages).
Kornbluth et al. "Multimeric Soluble 4-1BBL as a T Cell Stimulator for Adoptive Immunotherapy", The Journal of Immunology, 198(1) Suppl., May 1, 2017.
Supplementary European Search Report and the European Search Opinion Dated Dec. 20, 2021 From the European Patent Office Re. Application No. 21179906.9. (8 Pages).
Official Action Dated Jun. 1, 2022 from US Patent and Trademark Office Re. U.S. Appl. No. 17/258,170. (82 pages).
Request for Examination Dated May 11, 2022 From the (ROSPATENT), Federal Government Institution of Industrial Property of the Federal Service of Intellectual Property, Patents and Trademark of the Russian Federation Re. Application No. 2022103192 and Its Translation Into English. (5 Pages).
ABSS "US_20160200833_ABSS_Sequence_Comparisons", Generated by Examiner Using the ABSS, 1-7 P., May 17, 2022.
ABSS "US_20170095531_ABSS Sequence Comparison Findings 102", Generated by Examiner Using the ABSS Application, 1-5 P., May 17, 2022.
ABSS W0_2014121093 Abss Sequence Comparison, Generated by Examiner Using the ABSS Application, 1 P., May 16-17, 2022.
Translation Dated Jan. 30, 2023 of Request for Examination and Search Report Dated Jan. 12, 2023 From the (ROSPATENT), Federal Government Institution of Industrial Property of the Federal Service of Intellectual Property, Patents and Trademark of the Russian Federation Re. Application No. 2021101091. (9 pages).
English Summary Dated Jun. 16, 2023 of Notification of Office Action Dated Jun. 1, 2023 From the State Intellectual Property Office of the People's Republic of China Re. Application No. 201980052864.9. (3 pages).

(56) References Cited

OTHER PUBLICATIONS

English Summary Dated Jun. 19, 2023 of Notification of Office Action and Search Report Dated Jun. 2, 2023 From the State Intellectual Property Office of the People's Republic of China Re. Application No. 201980052845.6. (3 pages).
Official Action Dated Jun. 12, 2023 from the US Patent and Trademark Office Re. U.S. Appl. No. 16/027,382. (49 pages).
Requisition by the Examiner Dated Jun. 20, 2023 From the Innovation, Science and Economic Development Canada, Canadian Intellectual Property Office Re. Application No. 3,146,248. (8 pages).
Translation Dated Jun. 15, 2023 of Notice of Reason(s) for Rejection Dated May 23, 2023 From the Japan Patent Office Re. Application No. 2021-500829. (3 pages).
Notification on the Results of Checking the Patentability of An Invention Dated Aug. 25, 2023 From the Federal Government Institution, Federal Institute of Industrial Property of the Federal Service of Intellectual Property, Patents and Trademarks of the Russian Federation, FIPS Re. Application No. 2021101108 and Its Translation Into English. (7 pages).
Request for Examination and Search Report Dated Sep. 13, 2023 From the Federal Government Institution, Federal Institute of Industrial Property of the Federal Service of Intellectual Property, Patents and Trademarks of the Russian Federation, FIPS Re. Application No. 2022103192. (11 pages).
Badri et al. "Optimization of Radiation Dosing Schedules for Proneural Glioblastoma", Journal of Mathematical Biology, 72(5): 1301-1336, Jun. 21, 2015.
Baylot et al. "TCTP Has a Crucial Role in the Different Stages of Prostate Cancer Malignant 4 Progression 5", Results and Problems in Cell Differentiation, TCTP/tpt1—Remodeling Signaling from Stem Cell to Disease, 255-261, Nov. 18, 2017.
Restriction Official Action Dated Jan. 28, 2022 from US Patent and Trademark Office Re. U.S. Appl. No. 17/258,170. (8 pages).
Written Opinion Dated Jan. 18, 2022 From the Intellectual Property Office of Singapore, IPOS Re. Application No. 11201905681W. (8 Pages).
Persson et al. "Transforming Growth Factor (TGF-b)-specific Signaling by Chimeric TGF-b Type II Receptor with Intracellular Domain of Activin Type IIB Receptor", Cell Biologt and Metabolism, 272(34): 1187-21194, Aug. 1997.
Notice of the Results of the Patent Fee Check Dated May 30, 2022 From the Federal Government Institution, Federal Institute of Industrial Property of the Federal Service of Intellectual Property, Patents and Trademarks of the Russian Federation, FIPS Re. 2021101108. (3 Pages).
Requisition by the Examiner Dated Aug. 3, 2023 From the Innovation, Science and Economic Development Canada, Canadian Intellectual Property Office Re. Application No. 3,104,780. (9 Pages).
ABBS "US-16-473-631-1 Pep vs. US-17-258-170-13 Pep Align", ABSS Application, 1 P., May 18, 2022.
ABSS "US-17-400-179-2 Pep vs. US-17-258-170-13 Pep Align", ABSS Application, 1 P., May 18, 2018.
Translation Dated Dec. 23, 2022 of Request for Examination Dated Dec. 5, 2022 From the (ROSPATENT), Federal Government Institution of Industrial Property of the Federal Service of Intellectual Property, Patents and Trademark of the Russian Federation Re. Application No. 2021101108. (10 pages).
Edgar "T cell immunodeficiency", Journal of Clinical Pathology, 61(9): 988-993, Aug. 28, 2008.
Keskin et al. "A new, structurally nonredundant, diverse data set of protein-protein interfaces and its implications", Protein Science (2004), 13(4):1043-1055, Jan. 9, 2004.
Kosobokova et al. "Antibody-cytokine Fusion Proteins: Production, Functionality and Application Prospects in Oncology", Contemporary Technologies in Medicine 2013—5(4): 102-111, Jun. 27, 2013.
Pakula et al. "Genetic Analysis of Protein Stability and Function", Annual Review of Genetics, 23(1): 289-310, Dec. 1989.

Notice of Reason(s) for Rejection Dated Jul. 25, 2023 From the Japan Patent Office Re. Application No. 2022-132987 and Its Translation Into English. (7 Pages).
Communication Pursuant to Article 94(3) EPC Dated Jun. 1, 2017 From the European Patent Office Re. Application No. 13827047.5. (4 Pages).
Communication Pursuant to Article 94(3) EPC Dated Feb. 6, 2018 From the European Patent Office Re. Application No. 13827047.5. (5 Pages).
Communication Pursuant to Article 94(3) EPC Dated Sep. 26, 2016 From the European Patent Office Re. Application No. 13827047.5. (3 Pages).
Examination Report Dated Jul. 11, 2017 From the Australian Government, IP Australia Re. Application No. 2013371826.(4 Pages).
Examination Report Dated Mar. 28, 2018 From the Australian Government, IP Australia Re. Application No. 2013371826.(2 Pages).
Final Official Action Dated May 12, 2021 From the US Patent and Trademark Office Re. U.S. Appl. No. 16/027,382. (15 Pages).
International Preliminary Report on Patentability Dated Jul. 16, 2015 From the International Bureau of WIPO Re. Application No. PCT/IL2013/051098. (14 Pages).
International Preliminary Report on Patentability Dated Jul. 18, 2019 From the International Bureau of WIPO Re. Application No. PCT/IL2018/050014. (7 Pages).
International Preliminary Report on Patentability Dated Jul. 18, 2019 From the International Bureau of WIPO Re. Application No. PCT/IL2018/050015. (7 Pages).
International Preliminary Report on Patentability Dated Jul. 18, 2019 From the International Bureau of WIPO Re. Application No. PCT/IL2018/050016. (7 Pages).
International Preliminary Report on Patentability Dated Jul. 18, 2019 From the International Bureau of WIPO Re. Application No. PCT/IL2018/050017. (7 Pages).
International Preliminary Report on Patentability Dated Jan. 21, 2021 From the International Bureau of WIPO Re. Application No. PCT/IL2019/050782. (9 Pages).
International Preliminary Report on Patentability Dated Jan. 21, 2021 From the International Bureau of WIPO Re. Application No. PCT/IL2019/050783. (8 Pages).
International Search Report and the Written Opinion Dated Oct. 6, 2020 From the International Searching Authority Re. Application No. PCT/IL2020/050762. (13 Pages).
International Search Report and the Written Opinion Dated Mar. 13, 2018 From the International Searching Authority Re. Application No. PCT/IL2018/050015. (11 Pages).
International Search Report and the Written Opinion Dated Mar. 13, 2018 From the International Searching Authority Re. Application No. PCT/IL2018/050016. (11 Pages).
International Search Report and the Written Opinion Dated May 15, 2014 From the International Searching Authority Re. Application No. PCT/IL2013/051098. (19 Pages).
International Search Report and the Written Opinion Dated Sep. 16, 2019 From the International Searching Authority Re. Application No. PCT/IL2019/050783. (15 Pages).
International Search Report and the Written Opinion Dated Sep. 18, 2019 From the International Searching Authority Re. Application No. PCT/IL2019/050782. (16 Pages).
International Search Report and the Written Opinion Dated Feb. 25, 2018 From the International Searching Authority Re. Application No. PCT/IL2018/050017. (11 Pages).
International Search Report and the Written Opinion Dated Feb. 27, 2018 From the International Searching Authority Re. Application No. PCT/IL2018/050014. (11 Pages).
Notification of Office Action and Search Report Dated Dec. 15, 2017 From the State Intellectual Property Office of the People's Republic of China Re. Application No. 201380074192.4. (7 Pages).
Notification of Office Action Dated Jul. 10, 2018 From The State Intellectual Property Office of the People's Republic of China Re. Application No. 201380074192.4. and Its Summary In English. (5 Pages).
Office Action Dated Aug. 14, 2018 From the Israel Patent Office Re. Application No. 239671 and Its Translation Into English. (7 Pages).

(56) References Cited

OTHER PUBLICATIONS

Official Action Dated Oct. 6, 2017 From the US Patent and Trademark Office Re. U.S. Appl. No. 14/655,752. (9 pages).
Official Action Dated Nov. 13, 2020 from the US Patent and Trademark Office Re. U.S. Appl. No. 16/027,382. (41 pages).
Official Action Dated Mar. 29, 2021 From the US Patent and Trademark Office Re. U.S. Appl. No. 16/473,631. (34 Pages).
Official Action Dated Mar. 30, 2017 From the US Patent and Trademark Office Re. U.S. Appl. No. 14/655,752. (12 Pages).
Patent Examination Report Dated Apr. 6, 2021 From the Australian Government, IP Australia Re. Application No. 2018205890.(4 Pages).
Patent Examination Report Dated 26 Marcch 2021 From the Australian Government, IP Australia Re. Application No. 2018205888. (4 Pages).
Request for Examination and Search Report Dated Apr. 9, 2021 From the (ROSPATENT), Federal Government Institution of Industrial Property of the Federal Service of Intellectual Property, Patents and Trademark of the Russian Federation Re. Application No. 2019124676 and Its Translation Into English. (40 Pages).
Request for Examination Dated Apr. 9, 2021 Fom the (ROSPATENT), Federal Government Institution of Industrial Property of the Federal Service of Intellectual Property, Patents and Trademark of the Russian Federation Re. Application No. 2019124678 and Its Translation Into English. (33 Pages).
Restriction Official Action Dated Jun. 15, 2016 From the US Patent and Trademark Office Re. U.S. Appl. No. 14/655,752. (7 Pages).
Restriction Official Action Dated May 15, 2020 from the US Patent and Trademark Office Re. U.S. Appl. No. 16/027,382. (10 pages).
Restriction Official Action Dated Nov. 2, 2020 From the US Patent and Trademark Office Re. U.S. Appl. No. 16/473,631. (14 Pages).
Restriction Official Action Dated Mar. 26, 2021 from the US Patent and Trademark Office Re. U.S. Appl. No. 16/475,683. (9 pages).
Search Report and Written Opinion Dated Apr. 25, 2020 From the Intellectual Property Office of Singapore Re. Application No. 11201905679S.
Search Report and Written Opinion Dated Apr. 25, 2020 From the Intellectual Propery Office of Singapore Re. Application No. 11201905681W. (10 Pages).
Supplementary European Search Report and the European Search Opinion Dated Oct. 12, 2020 From the European Patent Office Re. Application No. 18735930.2. (8 Pages).
Supplementary European Search Report and the European Search Opinion Dated Nov. 19, 2020 From the European Patent Office Re. Application No. 18736642.2. (12 Pages).
Translation Dated Jul. 25, 2018 of Notification of Office Action Dated Jul. 10, 2018 From The State Intellectual Property Office of the People's Republic of China Re. Application No. 201380074192.4. (5 Pages).
Translation of Notification of Office Action and Search Report Dated Dec. 15, 2017 From the State Intellectual Property Office of the People's Republic of China Re. Application No. 201380074192.4. (9 Pages).
Absolute Antibody "Antibody Sequencing, Engineering & Recombinant Expression", Absolute Antibody, Home Products, Website, 3 P., 2019.
Absolute Antibody "Bispecific and Trispecific Antibodies", Absolute Antibody, Website, Home Products, Website, 3 P., 2019.
Absolute Antibody "Products Archive", Absolute Antibody, Home Products, Website, 2 P., 2019.
Antoniou et al. "Transgenes Excompassing Dual-Promoter CpG Islands From the Human TBPand HNRPA2B1 Loci Are Resistant to Heterochromatin-Mediated Silencing", Genomics, 82(3): 269-279, Sep. 2003.
Arora et al. "Belatacept: A New Biological Agent for Maintenance Immunosuppression in Kidney Transplantation", Expert Opinion on Biological Therapy, 12(7): 965-979, Published Online May 8, 2012.
Ascierto et al. "Clinical Experiences With Anti-CD137 and Anti-PD1 Therapeutic Antibodies", Seminars in Oncology, XP008175440, 27(5): 508-516, Oct. 1, 2010.

Beha et al. "IL-15-Based Trifunctional Antibody-Fusion Proteins With Costimulatory TNF-Superfamily Ligands in the Single-Chain Format for Cancer Immunotherapy", Molecular Cancer Therapeutics, p. 1-35, Published Ahead of Print Apr. 30, 2019.
Berry et al. "Substitution of Cysteine for Selenocysteine in Type I Iodothyronine Deiodinase Reduces the Catalytic Efficiency of the Protein But Enhances its Translation", Endocrinology,131(4): 1848-1852, Oct. 1, 1992.
Chen et al. "Fusion Protein Linkers: Property, Design and Functionality", Advanced Drug Delivery Reviews, 65(10): 1357-1369, Oct. 15, 2013.
Dranitzki-Elhalel et al. CD40•FasL Inhibits Human T Cells: Evidence for An Auto-Inhibitory Loop-Back Mechanism, International Immunology, XP001668353, 19(4): 355-363, Advance Access Publication Feb. 20, 2007.
Eisele et al. "APO010, A Synthetic Hexameric CD95 Ligand, Induces Human Glioma Cell Death In Vitro and In Vivo", Neuro-Oncology, 13(2): 155-164, Published Online Dec. 22, 2010.
Fellermeier et al. "Advancing Targeted Co-Stimulation With Antibody-Fusion Proteins by Introducing TNF Superfamily Members in A Single-Chain Format", Oncoimmunology, 5(11): e1238540-1-e1238540-11, Sep. 27, 2016.
Feng et al. "CTLA4-Fas Ligand Gene Transfer Mediated by Adenovirus Induce Long-Time Survival of Murine Cardiac Allografts", Transplantation Proceedings, 37(5): 2379-2381, Jun. 2005.
Frankel et al. Characterization Of Diphtheria Fusion Proteins Targeted To The Human Interleukin-3 Receptor', Protein Engineering, Design and Selection, 13(8);575-581, Aug. 1, 2000.
Gasser et al. "Antibody Production With Yeasts And Filamentous Fungi: On The Road To Large Scale?", Biotechnology Letters, 29: 201-212, Nov. 22, 2006.
Gozlan et al. "Abstract A076: DSP107-A novel SIRPa-4-1 BBL Dual Signaling Protein (DSP) for Cancer Immunotherapy", Cancer Immunology Research, XP55734527A,7(2): 2P., Feb. 2019.
Grewal et al. "CD40 and CD154 in Cell-Mediated Immunity", Annual Review of Immunology, 16:111-135, Publication date: Apr. 1998.
Halin et al. "Synergistic Therapeutic Effects of a Tumor Targeting Antibody Fragment, Fused to Interleukin 12 and to Tumor Necrosis Factor α", Cancer Research, 63(12):3202-3210, Jun. 15, 2003.
Herrero-Beaumont et al. "Abatacept Mechanism of Action: Concordance With Its Clinical Profile?", Reumatologia Clinica, 8(2): 78-83, Available Online Feb. 15, 2012.
Holler et al. "Two Adjacent Trimeric Fas Ligands Are Required for Fas Signaling and Formation of A Death-Inducing Signaling Complex", Molecular and Cellular Biology, XP002258597, 23(4): 1428-1440, Feb. 2003. Abstract.
Huang et al. "CTLA-4-Fas Ligand Functions as A Trans Signal Converter Protein in Bridging Antigen-Presenting Cells and T Cells", International Immunology, XP001147390, 13(4): 529-539, Apr. 1, 2001. p. 537, r-h Col., Last Para, Fig. 1.
Jin et al. "Simultaneous Stimulation of Fas-Mediated Apoptosis and Blockade of Costimualtion Prevent Autoimmune Diabetes in Mice Induced by Multiple Low-Dose Streptozotocin", Gene Therapy, 11(12): 982-991, Published Online Mar. 25, 2004.
Kahr Medical "DSP105 (PD1-41BBL): Targeted Immune Activation Leading to T- Cell Mediated Tumor Destruction", Kahr Medical, Product Description, p. 1-4, Apr. 29, 2018.
Kaiko et al. "Immunological Decision-Making: How Does The Immune System Decide To Mount A Helper T-Cell Response", Immunology,123(3):326-338, Jan. 18, 2008.
Kontermann et al. "Bispecific Antibodies", Drug Discovery Today, 20(7): 838-847, Jul. 2015.
Lazar-Molnar et al. "Crystal Structure of the Complex Between Programmed Death-1 (PD-1) and Its Ligand PD-2", Proc. Natl. Acad. Sci. USA, PNAS, 105(30): 10483-10488, Jul. 29, 2008.
Locksley et al. "The TNF and TNF Receptor Superfamilies: Integrating Mammalian Biology", Cell, 104(4): 487-501, Feb. 23, 2001.
Maeda et al. "Engineering of Functional Chimeric Protein G-VargulaLuciferase", Analytical Biochemistry,249(2): 147-152, Jul. 1, 1997.

(56) References Cited

OTHER PUBLICATIONS

Maute et al. "Engineering High-Affinity PD-1 Variants for Optimized Immunotherapy and Ommuno-PET Omaging", Proceedings of the National Academy of Sciences, 112 (47): E6506-E6514, Published Online Nov. 10, 2015.

Merchant et al. "An Efficient Route to Human Bispecific IgG", Nature Biotechnology, 16(7): 677-681, Jul. 1998.

Muller et al. "Spliceosomal peptide P140 forImmunotherapy of Systemic Lupus Erythematosus: Results of an Early Phase II Clinical Trial*", Arthritis and Rheumatology, 58(12): 3873-3883, Nov. 26, 2008.

Nalamalpu et al. "Booster for Driving Long Onchip Interconnects—Design Issues, Interconnect Synthesis, and Comparison With Repeaters", IEEE Transactions on Computer-Aided Design of Integrated Circuits and Systems, 21(1): 50-62, Jan. 2002.

Orbach et al. "CD40•FasL and CTLA-4. FasL Fusion Proteins Induce Apoptosis in Malignant Cell Lines by Dual Signaling", The American Journal of Pathology, XP009155963, 177(6): 3159-3168, Dec. 2010. Abstract.

Orbach et al. "CTLA-4 • FasL Induces Early Apoptosis of Activated T Cells by Interfering With Anti-Apoptotic Signals", The Journal of Immunology, XP002668354, 179(11): 7287-7294, Dec. 1, 2007.

Pereg "Kahr Medical Dual Signaling Proteins (DSP) Platform—The Next Generation of Cancer Immunotherapy", Kahr Medical, Abstract Template for Company Presentations, 1 P., May 11, 2018.

Sanmamed et al. "Agonists of Co-Stimulation in Cancer Immunotherapy Directed Against CD137, OX40, Gitr, CD27, CD28, and ICOS", Seminars in Oncology, XP055410294, 42(4): 640-655, Aug. 1, 2015.

Shi et al. "Prolongation of Corneal Allograft Survival by CTLA4-FasL in A Murine Model", Graefe's Archive for Clinical and Experimental Ophthalmology, XP019542074, 245(11): 1691-1697, Published Online May 31, 2007.

Shrimali et al. "Concurrent PD-1 Blockade Negates the Effects of OX40 Agonist in Combination Immunotherapy Through Inducing T-Cell Apoptosis", Cancer Immunology Research, 5(9): 755-766, Published Online Aug. 28, 2017.

Slavin et al. "Spontaneous Murine B-Cell Leukaemia", Nature, 272(5654): 624-626, Apr. 13, 1978.

Tansey et al. "The TNF Superfamily in 2009: New Pathways, New Indications, and New Drugs", Drug Discovery Today, 14(23/24): 1082-1088, Dec. 2009.

Weiskopf et al. "Engineered SIRP-alpha Variants as Immunotherapeutic Adjuvants to Anti-cancer Antibodies," Science, 341 (6141): 88-91, Jul. 5, 2013.

Wyzgol et al. "Trimer Stabilization, Oligomerization, and Antibody-Mediated Cell Surface Immobilization Improve the Activity of Soluble Trimers of CD27L, CD40L, 41BBL, and Glucocorticoid-InducedTNF Receptor Ligands", The Journal of Immunology, 183(3): 1851-1861, Published Online Jun. 13, 2009.

Xiao et al. "Soluble PD-1 Facilitates 4-1BBL-Triggered Antitumor Immunity Against Murine H22 Hepatocarcinoma In Vivo", Clinical Cancer Research, XP055144430, 13(6): 1823-1830, Published Online Feb. 26, 2007.

Yang et al. "High-Level Expression And Deletion Mutagenesis Of Human Tryptophan Hydroxylase", Proceedings of the National Academy of Sciences ofthe United States of America, 91(14): 6659-6663, Jul. 5, 1994.

Yu et al. "The Surface Protein TIGIT Suppresses T Cell Activation by Promoting the Generation of Mature Immunoregulatory Dendritic Cells", Nature Immunology, 10: 48-57, 2009.

Zhang et al. "Intraarticular Gene Delivery of CTLA4-FasL Suppresses Experimental Arthritis", International Immunology, 24(6): 379-388, Advance Access Publicaiton 21 Februay 2012.

Zhang et al. "Targeted and Untargeted CD137L Fusion Proteins for the Immunotherapy of Experimental Solid Tumors", Clinical Cancer Research, XP055186494, 13(9): 2758-2767, May 1, 2007.

Interview Summary Dated Aug. 5, 2021 from the US Patent and Trademark Office Re. U.S. Appl. No. 16/027,382. (2 pages).

Kadagidze et al. Targeted Immunotherapy in Oncology, Allergiology and Immunology, 16(4):352, Nov. 2015, Abstract with English Translation.

Prokofieva et al. "Course of Lectures on General Pharmacology: Teaching Aid, Ulyanovsk", Ulyanovsk State University, 155 pages, pp. 65-77. 2017, with its Translation into English.

Translation Dated Nov. 17, 2022 of Notification of Office Action Dated Sep. 28, 2022 From the State Intellectual Property Office of the People's Republic of China Re. Application No. 201880015833. 1. (9 Pages).

Notification of Office Action and Search Report Dated Oct. 9, 2022 From the State Intellectual Property Office of the People's Republic of China Re Application No. 201880016069.X. (13 Pages).

Official Action Dated Oct. 17, 2022 from US Patent and Trademark Office Re. U.S. Appl. No. 16/027,382. (16 pages).

Summary Dated Oct. 18, 2022 of Notification of Office Action Dated Sep. 28, 2022 From the State Intellectual Property Office of the People's Republic of China Re. Application No. 201880015833. 1. (1 Pages).

Official Action Dated Jun. 24, 2022 from US Patent and Trademark Office Re. U.S. Appl. No. 16/475,139. (97 pages).

Communication Pursuant to Article 94(3) EPC Dated Oct. 1, 2021 From the European Patent Office Re. Application No. 18736642.2. (7 Pages).

Notice of Reason(s) for Rejection Dated Sep. 28, 2021 From the Japan Patent Office Re. Application No. 2019-536308 and Its Translation Into English. (8 Pages).

Translation Dated Oct. 1, 2021 of Request for Examination Dated Sep. 8, 2021 From the (ROSPATENT), Federal Government Institution of Industrial Property of the Federal Service of Intellectual Property, Patents and Trademark of the Russian Federation Re. Application No. 2019124678. (8 Pages).

Translation Dated Oct. 5, 2021 of Request for Examination Dated Sep. 8, 2021 From the Federal Government Institution, Federal Institute of Industrial Property of the Federal Service of Intellectual Property, Patents and Trademarks of the Russian Federation, FIPS Re. Application No. 2019124676. (11 Pages).

Written Opinion Dated Sep. 28, 2021 From the Intellectual Property Office of Singapore Re. Application No. 11201905679S. (9 Pages).

English Summary Dated Dec. 11, 2023 of Notification of Office Action Dated Nov. 23, 2023 From the State Intellectual Property Office of the People's Republic of China Re. Application No. 201980052864.9. (2 Pages).

Requisition by the Examiner Dated Sep. 27, 2023 From the Innovation, Science and Economic Development Canada, Canadian Intellectual Property Office Re. Application No. 3,047,708. (5 Pages).

Summary Dated Dec. 5, 2023 of Notification of Office Action Dated Nov. 25, 2023 From the State Intellectual Property Office of the People's Republic of China Rc. Application No. 201980052845.6. (2 Pages).

Translation Dated Dec. 12, 2023 of Notice of Reason(s) for Rejection Dated Nov. 28, 2023 From the Japan Patent Office Re. Application No. 2021-500829. (2 pages).

Notification of Office Action Dated Dec. 14, 2023 From the State Intellectual Property Office of the People's Republic of China Re. Application No. 202080063464.0 and Its Machine Translation Into English. (13 Pages).

Examination Report Under Sections 12 & 13 of the Patents Act, 1970 and the Patents Rules, 2003 Dated Dec. 1, 2023 From the Government of India, Intellectual Property India, Patents, Designs, Trade Marks, Geographical Indications, The Patent Office Re. Application No. 201927030333. (5 pages).

Notice of Reason(s) for Rejection Dated Nov. 28, 2023 From the Japan Patent Office Re. Application No. 2021-500829. (2 pages).

Written Opinion Dated Jan. 8, 2023 From the Intellectual Property Office of Singapore, IPOS Re. Application No. 11202200041R. (10 Pages).

Written Opinion Dated Jan. 8, 2024 From the Intellectual Property Office of Singapore, IPOS Re. Application No. 11202013167U. (8 Pages).

(56) References Cited

OTHER PUBLICATIONS

Machine Translation Dated Nov. 28, 2023 of Notification of Office Action Dated Nov. 23, 2023 From the State Intellectual Property Office of the People's Republic of China Re. Application No. 201980052864.9. (9 Pages).
Machine Translation Dated Nov. 29, 2023 of Notification of Office Action Dated Nov. 25, 2023 From the State Intellectual Property Office of the People's Republic of China Re. Application No. 201980052845.6. (5 Pages).
Notification of Office Action Dated Nov. 23, 2023 From the State Intellectual Property Office of the People's Republic of China Re. Application No. 201980052864.9. (4 Pages).
Notification of Office Action Dated Nov. 25, 2023 From the State Intellectual Property Office of the People's Republic of China Re. Application No. 201980052845.6. (5 Pages).
Official Action Dated Nov. 6, 2023 from the US Patent and Trademark Office Re. U.S. Appl. No. 17/695,898. (159 pages).
Written Opinion Dated Oct. 9, 2023 From the Intellectual Property Office of Singapore, IPOS Re. Application No. 11201905681W. (7 Pages).
Translation Dated Oct. 10, 2023 of Request for Examination and Search Report Dated Sep. 13, 2023 From the Federal Government Institution, Federal Institute of Industrial Property of the Federal Service of Intellectual Property, Patents and Trademarks of the Russian Federation, FIPS Re. Application No. 2022103192. (6 pages).
Written Opinion Dated Feb. 1, 2024 From the Intellectual Property Office of Singapore, IPOS Re. Application No. 11202013170R. (6 Pages).
English Summary Dated Nov. 10, 2023 of Request for Examination and Search Report Dated Nov. 2, 2023 From the (ROSPATENT), Federal Government Institution of Industrial Property of the Federal Service of Intellectual Property, Patents and Trademark of the Russian Federation Re. Application No. 2021101091. (4 Pages).
Official Action Dated Nov. 9, 2023 from the US Patent and Trademark Office Re. Application No. 17/258, 170. (62 pages).
Request for Examination and Search Report Dated Nov. 2, 2023 From the (ROSPATENT), Federal Government Institution of Industrial Property of the Federal Service of Intellectual Property, Patents and Trademark of the Russian Federation Re. Application No. 2021101091. (9 Pages).
Requisition by the Examiner Dated Nov. 7, 2023 From the Innovation, Science and Economic Development Canada, Canadian Intellectual Property Office Re. Application No. 3,104,778. (5 Pages).
Crasto et al. "Linker: A Program to Generate Linker Sequences for Fusion Proteins", Protein Engineering, 13(5): 309-312, May 1, 2000.
English Summary Dated Dec. 27, 2023 of Notification of Office Action Dated Dec. 14, 2023 From the State Intellectual Property Office of the People's Republic of China Re. Application No. 202080063464.0. (5 Pages).
Requisition by the Examiner Dated Nov. 15, 2023 From the Innovation, Science and Economic Development Canada, Canadian Intellectual Property Office Re. Application No. 3,047,707. (9 Pages).
Translation Dated Nov. 22, 2023 of Request for Examination and Search Report Dated Nov. 2, 2023 From the (ROSPATENT), Federal Government Institution of Industrial Property of the Federal Service of Intellectual Property, Patents and Trademark of the Russian Federation Re. Application No. 2021101091. (7 Pages).
Machine Translation Dated Jun. 10, 2024 of Notice of Reasons for Rejection Dated May 28, 2024 From the Japan Patent Office Re. Application No. 2019-536286.(2 pages).
Notice of Reasons for Rejection Dated May 28, 2024 From the Japan Patent Office Re. Application No. 2019-536286.(3 pages).
Restriction Official Action Dated Jun. 11, 2024 from the US Patent and Trademark Office Re. U.S. Appl. No. 18/101,601. (9 pages).
Notice of Allowance Dated Jun. 27, 2024 together with Interview Summary Dated Jun. 3, 2024 from the US Patent and Trademark Office Re. U.S. Appl. No. 17/258,170. (20 Pages).
Notice of Reason(s) for Rejection Dated Jun. 18, 2024 From the Japan Patent Office Re. Application No. 2022-501004 and Its Translation Into English. (14 Pages).
Restriction Official Action Dated Jun. 24, 2024 From the US Patent and Trademark Office Re. U.S. Appl. No. 18/537,886. (12 pages).
International Preliminary Report on Patentability Dated Jul. 4, 2024 From the International Bureau of WIPO Re. Application No. PCT/IL2022/051378. (7 Pages).

\* cited by examiner

FIG. 1

MEAPAQLLFLLLLWLPDTTGHHHHHHPGWFLDSPDRPWNPPTFS
PALLVVTEGDNATFTCSFSNTSESFVLNWYRMSPSNQTDKLAAF
PEDRSQPGQDCRFRVTQLPNGRDFHMSVVRARRNDSGTYLCGAI
SLAPKAQIKESLRAELRVTERRAEVPTAHPSPSPRPAGQFQTLV
GACPWAVSGARASPGSAASPRLREGPELSPDDPAGLLDLRQGMF
AQLVAQNVLLIDGPLSWYSDPGLAGVSLTGGLSYKEDTKELVVA
KAGVYYVFFQLELRRVVAGEGSGSVSLALHLQPLRSAAGAAALA
LTVDLPPASSEARNSAFGFQGRLLHLSAGQRLGVHLHTEARARH
AWQLTQGATVLGLFRVTPEIPAGLPSPRSE

FIG. 2A

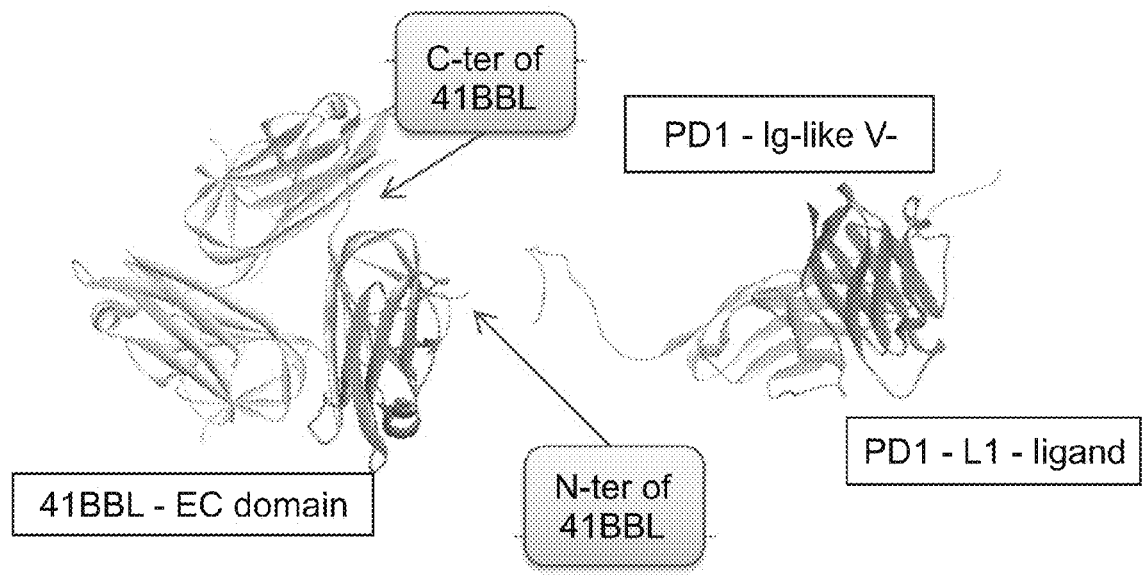

FIG. 2B

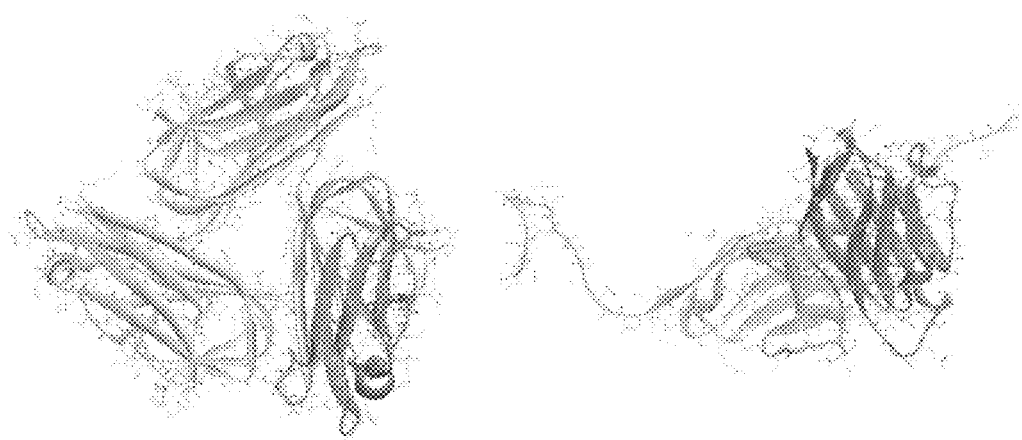

FIG. 2C
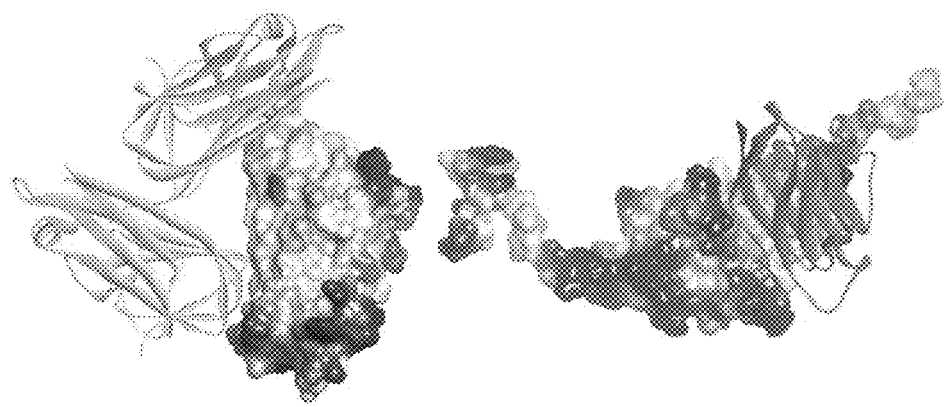
FIG. 2D
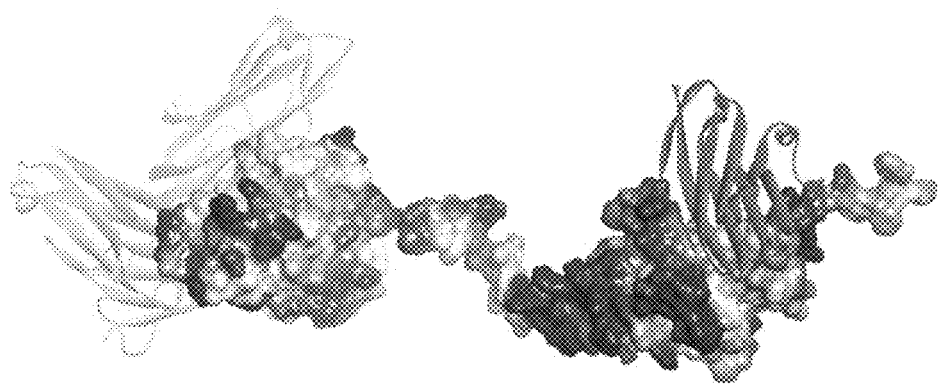
FIG. 3
PGWFLDSPDRPWNP...
...ERRAE
VPTAHPSPSRPAGQFQTLNG ACPWAVSGARASPGSAASPRLREGPELSPL DPAGLIDLRQGMFA
QLVAQNVLLIDGPLSWYSDPGLAGVSLTGGLSYKEDTKELVVAKAGVYYVFFQLELRRVAGEGS
GSVSLALHLQPLRSACAAALALTVDLPPASSEARNSAFGFQGRLLHLSAQQRLGVHLHTEARAF
HAWQLTQGATVLGLPRVTPEIPAGLPSPRSE FIG. 4
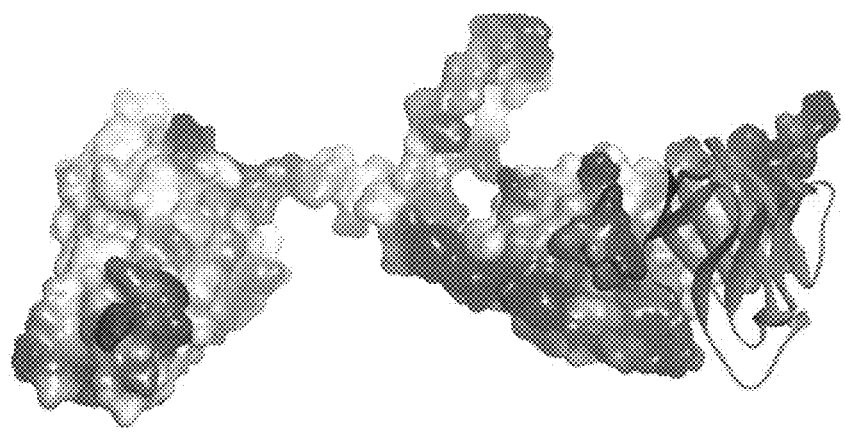
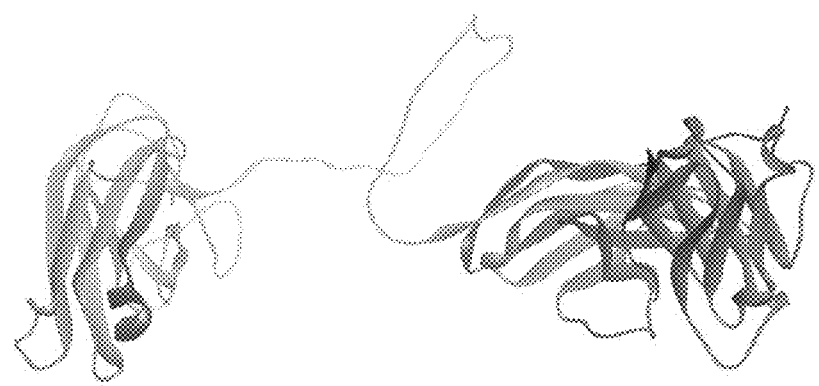

FIG. 5
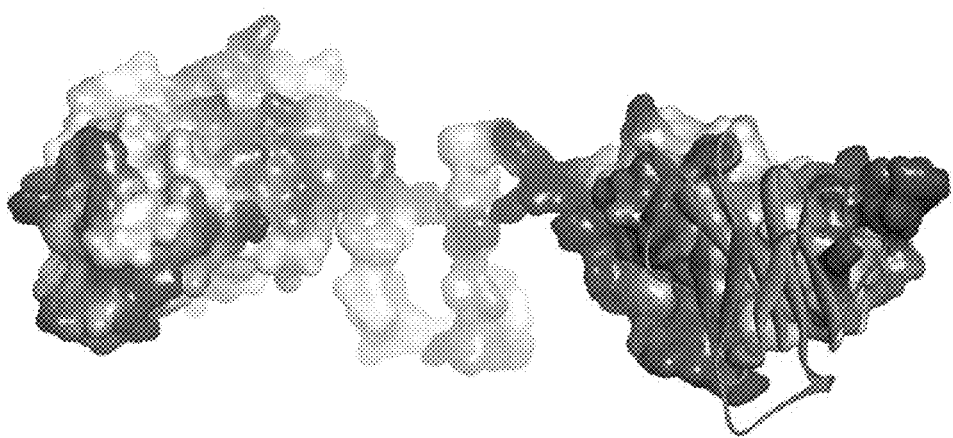
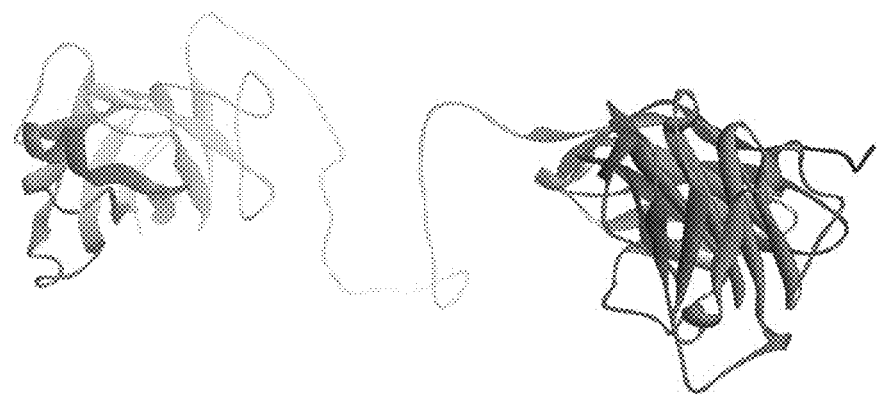

FIG. 6
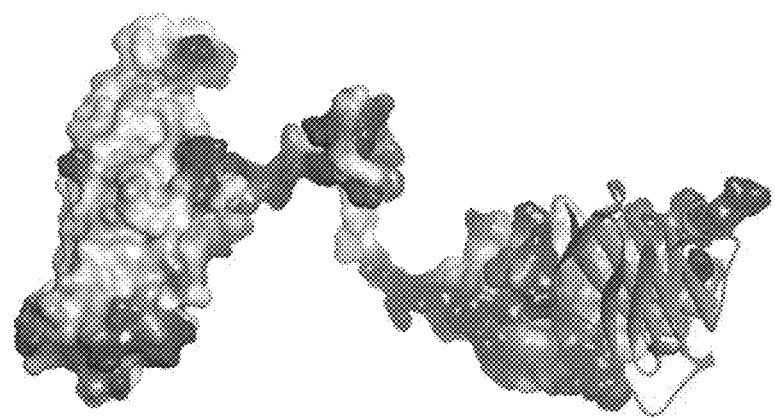
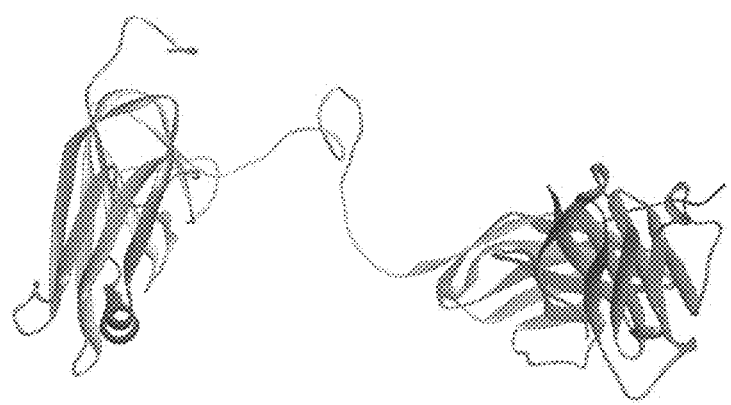

Reduced

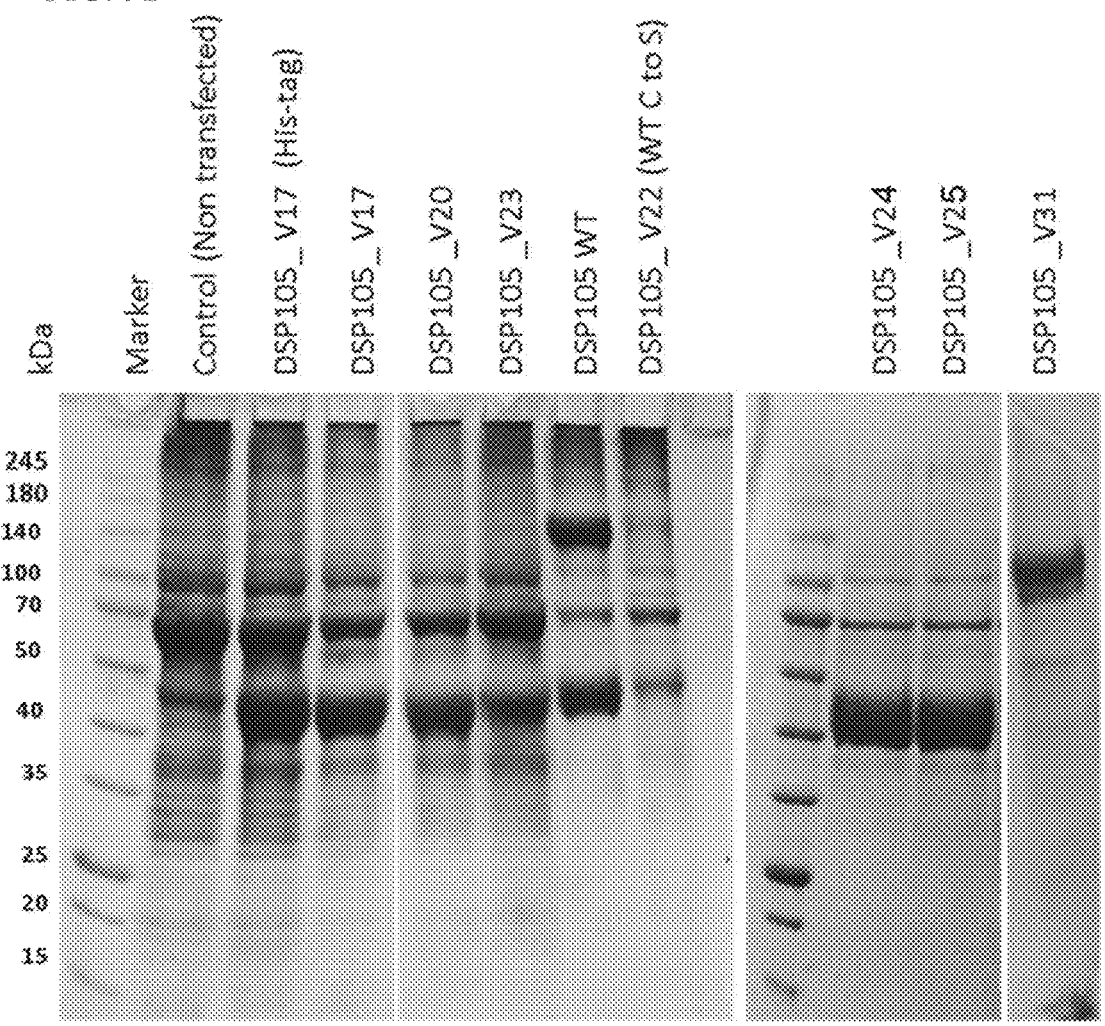

FIG. 10A
PDL1 expression on DLD1-PDL1 cells
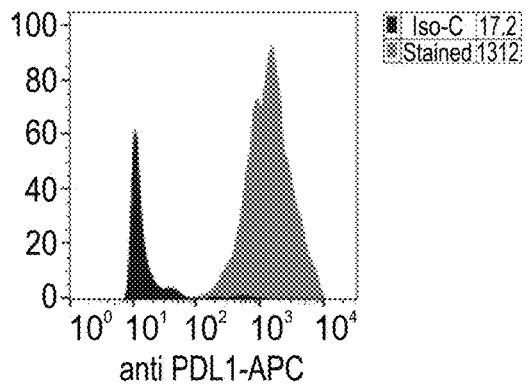
41BB expression on HT1080-41BB cells
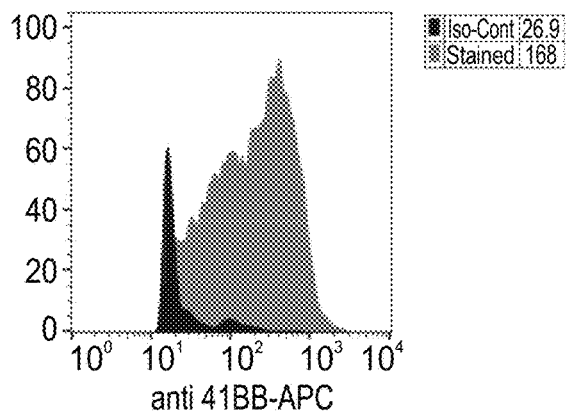
FIG. 10B
Binding of His-tagged DSP105_var17 to DLD1-PDL1 cells
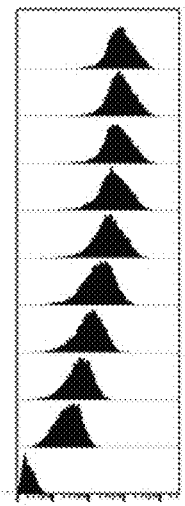
| 12.5ug/ml His-tagged DSP105_var17 | 763 |
|---|---|
| 6.25ug/ml | 751 |
| 3.125ug/ml | 629 |
| 1.6ug/ml | 484 |
| 0.8ug/ml | 350 |
| 0.4ug/ml | 182 |
| 0.2ug/ml | 102 |
| 0.1ug/ml | 53.3 |
| 0.05ug/ml | 26.4 |
| Unstained | 2.19 |
anti 41BBL-APC
Binding of His-tagged DSP105_var17 to HT1080-41BB cells
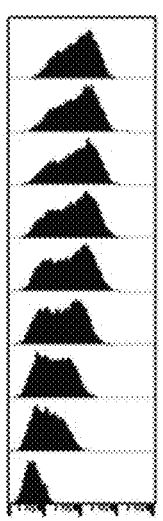
| 1:8 His-tagged DSP105_var17 | 77.3 |
|---|---|
| 1:16 | 74.0 |
| 1:32 | 68.9 |
| 1:64 | 58.2 |
| 1:128 | 46.5 |
| 1:256 | 30.3 |
| 1:512 | 18.4 |
| 1:1024 | 12.7 |
| 0 | 5.07 |
anti PD1-APC

FIG. 10C
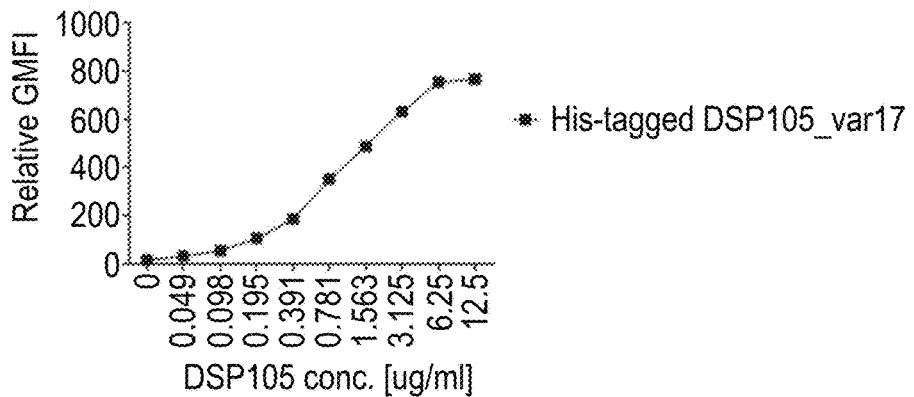
Graphic presentation of His-tagged DSP105_var17 binding to DLD1-PDL1 cells
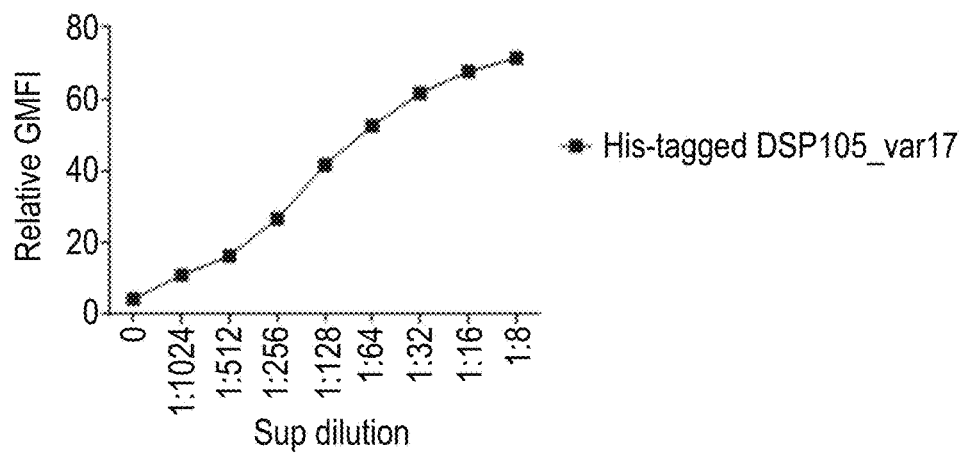
Graphic presentation of His-tagged DSP105_var17 binding to HT1080-41BB cells
FIG. 11
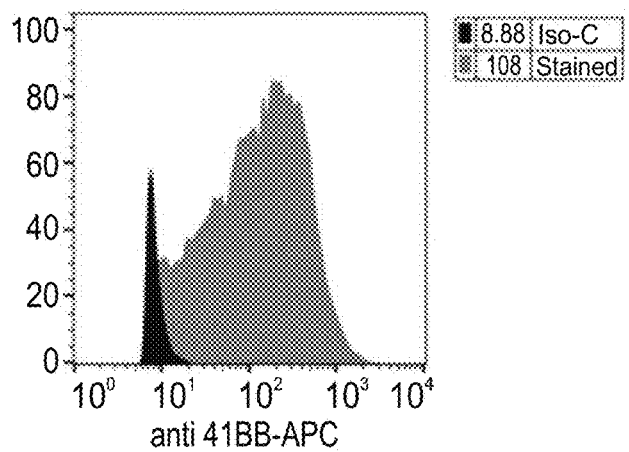
41BB expression on HT1080-41BB cells

SEQUENCE LISTING

```
<160> NUMBER OF SEQ ID NOS: 179

<210> SEQ ID NO 1
<211> LENGTH: 362
<212> TYPE: PRT
<213> ORGANISM: Artificial sequence
<220> FEATURE:
<223> OTHER INFORMATION: ORIGINAL PD1-41BBL with signal peptide and His
      Tag

<400> SEQUENCE: 1

His His His His His His Pro Gly Trp Phe Leu Asp Ser Pro Asp Arg
```

```
             1               5                  10                 15
          Pro Trp Asn Pro Pro Thr Phe Ser Pro Ala Leu Leu Val Val Thr Glu
                          20                  25                  30

Gly Asp Asn Ala Thr Phe Thr Cys Ser Phe Ser Asn Thr Ser Glu Ser
                          35                  40                  45

Phe Val Leu Asn Trp Tyr Arg Met Ser Pro Ser Asn Gln Thr Asp Lys
                          50                  55                  60

Leu Ala Ala Phe Pro Glu Asp Arg Ser Gln Pro Gly Gln Asp Cys Arg
           65                 70                  75                  80

Phe Arg Val Thr Gln Leu Pro Asn Gly Arg Asp Phe His Met Ser Val
                          85                  90                  95

Val Arg Ala Arg Arg Asn Asp Ser Gly Thr Tyr Leu Cys Gly Ala Ile
                         100                 105                 110

Ser Leu Ala Pro Lys Ala Gln Ile Lys Glu Ser Leu Arg Ala Glu Leu
                         115                 120                 125

Arg Val Thr Glu Arg Arg Ala Glu Val Pro Thr Ala His Pro Ser Pro
                         130                 135                 140

Ser Pro Arg Pro Ala Gly Gln Phe Gln Thr Leu Val Gly Ala Cys Pro
          145                 150                 155                 160

Trp Ala Val Ser Gly Ala Arg Ala Ser Pro Gly Ser Ala Ala Ser Pro
                         165                 170                 175

Arg Leu Arg Glu Gly Pro Glu Leu Ser Pro Asp Asp Pro Ala Gly Leu
                         180                 185                 190

Leu Asp Leu Arg Gln Gly Met Phe Ala Gln Leu Val Ala Gln Asn Val
                         195                 200                 205

Leu Leu Ile Asp Gly Pro Leu Ser Trp Tyr Ser Asp Pro Gly Leu Ala
                         210                 215                 220

Gly Val Ser Leu Thr Gly Gly Leu Ser Tyr Lys Glu Asp Thr Lys Glu
          225                 230                 235                 240

Leu Val Val Ala Lys Ala Gly Val Tyr Tyr Val Phe Phe Gln Leu Glu
                         245                 250                 255

Leu Arg Arg Val Val Ala Gly Glu Gly Ser Gly Ser Val Ser Leu Ala
                         260                 265                 270

Leu His Leu Gln Pro Leu Arg Ser Ala Ala Gly Ala Ala Ala Leu Ala
                         275                 280                 285

Leu Thr Val Asp Leu Pro Pro Ala Ser Ser Glu Ala Arg Asn Ser Ala
                         290                 295                 300

Phe Gly Phe Gln Gly Arg Leu Leu His Leu Ser Ala Gly Gln Arg Leu
          305                 310                 315                 320

Gly Val His Leu His Thr Glu Ala Arg Ala Arg His Ala Trp Gln Leu
                         325                 330                 335

Thr Gln Gly Ala Thr Val Leu Gly Leu Phe Arg Val Thr Pro Glu Ile
                         340                 345                 350

Pro Ala Gly Leu Pro Ser Pro Arg Ser Glu
                         355                 360

<210> SEQ ID NO 2
          <211> LENGTH: 150
          <212> TYPE: PRT
          <213> ORGANISM: Artificial sequence
          <220> FEATURE:
          <223> OTHER INFORMATION: ORIGINAL PD1 DOMAIN

<400> SEQUENCE: 2

Pro Gly Trp Phe Leu Asp Ser Pro Asp Arg Pro Trp Asn Pro Pro Thr
```

```
1               5                  10                 15
Phe Ser Pro Ala Leu Leu Val Val Thr Glu Gly Asp Asn Ala Thr Phe
               20                 25                 30

Thr Cys Ser Phe Ser Asn Thr Ser Glu Ser Phe Val Leu Asn Trp Tyr
               35                 40                 45

Arg Met Ser Pro Ser Asn Gln Thr Asp Lys Leu Ala Ala Phe Pro Glu
               50                 55                 60

Asp Arg Ser Gln Pro Gly Gln Asp Cys Arg Phe Arg Val Thr Gln Leu
65             70                 75                 80

Pro Asn Gly Arg Asp Phe His Met Ser Val Val Arg Ala Arg Arg Asn
               85                 90                 95

Asp Ser Gly Thr Tyr Leu Cys Gly Ala Ile Ser Leu Ala Pro Lys Ala
               100                105                110

Gln Ile Lys Glu Ser Leu Arg Ala Glu Leu Arg Val Thr Glu Arg Arg
               115                120                125

Ala Glu Val Pro Thr Ala His Pro Ser Pro Ser Pro Arg Pro Ala Gly
               130                135                140

Gln Phe Gln Thr Leu Val
145            150

<210> SEQ ID NO 3
<211> LENGTH: 205
<212> TYPE: PRT
<213> ORGANISM: Artificial sequence
<220> FEATURE:
<223> OTHER INFORMATION: ORIGINAL 41BBL DOMAIN

<400> SEQUENCE: 3

Ala Cys Pro Trp Ala Val Ser Gly Ala Arg Ala Ser Pro Gly Ser Ala
1              5                  10                 15

Ala Ser Pro Arg Leu Arg Glu Gly Pro Glu Leu Ser Pro Asp Asp Pro
               20                 25                 30

Ala Gly Leu Leu Asp Leu Arg Gln Gly Met Phe Ala Gln Leu Val Ala
               35                 40                 45

Gln Asn Val Leu Leu Ile Asp Gly Pro Leu Ser Trp Tyr Ser Asp Pro
               50                 55                 60

Gly Leu Ala Gly Val Ser Leu Thr Gly Gly Leu Ser Tyr Lys Glu Asp
65             70                 75                 80

Thr Lys Glu Leu Val Val Ala Lys Ala Gly Val Tyr Tyr Val Phe Phe
               85                 90                 95

Gln Leu Glu Leu Arg Arg Val Val Ala Gly Glu Gly Ser Gly Ser Val
               100                105                110

Ser Leu Ala Leu His Leu Gln Pro Leu Arg Ser Ala Ala Gly Ala Ala
               115                120                125

Ala Leu Ala Leu Thr Val Asp Leu Pro Pro Ala Ser Ser Glu Ala Arg
               130                135                140

Asn Ser Ala Phe Gly Phe Gln Gly Arg Leu Leu His Leu Ser Ala Gly
145            150                155                160

Gln Arg Leu Gly Val His Leu His Thr Glu Ala Arg Ala Arg His Ala
               165                170                175

Trp Gln Leu Thr Gln Gly Ala Thr Val Leu Gly Leu Phe Arg Val Thr
               180                185                190

Pro Glu Ile Pro Ala Gly Leu Pro Ser Pro Arg Ser Glu
               195                200                205
```

<210> SEQ ID NO 4
<211> LENGTH: 20
<212> TYPE: PRT
<213> ORGANISM: Artificial sequence
<220> FEATURE:
<223> OTHER INFORMATION: SIGNAL PEPTIDE

<400> SEQUENCE: 4

Met Glu Ala Pro Ala Gln Leu Leu Phe Leu Leu Leu Trp Leu Pro
1               5                   10                  15

Asp Thr Thr Gly
            20

<210> SEQ ID NO 5
<211> LENGTH: 356
<212> TYPE: PRT
<213> ORGANISM: Artificial sequence
<220> FEATURE:
<223> OTHER INFORMATION: ORIGINAL PD1-41BBL without His Tag

<400> SEQUENCE: 5

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Ala Cys Pro Trp Ala Val Ser Gly Ala
145                 150                 155                 160

Arg Ala Ser Pro Gly Ser Ala Ala Ser Pro Arg Leu Arg Glu Gly Pro
                165                 170                 175

Glu Leu Ser Pro Asp Asp Pro Ala Gly Leu Leu Asp Leu Arg Gln Gly
            180                 185                 190

Met Phe Ala Gln Leu Val Ala Gln Asn Val Leu Leu Ile Asp Gly Pro
        195                 200                 205

Leu Ser Trp Tyr Ser Asp Pro Gly Leu Ala Gly Val Ser Leu Thr Gly
    210                 215                 220

Gly Leu Ser Tyr Lys Glu Asp Thr Lys Glu Leu Val Val Ala Lys Ala
225                 230                 235                 240

Gly Val Tyr Tyr Val Phe Phe Gln Leu Glu Leu Arg Arg Val Val Ala
                245                 250                 255

Gly Glu Gly Ser Gly Ser Val Ser Leu Ala Leu His Leu Gln Pro Leu
            260                 265                 270

Arg Ser Ala Ala Gly Ala Ala Ala Leu Ala Leu Thr Val Asp Leu Pro
        275                 280                 285

```
Pro Ala Ser Ser Glu Ala Arg Asn Ser Ala Phe Gly Phe Gln Gly Arg
    290                 295                 300

Leu Leu His Leu Ser Ala Gly Gln Arg Leu Gly Val His Leu His Thr
305                 310                 315                 320

Glu Ala Arg Ala Arg His Ala Trp Gln Leu Thr Gln Gly Ala Thr Val
                325                 330                 335

Leu Gly Leu Phe Arg Val Thr Pro Glu Ile Pro Ala Gly Leu Pro Ser
                340                 345                 350

Pro Arg Ser Glu
        355

<210> SEQ ID NO 6
<211> LENGTH: 21
<212> TYPE: PRT
<213> ORGANISM: Artificial sequence
<220> FEATURE:
<223> OTHER INFORMATION: C-terminal segment of PD1

<400> SEQUENCE: 6

Glu Val Pro Thr Ala His Pro Ser Pro Ser Pro Arg Pro Ala Gly Gln
1               5                   10                  15

Phe Gln Thr Leu Val
            20

<210> SEQ ID NO 7
<211> LENGTH: 30
<212> TYPE: PRT
<213> ORGANISM: Artificial sequence
<220> FEATURE:
<223> OTHER INFORMATION: N-terminal segment of the 4-1BBL

<400> SEQUENCE: 7

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp
            20                  25                  30

<210> SEQ ID NO 8
<211> LENGTH: 5
<212> TYPE: PRT
<213> ORGANISM: Artificial sequence
<220> FEATURE:
<223> OTHER INFORMATION: segment of five residues at the N-terminal of
      PD1

<400> SEQUENCE: 8

Pro Gly Trp Phe Leu
1               5

<210> SEQ ID NO 9
<211> LENGTH: 5
<212> TYPE: PRT
<213> ORGANISM: Artificial sequence
<220> FEATURE:
<223> OTHER INFORMATION: segment of five residues at the C-terminal of
      PD1

<400> SEQUENCE: 9

Phe Gln Thr Leu Val
1               5

<210> SEQ ID NO 10
<211> LENGTH: 14
<212> TYPE: PRT
```

```
<213> ORGANISM: Artificial sequence
<220> FEATURE:
<223> OTHER INFORMATION: N-terminal segment of the 4-1BBL domain

<400> SEQUENCE: 10

Ala Cys Pro Trp Ala Val Ser Gly Ala Arg Ala Ser Pro Gly
1               5                   10

<210> SEQ ID NO 11
<211> LENGTH: 6
<212> TYPE: PRT
<213> ORGANISM: Artificial sequence
<220> FEATURE:
<223> OTHER INFORMATION: N-terminal segment of the 4-1BBL domain

<400> SEQUENCE: 11

Ala Cys Pro Trp Ala Val
1               5

<210> SEQ ID NO 12
<211> LENGTH: 332
<212> TYPE: PRT
<213> ORGANISM: Artificial sequence
<220> FEATURE:
<223> OTHER INFORMATION: K105_var1 without His Tag

<400> SEQUENCE: 12

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Gly Ser Ala Ala
    130                 135                 140

Ser Pro Arg Leu Arg Glu Gly Pro Glu Leu Ser Pro Asp Asp Pro Ala
145                 150                 155                 160

Gly Leu Leu Asp Leu Arg Gln Gly Met Phe Ala Gln Leu Val Ala Gln
                165                 170                 175

Asn Val Leu Leu Ile Asp Gly Pro Leu Ser Trp Tyr Ser Asp Pro Gly
            180                 185                 190

Leu Ala Gly Val Ser Leu Thr Gly Gly Leu Ser Tyr Lys Glu Asp Thr
        195                 200                 205

Lys Glu Leu Val Val Ala Lys Ala Gly Val Tyr Tyr Val Phe Phe Gln
    210                 215                 220

Leu Glu Leu Arg Arg Val Val Ala Gly Glu Gly Ser Gly Ser Val Ser
225                 230                 235                 240

Leu Ala Leu His Leu Gln Pro Leu Arg Ser Ala Ala Gly Ala Ala Ala
                245                 250                 255
```

```
Leu Ala Leu Thr Val Asp Leu Pro Ala Ser Ser Glu Ala Arg Asn
            260                 265                 270

Ser Ala Phe Gly Phe Gln Gly Arg Leu Leu His Leu Ser Ala Gly Gln
        275                 280                 285

Arg Leu Gly Val His Leu His Thr Glu Ala Arg Ala Arg His Ala Trp
        290                 295                 300

Gln Leu Thr Gln Gly Ala Thr Val Leu Gly Leu Phe Arg Val Thr Pro
305                 310                 315                 320

Glu Ile Pro Ala Gly Leu Pro Ser Pro Arg Ser Glu
                325                 330

<210> SEQ ID NO 13
<211> LENGTH: 338
<212> TYPE: PRT
<213> ORGANISM: Artificial sequence
<220> FEATURE:
<223> OTHER INFORMATION: K105_var1 with His Tag

<400> SEQUENCE: 13

His His His His His His Asp Ser Pro Asp Arg Pro Trp Asn Pro Pro
1               5                   10                  15

Thr Phe Ser Pro Ala Leu Leu Val Val Thr Glu Gly Asp Asn Ala Thr
            20                  25                  30

Phe Thr Cys Ser Phe Ser Asn Thr Ser Glu Ser Phe Val Leu Asn Trp
        35                  40                  45

Tyr Arg Met Ser Pro Ser Asn Gln Thr Asp Lys Leu Ala Ala Phe Pro
    50                  55                  60

Glu Asp Arg Ser Gln Pro Gly Gln Asp Cys Arg Phe Arg Val Thr Gln
65                  70                  75                  80

Leu Pro Asn Gly Arg Asp Phe His Met Ser Val Val Arg Ala Arg Arg
                85                  90                  95

Asn Asp Ser Gly Thr Tyr Leu Cys Gly Ala Ile Ser Leu Ala Pro Lys
            100                 105                 110

Ala Gln Ile Lys Glu Ser Leu Arg Ala Glu Leu Arg Val Thr Glu Arg
        115                 120                 125

Arg Ala Glu Val Pro Thr Ala His Pro Ser Pro Ser Pro Arg Pro Ala
    130                 135                 140

Gly Gln Gly Ser Ala Ala Ser Pro Arg Leu Arg Glu Gly Pro Glu Leu
145                 150                 155                 160

Ser Pro Asp Asp Pro Ala Gly Leu Leu Asp Leu Arg Gln Gly Met Phe
                165                 170                 175

Ala Gln Leu Val Ala Gln Asn Val Leu Leu Ile Asp Gly Pro Leu Ser
            180                 185                 190

Trp Tyr Ser Asp Pro Gly Leu Ala Gly Val Ser Leu Thr Gly Gly Leu
        195                 200                 205

Ser Tyr Lys Glu Asp Thr Lys Glu Leu Val Val Ala Lys Ala Gly Val
    210                 215                 220

Tyr Tyr Val Phe Phe Gln Leu Glu Leu Arg Arg Val Val Ala Gly Glu
225                 230                 235                 240

Gly Ser Gly Ser Val Ser Leu Ala Leu His Leu Gln Pro Leu Arg Ser
                245                 250                 255

Ala Ala Gly Ala Ala Ala Leu Ala Leu Thr Val Asp Leu Pro Pro Ala
            260                 265                 270

Ser Ser Glu Ala Arg Asn Ser Ala Phe Gly Phe Gln Gly Arg Leu Leu
        275                 280                 285
```

```
His Leu Ser Ala Gly Gln Arg Leu Gly Val His Leu His Thr Glu Ala
    290                 295                 300

Arg Ala Arg His Ala Trp Gln Leu Thr Gln Gly Ala Thr Val Leu Gly
305                 310                 315                 320

Leu Phe Arg Val Thr Pro Glu Ile Pro Ala Gly Leu Pro Ser Pro Arg
                325                 330                 335

Ser Glu

<210> SEQ ID NO 14
<211> LENGTH: 338
<212> TYPE: PRT
<213> ORGANISM: Artificial sequence
<220> FEATURE:
<223> OTHER INFORMATION: K105_var2 without His Tag

<400> SEQUENCE: 14

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Gly Ala Arg Ala
130                 135                 140

Ser Pro Gly Ser Ala Ala Ser Pro Arg Leu Arg Glu Gly Pro Glu Leu
145                 150                 155                 160

Ser Pro Asp Asp Pro Ala Gly Leu Leu Asp Leu Arg Gln Gly Met Phe
                165                 170                 175

Ala Gln Leu Val Ala Gln Asn Val Leu Leu Ile Asp Gly Pro Leu Ser
            180                 185                 190

Trp Tyr Ser Asp Pro Gly Leu Ala Gly Val Ser Leu Thr Gly Gly Leu
        195                 200                 205

Ser Tyr Lys Glu Asp Thr Lys Glu Leu Val Val Ala Lys Ala Gly Val
    210                 215                 220

Tyr Tyr Val Phe Phe Gln Leu Glu Leu Arg Arg Val Val Ala Gly Glu
225                 230                 235                 240

Gly Ser Gly Ser Val Ser Leu Ala Leu His Leu Gln Pro Leu Arg Ser
                245                 250                 255

Ala Ala Gly Ala Ala Ala Leu Ala Leu Thr Val Asp Leu Pro Pro Ala
            260                 265                 270

Ser Ser Glu Ala Arg Asn Ser Ala Phe Gly Phe Gln Gly Arg Leu Leu
        275                 280                 285

His Leu Ser Ala Gly Gln Arg Leu Gly Val His Leu His Thr Glu Ala
    290                 295                 300
```

```
Arg Ala Arg His Ala Trp Gln Leu Thr Gln Gly Ala Thr Val Leu Gly
305                 310                 315                 320

Leu Phe Arg Val Thr Pro Glu Ile Pro Ala Gly Leu Pro Ser Pro Arg
                325                 330                 335

Ser Glu

<210> SEQ ID NO 15
<211> LENGTH: 344
<212> TYPE: PRT
<213> ORGANISM: Artificial sequence
<220> FEATURE:
<223> OTHER INFORMATION: K105_var2 with His Tag

<400> SEQUENCE: 15

His His His His His His Asp Ser Pro Asp Arg Pro Trp Asn Pro Pro
1               5                   10                  15

Thr Phe Ser Pro Ala Leu Leu Val Val Thr Glu Gly Asp Asn Ala Thr
                20                  25                  30

Phe Thr Cys Ser Phe Ser Asn Thr Ser Glu Ser Phe Val Leu Asn Trp
            35                  40                  45

Tyr Arg Met Ser Pro Ser Asn Gln Thr Asp Lys Leu Ala Ala Phe Pro
50                  55                  60

Glu Asp Arg Ser Gln Pro Gly Gln Asp Cys Arg Phe Arg Val Thr Gln
65                  70                  75                  80

Leu Pro Asn Gly Arg Asp Phe His Met Ser Val Val Arg Ala Arg Arg
                85                  90                  95

Asn Asp Ser Gly Thr Tyr Leu Cys Gly Ala Ile Ser Leu Ala Pro Lys
            100                 105                 110

Ala Gln Ile Lys Glu Ser Leu Arg Ala Glu Leu Arg Val Thr Glu Arg
        115                 120                 125

Arg Ala Glu Val Pro Thr Ala His Pro Ser Pro Ser Pro Arg Pro Ala
130                 135                 140

Gly Gln Gly Ala Arg Ala Ser Pro Gly Ser Ala Ala Ser Pro Arg Leu
145                 150                 155                 160

Arg Glu Gly Pro Glu Leu Ser Pro Asp Asp Pro Ala Gly Leu Leu Asp
                165                 170                 175

Leu Arg Gln Gly Met Phe Ala Gln Leu Val Ala Gln Asn Val Leu Leu
            180                 185                 190

Ile Asp Gly Pro Leu Ser Trp Tyr Ser Asp Pro Gly Leu Ala Gly Val
        195                 200                 205

Ser Leu Thr Gly Gly Leu Ser Tyr Lys Glu Asp Thr Lys Glu Leu Val
210                 215                 220

Val Ala Lys Ala Gly Val Tyr Tyr Val Phe Phe Gln Leu Glu Leu Arg
225                 230                 235                 240

Arg Val Val Ala Gly Glu Gly Ser Gly Ser Val Ser Leu Ala Leu His
                245                 250                 255

Leu Gln Pro Leu Arg Ser Ala Ala Gly Ala Ala Ala Leu Ala Leu Thr
            260                 265                 270

Val Asp Leu Pro Pro Ala Ser Ser Glu Ala Arg Asn Ser Ala Phe Gly
        275                 280                 285

Phe Gln Gly Arg Leu Leu His Leu Ser Ala Gly Gln Arg Leu Gly Val
        290                 295                 300

His Leu His Thr Glu Ala Arg Ala Arg His Ala Trp Gln Leu Thr Gln
305                 310                 315                 320

Gly Ala Thr Val Leu Gly Leu Phe Arg Val Thr Pro Glu Ile Pro Ala
```

Gly Leu Pro Ser Pro Arg Ser Glu
                340

<210> SEQ ID NO 16
<211> LENGTH: 326
<212> TYPE: PRT
<213> ORGANISM: Artificial sequence
<220> FEATURE:
<223> OTHER INFORMATION: K105_var3 without His Tag

<400> SEQUENCE: 16

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Gly Leu Arg Glu
130                 135                 140

Gly Pro Glu Leu Ser Pro Asp Asp Pro Ala Gly Leu Leu Asp Leu Arg
145                 150                 155                 160

Gln Gly Met Phe Ala Gln Leu Val Ala Gln Asn Val Leu Leu Ile Asp
                165                 170                 175

Gly Pro Leu Ser Trp Tyr Ser Asp Pro Gly Leu Ala Gly Val Ser Leu
            180                 185                 190

Thr Gly Gly Leu Ser Tyr Lys Glu Asp Thr Lys Glu Leu Val Val Ala
        195                 200                 205

Lys Ala Gly Val Tyr Tyr Val Phe Phe Gln Leu Glu Leu Arg Arg Val
    210                 215                 220

Val Ala Gly Glu Gly Ser Gly Ser Val Ser Leu Ala Leu His Leu Gln
225                 230                 235                 240

Pro Leu Arg Ser Ala Ala Gly Ala Ala Ala Leu Ala Leu Thr Val Asp
                245                 250                 255

Leu Pro Pro Ala Ser Ser Glu Ala Arg Asn Ser Ala Phe Gly Phe Gln
            260                 265                 270

Gly Arg Leu Leu His Leu Ser Ala Gly Gln Arg Leu Gly Val His Leu
        275                 280                 285

His Thr Glu Ala Arg Ala Arg His Ala Trp Gln Leu Thr Gln Gly Ala
    290                 295                 300

Thr Val Leu Gly Leu Phe Arg Val Thr Pro Glu Ile Pro Ala Gly Leu
305                 310                 315                 320

Pro Ser Pro Arg Ser Glu
                325

-continued

```
<210> SEQ ID NO 17
<211> LENGTH: 332
<212> TYPE: PRT
<213> ORGANISM: Artificial sequence
<220> FEATURE:
<223> OTHER INFORMATION: K105_var3 with His Tag

<400> SEQUENCE: 17

His His His His His Asp Ser Pro Asp Arg Pro Trp Asn Pro Pro
1               5                   10                  15

Thr Phe Ser Pro Ala Leu Leu Val Val Thr Glu Gly Asp Asn Ala Thr
                20                  25                  30

Phe Thr Cys Ser Phe Ser Asn Thr Ser Glu Ser Phe Val Leu Asn Trp
            35                  40                  45

Tyr Arg Met Ser Pro Ser Asn Gln Thr Asp Lys Leu Ala Ala Phe Pro
    50                  55                  60

Glu Asp Arg Ser Gln Pro Gly Gln Asp Cys Arg Phe Arg Val Thr Gln
65                  70                  75                  80

Leu Pro Asn Gly Arg Asp Phe His Met Ser Val Val Arg Ala Arg Arg
                85                  90                  95

Asn Asp Ser Gly Thr Tyr Leu Cys Gly Ala Ile Ser Leu Ala Pro Lys
            100                 105                 110

Ala Gln Ile Lys Glu Ser Leu Arg Ala Glu Leu Arg Val Thr Glu Arg
        115                 120                 125

Arg Ala Glu Val Pro Thr Ala His Pro Ser Pro Ser Pro Arg Pro Ala
130                 135                 140

Gly Gln Gly Leu Arg Glu Gly Pro Glu Leu Ser Pro Asp Asp Pro Ala
145                 150                 155                 160

Gly Leu Leu Asp Leu Arg Gln Gly Met Phe Ala Gln Leu Val Ala Gln
                165                 170                 175

Asn Val Leu Leu Ile Asp Gly Pro Leu Ser Trp Tyr Ser Asp Pro Gly
            180                 185                 190

Leu Ala Gly Val Ser Leu Thr Gly Gly Leu Ser Tyr Lys Glu Asp Thr
        195                 200                 205

Lys Glu Leu Val Val Ala Lys Ala Gly Val Tyr Tyr Val Phe Phe Gln
210                 215                 220

Leu Glu Leu Arg Arg Val Val Ala Gly Glu Gly Ser Gly Ser Val Ser
225                 230                 235                 240

Leu Ala Leu His Leu Gln Pro Leu Arg Ser Ala Ala Gly Ala Ala Ala
                245                 250                 255

Leu Ala Leu Thr Val Asp Leu Pro Pro Ala Ser Ser Glu Ala Arg Asn
            260                 265                 270

Ser Ala Phe Gly Phe Gln Gly Arg Leu Leu His Leu Ser Ala Gly Gln
        275                 280                 285

Arg Leu Gly Val His Leu His Thr Glu Ala Arg Ala Arg His Ala Trp
    290                 295                 300

Gln Leu Thr Gln Gly Ala Thr Val Leu Gly Leu Phe Arg Val Thr Pro
305                 310                 315                 320

Glu Ile Pro Ala Gly Leu Pro Ser Pro Arg Ser Glu
                325                 330

<210> SEQ ID NO 18
<211> LENGTH: 140
<212> TYPE: PRT
<213> ORGANISM: Artificial sequence
<220> FEATURE:
<223> OTHER INFORMATION: 140 aa PD1 segment
```

<400> SEQUENCE: 18

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln
    130                 135                 140

<210> SEQ ID NO 19
<211> LENGTH: 128
<212> TYPE: PRT
<213> ORGANISM: Artificial sequence
<220> FEATURE:
<223> OTHER INFORMATION: 128 aa PD1 segment

<400> SEQUENCE: 19

Pro Trp Asn Pro Pro Thr Phe Ser Pro Ala Leu Leu Val Val Thr Glu
1               5                   10                  15

Gly Asp Asn Ala Thr Phe Thr Cys Ser Phe Ser Asn Thr Ser Glu Ser
            20                  25                  30

Phe Val Leu Asn Trp Tyr Arg Met Ser Pro Ser Asn Gln Thr Asp Lys
        35                  40                  45

Leu Ala Ala Phe Pro Glu Asp Arg Ser Gln Pro Gly Gln Asp Cys Arg
    50                  55                  60

Phe Arg Val Thr Gln Leu Pro Asn Gly Arg Asp Phe His Met Ser Val
65                  70                  75                  80

Val Arg Ala Arg Arg Asn Asp Ser Gly Thr Tyr Leu Cys Gly Ala Ile
                85                  90                  95

Ser Leu Ala Pro Lys Ala Gln Ile Lys Glu Ser Leu Arg Ala Glu Leu
            100                 105                 110

Arg Val Thr Glu Arg Arg Ala Glu Val Pro Thr Ala His Pro Ser Pro
        115                 120                 125

<210> SEQ ID NO 20
<211> LENGTH: 135
<212> TYPE: PRT
<213> ORGANISM: Artificial sequence
<220> FEATURE:
<223> OTHER INFORMATION: 135 aa PD1 segment

<400> SEQUENCE: 20

Pro Trp Asn Pro Pro Thr Phe Ser Pro Ala Leu Leu Val Val Thr Glu
1               5                   10                  15

Gly Asp Asn Ala Thr Phe Thr Cys Ser Phe Ser Asn Thr Ser Glu Ser
            20                  25                  30

-continued

```
Phe Val Leu Asn Trp Tyr Arg Met Ser Pro Ser Asn Gln Thr Asp Lys
        35                  40                  45

Leu Ala Ala Phe Pro Glu Asp Arg Ser Gln Pro Gly Gln Asp Cys Arg
 50                  55                  60

Phe Arg Val Thr Gln Leu Pro Asn Gly Arg Asp Phe His Met Ser Val
 65                  70                  75                  80

Val Arg Ala Arg Arg Asn Asp Ser Gly Thr Tyr Leu Cys Gly Ala Ile
                 85                  90                  95

Ser Leu Ala Pro Lys Ala Gln Ile Lys Glu Ser Leu Arg Ala Glu Leu
                100                 105                 110

Arg Val Thr Glu Arg Arg Ala Glu Val Pro Thr Ala His Pro Ser Pro
                115                 120                 125

Ser Pro Arg Pro Ala Gly Gln
                130                 135

<210> SEQ ID NO 21
<211> LENGTH: 133
<212> TYPE: PRT
<213> ORGANISM: Artificial sequence
<220> FEATURE:
<223> OTHER INFORMATION: 133 aa PD1 segment

<400> SEQUENCE: 21

Asp Ser Pro Asp Arg Pro Trp Asn Pro Thr Phe Ser Pro Ala Leu
 1               5                  10                  15

Leu Val Val Thr Glu Gly Asp Asn Ala Thr Phe Thr Cys Ser Phe Ser
                 20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
 50                  55                  60

Gly Gln Asp Cys Arg Phe Arg Val Thr Gln Leu Pro Asn Gly Arg Asp
 65                  70                  75                  80

Phe His Met Ser Val Val Arg Ala Arg Arg Asn Asp Ser Gly Thr Tyr
                 85                  90                  95

Leu Cys Gly Ala Ile Ser Leu Ala Pro Lys Ala Gln Ile Lys Glu Ser
                100                 105                 110

Leu Arg Ala Glu Leu Arg Val Thr Glu Arg Arg Ala Glu Val Pro Thr
                115                 120                 125

Ala His Pro Ser Pro
            130

<210> SEQ ID NO 22
<211> LENGTH: 191
<212> TYPE: PRT
<213> ORGANISM: Artificial sequence
<220> FEATURE:
<223> OTHER INFORMATION: 191 aa 41BBL segment

<400> SEQUENCE: 22

Ser Ala Ala Ser Pro Arg Leu Arg Glu Gly Pro Glu Leu Ser Pro Asp
 1               5                  10                  15

Asp Pro Ala Gly Leu Leu Asp Leu Arg Gln Gly Met Phe Ala Gln Leu
                 20                  25                  30

Val Ala Gln Asn Val Leu Leu Ile Asp Gly Pro Leu Ser Trp Tyr Ser
            35                  40                  45

Asp Pro Gly Leu Ala Gly Val Ser Leu Thr Gly Gly Leu Ser Tyr Lys
```

```
                50                  55                  60
Glu Asp Thr Lys Glu Leu Val Val Ala Lys Ala Gly Val Tyr Tyr Val
 65                  70                  75                  80

Phe Phe Gln Leu Glu Leu Arg Arg Val Val Ala Gly Glu Gly Ser Gly
                 85                  90                  95

Ser Val Ser Leu Ala Leu His Leu Gln Pro Leu Arg Ser Ala Ala Gly
                100                 105                 110

Ala Ala Ala Leu Ala Leu Thr Val Asp Leu Pro Pro Ala Ser Ser Glu
                115                 120                 125

Ala Arg Asn Ser Ala Phe Gly Phe Gln Gly Arg Leu Leu His Leu Ser
130                 135                 140

Ala Gly Gln Arg Leu Gly Val His Leu His Thr Glu Ala Arg Ala Arg
145                 150                 155                 160

His Ala Trp Gln Leu Thr Gln Gly Ala Thr Val Leu Gly Leu Phe Arg
                165                 170                 175

Val Thr Pro Glu Ile Pro Ala Gly Leu Pro Ser Pro Arg Ser Glu
                180                 185                 190

<210> SEQ ID NO 23
<211> LENGTH: 197
<212> TYPE: PRT
<213> ORGANISM: Artificial sequence
<220> FEATURE:
<223> OTHER INFORMATION: 197 aa 41BBL segment

<400> SEQUENCE: 23

Ala Arg Ala Ser Pro Gly Ser Ala Ala Ser Pro Arg Leu Arg Glu Gly
 1               5                  10                  15

Pro Glu Leu Ser Pro Asp Asp Pro Ala Gly Leu Leu Asp Leu Arg Gln
                20                  25                  30

Gly Met Phe Ala Gln Leu Val Ala Gln Asn Val Leu Leu Ile Asp Gly
                35                  40                  45

Pro Leu Ser Trp Tyr Ser Asp Pro Gly Leu Ala Gly Val Ser Leu Thr
 50                  55                  60

Gly Gly Leu Ser Tyr Lys Glu Asp Thr Lys Glu Leu Val Val Ala Lys
 65                  70                  75                  80

Ala Gly Val Tyr Tyr Val Phe Phe Gln Leu Glu Leu Arg Arg Val Val
                 85                  90                  95

Ala Gly Glu Gly Ser Gly Ser Val Ser Leu Ala Leu His Leu Gln Pro
                100                 105                 110

Leu Arg Ser Ala Ala Gly Ala Ala Ala Leu Ala Leu Thr Val Asp Leu
                115                 120                 125

Pro Pro Ala Ser Ser Glu Ala Arg Asn Ser Ala Phe Gly Phe Gln Gly
130                 135                 140

Arg Leu Leu His Leu Ser Ala Gly Gln Arg Leu Gly Val His Leu His
145                 150                 155                 160

Thr Glu Ala Arg Ala Arg His Ala Trp Gln Leu Thr Gln Gly Ala Thr
                165                 170                 175

Val Leu Gly Leu Phe Arg Val Thr Pro Glu Ile Pro Ala Gly Leu Pro
                180                 185                 190

Ser Pro Arg Ser Glu
                195

<210> SEQ ID NO 24
<211> LENGTH: 185
<212> TYPE: PRT
```

```
<213> ORGANISM: Artificial sequence
<220> FEATURE:
<223> OTHER INFORMATION: 185 aa 41BBL segment

<400> SEQUENCE: 24

Leu Arg Glu Gly Pro Glu Leu Ser Pro Asp Asp Pro Ala Gly Leu Leu
1               5                   10                  15

Asp Leu Arg Gln Gly Met Phe Ala Gln Leu Val Ala Gln Asn Val Leu
            20                  25                  30

Leu Ile Asp Gly Pro Leu Ser Trp Tyr Ser Asp Pro Gly Leu Ala Gly
        35                  40                  45

Val Ser Leu Thr Gly Gly Leu Ser Tyr Lys Glu Asp Thr Lys Glu Leu
50                  55                  60

Val Val Ala Lys Ala Gly Val Tyr Tyr Val Phe Phe Gln Leu Glu Leu
65                  70                  75                  80

Arg Arg Val Val Ala Gly Glu Gly Ser Gly Ser Val Ser Leu Ala Leu
                85                  90                  95

His Leu Gln Pro Leu Arg Ser Ala Ala Gly Ala Ala Leu Ala Leu
            100                 105                 110

Thr Val Asp Leu Pro Pro Ala Ser Ser Glu Ala Arg Asn Ser Ala Phe
            115                 120                 125

Gly Phe Gln Gly Arg Leu Leu His Leu Ser Ala Gly Gln Arg Leu Gly
        130                 135                 140

Val His Leu His Thr Glu Ala Arg Ala Arg His Ala Trp Gln Leu Thr
145                 150                 155                 160

Gln Gly Ala Thr Val Leu Gly Leu Phe Arg Val Thr Pro Glu Ile Pro
                165                 170                 175

Ala Gly Leu Pro Ser Pro Arg Ser Glu
            180                 185

<210> SEQ ID NO 25
<211> LENGTH: 199
<212> TYPE: PRT
<213> ORGANISM: Artificial sequence
<220> FEATURE:
<223> OTHER INFORMATION: 199 aa 41BBL segment

<400> SEQUENCE: 25

Ser Gly Ala Arg Ala Ser Pro Gly Ser Ala Ser Pro Arg Leu Arg
1               5                   10                  15

Glu Gly Pro Glu Leu Ser Pro Asp Asp Pro Ala Gly Leu Leu Asp Leu
            20                  25                  30

Arg Gln Gly Met Phe Ala Gln Leu Val Ala Gln Asn Val Leu Leu Ile
            35                  40                  45

Asp Gly Pro Leu Ser Trp Tyr Ser Asp Pro Gly Leu Ala Gly Val Ser
50                  55                  60

Leu Thr Gly Gly Leu Ser Tyr Lys Glu Asp Thr Lys Glu Leu Val Val
65                  70                  75                  80

Ala Lys Ala Gly Val Tyr Tyr Val Phe Phe Gln Leu Glu Leu Arg Arg
                85                  90                  95

Val Val Ala Gly Glu Gly Ser Gly Ser Val Ser Leu Ala Leu His Leu
            100                 105                 110

Gln Pro Leu Arg Ser Ala Ala Gly Ala Ala Leu Ala Leu Thr Val
            115                 120                 125

Asp Leu Pro Pro Ala Ser Ser Glu Ala Arg Asn Ser Ala Phe Gly Phe
        130                 135                 140
```

-continued

```
Gln Gly Arg Leu Leu His Leu Ser Ala Gly Gln Arg Leu Gly Val His
145                 150                 155                 160

Leu His Thr Glu Ala Arg Ala Arg His Ala Trp Gln Leu Thr Gln Gly
                165                 170                 175

Ala Thr Val Leu Gly Leu Phe Arg Val Thr Pro Glu Ile Pro Ala Gly
            180                 185                 190

Leu Pro Ser Pro Arg Ser Glu
        195

<210> SEQ ID NO 26
<211> LENGTH: 381
<212> TYPE: PRT
<213> ORGANISM: Artificial sequence
<220> FEATURE:
<223> OTHER INFORMATION: ORIGINAL PD1-41BBL with signal peptide and His
      Tag

<400> SEQUENCE: 26

Met Gly Trp Ser Cys Ile Ile Leu Phe Leu Val Ala Thr Ala Thr Gly
1               5                   10                  15

Val His Ser His His His His His His Pro Gly Trp Phe Leu Asp Ser
            20                  25                  30

Pro Asp Arg Pro Trp Asn Pro Thr Phe Ser Pro Ala Leu Leu Val
        35                  40                  45

Val Thr Glu Gly Asp Asn Ala Thr Phe Thr Cys Ser Phe Ser Asn Thr
50                  55                  60

Ser Glu Ser Phe Val Leu Asn Trp Tyr Arg Met Ser Pro Ser Asn Gln
65                  70                  75                  80

Thr Asp Lys Leu Ala Ala Phe Pro Glu Asp Arg Ser Gln Pro Gly Gln
            85                  90                  95

Asp Cys Arg Phe Arg Val Thr Gln Leu Pro Asn Gly Arg Asp Phe His
        100                 105                 110

Met Ser Val Val Arg Ala Arg Arg Asn Asp Ser Gly Thr Tyr Leu Cys
            115                 120                 125

Gly Ala Ile Ser Leu Ala Pro Lys Ala Gln Ile Lys Glu Ser Leu Arg
    130                 135                 140

Ala Glu Leu Arg Val Thr Glu Arg Arg Ala Glu Val Pro Thr Ala His
145                 150                 155                 160

Pro Ser Pro Ser Pro Arg Pro Ala Gly Gln Phe Gln Thr Leu Val Gly
                165                 170                 175

Ala Cys Pro Trp Ala Val Ser Gly Ala Arg Ala Ser Pro Gly Ser Ala
            180                 185                 190

Ala Ser Pro Arg Leu Arg Glu Gly Pro Glu Leu Ser Pro Asp Asp Pro
        195                 200                 205

Ala Gly Leu Leu Asp Leu Arg Gln Gly Met Phe Ala Gln Leu Val Ala
    210                 215                 220

Gln Asn Val Leu Leu Ile Asp Gly Pro Leu Ser Trp Tyr Ser Asp Pro
225                 230                 235                 240

Gly Leu Ala Gly Val Ser Leu Thr Gly Gly Leu Ser Tyr Lys Glu Asp
                245                 250                 255

Thr Lys Glu Leu Val Val Ala Lys Ala Gly Val Tyr Tyr Val Phe Phe
            260                 265                 270

Gln Leu Glu Leu Arg Arg Val Val Ala Gly Glu Gly Ser Gly Ser Val
        275                 280                 285

Ser Leu Ala Leu His Leu Gln Pro Leu Arg Ser Ala Ala Gly Ala Ala
    290                 295                 300
```

```
Ala Leu Ala Leu Thr Val Asp Leu Pro Pro Ala Ser Ser Glu Ala Arg
305                 310                 315                 320

Asn Ser Ala Phe Gly Phe Gln Gly Arg Leu Leu His Leu Ser Ala Gly
            325                 330                 335

Gln Arg Leu Gly Val His Leu His Thr Glu Ala Arg Ala Arg His Ala
            340                 345                 350

Trp Gln Leu Thr Gln Gly Ala Thr Val Leu Gly Leu Phe Arg Val Thr
        355                 360                 365

Pro Glu Ile Pro Ala Gly Leu Pro Ser Pro Arg Ser Glu
    370                 375                 380

<210> SEQ ID NO 27
<211> LENGTH: 288
<212> TYPE: PRT
<213> ORGANISM: Artificial sequence
<220> FEATURE:
<223> OTHER INFORMATION: aa sequence of full length PD1

<400> SEQUENCE: 27

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 28
<211> LENGTH: 867
<212> TYPE: DNA
<213> ORGANISM: Artificial sequence
<220> FEATURE:
<223> OTHER INFORMATION: na sequence of full length PD1

<400> SEQUENCE: 28

| | | | | | |
|---|---|---|---|---|---|
| atgcagatcc | cacaggcgcc | ctggccagtc | gtctgggcgg | tgctacaact | gggctggcgg | 60 |
| ccaggatggt | tcttagactc | cccagacagg | ccctggaacc | cccccacctt | ctccccagcc | 120 |
| ctgctcgtgg | tgaccgaagg | ggacaacgcc | accttcacct | gcagcttctc | caacacatcg | 180 |
| gagagcttcg | tgctaaactg | gtaccgcatg | agccccagca | accagacgga | caagctggcc | 240 |
| gccttccccg | aggaccgcag | ccagcccggc | caggactgcc | gcttccgtgt | cacacaactg | 300 |
| cccaacgggc | gtgacttcca | catgagcgtg | gtcagggccc | ggcgcaatga | cagcggcacc | 360 |
| tacctctgtg | ggccatctcc | ctggcccccc | aagcgcagaa | tcaaagagag | cctgcgggca | 420 |
| gagctcaggg | tgacagagag | aagggcagaa | gtgcccacag | cccaccccag | ccctcacccc | 480 |
| aggccagccg | ccagttccaa | accctggtg | gttggtgtcg | tgggcggcct | gctgggcagc | 540 |
| ctggtgctgc | tagtctgggt | cctggccgtc | atctgctccc | gggccgcacg | agggacaata | 600 |
| ggagccaggc | gcaccggcca | gcccctgaag | gaggacccct | cagccgtgcc | tgtgttctct | 660 |
| gtggactatg | gggagctgga | tttccagtgg | cgagagaaga | cccggagcc | cccgtgccc | 720 |
| tgtgtccctg | agcagacgga | gtatgccacc | attgtctttc | ctagcggaat | gggcacctca | 780 |
| tcccccgccc | gcagggctc | agctgacggc | cctcggagtg | cccagccact | gaggcctgag | 840 |
| gatggacact | gctcttggcc | cctctga | | | | 867 |

<210> SEQ ID NO 29
<211> LENGTH: 450
<212> TYPE: DNA
<213> ORGANISM: Artificial sequence
<220> FEATURE:
<223> OTHER INFORMATION: na sequence encoding SEQ ID NO: 2

<400> SEQUENCE: 29

| | | | | | |
|---|---|---|---|---|---|
| ccaggatggt | tcttagactc | cccagacagg | ccctggaacc | cccccacctt | ctccccagcc | 60 |
| ctgctcgtgg | tgaccgaagg | ggacaacgcc | accttcacct | gcagcttctc | caacacatcg | 120 |
| gagagcttcg | tgctaaactg | gtaccgcatg | agccccagca | accagacgga | caagctggcc | 180 |
| gccttccccg | aggaccgcag | ccagcccggc | caggactgcc | gcttccgtgt | cacacaactg | 240 |
| cccaacgggc | gtgacttcca | catgagcgtg | gtcagggccc | ggcgcaatga | cagcggcacc | 300 |
| tacctctgtg | ggccatctcc | ctggcccccc | aagcgcagaa | tcaaagagag | cctgcgggca | 360 |
| gagctcaggg | tgacagagag | aagggcagaa | gtgcccacag | cccaccccag | ccctcacccc | 420 |
| aggccagccg | ccagttccaa | accctggtg | | | | 450 |

<210> SEQ ID NO 30
<211> LENGTH: 167
<212> TYPE: PRT
<213> ORGANISM: Artificial sequence
<220> FEATURE:
<223> OTHER INFORMATION: PD1 amino acid sequence

<400> SEQUENCE: 30

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
 50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
130                 135                 140

Thr Glu Arg Arg Ala Glu Val Pro Thr Ala His Pro Ser Pro Ser Pro
145                 150                 155                 160

Arg Pro Ala Gly Gln Phe Gln
                165

<210> SEQ ID NO 31
<211> LENGTH: 122
<212> TYPE: PRT
<213> ORGANISM: Artificial sequence
<220> FEATURE:
<223> OTHER INFORMATION: PD1 amino acid sequence

<400> SEQUENCE: 31

Asp Ser Pro Asp Arg Pro Trp Asn Pro Pro Thr Phe Ser Pro Ala Leu
 1               5                  10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
 50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg
        115                 120

<210> SEQ ID NO 32
<211> LENGTH: 420
<212> TYPE: DNA
<213> ORGANISM: Artificial sequence
<220> FEATURE:
<223> OTHER INFORMATION: na sequence encoding SEQ ID NO: 18

<400> SEQUENCE: 32
gactcccctg acagaccttg aaccctccca accttctctc ccgctctgct ggtggttacc     60
gagggcgaca atgccacctt cacctgttcc ttcagcaaca cctccgagtc cttcgtgctg    120

```
aactggtaca gaatgtcccc tagcaaccag accgacaagc tggccgcctt tcctgaggac    180
agatctcagc caggccagga ctgccggttc agagttaccc agctgcctaa cggccgggac    240
ttccacatgt ctgttgtgcg ggccagacgg aacgactctg gcacatatct gtgcggcgcc    300
atctctctgg ctcccaaggc tcagatcaaa gagtctctgc gggccgagct gagagtgaca    360
gaaagacgag ctgaggtgcc caccgctcat ccctcacctt ctccaagacc tgccggccag    420
```

<210> SEQ ID NO 33
<211> LENGTH: 384
<212> TYPE: DNA
<213> ORGANISM: Artificial sequence
<220> FEATURE:
<223> OTHER INFORMATION: na sequence encoding SEQ ID NO: 19

<400> SEQUENCE: 33

```
ccttggaacc ctccaacctt ctctcccgct ctgctggtgg ttaccgaggg cgacaatgcc     60
accttcacct gttccttcag caacacctcc gagtccttcg tgctgaactg gtacagaatg    120 tccccctagca accagaccga caagctggcc gcctttcctg aggacagatc tcagccaggc   180
caggactgcc ggttcagagt acccagctg cctaacggcc gggacttcca catgtctgtt    240
gtgcgggcca gacggaacga ctctggcaca tatctgtgcg cgccatctc tctggctccc    300 aaggctcaga tcaaagagtc tctgcgggcc gagctgagag tgacagaaag acgagctgag   360
gtgcccaccg ctcatccctc acct                                          384
```

<210> SEQ ID NO 34
<211> LENGTH: 405
<212> TYPE: DNA
<213> ORGANISM: Artificial sequence
<220> FEATURE:
<223> OTHER INFORMATION: na sequence encoding SEQ ID NO: 20

<400> SEQUENCE: 34

```
ccttggaacc ctccaacctt ctctcccgct ctgctggtgg ttaccgaggg cgacaatgcc     60
accttcacct gttccttcag caacacctcc gagtccttcg tgctgaactg gtacagaatg    120 tccccctagca accagaccga caagctggcc gcctttcctg aggacagatc tcagccaggc   180
caggactgcc ggttcagagt acccagctg cctaacggcc gggacttcca catgtctgtt    240
gtgcgggcca gacggaacga ctctggcaca tatctgtgcg cgccatctc tctggctccc    300 aaggctcaga tcaaagagtc tctgcgggcc gagctgagag tgacagaaag acgagctgag   360
gtgcccaccg ctcatccctc accttctcca agacctgccg gccag                   405
```

<210> SEQ ID NO 35
<211> LENGTH: 399
<212> TYPE: DNA
<213> ORGANISM: Artificial sequence
<220> FEATURE:
<223> OTHER INFORMATION: na sequence encoding SEQ ID NO: 21

<400> SEQUENCE: 35

```
gactcccctg acagaccttg gaaccctcca accttctctc ccgctctgct ggtggttacc     60
gagggcgaca atgccacctt cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctgccggttc agagttaccc agctgcctaa cggccgggac    240
ttccacatgt ctgttgtgcg ggccagacgg aacgactctg gcacatatct gtgcggcgcc    300
atctctctgg ctcccaaggc tcagatcaaa gagtctctgc gggccgagct gagagtgaca    360
```
gaaagacgag ctgaggtgcc caccgctcat ccctcacct                                399

<210> SEQ ID NO 36
<211> LENGTH: 254
<212> TYPE: PRT
<213> ORGANISM: Artificial sequence
<220> FEATURE:
<223> OTHER INFORMATION: aa sequence of full length 41BBL

<400> SEQUENCE: 36

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
            20                  25                  30

Ala Gly Leu Leu Leu Leu Leu Leu Ala Ala Ala Cys Ala Val Phe
        35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
            100                 105                 110

Pro Gly Leu Ala Gly Val Ser Leu Thr Gly Gly Leu Ser Tyr Lys Glu
        115                 120                 125

Asp Thr Lys Glu Leu Val Val Ala Lys Ala Gly Val Tyr Tyr Val Phe
    130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
        195                 200                 205

Gly Gln Arg Leu Gly Val His Leu His Thr Glu Ala Arg Ala Arg His
    210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 37
<211> LENGTH: 765
<212> TYPE: DNA
<213> ORGANISM: Artificial sequence
<220> FEATURE:
<223> OTHER INFORMATION: na sequence of full length 41BBL

<400> SEQUENCE: 37
atggaatacg cctctgacgc ttcactggac cccgaagccc cgtggcctcc cgcgccccgc     60
gctcgcgcct gccgcgtact gccttgggcc ctggtcgcgg gctgctgct gctgctgctg    120 ctcgctgccg cctgcgccgt cttcctcgcc tgccccctgg gccgtgtccgg ggctcgcgcc   180 tcgcccggct ccgcggccag cccgagactc cgcgagggtc cgagctttc gcccgacgat    240

```
cccgccggcc tcttggacct gcggcagggc atgtttgcgc agctggtggc ccaaaatgtt      300
ctgctgatcg atgggcccct gagctggtac agtgacccag gcctggcagg cgtgtccctg      360 acgggggggcc tgagctacaa agaggacacg aaggagctgg tggtggccaa ggctggagtc     420
tactatgtct tctttcaact agagctgcgg cgcgtggtgg ccggcgaggg ctcaggctcc      480
gtttcacttg cgctgcacct gcagccactg cgctctgctg ctggggccgc cgccctggct      540
ttgaccgtgg acctgccacc cgcctcctcc gaggctcgga actcggcctt cggtttccag      600
ggccgcttgc tgcacctgag tgccggccag cgcctgggcg tccatcttca cactgaggcc      660
agggcacgcc atgcctggca gcttacccag ggcgccacag tcttgggact cttccgggtg      720 accccccgaaa tcccagccgg actcccttca ccgaggtcgg aataa                     765
```

```
<210> SEQ ID NO 38
<211> LENGTH: 615
<212> TYPE: DNA
<213> ORGANISM: Artificial sequence
<220> FEATURE:
<223> OTHER INFORMATION: na sequence encoding SEQ ID NO: 3

<400> SEQUENCE: 38
gcctgcccct gggccgtgtc cggggctcgc gcctcgcccg gctccgcggc cagcccgaga       60
ctccgcgagg gtcccgagct ttcgcccgac gatcccgccg gcctcttgga cctgcggcag      120
ggcatgtttg cgcagctggt ggcccaaaat gttctgctga tcgatgggcc cctgagctgg      180
tacagtgacc caggcctggc aggcgtgtcc ctgacggggg gcctgagcta caaagaggac      240
acgaaggagc tggtggtggc caaggctgga gtctactatg tcttctttca actagagctg      300
cggcgcgtgg tggccggcga gggctcaggc tccgtttcac ttgcgctgca cctgcagcca      360
ctgcgctctg ctgctggggc cgccgccctg gctttgaccg tggacctgcc acccgcctcc      420
tccgaggctc ggaactcggc cttcggtttc cagggccgct tgctgcacct gagtgccggc      480
cagcgcctgg gcgtccatct tcacactgag gccagggcac gccatgcctg gcagcttacc      540
cagggcgcca cagtcttggg actcttccgg gtgaccccccg aaatcccagc cggactccct      600
tcaccgaggt cggaa                                                       615
```

```
<210> SEQ ID NO 39
<211> LENGTH: 573
<212> TYPE: DNA
<213> ORGANISM: Artificial sequence
<220> FEATURE:
<223> OTHER INFORMATION: na sequence encoding SEQ ID NO: 22

<400> SEQUENCE: 39
tctgccgctt ctcccagact gagagaagga cctgagctga gccctgatga tcctgctgga       60
ctgctggatc tgcggcaggg catgtttgct cagttggtgg cccagaacgt gctgctgatc      120
gatggccctc tgtcctggta ctctgatcca ggattggctg gcgtgtccct gactggcggc      180
ctgtcttaca aagaggacac caaagaactg gtggtggcca aggccggcgt gtactacgtg      240
ttctttcagc tggaactgcg gagagtggtg gctggcgaag atctggatc tgtgtctctg      300 gccctgcatc tgcagcctct gagaagtgct gcaggcgctg ctgcactggc tctgacagtt      360
gatctgcctc ctgcctcctc cgaggccaga aactccgcct ttggcttcca aggcagactg      420
ctgcacctgt ccgctggaca gagactggga gtccatctgc acacagaggc cagagctaga      480
cacgcttggc agttgacaca gggcgctaca gtgctgggcc tgtttagagt gacccctgag      540
attccagccg gcctgccatc tcctagatct gag                                   573
```

<210> SEQ ID NO 40
<211> LENGTH: 591
<212> TYPE: DNA
<213> ORGANISM: Artificial sequence
<220> FEATURE:
<223> OTHER INFORMATION: na sequence encoding SEQ ID NO: 23

<400> SEQUENCE: 40

```
gctagagctt ctcctggctc tgccgcttct cccagactga gagaaggacc tgagctgagc      60
cctgatgatc ctgctggact gctggatctg cggcagggca tgtttgctca gttggtggcc     120
cagaacgtgc tgctgatcga tggccctctg tcctggtact ctgatccagg attggctggc     180
gtgtccctga ctggcggcct gtcttacaaa gaggacacca agaactggt ggtggccaag     240 gccggcgtgt actacgtgtt ctttcagctg gaactgcgga gagtggtggc tggcgaagga     300
tctggatctg tgtctctggc cctgcatctg cagcctctga aagtgctgc aggcgctgct     360 gcactggctc tgacagttga tctgcctcct gcctcctccg aggccagaaa ctccgccttt     420
ggcttccaag gcagactgct gcacctgtcc gctggacaga gactgggagt ccatctgcac     480
acagaggcca gagctagaca cgcttggcag ttgacacagg cgctacagt gctgggcctg     540 tttagagtga cccctgagat ccagccggc ctgccatctc ctagatctga g              591
```

<210> SEQ ID NO 41
<211> LENGTH: 555
<212> TYPE: DNA
<213> ORGANISM: Artificial sequence
<220> FEATURE:
<223> OTHER INFORMATION: na sequence encoding SEQ ID NO: 24

<400> SEQUENCE: 41

```
ctgagagaag gacctgagct gagccctgat gatcctgctg gactgctgga tctgcggcag      60
ggcatgtttg ctcagttggt ggcccagaac gtgctgctga tcgatggccc tctgtcctgg     120
tactctgatc caggattggc tggcgtgtcc ctgactggcg gcctgtctta caaagaggac     180
accaaagaac tggtggtggc caaggccggc gtgtactacg tgttctttca gctggaactg     240
cggagagtgg tggctggcga aggatctgga tctgtgtctc tggcccctgca tctgcagcct     300 ctgagaagtg ctgcaggcgc tgctgcactg gctctgacag ttgatctgcc tcctgcctcc     360
tccgaggcca gaaactccgc ctttggcttc caaggcagac tgctgcacct gtccgctgga     420
cagagactgg gagtccatct gcacacagag gccagagcta gacacgcttg gcagttgaca     480
cagggcgcta cagtgctggg cctgtttaga gtgacccctg agattccagc cggcctgcca     540
tctcctagat ctgag                                                      555
```

<210> SEQ ID NO 42
<211> LENGTH: 597
<212> TYPE: DNA
<213> ORGANISM: Artificial sequence
<220> FEATURE:
<223> OTHER INFORMATION: na sequence encoding SEQ ID NO: 25

<400> SEQUENCE: 42

```
tctggcgcta gagcttctcc tggctctgcc gcttctccca gactgagaga aggacctgag      60
ctgagccctg atgatcctgc tggactgctg atctgcggc agggcatgtt tgctcagttg     120
gtggcccaga acgtgctgct gatcgatggc cctctgtcct ggtactctga tccaggattg     180
gctggcgtgt ccctgactgg cggcctgtct tacaaagagg acaccaaaga actggtggtg     240
```

```
gccaaggccg gcgtgtacta cgtgttcttt cagctggaac tgcggagagt ggtggctggc      300
gaaggatctg gatctgtgtc tctggccctg catctgcagc ctctgagaag tgctgcaggc      360
gctgctgcac tggctctgac agttgatctg cctcctgcct cctccgaggc cagaaactcc      420
gcctttggct tccaaggcag actgctgcac ctgtccgctg gacagagact gggagtccat      480
ctgcacacag aggccagagc tagacacgct tggcagttga cacagggcgc tacagtgctg      540
ggcctgttta gagtgacccc tgagattcca gccggcctgc atctcctag atctgag         597
```

<210> SEQ ID NO 43

<400> SEQUENCE: 43

000

<210> SEQ ID NO 44
<211> LENGTH: 340
<212> TYPE: PRT
<213> ORGANISM: Artificial sequence
<220> FEATURE:
<223> OTHER INFORMATION: var 4

<400> SEQUENCE: 44

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Gly Ser Gly Ala
    130                 135                 140

Arg Ala Ser Pro Gly Ser Ala Ala Ser Pro Arg Leu Arg Glu Gly Pro
145                 150                 155                 160

Glu Leu Ser Pro Asp Asp Pro Ala Gly Leu Leu Asp Leu Arg Gln Gly
                165                 170                 175

Met Phe Ala Gln Leu Val Ala Gln Asn Val Leu Leu Ile Asp Gly Pro
            180                 185                 190

Leu Ser Trp Tyr Ser Asp Pro Gly Leu Ala Gly Val Ser Leu Thr Gly
        195                 200                 205

Gly Leu Ser Tyr Lys Glu Asp Thr Lys Glu Leu Val Val Ala Lys Ala
    210                 215                 220

Gly Val Tyr Tyr Val Phe Phe Gln Leu Glu Leu Arg Arg Val Val Ala
225                 230                 235                 240

Gly Glu Gly Ser Gly Ser Val Ser Leu Ala Leu His Leu Gln Pro Leu
                245                 250                 255

Arg Ser Ala Ala Gly Ala Ala Ala Leu Ala Leu Thr Val Asp Leu Pro
            260                 265                 270
```

```
Pro Ala Ser Ser Glu Ala Arg Asn Ser Ala Phe Gly Phe Gln Gly Arg
            275                 280                 285

Leu Leu His Leu Ser Ala Gly Gln Arg Leu Gly Val His Leu His Thr
290                 295                 300

Glu Ala Arg Ala Arg His Ala Trp Gln Leu Thr Gln Gly Ala Thr Val
305                 310                 315                 320

Leu Gly Leu Phe Arg Val Thr Pro Glu Ile Pro Ala Gly Leu Pro Ser
                325                 330                 335

Pro Arg Ser Glu
            340

<210> SEQ ID NO 45
<211> LENGTH: 333
<212> TYPE: PRT
<213> ORGANISM: Artificial sequence
<220> FEATURE:
<223> OTHER INFORMATION: var 5

<400> SEQUENCE: 45

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Gly Ser Gly Ala Arg Ala Ser Pro Gly Ser Ala
130                 135                 140

Ala Ser Pro Arg Leu Arg Glu Gly Pro Glu Leu Ser Pro Asp Asp Pro
145                 150                 155                 160

Ala Gly Leu Leu Asp Leu Arg Gln Gly Met Phe Ala Gln Leu Val Ala
                165                 170                 175

Gln Asn Val Leu Leu Ile Asp Gly Pro Leu Ser Trp Tyr Ser Asp Pro
            180                 185                 190

Gly Leu Ala Gly Val Ser Leu Thr Gly Gly Leu Ser Tyr Lys Glu Asp
        195                 200                 205

Thr Lys Glu Leu Val Val Ala Lys Ala Gly Val Tyr Tyr Val Phe Phe
    210                 215                 220

Gln Leu Glu Leu Arg Arg Val Val Ala Gly Glu Gly Ser Gly Ser Val
225                 230                 235                 240

Ser Leu Ala Leu His Leu Gln Pro Leu Arg Ser Ala Ala Gly Ala Ala
                245                 250                 255

Ala Leu Ala Leu Thr Val Asp Leu Pro Pro Ala Ser Ser Glu Ala Arg
            260                 265                 270

Asn Ser Ala Phe Gly Phe Gln Gly Arg Leu Leu His Leu Ser Ala Gly
        275                 280                 285
```

```
Gln Arg Leu Gly Val His Leu His Thr Glu Ala Arg Ala Arg His Ala
        290                 295                 300

Trp Gln Leu Thr Gln Gly Ala Thr Val Leu Gly Leu Phe Arg Val Thr
305                 310                 315                 320

Pro Glu Ile Pro Ala Gly Leu Pro Ser Pro Arg Ser Glu
            325                 330
```

<210> SEQ ID NO 46
<211> LENGTH: 325
<212> TYPE: PRT
<213> ORGANISM: Artificial sequence
<220> FEATURE:
<223> OTHER INFORMATION: var 6

<400> SEQUENCE: 46

```
Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Gly Ser Ala Ala Ser Pro Arg Leu Arg Glu Gly
130                 135                 140

Pro Glu Leu Ser Pro Asp Asp Pro Ala Gly Leu Leu Asp Leu Arg Gln
145                 150                 155                 160

Gly Met Phe Ala Gln Leu Val Ala Gln Asn Val Leu Leu Ile Asp Gly
                165                 170                 175

Pro Leu Ser Trp Tyr Ser Asp Pro Gly Leu Ala Gly Val Ser Leu Thr
            180                 185                 190

Gly Gly Leu Ser Tyr Lys Glu Asp Thr Lys Glu Leu Val Val Ala Lys
        195                 200                 205

Ala Gly Val Tyr Tyr Val Phe Phe Gln Leu Glu Leu Arg Arg Val Val
210                 215                 220

Ala Gly Glu Gly Ser Gly Ser Val Ser Leu Ala Leu His Leu Gln Pro
225                 230                 235                 240

Leu Arg Ser Ala Ala Gly Ala Ala Ala Leu Ala Leu Thr Val Asp Leu
                245                 250                 255

Pro Pro Ala Ser Ser Glu Ala Arg Asn Ser Ala Phe Gly Phe Gln Gly
            260                 265                 270

Arg Leu Leu His Leu Ser Ala Gly Gln Arg Leu Gly Val His Leu His
        275                 280                 285

Thr Glu Ala Arg Ala Arg His Ala Trp Gln Leu Thr Gln Gly Ala Thr
290                 295                 300

Val Leu Gly Leu Phe Arg Val Thr Pro Glu Ile Pro Ala Gly Leu Pro
305                 310                 315                 320
```

Ser Pro Arg Ser Glu
            325

<210> SEQ ID NO 47
<211> LENGTH: 331
<212> TYPE: PRT
<213> ORGANISM: Artificial sequence
<220> FEATURE:
<223> OTHER INFORMATION: var 7

<400> SEQUENCE: 47

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Gly Ala Arg Ala Ser Pro Gly Ser Ala Ala Ser
130                 135                 140

Pro Arg Leu Arg Glu Gly Pro Glu Leu Ser Pro Asp Asp Pro Ala Gly
145                 150                 155                 160

Leu Leu Asp Leu Arg Gln Gly Met Phe Ala Gln Leu Val Ala Gln Asn
                165                 170                 175

Val Leu Leu Ile Asp Gly Pro Leu Ser Trp Tyr Ser Asp Pro Gly Leu
            180                 185                 190

Ala Gly Val Ser Leu Thr Gly Gly Leu Ser Tyr Lys Glu Asp Thr Lys
        195                 200                 205

Glu Leu Val Val Ala Lys Ala Gly Val Tyr Tyr Val Phe Phe Gln Leu
210                 215                 220

Glu Leu Arg Arg Val Val Ala Gly Glu Gly Ser Gly Ser Val Ser Leu
225                 230                 235                 240

Ala Leu His Leu Gln Pro Leu Arg Ser Ala Ala Gly Ala Ala Ala Leu
                245                 250                 255

Ala Leu Thr Val Asp Leu Pro Pro Ala Ser Ser Glu Ala Arg Asn Ser
            260                 265                 270

Ala Phe Gly Phe Gln Gly Arg Leu Leu His Leu Ser Ala Gly Gln Arg
        275                 280                 285

Leu Gly Val His Leu His Thr Glu Ala Arg Ala Arg His Ala Trp Gln
290                 295                 300

Leu Thr Gln Gly Ala Thr Val Leu Gly Leu Phe Arg Val Thr Pro Glu
305                 310                 315                 320

Ile Pro Ala Gly Leu Pro Ser Pro Arg Ser Glu
            325                 330

<210> SEQ ID NO 48

<211> LENGTH: 319
<212> TYPE: PRT
<213> ORGANISM: Artificial sequence
<220> FEATURE:
<223> OTHER INFORMATION: var 8

<400> SEQUENCE: 48

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Gly Leu Arg Glu Gly Pro Glu Leu Ser Pro Asp
    130                 135                 140

Asp Pro Ala Gly Leu Leu Asp Leu Arg Gln Gly Met Phe Ala Gln Leu
145                 150                 155                 160

Val Ala Gln Asn Val Leu Leu Ile Asp Gly Pro Leu Ser Trp Tyr Ser
                165                 170                 175

Asp Pro Gly Leu Ala Gly Val Ser Leu Thr Gly Gly Leu Ser Tyr Lys
            180                 185                 190

Glu Asp Thr Lys Glu Leu Val Val Ala Lys Ala Gly Val Tyr Tyr Val
        195                 200                 205

Phe Phe Gln Leu Glu Leu Arg Arg Val Val Ala Gly Glu Gly Ser Gly
    210                 215                 220

Ser Val Ser Leu Ala Leu His Leu Gln Pro Leu Arg Ser Ala Ala Gly
225                 230                 235                 240

Ala Ala Ala Leu Ala Leu Thr Val Asp Leu Pro Pro Ala Ser Ser Glu
                245                 250                 255

Ala Arg Asn Ser Ala Phe Gly Phe Gln Gly Arg Leu Leu His Leu Ser
            260                 265                 270

Ala Gly Gln Arg Leu Gly Val His Leu His Thr Glu Ala Arg Ala Arg
        275                 280                 285

His Ala Trp Gln Leu Thr Gln Gly Ala Thr Val Leu Gly Leu Phe Arg
    290                 295                 300

Val Thr Pro Glu Ile Pro Ala Gly Leu Pro Ser Pro Arg Ser Glu
305                 310                 315

<210> SEQ ID NO 49
<211> LENGTH: 328
<212> TYPE: PRT
<213> ORGANISM: Artificial sequence
<220> FEATURE:
<223> OTHER INFORMATION: var 9

<400> SEQUENCE: 49

Pro Trp Asn Pro Pro Thr Phe Ser Pro Ala Leu Leu Val Val Thr Glu

```
  1               5                  10                 15
Gly Asp Asn Ala Thr Phe Thr Cys Ser Phe Ser Asn Thr Ser Glu Ser
                 20                 25                 30

Phe Val Leu Asn Trp Tyr Arg Met Ser Pro Ser Asn Gln Thr Asp Lys
                 35                 40                 45

Leu Ala Ala Phe Pro Glu Asp Arg Ser Gln Pro Gly Gln Asp Cys Arg
                 50                 55                 60

Phe Arg Val Thr Gln Leu Pro Asn Gly Arg Asp Phe His Met Ser Val
 65              70                 75                 80

Val Arg Ala Arg Arg Asn Asp Ser Gly Thr Tyr Leu Cys Gly Ala Ile
                 85                 90                 95

Ser Leu Ala Pro Lys Ala Gln Ile Lys Glu Ser Leu Arg Ala Glu Leu
                100                105                110

Arg Val Thr Glu Arg Arg Ala Glu Val Pro Thr Ala His Pro Ser Pro
                115                120                125

Gly Ser Gly Ala Arg Ala Ser Pro Gly Ser Ala Ala Ser Pro Arg Leu
                130                135                140

Arg Glu Gly Pro Glu Leu Ser Pro Asp Asp Pro Ala Gly Leu Leu Asp
145                150                155                160

Leu Arg Gln Gly Met Phe Ala Gln Leu Val Ala Gln Asn Val Leu Leu
                165                170                175

Ile Asp Gly Pro Leu Ser Trp Tyr Ser Asp Pro Gly Leu Ala Gly Val
                180                185                190

Ser Leu Thr Gly Gly Leu Ser Tyr Lys Glu Asp Thr Lys Glu Leu Val
                195                200                205

Val Ala Lys Ala Gly Val Tyr Tyr Val Phe Phe Gln Leu Glu Leu Arg
                210                215                220

Arg Val Val Ala Gly Glu Gly Ser Gly Ser Val Ser Leu Ala Leu His
225                230                235                240

Leu Gln Pro Leu Arg Ser Ala Ala Gly Ala Ala Ala Leu Ala Leu Thr
                245                250                255

Val Asp Leu Pro Pro Ala Ser Ser Glu Ala Arg Asn Ser Ala Phe Gly
                260                265                270

Phe Gln Gly Arg Leu Leu His Leu Ser Ala Gly Gln Arg Leu Gly Val
                275                280                285

His Leu His Thr Glu Ala Arg Ala Arg His Ala Trp Gln Leu Thr Gln
                290                295                300

Gly Ala Thr Val Leu Gly Leu Phe Arg Val Thr Pro Glu Ile Pro Ala
305                310                315                320

Gly Leu Pro Ser Pro Arg Ser Glu
                325

<210> SEQ ID NO 50
<211> LENGTH: 320
<212> TYPE: PRT
<213> ORGANISM: Artificial sequence
<220> FEATURE:
<223> OTHER INFORMATION: var 10

<400> SEQUENCE: 50

Pro Trp Asn Pro Pro Thr Phe Ser Pro Ala Leu Leu Val Val Thr Glu
 1               5                  10                 15

Gly Asp Asn Ala Thr Phe Thr Cys Ser Phe Ser Asn Thr Ser Glu Ser
                 20                 25                 30

Phe Val Leu Asn Trp Tyr Arg Met Ser Pro Ser Asn Gln Thr Asp Lys
```

```
                  35                  40                  45
Leu Ala Ala Phe Pro Glu Asp Arg Ser Gln Pro Gly Gln Asp Cys Arg
 50                  55                  60

Phe Arg Val Thr Gln Leu Pro Asn Gly Arg Asp Phe His Met Ser Val
 65                  70                  75                  80

Val Arg Ala Arg Arg Asn Asp Ser Gly Thr Tyr Leu Cys Gly Ala Ile
                     85                  90                  95

Ser Leu Ala Pro Lys Ala Gln Ile Lys Glu Ser Leu Arg Ala Glu Leu
                    100                 105                 110

Arg Val Thr Glu Arg Arg Ala Glu Val Pro Thr Ala His Pro Ser Pro
                115                 120                 125

Gly Ser Ala Ala Ser Pro Arg Leu Arg Glu Gly Pro Glu Leu Ser Pro
130                 135                 140

Asp Asp Pro Ala Gly Leu Leu Asp Leu Arg Gln Gly Met Phe Ala Gln
145                 150                 155                 160

Leu Val Ala Gln Asn Val Leu Leu Ile Asp Gly Pro Leu Ser Trp Tyr
                    165                 170                 175

Ser Asp Pro Gly Leu Ala Gly Val Ser Leu Thr Gly Gly Leu Ser Tyr
                180                 185                 190

Lys Glu Asp Thr Lys Glu Leu Val Val Ala Lys Ala Gly Val Tyr Tyr
                195                 200                 205

Val Phe Phe Gln Leu Glu Leu Arg Arg Val Val Ala Gly Glu Gly Ser
210                 215                 220

Gly Ser Val Ser Leu Ala Leu His Leu Gln Pro Leu Arg Ser Ala Ala
225                 230                 235                 240

Gly Ala Ala Ala Leu Ala Leu Thr Val Asp Leu Pro Pro Ala Ser Ser
                    245                 250                 255

Glu Ala Arg Asn Ser Ala Phe Gly Phe Gln Gly Arg Leu Leu His Leu
                260                 265                 270

Ser Ala Gly Gln Arg Leu Gly Val His Leu His Thr Glu Ala Arg Ala
                275                 280                 285

Arg His Ala Trp Gln Leu Thr Gln Gly Ala Thr Val Leu Gly Leu Phe
                290                 295                 300

Arg Val Thr Pro Glu Ile Pro Ala Gly Leu Pro Ser Pro Arg Ser Glu
305                 310                 315                 320

<210> SEQ ID NO 51
<211> LENGTH: 326
<212> TYPE: PRT
<213> ORGANISM: Artificial sequence
<220> FEATURE:
<223> OTHER INFORMATION: var 11

<400> SEQUENCE: 51

Pro Trp Asn Pro Pro Thr Phe Ser Pro Ala Leu Leu Val Val Thr Glu
 1               5                  10                  15

Gly Asp Asn Ala Thr Phe Thr Cys Ser Phe Ser Asn Thr Ser Glu Ser
                 20                  25                  30

Phe Val Leu Asn Trp Tyr Arg Met Ser Pro Ser Asn Gln Thr Asp Lys
             35                  40                  45

Leu Ala Ala Phe Pro Glu Asp Arg Ser Gln Pro Gly Gln Asp Cys Arg
 50                  55                  60

Phe Arg Val Thr Gln Leu Pro Asn Gly Arg Asp Phe His Met Ser Val
 65                  70                  75                  80

Val Arg Ala Arg Arg Asn Asp Ser Gly Thr Tyr Leu Cys Gly Ala Ile
```

```
                85                  90                  95
Ser Leu Ala Pro Lys Ala Gln Ile Lys Glu Ser Leu Arg Ala Glu Leu
            100                 105                 110
Arg Val Thr Glu Arg Arg Ala Glu Val Pro Thr Ala His Pro Ser Pro
            115                 120                 125
Gly Ala Arg Ala Ser Pro Gly Ser Ala Ala Ser Pro Arg Leu Arg Glu
            130                 135                 140
Gly Pro Glu Leu Ser Pro Asp Asp Pro Ala Gly Leu Leu Asp Leu Arg
145                 150                 155                 160
Gln Gly Met Phe Ala Gln Leu Val Ala Gln Asn Val Leu Leu Ile Asp
                165                 170                 175
Gly Pro Leu Ser Trp Tyr Ser Asp Pro Gly Leu Ala Gly Val Ser Leu
                180                 185                 190
Thr Gly Gly Leu Ser Tyr Lys Glu Asp Thr Lys Glu Leu Val Val Ala
                195                 200                 205
Lys Ala Gly Val Tyr Tyr Val Phe Phe Gln Leu Glu Leu Arg Arg Val
            210                 215                 220
Val Ala Gly Glu Gly Ser Gly Ser Val Ser Leu Ala Leu His Leu Gln
225                 230                 235                 240
Pro Leu Arg Ser Ala Ala Gly Ala Ala Leu Ala Leu Thr Val Asp
                245                 250                 255
Leu Pro Pro Ala Ser Ser Glu Ala Arg Asn Ser Ala Phe Gly Phe Gln
                260                 265                 270
Gly Arg Leu Leu His Leu Ser Ala Gly Gln Arg Leu Gly Val His Leu
                275                 280                 285
His Thr Glu Ala Arg Ala Arg His Ala Trp Gln Leu Thr Gln Gly Ala
                290                 295                 300
Thr Val Leu Gly Leu Phe Arg Val Thr Pro Glu Ile Pro Ala Gly Leu
305                 310                 315                 320
Pro Ser Pro Arg Ser Glu
                325

<210> SEQ ID NO 52
<211> LENGTH: 314
<212> TYPE: PRT
<213> ORGANISM: Artificial sequence
<220> FEATURE:
<223> OTHER INFORMATION: var 12

<400> SEQUENCE: 52

Pro Trp Asn Pro Pro Thr Phe Ser Pro Ala Leu Leu Val Val Thr Glu
1               5                   10                  15
Gly Asp Asn Ala Thr Phe Thr Cys Ser Phe Ser Asn Thr Ser Glu Ser
                20                  25                  30
Phe Val Leu Asn Trp Tyr Arg Met Ser Pro Ser Asn Gln Thr Asp Lys
            35                  40                  45
Leu Ala Ala Phe Pro Glu Asp Arg Ser Gln Pro Gly Gln Asp Cys Arg
        50                  55                  60
Phe Arg Val Thr Gln Leu Pro Asn Gly Arg Asp Phe His Met Ser Val
65                  70                  75                  80
Val Arg Ala Arg Arg Asn Asp Ser Gly Thr Tyr Leu Cys Gly Ala Ile
                85                  90                  95
Ser Leu Ala Pro Lys Ala Gln Ile Lys Glu Ser Leu Arg Ala Glu Leu
            100                 105                 110
Arg Val Thr Glu Arg Arg Ala Glu Val Pro Thr Ala His Pro Ser Pro
```

```
            115                 120                 125
Gly Leu Arg Glu Gly Pro Glu Leu Ser Pro Asp Asp Pro Ala Gly Leu
    130                 135                 140

Leu Asp Leu Arg Gln Gly Met Phe Ala Gln Leu Val Ala Gln Asn Val
145                 150                 155                 160

Leu Leu Ile Asp Gly Pro Leu Ser Trp Tyr Ser Asp Pro Gly Leu Ala
                165                 170                 175

Gly Val Ser Leu Thr Gly Gly Leu Ser Tyr Lys Glu Asp Thr Lys Glu
            180                 185                 190

Leu Val Val Ala Lys Ala Gly Val Tyr Tyr Val Phe Phe Gln Leu Glu
        195                 200                 205

Leu Arg Arg Val Val Ala Gly Glu Gly Ser Gly Val Ser Leu Ala
    210                 215                 220

Leu His Leu Gln Pro Leu Arg Ser Ala Ala Gly Ala Ala Leu Ala
225                 230                 235                 240

Leu Thr Val Asp Leu Pro Pro Ala Ser Ser Glu Ala Arg Asn Ser Ala
                245                 250                 255

Phe Gly Phe Gln Gly Arg Leu Leu His Leu Ser Ala Gly Gln Arg Leu
            260                 265                 270

Gly Val His Leu His Thr Glu Ala Arg Ala Arg His Ala Trp Gln Leu
        275                 280                 285

Thr Gln Gly Ala Thr Val Leu Gly Leu Phe Arg Val Thr Pro Glu Ile
    290                 295                 300

Pro Ala Gly Leu Pro Ser Pro Arg Ser Glu
305                 310
```

<210> SEQ ID NO 53
<211> LENGTH: 335
<212> TYPE: PRT
<213> ORGANISM: Artificial sequence
<220> FEATURE:
<223> OTHER INFORMATION: var 13

<400> SEQUENCE: 53

```
Pro Trp Asn Pro Pro Thr Phe Ser Pro Ala Leu Leu Val Val Thr Glu
1               5                   10                  15

Gly Asp Asn Ala Thr Phe Thr Cys Ser Phe Ser Asn Thr Ser Glu Ser
            20                  25                  30

Phe Val Leu Asn Trp Tyr Arg Met Ser Pro Ser Asn Gln Thr Asp Lys
        35                  40                  45

Leu Ala Ala Phe Pro Glu Asp Arg Ser Gln Pro Gly Gln Asp Cys Arg
    50                  55                  60

Phe Arg Val Thr Gln Leu Pro Asn Gly Arg Asp Phe His Met Ser Val
65                  70                  75                  80

Val Arg Ala Arg Arg Asn Asp Ser Gly Thr Tyr Leu Cys Gly Ala Ile
                85                  90                  95

Ser Leu Ala Pro Lys Ala Gln Ile Lys Glu Ser Leu Arg Ala Glu Leu
            100                 105                 110

Arg Val Thr Glu Arg Arg Ala Glu Val Pro Thr Ala His Pro Ser Pro
        115                 120                 125

Ser Pro Arg Pro Ala Gly Gln Gly Ser Gly Ala Arg Ala Ser Pro Gly
    130                 135                 140

Ser Ala Ala Ser Pro Arg Leu Arg Glu Gly Pro Glu Leu Ser Pro Asp
145                 150                 155                 160

Asp Pro Ala Gly Leu Leu Asp Leu Arg Gln Gly Met Phe Ala Gln Leu
```

```
            165                 170                 175
Val Ala Gln Asn Val Leu Leu Ile Asp Gly Pro Leu Ser Trp Tyr Ser
                180                 185                 190

Asp Pro Gly Leu Ala Gly Val Ser Leu Thr Gly Gly Leu Ser Tyr Lys
        195                 200                 205

Glu Asp Thr Lys Glu Leu Val Ala Lys Ala Gly Val Tyr Tyr Val
        210                 215                 220

Phe Phe Gln Leu Glu Leu Arg Arg Val Ala Gly Glu Gly Ser Gly
225                 230                 235                 240

Ser Val Ser Leu Ala Leu His Leu Gln Pro Leu Arg Ser Ala Ala Gly
                245                 250                 255

Ala Ala Ala Leu Ala Leu Thr Val Asp Leu Pro Pro Ala Ser Ser Glu
                260                 265                 270

Ala Arg Asn Ser Ala Phe Gly Phe Gln Gly Arg Leu Leu His Leu Ser
                275                 280                 285

Ala Gly Gln Arg Leu Gly Val His Leu His Thr Glu Ala Arg Ala Arg
                290                 295                 300

His Ala Trp Gln Leu Thr Gln Gly Ala Thr Val Leu Gly Leu Phe Arg
305                 310                 315                 320

Val Thr Pro Glu Ile Pro Ala Gly Leu Pro Ser Pro Arg Ser Glu
                325                 330                 335

<210> SEQ ID NO 54
<211> LENGTH: 327
<212> TYPE: PRT
<213> ORGANISM: Artificial sequence
<220> FEATURE:
<223> OTHER INFORMATION: var 14

<400> SEQUENCE: 54

Pro Trp Asn Pro Pro Thr Phe Ser Pro Ala Leu Leu Val Val Thr Glu
1               5                   10                  15

Gly Asp Asn Ala Thr Phe Thr Cys Ser Phe Ser Asn Thr Ser Glu Ser
                20                  25                  30

Phe Val Leu Asn Trp Tyr Arg Met Ser Pro Ser Asn Gln Thr Asp Lys
            35                  40                  45

Leu Ala Ala Phe Pro Glu Asp Arg Ser Gln Pro Gly Gln Asp Cys Arg
        50                  55                  60

Phe Arg Val Thr Gln Leu Pro Asn Gly Arg Asp Phe His Met Ser Val
65                  70                  75                  80

Val Arg Ala Arg Arg Asn Asp Ser Gly Thr Tyr Leu Cys Gly Ala Ile
                85                  90                  95

Ser Leu Ala Pro Lys Ala Gln Ile Lys Glu Ser Leu Arg Ala Glu Leu
                100                 105                 110

Arg Val Thr Glu Arg Arg Ala Glu Val Pro Thr Ala His Pro Ser Pro
            115                 120                 125

Ser Pro Arg Pro Ala Gly Gln Gly Ser Ala Ala Ser Pro Arg Leu Arg
        130                 135                 140

Glu Gly Pro Glu Leu Ser Pro Asp Asp Pro Ala Gly Leu Leu Asp Leu
145                 150                 155                 160

Arg Gln Gly Met Phe Ala Gln Leu Val Ala Gln Asn Val Leu Leu Ile
                165                 170                 175

Asp Gly Pro Leu Ser Trp Tyr Ser Asp Pro Gly Leu Ala Gly Val Ser
                180                 185                 190

Leu Thr Gly Gly Leu Ser Tyr Lys Glu Asp Thr Lys Glu Leu Val Val
```

```
                195                 200                 205
Ala Lys Ala Gly Val Tyr Tyr Val Phe Phe Gln Leu Glu Leu Arg Arg
            210                 215                 220

Val Val Ala Gly Glu Gly Ser Gly Ser Val Ser Leu Ala Leu His Leu
225                 230                 235                 240

Gln Pro Leu Arg Ser Ala Ala Gly Ala Ala Ala Leu Ala Leu Thr Val
                245                 250                 255

Asp Leu Pro Pro Ala Ser Ser Glu Ala Arg Asn Ser Ala Phe Gly Phe
            260                 265                 270

Gln Gly Arg Leu Leu His Leu Ser Ala Gly Gln Arg Leu Gly Val His
                275                 280                 285

Leu His Thr Glu Ala Arg Ala Arg His Ala Trp Gln Leu Thr Gln Gly
            290                 295                 300

Ala Thr Val Leu Gly Leu Phe Arg Val Thr Pro Glu Ile Pro Ala Gly
305                 310                 315                 320

Leu Pro Ser Pro Arg Ser Glu
                325

<210> SEQ ID NO 55
<211> LENGTH: 333
<212> TYPE: PRT
<213> ORGANISM: Artificial sequence
<220> FEATURE:
<223> OTHER INFORMATION: var 15

<400> SEQUENCE: 55

Pro Trp Asn Pro Pro Thr Phe Ser Pro Ala Leu Leu Val Val Thr Glu
1               5                   10                  15

Gly Asp Asn Ala Thr Phe Thr Cys Ser Phe Ser Asn Thr Ser Glu Ser
            20                  25                  30

Phe Val Leu Asn Trp Tyr Arg Met Ser Pro Ser Asn Gln Thr Asp Lys
        35                  40                  45

Leu Ala Ala Phe Pro Glu Asp Arg Ser Gln Pro Gly Gln Asp Cys Arg
    50                  55                  60

Phe Arg Val Thr Gln Leu Pro Asn Gly Arg Asp Phe His Met Ser Val
65                  70                  75                  80

Val Arg Ala Arg Arg Asn Asp Ser Gly Thr Tyr Leu Cys Gly Ala Ile
                85                  90                  95

Ser Leu Ala Pro Lys Ala Gln Ile Lys Glu Ser Leu Arg Ala Glu Leu
            100                 105                 110

Arg Val Thr Glu Arg Arg Ala Glu Val Pro Thr Ala His Pro Ser Pro
        115                 120                 125

Ser Pro Arg Pro Ala Gly Gln Gly Ala Arg Ala Ser Pro Gly Ser Ala
    130                 135                 140

Ala Ser Pro Arg Leu Arg Glu Gly Pro Glu Leu Ser Pro Asp Asp Pro
145                 150                 155                 160

Ala Gly Leu Leu Asp Leu Arg Gln Gly Met Phe Ala Gln Leu Val Ala
                165                 170                 175

Gln Asn Val Leu Leu Ile Asp Gly Pro Leu Ser Trp Tyr Ser Asp Pro
            180                 185                 190

Gly Leu Ala Gly Val Ser Leu Thr Gly Gly Leu Ser Tyr Lys Glu Asp
        195                 200                 205

Thr Lys Glu Leu Val Val Ala Lys Ala Gly Val Tyr Tyr Val Phe Phe
    210                 215                 220

Gln Leu Glu Leu Arg Arg Val Val Ala Gly Glu Gly Ser Gly Ser Val
```

```
                    225                 230                 235                 240
                Ser Leu Ala Leu His Leu Gln Pro Leu Arg Ser Ala Ala Gly Ala Ala
                            245                 250                 255

Ala Leu Ala Leu Thr Val Asp Leu Pro Pro Ala Ser Ser Glu Ala Arg
                            260                 265                 270

Asn Ser Ala Phe Gly Phe Gln Gly Arg Leu Leu His Leu Ser Ala Gly
                            275                 280                 285

Gln Arg Leu Gly Val His Leu His Thr Glu Ala Arg Ala Arg His Ala
                            290                 295                 300

Trp Gln Leu Thr Gln Gly Ala Thr Val Leu Gly Leu Phe Arg Val Thr
                305                 310                 315                 320

Pro Glu Ile Pro Ala Gly Leu Pro Ser Pro Arg Ser Glu
                            325                 330

<210> SEQ ID NO 56
<211> LENGTH: 321
<212> TYPE: PRT
<213> ORGANISM: Artificial sequence
<220> FEATURE:
<223> OTHER INFORMATION: var 16

<400> SEQUENCE: 56

Pro Trp Asn Pro Pro Thr Phe Ser Pro Ala Leu Leu Val Val Thr Glu
                1               5                   10                  15

Gly Asp Asn Ala Thr Phe Thr Cys Ser Phe Ser Asn Thr Ser Glu Ser
                            20                  25                  30

Phe Val Leu Asn Trp Tyr Arg Met Ser Pro Ser Asn Gln Thr Asp Lys
                            35                  40                  45

Leu Ala Ala Phe Pro Glu Asp Arg Ser Gln Pro Gly Gln Asp Cys Arg
                    50                  55                  60

Phe Arg Val Thr Gln Leu Pro Asn Gly Arg Asp Phe His Met Ser Val
                65                  70                  75                  80

Val Arg Ala Arg Arg Asn Asp Ser Gly Thr Tyr Leu Cys Gly Ala Ile
                            85                  90                  95

Ser Leu Ala Pro Lys Ala Gln Ile Lys Glu Ser Leu Arg Ala Glu Leu
                            100                 105                 110

Arg Val Thr Glu Arg Arg Ala Glu Val Pro Thr Ala His Pro Ser Pro
                            115                 120                 125

Ser Pro Arg Pro Ala Gly Gln Gly Leu Arg Glu Gly Pro Glu Leu Ser
                            130                 135                 140

Pro Asp Asp Pro Ala Gly Leu Leu Asp Leu Arg Gln Gly Met Phe Ala
                145                 150                 155                 160

Gln Leu Val Ala Gln Asn Val Leu Leu Ile Asp Gly Pro Leu Ser Trp
                            165                 170                 175

Tyr Ser Asp Pro Gly Leu Ala Gly Val Ser Leu Thr Gly Gly Leu Ser
                            180                 185                 190

Tyr Lys Glu Asp Thr Lys Glu Leu Val Val Ala Lys Ala Gly Val Tyr
                            195                 200                 205

Tyr Val Phe Phe Gln Leu Glu Leu Arg Arg Val Val Ala Gly Glu Gly
                            210                 215                 220

Ser Gly Ser Val Ser Leu Ala Leu His Leu Gln Pro Leu Arg Ser Ala
                225                 230                 235                 240

Ala Gly Ala Ala Ala Leu Ala Leu Thr Val Asp Leu Pro Pro Ala Ser
                            245                 250                 255

Ser Glu Ala Arg Asn Ser Ala Phe Gly Phe Gln Gly Arg Leu Leu His
```

```
                    260                 265                 270
Leu Ser Ala Gly Gln Arg Leu Gly Val His Leu His Thr Glu Ala Arg
            275                 280                 285

Ala Arg His Ala Trp Gln Leu Thr Gln Gly Ala Thr Val Leu Gly Leu
        290                 295                 300

Phe Arg Val Thr Pro Glu Ile Pro Ala Gly Leu Pro Ser Pro Arg Ser
305                 310                 315                 320

Glu

<210> SEQ ID NO 57
<211> LENGTH: 1020
<212> TYPE: DNA
<213> ORGANISM: Artificial sequence
<220> FEATURE:
<223> OTHER INFORMATION: NA seq of SEQ ID NO: 44, var 4

<400> SEQUENCE: 57
gatagcccgg atcgcccgtg aacccgccg accttagcc cggcgctgct ggtggtgacc      60
gaaggcgata cgcgacctt tacctgcagc tttagcaaca ccagcgaaag ctttgtgctg     120
aactggtatc gcatgagccc gagcaaccag accgataaac tggcggcgtt tccggaagat    180
cgcagccagc cgggccagga ttgccgcttt cgcgtgaccc agctgccgaa cggccgcgat    240
tttcatatga gcgtggtgcg cgcgcgccgc aacgatagcg caccactatct gtgcggcgcg   300 attagcctgg cgccgaaagc gcagattaaa gaaagcctgc gcgcggaact gcgcgtgacc    360
gaacgccgcg cggaagtgcc gaccgcgcat ccgagcccga gccgcgcccc ggcgggccag    420
ggcagcggcg cgcgcgcgag cccgggcagc gcggcgagcc cgcgcctgcg cgaaggcccg    480
gaactgagcc cggatgatcc ggcgggcctg ctggatctgc gccagggcat gtttgcgcag    540
ctggtggcgc agaacgtgct gctgattgat ggcccgctga gctggtatag cgatccgggc    600
ctggcgggcg tgagcctgac cggcggcctg agctataaag aagataccaa agaactggtg    660
gtggcgaaag cgggcgtgta ttatgtgttt tttcagctgg aactgcgccg cgtggtggcg    720
ggcgaaggca gcggcagcgt gagcctggcg ctgcatctgc agccgctgcg cagcgcggcg    780 ggcgcggcg cgctggcgct gaccgtggat ctgccgccgg cgagcagcga agcgcgcaac    840
agcgcgtttg gctttcaggg ccgcctgctg catctgagcg cgggccagcg cctgggcgtg    900
catctgcata ccgaagcgcg cgcgcgccat gcgtggcagc tgacccaggg cgcgaccgtg    960
ctgggcctgt ttcgcgtgac cccggaaatt ccggcgggcc tgccgagccc gcgcagcgaa   1020

<210> SEQ ID NO 58
<211> LENGTH: 999
<212> TYPE: DNA
<213> ORGANISM: Artificial sequence
<220> FEATURE:
<223> OTHER INFORMATION: NA seq of SEQ ID NO: 45, var 5

<400> SEQUENCE: 58
gactctccag acagaccttg aaccctcca accttctctc ccgctctgct ggtggttacc      60
gagggcgaca atgccacctt cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctgccggttc agagttaccc agctgcctaa cggccgggac    240
ttccacatgt ctgttgtgcg ggccagacga aacgactctg cacatatct gtgcggcgcc    300 atctctctgg ctcccaaggc tcagatcaaa gagtctctgc gggccgagct gagagtgaca    360
```

```
gaaagacgag ctgaggtgcc caccgctcat ccctcacctg gatctggcgc tagagcatct      420
cctggctctg ctgcctctcc tagactgaga gagggacctg agctgtctcc tgatgatcct      480
gctggcctgc tggatctgag acagggcatg tttgctcagc tggtggccca gaacgtgctg      540
ctgattgatg gccctctgtc ctggtactct gatcctggat tggctggcgt gtccctgact      600
ggcggcctgt cttacaaaga ggacaccaaa gaactggtgg tggccaaggc cggcgtgtac      660
tacgtgttct ttcagctgga actgcggaga gtggtggccg cgaaggatc tggatctgtg       720 tctctggcac tgcatctgca gcccctgaga tctgctgcag gcgctgctgc tctggctctg      780
acagttgatc tgcctcctgc ctcctccgag gccagaaact ccgcctttgg cttccaaggc      840
agactgctgc atctgtctgc cggccagaga ctggagtcc atctgcatac agaggctaga       900
gccaggcacg cctggcagtt gacacaaggt gctacagtgc tgggcctgtt cagagtgacc      960
ccagagattc cagccggcct gccttctcca agatccgag                              999
```

<210> SEQ ID NO 59
<211> LENGTH: 975
<212> TYPE: DNA
<213> ORGANISM: Artificial sequence
<220> FEATURE:
<223> OTHER INFORMATION: NA seq of SEQ ID NO: 46, var 6

<400> SEQUENCE: 59

```
gactctccag acagaccttg gaaccctcca accttctctc ccgctctgct ggtggttacc       60
gagggcgaca atgccacctt cacctgttcc ttcagcaaca cctccgagtc cttcgtgctg      120
aactggtaca gaatgtcccc tagcaaccag accgacaagc tggccgcctt tcctgaggac      180
agatctcagc caggccagga ctgccggttc agagttaccc agctgcctaa cggccgggac      240
ttccacatgt ctgttgtgcg ggccagacgg aacgactctg gcacatatct gtgcggcgcc      300
atctctctgg ctcccaaggc tcagatcaaa gagtctctgc gggccgagct gagagtgaca      360
gaaagacgag ctgaggtgcc caccgctcat ccctcacctg gatctgctgc ttcccctaga      420
ctgagagagg gccctgagct gtcccctgat gatcctgctg gattgctgga cctgcggcag      480
ggcatgtttg ctcagttggt ggcccagaac gtgctgctga tcgatggccc tctgtcctgg      540
tactctgatc caggattggc tggcgtgtcc ctgactggcg gcctgtctta caaagaggac      600
accaaagaac tggtggtcgc caaggccggc gtgtactacg tgttctttca gctgaactg       660 cggagagtgg tggctggcga aggatctgga tctgtgtctc tggccctgca tctgcagcct      720
ctgagaagtg ctgcaggcgc tgctgcactg gctctgacag ttgatctgcc tcctgcctcc      780
tccgaggcca gaaactccgc ctttggcttc caaggcagac tgctgcatct gtctgccgga      840
cagagactgg gagtgcacct ccatacagag gccagagcta gacacgcttg gcagttgaca      900
cagggcgcta cagtgctggg cctgtttaga gtgacccctg agatcccagc tggcctgcca      960
tctcctagat ctgag                                                        975
```

<210> SEQ ID NO 60
<211> LENGTH: 992
<212> TYPE: DNA
<213> ORGANISM: Artificial sequence
<220> FEATURE:
<223> OTHER INFORMATION: NA seq of SEQ ID NO: 47, var 7

<400> SEQUENCE: 60

```
actctccaga cagaccttgg aaccctccaa ccttctctcc cgctctgctg gtggttaccg       60
agggcgacaa tgccaccttc acctgttcct tcagcaacac ctccgagtcc ttcgtgctga      120
```

```
actggtacag aatgtcccct agcaaccaga ccgacaagct ggccgccttt cctgaggaca      180
gatctcagcc aggccaggac tgccggttca gagttaccca gctgcctaac ggccgggact      240
tccacatgtc tgttgtgcgg gccagacgga acgactctgg cacatatctg tgcggcgcca      300
tctctctggc tcccaaggct cagatcaaag agtctctgcg ggccgagctg agagtgacag      360
aaagacgagc tgaggtgccc accgctcatc cctcacctgg agccagagct tctcctggat      420
ctgctgcttc ccctagactg agagagggcc ctgagctgtc ccctgatgat cctgctggat      480
tgctggacct gcggcagggc atgtttgctc agttggtggc ccagaacgtg ctgctgatcg      540
atggccctct gtcctggtac tctgatccag gattggctgg cgtgtccctg actggcggcc      600
tgtcttacaa agaggacacc aaagaactgg tggtcgccaa ggccggcgtg tactacgtgt      660
tctttcagct ggaactgcgg agagtggtgg ctggcgaagg atctggatct gtgtctctgg      720
ccctgcatct gcagcctctg agaagtgctg caggcgctgc tgcactggct ctgacagttg      780
atctgcctcc tgcctcctcc gaggccagaa actccgcctt ggcttccaa ggcagactgc      840 tgcatctgtc tgccggacag agactgggag tgcacctcca tacagaggcc agagctagac      900
acgcttggca gttgacacag ggcgctacag tgctgggcct gtttagagtg acccctgaga      960
tcccagctgg cctgccatct cctagatctg ag                                   992

<210> SEQ ID NO 61
<211> LENGTH: 956
<212> TYPE: DNA
<213> ORGANISM: Artificial sequence
<220> FEATURE:
<223> OTHER INFORMATION: NA seq of SEQ ID NO: 48, var 8

<400> SEQUENCE: 61
actctccaga cagaccttgg aaccctccaa ccttctctcc cgctctgctg gtggttaccg       60
agggcgacaa tgccaccttc acctgttcct tcagcaacac ctccgagtcc ttcgtgctga      120
actggtacag aatgtcccct agcaaccaga ccgacaagct ggccgccttt cctgaggaca      180
gatctcagcc aggccaggac tgccggttca gagttaccca gctgcctaac ggccgggact      240
tccacatgtc tgttgtgcgg gccagacgga acgactctgg cacatatctg tgcggcgcca      300
tctctctggc tcccaaggct cagatcaaag agtctctgcg ggccgagctg agagtgacag      360
aaagacgagc tgaggtgccc accgctcatc cctcacctgg actgagagag ggccctgagc      420
tgtcccctga tgatcctgct ggattgctgg acctgcggca gggcatgttt gctcagttgg      480
tggcccagaa cgtgctgctg atcgatggcc ctctgtcctg gtactctgat ccaggattgg      540
ctggcgtgtc cctgactggc ggcctgtctt acaaagagga caccaaagaa ctggtggtcg      600
ccaaggccgg cgtgtactac gtgttctttc agctggaact gcggagagtg gtggctggcg      660
aaggatctgg atctgtgtct ctggccctgc atctgcagcc tctgagaagt gctgcaggcg      720
ctgctgcact ggctctgaca gttgatctgc ctcctgcctc ctccgaggcc agaaactccg      780
cctttggctt ccaaggcaga ctgctgcatc tgtctgccgg acagagactg ggagtgcacc      840
tccatacaga ggccagagct agacacgctt ggcagttgac acagggcgct acagtgctgg      900
gcctgtttag agtgacccct gagatcccag ctggcctgcc atctcctaga tctgag         956

<210> SEQ ID NO 62
<211> LENGTH: 984
<212> TYPE: DNA
<213> ORGANISM: Artificial sequence
<220> FEATURE:
```

<223> OTHER INFORMATION: NA seq of SEQ ID NO: 49, var 9

<400> SEQUENCE: 62

```
ccttggaacc ctccaacctt ctctcccgct ctgctggtgg ttaccgaggg cgacaatgcc    60
accttcacct gttccttcag caacacctcc gagtccttcg tgctgaactg gtacagaatg   120
tcccctagca accagaccga caagctggcc gcctttcctg aggacagatc tcagccaggc   180
caggactgcc ggttcagagt tacccagctg cctaacggcc gggacttcca catgtctgtt   240
gtgcgggcca gacggaacga ctctggcaca tatctgtgcg gcgccatctc tctggctccc   300
aaggctcaga tcaaagagtc tctgcgggcc gagctgagag tgacagaaag acgagctgag   360
gtgcccaccg ctcatccctc acctggatct ggcgctagag catctcctgg ctctgctgcc   420
tctcctagac tgagagaggg acctgagctg tctcctgatg atcctgctgg cctgctggat   480
ctgagacagg gcatgtttgc tcagctggtg gcccagaacg tgctgctgat tgatggccct   540
ctgtcctggt actctgatcc tggattggct ggcgtgtccc tgactggcgg cctgtcttac   600
aaagaggaca ccaaagaact ggtggtggcc aaggccggcg tgtactacgt gttctttcag   660
ctggaactgc ggagagtggt ggccggcgaa ggatctggat ctgtgtctct ggcactgcat   720
ctgcagcccc tgagatctgc tgcaggcgct gctgctctgg ctctgacagt tgatctgcct   780
cctgcctcct ccgaggccag aaactccgcc tttggcttcc aaggcagact gctgcatctg   840
tctgccggcc agagactggg agtccatctg catacagagg ctagagccag gcacgcctgg   900
cagttgacac aaggtgctac agtgctgggc ctgttcagag tgaccccaga gattccagcc   960
ggcctgcctt ctccaagatc cgag                                           984
```

<210> SEQ ID NO 63
<211> LENGTH: 960
<212> TYPE: DNA
<213> ORGANISM: Artificial sequence
<220> FEATURE:
<223> OTHER INFORMATION: NA seq of SEQ ID NO: 50, var 10

<400> SEQUENCE: 63

```
ccttggaacc ctccaacctt ctctcccgct ctgctggtgg ttaccgaggg cgacaatgcc    60
accttcacct gttccttcag caacacctcc gagtccttcg tgctgaactg gtacagaatg   120
tcccctagca accagaccga caagctggcc gcctttcctg aggacagatc tcagccaggc   180
caggactgcc ggttcagagt tacccagctg cctaacggcc gggacttcca catgtctgtt   240
gtgcgggcca gacggaacga ctctggcaca tatctgtgcg gcgccatctc tctggctccc   300
aaggctcaga tcaaagagtc tctgcgggcc gagctgagag tgacagaaag acgagctgag   360
gtgcccaccg ctcatccctc acctggatct gctgcttccc ctagactgag agagggccct   420
gagctgtccc ctgatgatcc tgctggattg ctggacctgc ggcagggcat gtttgctcag   480
ttggtggccc agaacgtgct gctgatcgat ggccctctgt cctggtactc tgatccagga   540
ttggctggcg tgtccctgac tggcggcctg tcttacaaag aggacaccaa agaactggtg   600
gtcgccaagg ccggcgtgta ctacgtgttc tttcagctgg aactgcggag agtggtggct   660
ggcgaaggat ctggatctgt gtctctggcc ctgcatctgc agcctctgag aagtgctgca   720
ggcgctgctg cactggctct gacagttgat ctgcctcctg cctcctccga ggccagaaac   780
tccgcctttg gcttccaagg cagactgctg catctgtctg ccggacagag actgggagtg   840
cacctccata cagaggccag agctagacac gcttggcagt tgacagggg cgctacagtg   900
ctgggcctgt ttagagtgac ccctgagatc ccagctggcc tgccatctcc tagatctgag   960
```

<210> SEQ ID NO 64
<211> LENGTH: 978
<212> TYPE: DNA
<213> ORGANISM: Artificial sequence
<220> FEATURE:
<223> OTHER INFORMATION: NA seq of SEQ ID NO: 51, var 11

<400> SEQUENCE: 64

| ccttggaacc ctccaacctt ctctcccgct ctgctggtgg ttaccgaggg cgacaatgcc | 60 |
| accttcacct gttccttcag caacacctcc gagtccttcg tgctgaactg gtacagaatg | 120 |
| tcccctagca accagaccga caagctggcc gcctttcctg aggacagatc tcagccaggc | 180 |
| caggactgcc ggttcagagt tacccagctg cctaacggcc gggacttcca catgtctgtt | 240 |
| gtgcgggcca gacggaacga ctctggcaca tatctgtgcg gcgccatctc tctggctccc | 300 |
| aaggctcaga tcaaagagtc tctgcgggcc gagctgagag tgacagaaag acgagctgag | 360 |
| gtgcccaccg ctcatccctc acctggagcc agagcttctc ctggatctgc tgcttcccct | 420 |
| agactgagag agggccctga gctgtcccct gatgatcctg ctggattgct ggacctgcgg | 480 |
| cagggcatgt ttgctcagtt ggtggcccag aacgtgctgc tgatcgatgg ccctctgtcc | 540 |
| tggtactctg atccaggatt ggctggcgtg tccctgactg gcggcctgtc ttacaaagag | 600 |
| gacaccaaag aactggtggt cgccaaggcc ggcgtgtact acgtgttctt tcagctggaa | 660 |
| ctgcggagag tggtggctgg cgaaggatct ggatctgtgt ctctggccct gcatctgcag | 720 |
| cctctgagaa gtgctgcagg cgctgctgca ctggctctga cagttgatct gcctcctgcc | 780 |
| tcctccgagg ccagaaactc cgcctttggc ttccaaggca gactgctgca tctgtctgcc | 840 |
| ggacagagac tgggagtgca cctccataca gaggccagag ctagacacgc ttggcagttg | 900 |
| acacagggcg ctacagtgct gggcctgttt agagtgaccc ctgagatccc agctggcctg | 960 |
| ccatctccta gatctgag | 978 |

<210> SEQ ID NO 65
<211> LENGTH: 942
<212> TYPE: DNA
<213> ORGANISM: Artificial sequence
<220> FEATURE:
<223> OTHER INFORMATION: NA seq of SEQ ID NO: 52, var 12

<400> SEQUENCE: 65

| ccttggaacc ctccaacctt ctctcccgct ctgctggtgg ttaccgaggg cgacaatgcc | 60 |
| accttcacct gttccttcag caacacctcc gagtccttcg tgctgaactg gtacagaatg | 120 |
| tcccctagca accagaccga caagctggcc gcctttcctg aggacagatc tcagccaggc | 180 |
| caggactgcc ggttcagagt tacccagctg cctaacggcc gggacttcca catgtctgtt | 240 |
| gtgcgggcca gacggaacga ctctggcaca tatctgtgcg gcgccatctc tctggctccc | 300 |
| aaggctcaga tcaaagagtc tctgcgggcc gagctgagag tgacagaaag acgagctgag | 360 |
| gtgcccaccg ctcatccctc acctggactg agagagggcc ctgagctgtc ccctgatgat | 420 |
| cctgctggat tgctggacct gcggcagggc atgtttgctc agttggtggc ccagaacgtg | 480 |
| ctgctgatcg atggccctct gtcctggtac tctgatccag gattggctgg cgtgtccctg | 540 |
| actggcggcc tgtcttacaa agaggacacc aaagaactgg tggtcgccaa ggccggcgtg | 600 |
| tactacgtgt tctttcagct ggaactgcgg agagtggtgg ctggcgaagg atctggatct | 660 |
| gtgtctctgg ccctgcatct gcagcctctg agaagtgctg caggcgctgc tgcactggct | 720 |

```
ctgacagttg atctgcctcc tgcctcctcc gaggccagaa actccgcctt tggcttccaa      780
ggcagactgc tgcatctgtc tgccggacag agactgggag tgcacctcca tacagaggcc      840
agagctagac acgcttggca gttgacacag ggcgctacag tgctgggcct gtttagagtg      900
acccctgaga tcccagctgg cctgccatct cctagatctg ag                         942
```

<210> SEQ ID NO 66
<211> LENGTH: 1005
<212> TYPE: DNA
<213> ORGANISM: Artificial sequence
<220> FEATURE:
<223> OTHER INFORMATION: NA seq of SEQ ID NO: 53, var 13

<400> SEQUENCE: 66

```
ccttggaacc ctccaacctt ctctcccgct ctgctggtgg ttaccgaggg cgacaatgcc       60
accttcacct gttccttcag caacacctcc gagtccttcg tgctgaactg gtacagaatg      120
tcccctagca accagaccga caagctggcc gcctttcctg aggacagatc tcagccaggc      180
caggactgcc ggttcagagt tacccagctg cctaacggcc gggacttcca catgtctgtt      240
gtgcgggcca gacggaacga ctctggcaca tatctgtgcg gcgccatctc tctggctccc      300
aaggctcaga tcaaagagtc tctgcgggcc gagctgagag tgacagaaag acgagctgag      360
gtgcccaccg ctcatccctc accttctcca agacctgctg gccagggatc tggcgctaga      420
gcatctcctg gctctgctgc ctctcctaga ctgagagagg acctgagct gtctcctgat       480 gatcctgctg gcctgctgga tctgagacag ggcatgtttg ctcagctggt ggcccagaac      540
gtgctgctga ttgatggccc tctgtcctgg tactctgatc ctggattggc tggcgtgtcc      600
ctgactggcg gcctgtctta caaagaggac accaagaac tggtggtggc caaggccggc      660
gtgtactacg tgttctttca gctggaactg cggagagtgg tggccggcga aggatctgga      720
tctgtgtctc tggcactgca tctgcagccc ctgagatctg ctgcaggcgc tgctgctctg      780
gctctgacag ttgatctgcc tcctgcctcc tccgaggcca gaaactccgc cttttggcttc      840 caaggcagac tgctgcatct gtctgccggc cagagactgg gagtccatct gcatacagag      900
gctagagcca ggcacgcctg gcagttgaca caaggtgcta cagtgctggg cctgttcaga      960 gtgacccag agattccagc cggcctgcct tctccaagat ccgag                     1005
```

<210> SEQ ID NO 67
<211> LENGTH: 981
<212> TYPE: DNA
<213> ORGANISM: Artificial sequence
<220> FEATURE:
<223> OTHER INFORMATION: NA seq of SEQ ID NO: 54, var 14

<400> SEQUENCE: 67

```
ccttggaacc ctccaacctt ctctcccgct ctgctggtgg ttaccgaggg cgacaatgcc       60
accttcacct gttccttcag caacacctcc gagtccttcg tgctgaactg gtacagaatg      120
tcccctagca accagaccga caagctggcc gcctttcctg aggacagatc tcagccaggc      180
caggactgcc ggttcagagt tacccagctg cctaacggcc gggacttcca catgtctgtt      240
gtgcgggcca gacggaacga ctctggcaca tatctgtgcg gcgccatctc tctggctccc      300
aaggctcaga tcaaagagtc tctgcgggcc gagctgagag tgacagaaag acgagctgag      360
gtgcccaccg ctcatccctc accttctcca agacctgctg gccagggatc tgctgcttcc      420
cctagactga gagagggccc tgagctgtcc cctgatgatc ctgctggatt gctgacctg      480 cggcagggca tgtttgctca gttggtggcc cagaacgtgc tgctgatcga tggccctctg      540
```

```
tcctggtact ctgatccagg attggctggc gtgtccctga ctggcggcct gtcttacaaa    600
gaggacacca aagaactggt ggtcgccaag gccggcgtgt actacgtgtt ctttcagctg    660
gaactgcgga gagtggtggc tggcgaagga tctggatctg tgtctctggc cctgcatctg    720
cagcctctga aagtgctgca aggcgctgct gcactggctc tgacagttga tctgcctcct    780
gcctcctccg aggccagaaa ctccgccttt ggcttccaag gcagactgct gcatctgtct    840
gccggacaga gactgggagt gcacctccat acagaggcca gagctagaca cgcttggcag    900
ttgacacagg gcgctacagt gctgggcctg tttagagtga cccctgagat cccagctggc    960
ctgccatctc ctagatctga g                                              981

<210> SEQ ID NO 68
<211> LENGTH: 999
<212> TYPE: DNA
<213> ORGANISM: Artificial sequence
<220> FEATURE:
<223> OTHER INFORMATION: NA seq of SEQ ID NO: 55, var 15

<400> SEQUENCE: 68
ccttggaacc ctccaacctt ctctcccgct ctgctggtgg ttaccgaggg cgacaatgcc     60
accttcacct gttccttcag caacacctcc gagtccttcg tgctgaactg gtacagaatg    120 tccctagca accagaccga caagctggcc gcctttcctg aggacagatc tcagccaggc    180
caggactgcc ggttcagagt tacccagctg cctaacggcc gggacttcca catgtctgtt    240
gtgcgggcca gacggaacga ctctggcaca tatctgtgcg cgccatctc tctggctccc    300 aaggctcaga tcaaagagtc tctgcgggcc gagctgagag tgacagaaag acgagctgag    360
gtgcccaccg ctcatccctc accttctcca agacctgctg gccagggagc cagagcttct    420
cctggatctg ctgcttcccc tagactgaga gagggccctg agctgtcccc tgatgatcct    480
gctggattgc tggaccctgcg gcagggcatg tttgctcagt tggtggccca gaacgtgctg    540
ctgatcgatg gccctctgtc ctggtactct gatccaggat tggctggcgt gtccctgact    600
ggcggcctgt cttacaaaga ggacaccaaa gaactggtgg tcgccaaggc cggcgtgtac    660
tacgtgttct ttcagctgga actgcggaga gtggtggctg gcgaaggatc tggatctgtg    720
tctctggccc tgcatctgca gcctctgaga agtgctgcag gcgctgctgc actggctctg    780
acagttgatc tgcctcctgc ctcctccgag gccagaaact ccgcctttgg cttccaaggc    840
agactgctgc atctgtctgc cggacagaga ctgggagtgc acctccatac agaggccaga    900
gctagacacg cttggcagtt gacacagggc gctacagtgc tgggcctgtt tagagtgacc    960
cctgagatcc agctggcct gccatctcct agatctgag                            999

<210> SEQ ID NO 69
<211> LENGTH: 963
<212> TYPE: DNA
<213> ORGANISM: Artificial sequence
<220> FEATURE:
<223> OTHER INFORMATION: NA seq of SEQ ID NO: 56, var 16

<400> SEQUENCE: 69
ccttggaacc ctccaacctt ctctcccgct ctgctggtgg ttaccgaggg cgacaatgcc     60
accttcacct gttccttcag caacacctcc gagtccttcg tgctgaactg gtacagaatg    120 tccctagca accagaccga caagctggcc gcctttcctg aggacagatc tcagccaggc    180
caggactgcc ggttcagagt tacccagctg cctaacggcc gggacttcca catgtctgtt    240
```

```
gtgcgggcca gacggaacga ctctggcaca tatctgtgcg cgccatctc tctggctccc      300
aaggctcaga tcaaagagtc tctgcgggcc gagctgagag tgacagaaag acagagctgag   360
gtgcccaccg ctcatccctc accttctcca agacctgctg gccagggact gagagagggc    420
cctgagctgt ccctgatga tcctgctgga ttgctgacc tgcggcaggg catgtttgct      480
cagttggtgg cccagaacgt gctgctgatc gatggccctc tgtcctggta ctctgatcca    540
ggattggctg gcgtgtccct gactggcggc ctgtcttaca aagaggacac caaagaactg    600
gtggtcgcca aggccggcgt gtactacgtg ttctttcagc tggaactgcg gagagtggtg    660
gctggcgaag gatctggatc tgtgtctctg gccctgcatc tgcagcctct gagaagtgct    720
gcaggcgctg ctgcactggc tctgacagtt gatctgcctc ctgcctcctc cgaggccaga    780
aactccgcct ttggcttcca aggcagactg ctgcatctgt ctgccggaca gagactggga    840
gtgcacctcc atacagaggc cagagctaga cacgcttggc agttgacaca gggcgctaca    900
gtgctgggcc tgtttagagt gacccctgag atcccagctg gcctgccatc tcctagatct    960
gag                                                                  963
```

<210> SEQ ID NO 70
<211> LENGTH: 996
<212> TYPE: DNA
<213> ORGANISM: Artificial sequence
<220> FEATURE:
<223> OTHER INFORMATION: NA seq of SEQ ID NO: 12

<400> SEQUENCE: 70

```
gactctccag acagaccttg gaaccctcca accttctctc ccgctctgct ggtggttacc      60
gagggcgaca atgccaccct cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctgccggttc agagttaccc agctgcctaa cggccgggac    240
ttccacatgt ctgttgtgcg ggccagacgg aacgactctg gcacatatct gtgcggcgcc    300
atctctctgg ctcccaaggc tcagatcaaa gagtctctgc gggccgagct gagagtgaca    360
gaaagacgag ctgaggtgcc caccgctcat ccctcacctt ctccaagacc tgctggccag    420
ggatctgccg cttctcctag actgagagag ggccctgagc tgtctcctga tgatcctgct    480
ggactgctgg acctgagaca gggcatgttt gcccagctgg tggcccagaa tgtgctgctg    540
attgacggcc ctctgtcctg gtactctgat ccaggattgg ctggcgtgtc cctgactggc    600
ggcctgtctt acaaagagga caccaaagaa ctggtggtcg ccaaggccgg cgtgtactac    660
gtgttctttc agctggaact gcggagagtg gtggctggcg aaggatctgg atctgtgtct    720
ctggccctgc atctgcagcc tctgagaagt gctgcaggcg ctgctgcact ggctctgaca    780
gttgatctgc ctcctgcctc ctccgaggcc agaaactccg cctttggctt ccaaggcaga    840
ctgctgcatc tgtctgccgg acagagactg gagtgcacc tccatacaga ggccagagct    900
agacacgctt ggcagttgac acagggcgct acagtgctgg gcctgtttag agtgaccct    960
gagattccag ccggcctgcc atctccaaga tctgag                              996
```

<210> SEQ ID NO 71
<211> LENGTH: 1014
<212> TYPE: DNA
<213> ORGANISM: Artificial sequence
<220> FEATURE:
<223> OTHER INFORMATION: NA seq of SEQ ID NO: 14

<400> SEQUENCE: 71

```
gactctccag acagaccttg aaccctcca accttctctc ccgctctgct ggtggttacc      60
gagggcgaca atgccacctt cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctgccggttc agagttaccc agctgcctaa cggccgggac    240
ttccacatgt ctgttgtgcg ggccagacgg aacgactctg gcacatatct gtgcggcgcc    300
atctctctgg ctcccaaggc tcagatcaaa gagtctctgc gggccgagct gagagtgaca    360
gaaagacgag ctgaggtgcc caccgctcat ccctcacctt ctccaagacc tgctggacag    420
ggcgccagag cttctcctgg atctgctgct ccccctagac tgagagaggg ccctgagctg    480
tcccctgatg atcctgctgg attgctggac ctgcggcagg gcatgtttgc tcagttggtg    540
gcccagaacg tgctgctgat cgatggcccc tgtcctggt actctgatcc aggattggct     600
ggcgtgtccc tgactggcgg cctgtcttac aaagaggaca ccaaagaact ggtggtcgcc    660
aaggccggcg tgtactacgt gttctttcag ctggaactgc ggagagtggt ggctggcgaa    720
ggatctggat ctgtgtctct ggccctgcat ctgcagcctc tgagaagtgc tgcaggcgct    780
gctgcactgg ctctgacagt tgatctgcct cctgcctcct ccgaggccag aaactccgcc    840
tttggcttcc aaggcagact gctgcatctg tctgccggac agagactggg agtgcacctc    900
catacagagg ccagagctag acacgcttgg cagttgacac agggcgctac agtgctgggc    960
ctgtttagag tgaccoctga gatcccagct ggcctgccat ctcctagatc tgag         1014

<210> SEQ ID NO 72
<211> LENGTH: 978
<212> TYPE: DNA
<213> ORGANISM: Artificial sequence
<220> FEATURE:
<223> OTHER INFORMATION: NA seq of SEQ ID NO: 16

<400> SEQUENCE: 72
gactctccag acagaccttg aaccctcca accttctctc ccgctctgct ggtggttacc      60
gagggcgaca atgccacctt cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctgccggttc agagttaccc agctgcctaa cggccgggac    240
ttccacatgt ctgttgtgcg ggccagacgg aacgactctg gcacatatct gtgcggcgcc    300
atctctctgg ctcccaaggc tcagatcaaa gagtctctgc gggccgagct gagagtgaca    360
gaaagacgag ctgaggtgcc caccgctcat ccctcacctt ctccaagacc tgctggccag    420
ggactgagag agggacctga actgtctcct gatgatcctg ccggcctgct ggatctgaga    480
cagggcatgt ttgcccagct ggtggcccag aatgtgctgc tgattgacgg ccctctgtcc    540
tggtactctg atccaggatt ggctggcgtg tccctgactg gcggcctgtc ttacaaagag    600
gacaccaaag aactggtggt cgccaaggcc ggcgtgtact acgtgttctt tcagctggaa    660
ctgcggagag tggtggctgg cgaaggatct ggatctgtgt ctctggccct gcatctgcag    720
cctctgagaa gtgctgcagg cgctgctgca ctggctctga cagttgatct gcctcctgcc    780
tcctccgagg ccagaaactc cgcctttggc ttcaaggca gactgctgca tctgtctgcc     840
ggacagagac tgggagtgca cctccataca gaggccagag ctagacacgc ttggcagttg    900
acacagggcg ctacagtgct gggcctgttt agagtgaccc ctgagatccc tgctggactg    960
ccctctccaa gatctgag                                                  978
```

<210> SEQ ID NO 73
<211> LENGTH: 150
<212> TYPE: PRT
<213> ORGANISM: Artificial sequence
<220> FEATURE:
<223> OTHER INFORMATION: 73  PD1 ECD Full with CYS73>SER SUBSTITUTION

<400> SEQUENCE: 73

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Ser Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150
```

<210> SEQ ID NO 74
<211> LENGTH: 450
<212> TYPE: DNA
<213> ORGANISM: Artificial sequence
<220> FEATURE:
<223> OTHER INFORMATION: na sequence encoding SEQ ID NO:73

<400> SEQUENCE: 74

```
cccggctggt ttctggactc tccagacaga ccttggaacc ctccaacctt ctctcccgct    60
ctgctggtgg ttaccgaggg cgacaatgcc accttcacct gttccttcag caacacctcc   120
gagtccttcg tgctgaactg gtacagaatg tcccctagca accagaccga caagctggcc   180
gcctttcctg aggacagatc tcagccaggc caggactctc ggttcagagt acccagctg    240
cctaacggcc gggacttcca catgtctgtt gtgcgggcca gacggaacga ctctggcaca   300
tatctgtgcg gcgccatctc tctggctccc aaggctcaga tcaaagagtc tctgcgggcc   360
gagctgagag tgacagaaag acgagctgag gtgcccaccg ctcatccctc accttctcca   420
agacctgctg gccagtttca gacactcgtg                                    450
```

<210> SEQ ID NO 75
<211> LENGTH: 140
<212> TYPE: PRT
<213> ORGANISM: Artificial sequence
<220> FEATURE:
<223> OTHER INFORMATION: PD1 -5-5 from var17 (DSP105 var 1 with
      CYS73>SER SUBSTITUTION)

<400> SEQUENCE: 75

```
Asp Ser Pro Asp Arg Pro Trp Asn Pro Pro Thr Phe Ser Pro Ala Leu
1               5                   10                  15
```

```
Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Ser Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln
    130                 135                 140

<210> SEQ ID NO 76
<211> LENGTH: 420
<212> TYPE: DNA
<213> ORGANISM: Artificial sequence
<220> FEATURE:
<223> OTHER INFORMATION: na sequence encoding SEQ ID NO: 75 420 bp

<400> SEQUENCE: 76
gactctccag acagaccttg gaaccctcca accttctctc ccgctctgct ggtggttacc      60
gagggcgaca atgccacctt cacctgttcc ttcagcaaca cctccgagtc cttcgtgctg     120
aactggtaca gaatgtcccc tagcaaccag accgacaagc tggccgcctt tcctgaggac     180
agatctcagc caggccagga ctctcggttc agagtgaccc agctgcctaa cggcagagac     240
ttccacatgt ccgtcgtgcg ggccagaaga aacgactctg gcacctatct gtgcggcgcc     300
atctctctgg ctcccaaggc tcagatcaaa gagtctctgc gggccgagct gagagtgaca     360
gaaagacgag ctgaggtgcc caccgctcat ccctcacctt ctccaagacc tgctggccag     420

<210> SEQ ID NO 77
<211> LENGTH: 146
<212> TYPE: PRT
<213> ORGANISM: Artificial sequence
<220> FEATURE:
<223> OTHER INFORMATION: PD1 -5-5 with His Tag with CYS73>SER
      SUBSTITUTION

<400> SEQUENCE: 77

His His His His His Asp Ser Pro Asp Arg Pro Trp Asn Pro Pro
1               5                   10                  15

Thr Phe Ser Pro Ala Leu Leu Val Val Thr Glu Gly Asp Asn Ala Thr
            20                  25                  30

Phe Thr Cys Ser Phe Ser Asn Thr Ser Glu Ser Phe Val Leu Asn Trp
        35                  40                  45

Tyr Arg Met Ser Pro Ser Asn Gln Thr Asp Lys Leu Ala Ala Phe Pro
    50                  55                  60

Glu Asp Arg Ser Gln Pro Gly Gln Asp Ser Arg Phe Arg Val Thr Gln
65                  70                  75                  80

Leu Pro Asn Gly Arg Asp Phe His Met Ser Val Val Arg Ala Arg Arg
                85                  90                  95

Asn Asp Ser Gly Thr Tyr Leu Cys Gly Ala Ile Ser Leu Ala Pro Lys
```

```
                100              105                110
Ala Gln Ile Lys Glu Ser Leu Arg Ala Glu Leu Arg Val Thr Glu Arg
            115                 120                 125

Arg Ala Glu Val Pro Thr Ala His Pro Ser Pro Ser Pro Arg Pro Ala
        130                 135                 140

Gly Gln
145

<210> SEQ ID NO 78
<211> LENGTH: 438
<212> TYPE: DNA
<213> ORGANISM: Artificial sequence
<220> FEATURE:
<223> OTHER INFORMATION: na sequence encoding SEQ ID NO:77 438 bp

<400> SEQUENCE: 78
caccaccacc atcaccacga ctctccagac agaccttgga accctccaac cttctctccc      60
gctctgctgg tggttaccga gggcgacaat gccaccttca cctgttcctt cagcaacacc    120
tccgagtcct tcgtgctgaa ctggtacaga atgtcccta gcaaccagac cgacaagctg     180
gccgcctttc ctgaggacag atctcagcca ggccaggact ctcggttcag agtgacccag    240
ctgcctaacg gcagagactt ccacatgtcc gtcgtgcggg ccagaagaaa cgactctggc    300
acctatctgt gcggcgccat ctctctggct cccaaggctc agatcaaaga gtctctgcgg    360
gccgagctga gagtgacaga aagacgagct gaggtgccca ccgctcatcc ctcaccttct    420
ccaagacctg ctggccag                                                  438

<210> SEQ ID NO 79
<211> LENGTH: 135
<212> TYPE: PRT
<213> ORGANISM: Artificial sequence
<220> FEATURE:
<223> OTHER INFORMATION: PD1 -10-5 (with CYS73>SER SUBSTITUTION)

<400> SEQUENCE: 79

Pro Trp Asn Pro Pro Thr Phe Ser Pro Ala Leu Leu Val Val Thr Glu
1               5                   10                  15

Gly Asp Asn Ala Thr Phe Thr Cys Ser Phe Ser Asn Thr Ser Glu Ser
            20                  25                  30

Phe Val Leu Asn Trp Tyr Arg Met Ser Pro Ser Asn Gln Thr Asp Lys
        35                  40                  45

Leu Ala Ala Phe Pro Glu Asp Arg Ser Gln Pro Gly Gln Asp Ser Arg
    50                  55                  60

Phe Arg Val Thr Gln Leu Pro Asn Gly Arg Asp Phe His Met Ser Val
65                  70                  75                  80

Val Arg Ala Arg Arg Asn Asp Ser Gly Thr Tyr Leu Cys Gly Ala Ile
                85                  90                  95

Ser Leu Ala Pro Lys Ala Gln Ile Lys Glu Ser Leu Arg Ala Glu Leu
            100                 105                 110

Arg Val Thr Glu Arg Arg Ala Glu Val Pro Thr Ala His Pro Ser Pro
        115                 120                 125

Ser Pro Arg Pro Ala Gly Gln
    130                 135

<210> SEQ ID NO 80
<211> LENGTH: 405
<212> TYPE: DNA
<213> ORGANISM: Artificial sequence
```

```
<220> FEATURE:
<223> OTHER INFORMATION: na sequence encoding SEQ ID NO:79 405 bp

<400> SEQUENCE: 80
ccttggaacc ctccaacctt ctctcccgct ctgctggtgg ttaccgaggg cgacaatgcc      60
accttcacct gttccttcag caacacctcc gagtccttcg tgctgaactg gtacagaatg     120
tcccctagca accagaccga caagctggcc gcctttcctg aggacagatc tcagccaggc     180
caggactctc ggttcagagt tacccagctg cctaacggcc gggacttcca catgtctgtt     240
gtgcgggcca gacggaacga ctctggcaca tatctgtgcg cgccatctc tctggctccc      300
aaggctcaga tcaaagagtc tctgcgggcc gagctgagag tgacagaaag acgagctgag     360
gtgcccaccg ctcatccctc accttctcca agacctgctg gccag                     405

<210> SEQ ID NO 81
<211> LENGTH: 128
<212> TYPE: PRT
<213> ORGANISM: Artificial sequence
<220> FEATURE:
<223> OTHER INFORMATION: PD1-10-12 (with CYS73>SER SUBSTITUTION)

<400> SEQUENCE: 81

Pro Trp Asn Pro Pro Thr Phe Ser Pro Ala Leu Leu Val Val Thr Glu
1               5                   10                  15
Gly Asp Asn Ala Thr Phe Thr Cys Ser Phe Ser Asn Thr Ser Glu Ser
                20                  25                  30
Phe Val Leu Asn Trp Tyr Arg Met Ser Pro Ser Asn Gln Thr Asp Lys
            35                  40                  45
Leu Ala Ala Phe Pro Glu Asp Arg Ser Gln Pro Gly Gln Asp Ser Arg
        50                  55                  60
Phe Arg Val Thr Gln Leu Pro Asn Gly Arg Asp Phe His Met Ser Val
65                  70                  75                  80
Val Arg Ala Arg Arg Asn Asp Ser Gly Thr Tyr Leu Cys Gly Ala Ile
                85                  90                  95
Ser Leu Ala Pro Lys Ala Gln Ile Lys Glu Ser Leu Arg Ala Glu Leu
                100                 105                 110
Arg Val Thr Glu Arg Arg Ala Glu Val Pro Thr Ala His Pro Ser Pro
            115                 120                 125

<210> SEQ ID NO 82
<211> LENGTH: 384
<212> TYPE: DNA
<213> ORGANISM: Artificial sequence
<220> FEATURE:
<223> OTHER INFORMATION: na sequence encoding SEQ ID NO:81 384 bp

<400> SEQUENCE: 82
ccttggaacc ctccaacctt ctctcccgct ctgctggtgg ttaccgaggg cgacaatgcc      60
accttcacct gttccttcag caacacctcc gagtccttcg tgctgaactg gtacagaatg     120
tcccctagca accagaccga caagctggcc gcctttcctg aggacagatc tcagccaggc     180
caggactctc ggttcagagt tacccagctg cctaacggcc gggacttcca catgtctgtt     240
gtgcgggcca gacggaacga ctctggcaca tatctgtgcg cgccatctc tctggctccc      300
aaggctcaga tcaaagagtc tctgcgggcc gagctgagag tgacagaaag acgagctgag     360
gtgcccaccg ctcatccctc acct                                            384

<210> SEQ ID NO 83
```

```
<211> LENGTH: 133
<212> TYPE: PRT
<213> ORGANISM: Artificial sequence
<220> FEATURE:
<223> OTHER INFORMATION: PD1 -5-12 (New, from V20) (with CYS73>SER
      SUBSTITUTION)

<400> SEQUENCE: 83
```

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Ser Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro
    130

```
<210> SEQ ID NO 84
<211> LENGTH: 399
<212> TYPE: DNA
<213> ORGANISM: Artificial sequence
<220> FEATURE:
<223> OTHER INFORMATION: na sequence encoding SEQ ID NO:83 399 bp

<400> SEQUENCE: 84
```
gactctccag acagaccttg aaccctcca accttctctc ccgctctgct ggtggttacc      60
gagggcgaca atgccacctt cacctgttcc ttcagcaaca cctccgagtc cttcgtgctg     120
aactggtaca gaatgtcccc tagcaaccag accgacaagc tggccgcctt tcctgaggac     180
agatctcagc caggccagga ctctcggttc agagttaccc agctgcctaa cggccgggac     240
ttccacatgt ctgttgtgcg ggccagacgg aacgactctg gcacatatct gtgcggcgcc     300
atctctctgg ctcccaaggc tcagatcaaa gagtctctgc gggccgagct gagagtgaca     360
gaaagacgag ctgaggtgcc caccgctcat ccctcacct                            399

```
<210> SEQ ID NO 85
<211> LENGTH: 127
<212> TYPE: PRT
<213> ORGANISM: Artificial sequence
<220> FEATURE:
<223> OTHER INFORMATION: PD1 -11-12

<400> SEQUENCE: 85
```

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Cys Arg Phe
            50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Gly Ala Ile Ser
                85                  90                  95

Leu Ala Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro
            115                 120                 125

<210> SEQ ID NO 86
<211> LENGTH: 381
<212> TYPE: DNA
<213> ORGANISM: Artificial sequence
<220> FEATURE:
<223> OTHER INFORMATION: na sequence encoding SEQ ID NO: 85 381 bp

<400> SEQUENCE: 86
tggaaccctc aaccttctc tcccgctctg ctggtggtta ccgagggcga caatgccacc    60
ttcacctgtt ccttcagcaa cacctccgag tccttcgtgc tgaactggta cagaatgtcc   120
cctagcaacc agaccgacaa gctggccgcc tttcctgagg acagatctca gccaggccag   180
gactgtcggt tcagagtgac ccagctgcct aacggcagag acttccacat gtccgtcgtg   240
cgggccagaa gaaacgactc tggcacctat ctgtgcggcg ccatctctct ggctcccaag   300
gctcagatca agagtctctc gcgggccgag ctgagagtga cagaaagacg agctgaggtg   360
cccaccgctc atccctcacc t                                              381

<210> SEQ ID NO 87
<211> LENGTH: 127
<212> TYPE: PRT
<213> ORGANISM: Artificial sequence
<220> FEATURE:
<223> OTHER INFORMATION: PD1 -11-12 (New, from V18) (with CYS73>SER
      SUBSTITUTION)

<400> SEQUENCE: 87

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Ser Arg Phe
            50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Gly Ala Ile Ser
                85                  90                  95

Leu Ala Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro
            115                 120                 125

<210> SEQ ID NO 88
<211> LENGTH: 381
<212> TYPE: DNA
<213> ORGANISM: Artificial sequence
<220> FEATURE:
<223> OTHER INFORMATION: na sequence encoding SEQ ID NO: 87 381 bp

<400> SEQUENCE: 88

```
tggaaccctc caaccttctc tcccgctctg ctggtggtta ccgagggcga caatgccacc        60
ttcacctgtt ccttcagcaa cacctccgag tccttcgtgc tgaactggta cagaatgtcc       120
cctagcaacc agaccgacaa gctggccgcc tttcctgagg acagatctca gccaggccag       180
gactctcggt tcagagtgac ccagctgcct aacggcagag acttccacat gtccgtcgtg       240
cgggccagaa gaaacgactc tggcacctat ctgtgcggcg ccatctctct ggctcccaag       300
gctcagatca aagagtctct gcgggccgag ctgagagtga cagaaagacg agctgaggtg       360
cccaccgctc atccctcacc t                                                 381
```

<210> SEQ ID NO 89
<211> LENGTH: 134
<212> TYPE: PRT
<213> ORGANISM: Artificial sequence
<220> FEATURE:
<223> OTHER INFORMATION: PD1-11-5

<400> SEQUENCE: 89

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Cys Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Gly Ala Ile Ser
                85                  90                  95

Leu Ala Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro Arg Pro Ala Gly Gln
    130
```

<210> SEQ ID NO 90
<211> LENGTH: 402
<212> TYPE: DNA
<213> ORGANISM: Artificial sequence
<220> FEATURE:
<223> OTHER INFORMATION: na sequence encoding SEQ ID NO: 89 402 bp

<400> SEQUENCE: 90

```
tggaaccctc caaccttctc tcccgctctg ctggtggtta ccgagggcga caatgccacc        60
ttcacctgtt ccttcagcaa cacctccgag tccttcgtgc tgaactggta cagaatgtcc       120
cctagcaacc agaccgacaa gctggccgcc tttcctgagg acagatctca gccaggccag       180
gactgtcggt tcagagtgac ccagctgcct aacggcagag acttccacat gtccgtcgtg       240
cgggccagaa gaaacgactc tggcacctat ctgtgcggcg ccatctctct ggctcccaag       300
gctcagatca aagagtctct gcgggccgag ctgagagtga cagaaagacg agctgaggtg       360
cccaccgctc atccctcacc ttctccaaga cctgctggcc ag                          402
```

<210> SEQ ID NO 91
<211> LENGTH: 134
<212> TYPE: PRT
<213> ORGANISM: Artificial sequence
<220> FEATURE:
<223> OTHER INFORMATION: PD1 -11-5 (New, from V19) (with CYS73>SER SUBSTITUTION)

<400> SEQUENCE: 91

Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Ser Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Gly Ala Ile Ser
                85                  90                  95

Leu Ala Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro Ser
        115                 120                 125

Pro Arg Pro Ala Gly Gln
    130

<210> SEQ ID NO 92
<211> LENGTH: 402
<212> TYPE: DNA
<213> ORGANISM: Artificial sequence
<220> FEATURE:
<223> OTHER INFORMATION: na sequence encoding SEQ ID NO: 91 402 bp

<400> SEQUENCE: 92
tggaaccctc caaccttctc tcccgctctg ctggtggtta ccgagggcga caatgccacc    60
ttcacctgtt ccttcagcaa cacctccgag tccttcgtgc tgaactggta cagaatgtcc   120
cctagcaacc agaccgacaa gctggccgcc tttcctgagg acagatctca gccaggccag   180
gactctcggt tcagagtgac ccagctgcct aacggcagag acttccacat gtccgtcgtg   240
cgggccagaa gaaacgactc tggcacctat ctgtgcggcg ccatctctct ggctcccaag   300
gctcagatca agagtctct gcgggccgag ctgagagtga cagaaagacg agctgaggtg   360
cccaccgctc atccctcacc ttctccaaga cctgctggcc ag                      402

<210> SEQ ID NO 93
<211> LENGTH: 138
<212> TYPE: PRT
<213> ORGANISM: Artificial sequence
<220> FEATURE:
<223> OTHER INFORMATION: PD1 -5-7

<400> SEQUENCE: 93

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala
    130                 135

<210> SEQ ID NO 94
<211> LENGTH: 414
<212> TYPE: DNA
<213> ORGANISM: Artificial sequence
<220> FEATURE:
<223> OTHER INFORMATION: na sequence encoding SEQ ID NO: 93 414 bp

<400> SEQUENCE: 94
gactctccag acagaccttg aaccctcca accttctctc cgctctgct ggtggttacc      60 gagggcgaca atgccacctt cacctgttcc ttcagcaaca cctccgagtc cttcgtgctg     120
aactggtaca gaatgtcccc tagcaaccag accgacaagc tggccgcctt tcctgaggac     180
agatctcagc caggccagga ctgtcggttc agagtgaccc agctgcctaa cggcagagac     240
ttccacatgt ccgtcgtgcg ggccagaaga aacgactctg gcacctatct gtgcggcgcc     300
atctctctgg ctcccaaggc tcagatcaaa gagtctctgc gggccgagct gagagtgaca     360
gaaagacgag ctgaggtgcc caccgctcat ccctcacctt ctccaagacc tgct           414

<210> SEQ ID NO 95
<211> LENGTH: 138
<212> TYPE: PRT
<213> ORGANISM: Artificial sequence
<220> FEATURE:
<223> OTHER INFORMATION: PD1 -5-7 (New, from V21) (with CYS73>SER
      SUBSTITUTION)

<400> SEQUENCE: 95

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
    50                  55                  60

Gly Gln Asp Ser Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala
    130                 135

<210> SEQ ID NO 96
<211> LENGTH: 414
<212> TYPE: DNA
<213> ORGANISM: Artificial sequence
<220> FEATURE:
<223> OTHER INFORMATION: na sequence encoding SEQ ID NO: 95 414 bp

<400> SEQUENCE: 96
gactctccag acagaccttg gaaccctcca accttctctc ccgctctgct ggtggttacc     60
gagggcgaca atgccacctt cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctctcggttc agagtgaccc agctgcctaa cggcagagac    240
ttccacatgt ccgtcgtgcg ggccagaaga aacgactctg gcacctatct gtgcggcgcc    300
atctctctgg ctcccaaggc tcagatcaaa gagtctctgc gggccgagct gagagtgaca    360
gaaagacgag ctgaggtgcc caccgctcat ccctcacctt ctccaagacc tgct          414

<210> SEQ ID NO 97
<211> LENGTH: 332
<212> TYPE: PRT
<213> ORGANISM: Artificial sequence
<220> FEATURE:
<223> OTHER INFORMATION: DSP105 var17 (var1 with substitution of CYS73
      in the PD1 domain to SER) without His tag

<400> SEQUENCE: 97

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Ser Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Gly Ser Ala Ala
    130                 135                 140

Ser Pro Arg Leu Arg Glu Gly Pro Glu Leu Ser Pro Asp Asp Pro Ala
145                 150                 155                 160

Gly Leu Leu Asp Leu Arg Gln Gly Met Phe Ala Gln Leu Val Ala Gln
                165                 170                 175

Asn Val Leu Leu Ile Asp Gly Pro Leu Ser Trp Tyr Ser Asp Pro Gly
            180                 185                 190

Leu Ala Gly Val Ser Leu Thr Gly Gly Leu Ser Tyr Lys Glu Asp Thr
        195                 200                 205

Lys Glu Leu Val Val Ala Lys Ala Gly Val Tyr Tyr Val Phe Phe Gln

```
                 210                 215                 220
Leu Glu Leu Arg Arg Val Val Ala Gly Glu Gly Ser Gly Ser Val Ser
225                 230                 235                 240

Leu Ala Leu His Leu Gln Pro Leu Arg Ser Ala Ala Gly Ala Ala Ala
            245                 250                 255

Leu Ala Leu Thr Val Asp Leu Pro Pro Ala Ser Ser Glu Ala Arg Asn
            260                 265                 270

Ser Ala Phe Gly Phe Gln Gly Arg Leu Leu His Leu Ser Ala Gly Gln
        275                 280                 285

Arg Leu Gly Val His Leu His Thr Glu Ala Arg Ala Arg His Ala Trp
290                 295                 300

Gln Leu Thr Gln Gly Ala Thr Val Leu Gly Leu Phe Arg Val Thr Pro
305                 310                 315                 320

Glu Ile Pro Ala Gly Leu Pro Ser Pro Arg Ser Glu
                325                 330
```

<210> SEQ ID NO 98
<211> LENGTH: 996
<212> TYPE: DNA
<213> ORGANISM: Artificial sequence
<220> FEATURE:
<223> OTHER INFORMATION: na sequence encoding SEQ ID NO: 97 996 bp

<400> SEQUENCE: 98

```
gactctccag acagaccttg aaccctcca accttctctc ccgctctgct ggtggttacc      60
gagggcgaca atgccacctt cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctctcggttc agagtgaccc agctgcctaa cggcagagac    240
ttccacatgt ccgtcgtgcg ggccagaaga aacgactctg gcacctatct gtgcggcgcc    300
atctctctgg ctcccaaggc tcagatcaaa gagtctctgc gggccgagct gagagtgaca    360
gaaagacgag ctgaggtgcc caccgctcat ccctcacctt ctccaagacc tgctggccag    420
ggatctgccg cttctcctag actgagagag ggccctgagc tgtctcctga tgatcctgct    480
ggactgctgg acctgagaca gggcatgttt gctcagctgg tggcccagaa cgtgctgctg    540
attgatggcc ctctgtcctg gtactctgat cctggattgg ctggcgtgtc cctgactggc    600
ggcctgtctt acaaagagga caccaaagaa ctggtggtcg ccaaggccgg cgtgtactac    660
gtgttctttc agctggaact gcggagagtg gtggctggcg aaggatctgg atctgtgtct    720
ctggccctgc atctgcagcc tctgagaagt gctgcaggcg ctgctgcact ggctctgaca    780
gttgatctgc ctcctgcctc ctccgaggcc agaaactccg cctttggctt ccaaggcaga    840
ctgctgcatc tgtctgccgg acagagactg ggagtgcacc tccatacaga ggccagagct    900
agacacgctt ggcagttgac acagggcgct acagtgctgg gcctgtttag agtgacacct    960
gagatcccag ccggcctgcc atctccaaga tctgaa                              996
```

<210> SEQ ID NO 99
<211> LENGTH: 338
<212> TYPE: PRT
<213> ORGANISM: Artificial sequence
<220> FEATURE:
<223> OTHER INFORMATION: DSP105 var17 (var1 with substitution of CYS73 in the PD1 domain to SER) with His tag

<400> SEQUENCE: 99

His His His His His His Asp Ser Pro Asp Arg Pro Trp Asn Pro Pro

```
1               5                  10                 15
Thr Phe Ser Pro Ala Leu Leu Val Val Thr Glu Gly Asp Asn Ala Thr
                20                 25                 30

Phe Thr Cys Ser Phe Ser Asn Thr Ser Glu Ser Phe Val Leu Asn Trp
                35                 40                 45

Tyr Arg Met Ser Pro Ser Asn Gln Thr Asp Lys Leu Ala Ala Phe Pro
    50                 55                 60

Glu Asp Arg Ser Gln Pro Gly Gln Asp Ser Arg Phe Arg Val Thr Gln
65                  70                 75                 80

Leu Pro Asn Gly Arg Asp Phe His Met Ser Val Arg Ala Arg
                85                 90                 95

Asn Asp Ser Gly Thr Tyr Leu Cys Gly Ala Ile Ser Leu Ala Pro Lys
                100                105                110

Ala Gln Ile Lys Glu Ser Leu Arg Ala Glu Leu Arg Val Thr Glu Arg
                115                120                125

Arg Ala Glu Val Pro Thr Ala His Pro Ser Pro Ser Pro Arg Pro Ala
130                 135                140

Gly Gln Gly Ser Ala Ala Ser Pro Arg Leu Arg Glu Gly Pro Glu Leu
145                 150                155                160

Ser Pro Asp Asp Pro Ala Gly Leu Leu Asp Leu Arg Gln Gly Met Phe
                165                170                175

Ala Gln Leu Val Ala Gln Asn Val Leu Leu Ile Asp Gly Pro Leu Ser
                180                185                190

Trp Tyr Ser Asp Pro Gly Leu Ala Gly Val Ser Leu Thr Gly Gly Leu
                195                200                205

Ser Tyr Lys Glu Asp Thr Lys Glu Leu Val Val Ala Lys Ala Gly Val
    210                215                220

Tyr Tyr Val Phe Phe Gln Leu Glu Leu Arg Arg Val Val Ala Gly Glu
225                 230                235                240

Gly Ser Gly Ser Val Ser Leu Ala Leu His Leu Gln Pro Leu Arg Ser
                245                250                255

Ala Ala Gly Ala Ala Ala Leu Ala Leu Thr Val Asp Leu Pro Pro Ala
                260                265                270

Ser Ser Glu Ala Arg Asn Ser Ala Phe Gly Phe Gln Gly Arg Leu Leu
    275                280                285

His Leu Ser Ala Gly Gln Arg Leu Gly Val His Leu His Thr Glu Ala
    290                295                300

Arg Ala Arg His Ala Trp Gln Leu Thr Gln Gly Ala Thr Val Leu Gly
305                 310                315                320

Leu Phe Arg Val Thr Pro Glu Ile Pro Ala Gly Leu Pro Ser Pro Arg
                325                330                335

Ser Glu

<210> SEQ ID NO 100
<211> LENGTH: 1014
<212> TYPE: DNA
<213> ORGANISM: Artificial sequence
<220> FEATURE:
<223> OTHER INFORMATION: na sequence encoding SEQ ID NO: 99 1014 bp

<400> SEQUENCE: 100
caccaccacc atcaccacga ctctccagac agaccttgga accctccaac cttctctccc      60
gctctgctgg tggttaccga gggcgacaat gccaccttca cctgttcctt cagcaacacc     120
tccgagtcct tcgtgctgaa ctggtacaga atgtccccta gcaaccagac cgacaagctg     180
```

```
gccgcctttc ctgaggacag atctcagcca ggccaggact ctcggttcag agtgacccag    240
ctgcctaacg gcagagactt ccacatgtcc gtcgtgcggg ccagaagaaa cgactctggc    300
acctatctgt gcggcgccat ctctctggct cccaaggctc agatcaaaga gtctctgcgg    360
gccgagctga gagtgacaga aagacgagct gaggtgccca ccgctcatcc ctcaccttct    420
ccaagacctg ctggccaggg atctgccgct tctcctagac tgagagaggg ccctgagctg    480
tctcctgatg atcctgctgg actgctggac ctgagacagg gcatgtttgc tcagctggtg    540
gcccagaacg tgctgctgat tgatggccct ctgtcctggt actctgatcc tggattggct    600
ggcgtgtccc tgactggcgg cctgtcttac aaagaggaca ccaaagaact ggtggtcgcc    660
aaggccggcg tgtactacgt gttctttcag ctggaactgc ggagagtggt ggctggcgaa    720
ggatctggat ctgtgtctct ggccctgcat ctgcagcctc tgagaagtgc tgcaggcgct    780
gctgcactgg ctctgacagt tgatctgcct cctgcctcct ccgaggccag aaactccgcc    840
tttggcttcc aaggcagact gctgcatctg tctgccggac agagactggg agtgcacctc    900
catacagagg ccagagctag acacgcttgg cagttgacac agggcgctac agtgctgggc    960
ctgtttagag tgacacctga gatcccagcc ggcctgccat ctccaagatc tgaa         1014
```

<210> SEQ ID NO 101
<211> LENGTH: 319
<212> TYPE: PRT
<213> ORGANISM: Artificial sequence
<220> FEATURE:
<223> OTHER INFORMATION: DSP105 var18

<400> SEQUENCE: 101

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Met Ser Pro Ser Asn Gln Thr Asp Lys Leu
        35                  40                  45

Ala Ala Phe Pro Glu Asp Arg Ser Gln Pro Gly Gln Asp Ser Arg Phe
    50                  55                  60

Arg Val Thr Gln Leu Pro Asn Gly Arg Asp Phe His Met Ser Val Val
65                  70                  75                  80

Arg Ala Arg Arg Asn Asp Ser Gly Thr Tyr Leu Cys Gly Ala Ile Ser
                85                  90                  95

Leu Ala Pro Lys Ala Gln Ile Lys Glu Ser Leu Arg Ala Glu Leu Arg
            100                 105                 110

Val Thr Glu Arg Arg Ala Glu Val Pro Thr Ala His Pro Ser Pro Gly
        115                 120                 125

Ser Ala Ala Ser Pro Arg Leu Arg Glu Gly Pro Glu Leu Ser Pro Asp
    130                 135                 140

Asp Pro Ala Gly Leu Leu Asp Leu Arg Gln Gly Met Phe Ala Gln Leu
145                 150                 155                 160

Val Ala Gln Asn Val Leu Leu Ile Asp Gly Pro Leu Ser Trp Tyr Ser
                165                 170                 175

Asp Pro Gly Leu Ala Gly Val Ser Leu Thr Gly Gly Leu Ser Tyr Lys
            180                 185                 190

Glu Asp Thr Lys Glu Leu Val Val Ala Lys Ala Gly Val Tyr Tyr Val
        195                 200                 205

Phe Phe Gln Leu Glu Leu Arg Arg Val Val Ala Gly Glu Gly Ser Gly
```

```
                210              215                  220
Ser Val Ser Leu Ala Leu His Leu Gln Pro Leu Arg Ser Ala Ala Gly
225                 230                 235                 240

Ala Ala Ala Leu Ala Leu Thr Val Asp Leu Pro Pro Ala Ser Ser Glu
                245                 250                 255

Ala Arg Asn Ser Ala Phe Gly Phe Gln Gly Arg Leu Leu His Leu Ser
            260                 265                 270

Ala Gly Gln Arg Leu Gly Val His Leu His Thr Glu Ala Arg Ala Arg
        275                 280                 285

His Ala Trp Gln Leu Thr Gln Gly Ala Thr Val Leu Gly Leu Phe Arg
    290                 295                 300

Val Thr Pro Glu Ile Pro Ala Gly Leu Pro Ser Pro Arg Ser Glu
305                 310                 315
```

<210> SEQ ID NO 102
<211> LENGTH: 957
<212> TYPE: DNA
<213> ORGANISM: Artificial sequence
<220> FEATURE:
<223> OTHER INFORMATION: na sequence encoding SEQ ID NO: 101 957 bp

<400> SEQUENCE: 102

```
tggaaccctc caaccttctc tcccgctctg ctggtggtta ccgagggcga caatgccacc    60
ttcacctgtt ccttcagcaa cacctccgag tccttcgtgc tgaactggta cagaatgtcc   120
cctagcaacc agaccgacaa gctggccgcc tttcctgagg acagatctca gccaggccag   180
gactctcggt tcagagtgac ccagctgcct aacggcagag acttccacat gtccgtcgtg   240
cgggccagaa gaaacgactc tggcacctat ctgtgcggcg ccatctctct ggctcccaag   300
gctcagatca aagagtctct gcgggccgag ctgagagtga cagaaagacg agctgaggtg   360
cccaccgctc atccctcacc tggatctgcc gcttctccta gactgagaga gggccctgag   420
ctgtctcctg atgatcctgc tggactgctg gacctgagac agggcatgtt tgctcagctg   480
gtggcccaga acgtgctgct gattgatggc cctctgtcct ggtactctga tcctggattg   540
gctgccgtgt ccctgactgg cggcctgtct tacaaagagg acaccaaaga actggtggtc   600
gccaaggccg gcgtgtacta cgtgttcttt cagctggaac tgcggagagt ggtggctggc   660
gaaggatctg atctgtgtc tctggccctg catctgcagc ctctgagaag tgctgcaggc   720
gctgctgcac tggctctgac agttgatctg cctcctgcct cctccgaggc cagaaactcc   780
gcctttggct tccaaggcag actgctgcat ctgtctgccg gacagagact gggagtgcac   840
ctccatacag aggccagagc tagacacgct tggcagttga cagggcgc tacagtgctg   900
ggcctgttta gagtgacacc tgagatccca gccggcctgc catctccaag atctgaa     957
```

<210> SEQ ID NO 103
<211> LENGTH: 326
<212> TYPE: PRT
<213> ORGANISM: Artificial sequence
<220> FEATURE:
<223> OTHER INFORMATION: DSP105 var19

<400> SEQUENCE: 103

```
Trp Asn Pro Pro Thr Phe Ser Pro Ala Leu Leu Val Val Thr Glu Gly
1               5                   10                  15

Asp Asn Ala Thr Phe Thr Cys Ser Phe Ser Asn Thr Ser Glu Ser Phe
            20                  25                  30

Val Leu Asn Trp Tyr Arg Met Ser Pro Ser Asn Gln Thr Asp Lys Leu
```

```
                35                  40                  45
Ala Ala Phe Pro Glu Asp Arg Ser Gln Pro Gly Gln Asp Ser Arg Phe
        50                  55                  60
Arg Val Thr Gln Leu Pro Asn Gly Arg Asp Phe His Met Ser Val Val
65                  70                  75                  80
Arg Ala Arg Arg Asn Asp Ser Gly Thr Tyr Leu Cys Gly Ala Ile Ser
                85                  90                  95
Leu Ala Pro Lys Ala Gln Ile Lys Glu Ser Leu Arg Ala Glu Leu Arg
            100                 105                 110
Val Thr Glu Arg Arg Ala Glu Val Pro Thr Ala His Pro Ser Pro Ser
        115                 120                 125
Pro Arg Pro Ala Gly Gln Gly Ser Ala Ala Ser Pro Arg Leu Arg Glu
    130                 135                 140
Gly Pro Glu Leu Ser Pro Asp Asp Pro Ala Gly Leu Leu Asp Leu Arg
145                 150                 155                 160
Gln Gly Met Phe Ala Gln Leu Val Ala Gln Asn Val Leu Leu Ile Asp
                165                 170                 175
Gly Pro Leu Ser Trp Tyr Ser Asp Pro Gly Leu Ala Gly Val Ser Leu
            180                 185                 190
Thr Gly Gly Leu Ser Tyr Lys Glu Asp Thr Lys Glu Leu Val Val Ala
        195                 200                 205
Lys Ala Gly Val Tyr Tyr Val Phe Phe Gln Leu Glu Leu Arg Arg Val
    210                 215                 220
Val Ala Gly Glu Gly Ser Gly Ser Val Ser Leu Ala Leu His Leu Gln
225                 230                 235                 240
Pro Leu Arg Ser Ala Ala Gly Ala Ala Ala Leu Ala Leu Thr Val Asp
                245                 250                 255
Leu Pro Pro Ala Ser Ser Glu Ala Arg Asn Ser Ala Phe Gly Phe Gln
            260                 265                 270
Gly Arg Leu Leu His Leu Ser Ala Gly Gln Arg Leu Gly Val His Leu
        275                 280                 285
His Thr Glu Ala Arg Ala Arg His Ala Trp Gln Leu Thr Gln Gly Ala
    290                 295                 300
Thr Val Leu Gly Leu Phe Arg Val Thr Pro Glu Ile Pro Ala Gly Leu
305                 310                 315                 320
Pro Ser Pro Arg Ser Glu
            325

<210> SEQ ID NO 104
<211> LENGTH: 978
<212> TYPE: DNA
<213> ORGANISM: Artificial sequence
<220> FEATURE:
<223> OTHER INFORMATION: na sequence encoding SEQ ID NO: 103 977 bp

<400> SEQUENCE: 104
tggaaccctc caaccttctc tcccgctctg ctggtggtta ccgagggcga caatgccacc      60
ttcacctgtt ccttcagcaa cacctccgag tccttcgtgc tgaactggta cagaatgtcc     120
cctagcaacc agaccgacaa gctggccgcc tttcctgagg acagatctca gccaggccag     180
gactctcggt tcagagtgac ccagctgcct aacggcagag acttccacat gtccgtcgtg     240
cgggccagaa gaaacgactc tggcacctat ctgtgcggcg ccatctctct ggctcccaag     300
gctcagatca agagtctctc gcgggccgag ctgagagtga cagaaagacg agctgaggtg     360
cccaccgctc atccctcacc ttctccaaga cctgctggcc agggatctgc cgcttctcct     420
```

```
agactgagag agggccctga gctgtctcct gatgatcctg ctggactgct ggacctgaga      480
cagggcatgt ttgctcagct ggtggcccag aacgtgctgc tgattgatgg ccctctgtcc      540
tggtactctg atcctggatt ggctggcgtg tccctgactg gcggcctgtc ttacaaagag      600
gacaccaaag aactggtggt cgccaaggcc ggcgtgtact acgtgttctt tcagctggaa      660
ctgcggagag tggtggctgg cgaaggatct ggatctgtgt ctctggccct gcatctgcag      720
cctctgagaa gtgctgcagg cgctgctgca ctggctctga cagttgatct gcctcctgcc      780
tcctccgagg ccagaaactc cgcctttggc ttccaaggca gactgctgca tctgtctgcc      840
ggacagagac tgggagtgca cctccataca gaggccagag ctagacacgc ttggcagttg      900
acacagggcg ctacagtgct gggcctgttt agagtgacac ctgagatccc agccggcctg      960
ccatctccaa gatctgaa                                                    978
```

<210> SEQ ID NO 105
<211> LENGTH: 325
<212> TYPE: PRT
<213> ORGANISM: Artificial sequence
<220> FEATURE:
<223> OTHER INFORMATION: DSP105 var20

<400> SEQUENCE: 105

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Ser Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Gly Ser Ala Ala Ser Pro Arg Leu Arg Glu Gly
    130                 135                 140

Pro Glu Leu Ser Pro Asp Asp Pro Ala Gly Leu Leu Asp Leu Arg Gln
145                 150                 155                 160

Gly Met Phe Ala Gln Leu Val Ala Gln Asn Val Leu Leu Ile Asp Gly
                165                 170                 175

Pro Leu Ser Trp Tyr Ser Asp Pro Gly Leu Ala Gly Val Ser Leu Thr
            180                 185                 190

Gly Gly Leu Ser Tyr Lys Glu Asp Thr Lys Glu Leu Val Val Ala Lys
        195                 200                 205

Ala Gly Val Tyr Tyr Val Phe Phe Gln Leu Glu Leu Arg Arg Val Val
    210                 215                 220

Ala Gly Glu Gly Ser Gly Ser Val Ser Leu Ala Leu His Leu Gln Pro
225                 230                 235                 240

Leu Arg Ser Ala Ala Gly Ala Ala Ala Leu Ala Leu Thr Val Asp Leu
                245                 250                 255
```

Pro Pro Ala Ser Ser Glu Ala Arg Asn Ser Ala Phe Gly Phe Gln Gly
            260                 265                 270

Arg Leu Leu His Leu Ser Ala Gly Gln Arg Leu Gly Val His Leu His
        275                 280                 285

Thr Glu Ala Arg Ala Arg His Ala Trp Gln Leu Thr Gln Gly Ala Thr
    290                 295                 300

Val Leu Gly Leu Phe Arg Val Thr Pro Glu Ile Pro Ala Gly Leu Pro
305                 310                 315                 320

Ser Pro Arg Ser Glu
            325

<210> SEQ ID NO 106
<211> LENGTH: 975
<212> TYPE: DNA
<213> ORGANISM: Artificial sequence
<220> FEATURE:
<223> OTHER INFORMATION: na sequence encoding SEQ ID NO: 105 1062 bp

<400> SEQUENCE: 106
gactctccag acagaccttg aaccctcca accttctctc ccgctctgct ggtggttacc      60
gagggcgaca atgccacctt cacctgttcc ttcagcaaca cctccgagtc cttcgtgctg     120
aactggtaca gaatgtcccc tagcaaccag accgacaagc tggccgcctt tcctgaggac     180
agatctcagc caggccagga ctctcggttc agagtgaccc agctgcctaa cggcagagac     240
ttccacatgt ccgtcgtgcg ggccagaaga aacgactctg caacctatct gtgcggcgcc     300
atctctctgg ctcccaaggc tcagatcaaa gagtctctgc gggccgagct gagagtgaca     360
gaaagacgag ctgaggtgcc caccgctcat ccctcacctg atctgccgc ttctcctaga      420
ctgagagagg gccctgagct gtctcctgat gatcctgctg gactgctgga cctgagacag     480
ggcatgtttg ctcagctggt ggcccagaac gtgctgctga ttgatggccc tctgtcctgg     540
tactctgatc ctggattggc tggcgtgtcc ctgactggcg gcctgtctta caaagaggac     600
accaaagaac tggtggtcgc caaggccggc gtgtactacg tgttctttca gctggaactg     660
cggagagtgg tggctggcga aggatctgga tctgtgtctc tggccctgca tctgcagcct     720
ctgagaagtg ctgcaggcgc tgctgcactg gctctgacag ttgatctgcc tcctgcctcc     780
tccgaggcca gaaactccgc ctttggcttc aaggcagac tgctgcatct gtctgccgga     840
cagagactgg gagtgcacct ccatacagag gccagagcta gacacgcttg gcagttgaca     900
cagggcgcta cagtgctggg cctgtttaga gtgacacctg agatcccagc cggcctgcca     960
tctccaagat ctgaa                                                      975

<210> SEQ ID NO 107
<211> LENGTH: 330
<212> TYPE: PRT
<213> ORGANISM: Artificial sequence
<220> FEATURE:
<223> OTHER INFORMATION: DSP105 var21

<400> SEQUENCE: 107

Asp Ser Pro Asp Arg Pro Trp Asn Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro

```
                    50                  55                  60
Gly Gln Asp Ser Arg Phe Arg Val Thr Gln Leu Pro Asn Gly Arg Asp
 65                      70                  75                  80

Phe His Met Ser Val Val Arg Ala Arg Arg Asn Asp Ser Gly Thr Tyr
                     85                  90                  95

Leu Cys Gly Ala Ile Ser Leu Ala Pro Lys Ala Gln Ile Lys Glu Ser
                100                 105                 110

Leu Arg Ala Glu Leu Arg Val Thr Glu Arg Arg Ala Glu Val Pro Thr
            115                 120                 125

Ala His Pro Ser Pro Ser Pro Arg Pro Ala Gly Ser Ala Ala Ser Pro
130                 135                 140

Arg Leu Arg Glu Gly Pro Glu Leu Ser Pro Asp Asp Pro Ala Gly Leu
145                 150                 155                 160

Leu Asp Leu Arg Gln Gly Met Phe Ala Gln Leu Val Ala Gln Asn Val
                165                 170                 175

Leu Leu Ile Asp Gly Pro Leu Ser Trp Tyr Ser Asp Pro Gly Leu Ala
                180                 185                 190

Gly Val Ser Leu Thr Gly Gly Leu Ser Tyr Lys Glu Asp Thr Lys Glu
            195                 200                 205

Leu Val Val Ala Lys Ala Gly Val Tyr Tyr Val Phe Phe Gln Leu Glu
210                 215                 220

Leu Arg Arg Val Val Ala Gly Glu Gly Ser Gly Ser Val Ser Leu Ala
225                 230                 235                 240

Leu His Leu Gln Pro Leu Arg Ser Ala Ala Gly Ala Ala Ala Leu Ala
                245                 250                 255

Leu Thr Val Asp Leu Pro Pro Ala Ser Ser Glu Ala Arg Asn Ser Ala
                260                 265                 270

Phe Gly Phe Gln Gly Arg Leu Leu His Leu Ser Ala Gly Gln Arg Leu
            275                 280                 285

Gly Val His Leu His Thr Glu Ala Arg Ala Arg His Ala Trp Gln Leu
290                 295                 300

Thr Gln Gly Ala Thr Val Leu Gly Leu Phe Arg Val Thr Pro Glu Ile
305                 310                 315                 320

Pro Ala Gly Leu Pro Ser Pro Arg Ser Glu
                325                 330

<210> SEQ ID NO 108
<211> LENGTH: 990
<212> TYPE: DNA
<213> ORGANISM: Artificial sequence
<220> FEATURE:
<223> OTHER INFORMATION: na sequence encoding SEQ ID NO: 107 1077 bp

<400> SEQUENCE: 108
gactctccag acagaccttg aaccctcca accttctctc ccgctctgct ggtggttacc      60
gagggcgaca atgccacctt cacctgttcc ttcagcaaca cctccgagtc cttcgtgctg     120
aactggtaca gaatgtcccc tagcaaccag accgacaagc tggccgcctt tcctgaggac     180
agatctcagc caggccagga ctctcggttc agagtgaccc agctgcctaa cggcagagac     240
ttccacatgt ccgtcgtgcg ggccagaaga aacgactctg gcacctatct gtgcggcgcc     300
atctctctgg ctcccaaggc tcagatcaaa gagtctctgc gggccgagct gagagtgaca     360
gaaagacgag ctgaggtgcc caccgctcat ccctcacctt ctccaagacc tgctggatct     420
gccgcttctc ctagactgag agagggccct gagctgtctc ctgatgatcc tgctggactg     480
```

```
ctggacctga  gacagggcat  gtttgctcag  ctggtggccc  agaacgtgct  gctgattgat      540
ggccctctgt  cctggtactc  tgatcctgga  ttggctggcg  tgtccctgac  tggcggcctg      600
tcttacaaag  aggacaccaa  agaactggtg  gtcgccaagg  ccggcgtgta  ctacgtgttc      660
tttcagctgg  aactgcggag  agtggtggct  ggcgaaggat  ctggatctgt  gtctctggcc      720
ctgcatctgc  agcctctgag  aagtgctgca  ggcgctgctg  cactggctct  gacagttgat      780
ctgcctcctg  cctcctccga  ggccagaaac  tccgcctttg  gcttccaagg  cagactgctg      840
catctgtctg  ccggacagag  actgggagtg  cacctccata  cagaggccag  agctagacac      900
gcttggcagt  tgacacaggg  cgctacagtg  ctgggcctgt  ttagagtgac  acctgagatc      960
ccagccggcc  tgccatctcc  aagatctgaa                                         990
```

<210> SEQ ID NO 109
<211> LENGTH: 362
<212> TYPE: PRT
<213> ORGANISM: Artificial sequence
<220> FEATURE:
<223> OTHER INFORMATION: DSP105 var22 362 aa with His tag

<400> SEQUENCE: 109

```
His His His His His His Pro Gly Trp Phe Leu Asp Ser Pro Asp Arg
1               5                   10                  15

Pro Trp Asn Pro Pro Thr Phe Ser Pro Ala Leu Leu Val Val Thr Glu
            20                  25                  30

Gly Asp Asn Ala Thr Phe Thr Cys Ser Phe Ser Asn Thr Ser Glu Ser
        35                  40                  45

Phe Val Leu Asn Trp Tyr Arg Met Ser Pro Ser Asn Gln Thr Asp Lys
    50                  55                  60

Leu Ala Ala Phe Pro Glu Asp Arg Ser Gln Pro Gly Gln Asp Ser Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Ala Gln Ile Lys Glu Ser Leu Arg Ala Glu Leu
        115                 120                 125

Arg Val Thr Glu Arg Arg Ala Glu Val Pro Thr Ala His Pro Ser Pro
    130                 135                 140

Ser Pro Arg Pro Ala Gly Gln Phe Gln Thr Leu Val Gly Ala Cys Pro
145                 150                 155                 160

Trp Ala Val Ser Gly Ala Arg Ala Ser Pro Gly Ser Ala Ala Ser Pro
                165                 170                 175

Arg Leu Arg Glu Gly Pro Glu Leu Ser Pro Asp Pro Ala Gly Leu
            180                 185                 190

Leu Asp Leu Arg Gln Gly Met Phe Ala Gln Leu Val Ala Gln Asn Val
        195                 200                 205

Leu Leu Ile Asp Gly Pro Leu Ser Trp Tyr Ser Asp Pro Gly Leu Ala
    210                 215                 220

Gly Val Ser Leu Thr Gly Gly Leu Ser Tyr Lys Glu Asp Thr Lys Glu
225                 230                 235                 240

Leu Val Val Ala Lys Ala Gly Val Tyr Tyr Val Phe Phe Gln Leu Glu
                245                 250                 255

Leu Arg Arg Val Val Ala Gly Glu Gly Ser Gly Ser Val Ser Leu Ala
            260                 265                 270
```

```
Leu His Leu Gln Pro Leu Arg Ser Ala Ala Gly Ala Ala Ala Leu Ala
            275                 280                 285
Leu Thr Val Asp Leu Pro Pro Ala Ser Ser Glu Ala Arg Asn Ser Ala
        290                 295                 300
Phe Gly Phe Gln Gly Arg Leu Leu His Leu Ser Ala Gly Gln Arg Leu
305                 310                 315                 320
Gly Val His Leu His Thr Glu Ala Arg Ala Arg His Ala Trp Gln Leu
                325                 330                 335
Thr Gln Gly Ala Thr Val Leu Gly Leu Phe Arg Val Thr Pro Glu Ile
            340                 345                 350
Pro Ala Gly Leu Pro Ser Pro Arg Ser Glu
            355                 360

<210> SEQ ID NO 110
<211> LENGTH: 1086
<212> TYPE: DNA
<213> ORGANISM: Artificial sequence
<220> FEATURE:
<223> OTHER INFORMATION: na sequence encoding SEQ ID NO: 109 1086 bp

<400> SEQUENCE: 110
caccatcatc accaccatcc tggctggttt ctggacagcc ccgacagacc ttggaaccct        60
cctacattca gccccgctct gctggtggtt accgagggcg ataatgccac cttcacctgt       120
agcttcagca caccagcga gagcttcgtg ctgaactggt acagaatgag ccccagcaac       180
cagaccgaca agctggccgc cttcctgag gatagatctc agcccggcca ggactctcgg       240
ttcagagtta cacagctgcc aacggccgg gacttccaca tgtctgtcgt ccgggccaga       300
agaaacgaca gcggcacata tctgtgcggc gccatttctc tggccccctaa ggctcagatc       360
aaagagagcc tgagagccga gctgagagtg acagaaagac gggccgaagt gcccacagct       420
cacccttcac cttctccaag acctgccggc cagtttcaga cactcgtggg agcttgtcct       480
tgggccgttt ctggcgctag agcctctcct ggatctgccg cttctcccag actgagagag       540
ggacctgagc tgagccctga tgatcctgct ggactgctgg atctgagaca gggcatgttt       600
gcccagctgg tggcccagaa tgtgctgctg attgatggcc ctctgtcctg gtacagcgat       660
cctggacttg ctggcgttag cctgactggc ggcctgagct acaaagagga caccaaagaa       720
ctggtggtgg ccaaggccgg cgtgtactac gtgttctttc agctggaact gcggagagtg       780
gtggccggcg aaggatctgg atctgtgtct ctggctctgc atctgcagcc tctgagatct       840
gctgctggtg ctgctgctct ggccctgaca gttgatctgc ctcctgcctc tagcgaggcc       900
agaaactccg cctttggctt ccaaggcaga ctgctgcacc tgagcgctgg acagagactg       960
ggagtccatc tgcacacaga agccagagct agacacgcct ggcagctgac acaaggcgct      1020
acagtgctgg gcctgttcag agtgaccct gagattccag ccggcctgcc atctcctaga      1080
tctgag                                                                1086

<210> SEQ ID NO 111
<211> LENGTH: 356
<212> TYPE: PRT
<213> ORGANISM: Artificial sequence
<220> FEATURE:
<223> OTHER INFORMATION: DSP105 var22 362 aa

<400> SEQUENCE: 111

Pro Gly Trp Phe Leu Asp Ser Pro Asp Arg Pro Trp Asn Pro Pro Thr
1               5                   10                  15
```

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
50                  55                  60

Asp Arg Ser Gln Pro Gly Gln Asp Ser Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Gly Ala Cys Pro Trp Ala Val Ser Gly Ala
145                 150                 155                 160

Arg Ala Ser Pro Gly Ser Ala Ala Ser Pro Arg Leu Arg Glu Gly Pro
                165                 170                 175

Glu Leu Ser Pro Asp Asp Pro Ala Gly Leu Leu Asp Leu Arg Gln Gly
            180                 185                 190

Met Phe Ala Gln Leu Val Ala Gln Asn Val Leu Leu Ile Asp Gly Pro
        195                 200                 205

Leu Ser Trp Tyr Ser Asp Pro Gly Leu Ala Gly Val Ser Leu Thr Gly
210                 215                 220

Gly Leu Ser Tyr Lys Glu Asp Thr Lys Glu Leu Val Val Ala Lys Ala
225                 230                 235                 240

Gly Val Tyr Tyr Val Phe Phe Gln Leu Glu Leu Arg Arg Val Val Ala
                245                 250                 255

Gly Glu Gly Ser Gly Ser Val Ser Leu Ala Leu His Leu Gln Pro Leu
            260                 265                 270

Arg Ser Ala Ala Gly Ala Ala Ala Leu Ala Leu Thr Val Asp Leu Pro
        275                 280                 285

Pro Ala Ser Ser Glu Ala Arg Asn Ser Ala Phe Gly Phe Gln Gly Arg
290                 295                 300

Leu Leu His Leu Ser Ala Gly Gln Arg Leu Gly Val His Leu His Thr
305                 310                 315                 320

Glu Ala Arg Ala Arg His Ala Trp Gln Leu Thr Gln Gly Ala Thr Val
                325                 330                 335

Leu Gly Leu Phe Arg Val Thr Pro Glu Ile Pro Ala Gly Leu Pro Ser
            340                 345                 350

Pro Arg Ser Glu
        355

<210> SEQ ID NO 112
<211> LENGTH: 1068
<212> TYPE: DNA
<213> ORGANISM: Artificial sequence
<220> FEATURE:
<223> OTHER INFORMATION: na sequence encoding SEQ ID NO: 111 1086 bp

<400> SEQUENCE: 112
cctggctggt ttctggacag ccccgacaga ccttggaacc ctcctacatt cagccccgct      60
ctgctggtgg ttaccgaggg cgataatgcc accttcacct gtagcttcag caacaccagc     120

```
gagagcttcg tgctgaactg gtacagaatg agccccagca accagaccga caagctggcc    180
gcctttcctg aggatagatc tcagcccggc caggactctc ggttcagagt tacacagctg    240
cccaacggcc gggacttcca catgtctgtc gtccgggcca agaaaacga cagcggcaca    300
tatctgtgcg gcgccatttc tctggcccct aaggctcaga tcaaagagag cctgagagcc    360
gagctgagag tgacagaaag acgggccgaa gtgcccacag ctcacccttc accttctcca    420
agacctgccg gccagtttca gacactcgtg ggagcttgtc cttgggccgt ttctggcgct    480
agagcctctc ctggatctgc cgcttctccc agactgagag agggacctga gctgagccct    540
gatgatcctg ctggactgct ggatctgaga cagggcatgt ttgcccagct ggtggcccag    600
aatgtgctgc tgattgatgg ccctctgtcc tggtacagcg atcctggact tgctggcgtt    660
agcctgactg gcggcctgag ctacaaagag gacaccaaag aactggtggt ggccaaggcc    720
ggcgtgtact acgtgttctt tcagctggaa ctgcggagag tggtggccgg cgaaggatct    780
ggatctgtgt ctctggctct gcatctgcag cctctgagat ctgctgctgg tgctgctgct    840
ctggccctga cagttgatct gcctcctgcc tctagcgagg ccagaaactc cgcctttggc    900
ttccaaggca gactgctgca cctgagcgct ggacagagac tgggagtcca tctgcacaca    960
gaagccagag ctagacacgc ctggcagctg acacaaggcg ctacagtgct gggcctgttc   1020
agagtgaccc ctgagattcc agccggcctg ccatctccta gatctgag                1068

<210> SEQ ID NO 113
<211> LENGTH: 330
<212> TYPE: PRT
<213> ORGANISM: Artificial sequence
<220> FEATURE:
<223> OTHER INFORMATION: DSP105 var23 amino acid sequence

<400> SEQUENCE: 113

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Ser Ala Ala Ser Pro
    130                 135                 140

Arg Leu Arg Glu Gly Pro Glu Leu Ser Pro Asp Asp Pro Ala Gly Leu
145                 150                 155                 160

Leu Asp Leu Arg Gln Gly Met Phe Ala Gln Leu Val Ala Gln Asn Val
                165                 170                 175

Leu Leu Ile Asp Gly Pro Leu Ser Trp Tyr Ser Asp Pro Gly Leu Ala
            180                 185                 190
```

```
Gly Val Ser Leu Thr Gly Gly Leu Ser Tyr Lys Glu Asp Thr Lys Glu
            195                 200                 205

Leu Val Val Ala Lys Ala Gly Val Tyr Tyr Val Phe Phe Gln Leu Glu
        210                 215                 220

Leu Arg Arg Val Val Ala Gly Glu Gly Ser Gly Ser Val Ser Leu Ala
225                 230                 235                 240

Leu His Leu Gln Pro Leu Arg Ser Ala Ala Gly Ala Ala Leu Ala
            245                 250                 255

Leu Thr Val Asp Leu Pro Pro Ala Ser Ser Glu Ala Arg Asn Ser Ala
        260                 265                 270

Phe Gly Phe Gln Gly Arg Leu Leu His Leu Ser Ala Gly Gln Arg Leu
            275                 280                 285

Gly Val His Leu His Thr Glu Ala Arg Ala Arg His Ala Trp Gln Leu
        290                 295                 300

Thr Gln Gly Ala Thr Val Leu Gly Leu Phe Arg Val Thr Pro Glu Ile
305                 310                 315                 320

Pro Ala Gly Leu Pro Ser Pro Arg Ser Glu
            325                 330
```

<210> SEQ ID NO 114
<211> LENGTH: 990
<212> TYPE: DNA
<213> ORGANISM: Artificial sequence
<220> FEATURE:
<223> OTHER INFORMATION: DSP105 var23 nucleic acid sequence

<400> SEQUENCE: 114

```
gactctccag acagaccttg aaccctcca accttctctc ccgctctgct ggtggttacc      60
gagggcgaca atgccacctt cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctgtcggttc agagtgaccc agctgcctaa cggcagagac    240
ttccacatgt ccgtcgtgcg ggccagaaga aacgactctg gcacctatct gtgcggcgcc    300
atctctctgg ctcccaaggc tcagatcaaa gagtctctgc gggccgagct gagagtgaca    360
gaaagacgag ctgaggtgcc caccgctcat ccctcacctt ctccaagacc tgctggatct    420
gccgcttctc ctagactgag agagggccct gagctgtctc ctgatgatcc tgctggactg    480
ctggacctga cagggcat gttttgctcag ctggtggccc agaacgtgct gctgattgat    540
ggccctctgt cctggtactc tgatcctgga ttggctggcg tgtccctgac tgcggcctg    600
tcttacaaag aggacaccaa agaactggtg gtcgccaagg ccggcgtgta ctacgtgttc    660
tttcagctgg aactgcggag agtggtggct ggcgaaggat ctggatctgt gtctctggcc    720
ctgcatctgc agcctctgag aagtgctgca ggcgctgctg cactggctct gacagttgat    780
ctgcctcctg cctcctccga ggccagaaac tccgcctttg gcttccaagg cagactgctg    840
catctgtctg ccggacagag actgggagtg cacctccata cagaggccag agctagacac    900
gcttggcagt tgacacaggg cgctacagtg ctgggcctgt ttagagtgac acctgagatc    960
ccagccggcc tgccatctcc aagatctgaa                                     990
```

<210> SEQ ID NO 115
<211> LENGTH: 136
<212> TYPE: PRT
<213> ORGANISM: Artificial sequence
<220> FEATURE:
<223> OTHER INFORMATION: PD1 variant amino acid sequence

<400> SEQUENCE: 115

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
                100                 105                 110

Leu Arg Ala Glu Leu Arg Val Thr Glu Arg Arg Ala Glu Val Pro Thr
            115                 120                 125

Ala His Pro Ser Pro Ser Pro Arg
        130                 135

<210> SEQ ID NO 116
<211> LENGTH: 408
<212> TYPE: DNA
<213> ORGANISM: Artificial sequence
<220> FEATURE:
<223> OTHER INFORMATION: PD1 variant nucleic acid sequence

<400> SEQUENCE: 116
gactctccag acagaccttg aaccctcca accttctctc ccgctctgct ggtggttacc      60
gagggcgaca atgccacctt cacctgttcc ttcagcaaca cctccgagtc cttcgtgctg     120
aactggtaca gaatgtcccc tagcaaccag accgacaagc tggccgcctt tcctgaggac     180
agatctcagc caggccagga ctgtcggttc agagttaccc agctgcctaa cggccgggac     240
ttccacatgt ctgttgtgcg ggccagacgg aacgactctg gcacatatct gtgcggcgcc     300
atctctctgg ctcccaaggc tcagatcaaa gagtctctgc gggccgagct gagagtgaca     360
gaaagacgag ctgaggtgcc caccgctcat ccctcacctt ctccaaga                  408

<210> SEQ ID NO 117
<211> LENGTH: 145
<212> TYPE: PRT
<213> ORGANISM: Artificial sequence
<220> FEATURE:
<223> OTHER INFORMATION: PD1 variant amino acid sequence

<400> SEQUENCE: 117

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn

```
                    85                  90                  95
Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln
145

<210> SEQ ID NO 118
<211> LENGTH: 435
<212> TYPE: DNA
<213> ORGANISM: Artificial sequence
<220> FEATURE:
<223> OTHER INFORMATION: PD1 variant nucleic acid sequence

<400> SEQUENCE: 118
cccggctggt ttctggactc tccagacaga ccttggaacc ctccaacctt ctctcccgct      60
ctgctggtgg ttaccgaggg cgacaatgcc accttcacct gttccttcag caacacctcc     120
gagtccttcg tgctgaactg gtacagaatg tcccctagca accagaccga caagctggcc     180
gcctttcctg aggacagatc tcagccaggc caggactgtc ggttcagagt acccagctg      240 cctaacggcc gggacttcca catgtctgtt gtgcgggcca gacggaacga ctctggcaca     300
tatctgtgcg gcgccatctc tctggctccc aaggctcaga tcaaagagtc tctgcgggcc     360
gagctgagag tgacagaaag acgagctgag gtgcccaccg ctcatccctc accttctcca     420
agacctgctg gccag                                                       435

<210> SEQ ID NO 119
<211> LENGTH: 143
<212> TYPE: PRT
<213> ORGANISM: Artificial sequence
<220> FEATURE:
<223> OTHER INFORMATION: PD1 variant amino acid sequence

<400> SEQUENCE: 119

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala
    130                 135                 140

<210> SEQ ID NO 120
```

```
<211> LENGTH: 429
<212> TYPE: DNA
<213> ORGANISM: Artificial sequence
<220> FEATURE:
<223> OTHER INFORMATION: PD1 variant nucleic acid sequence

<400> SEQUENCE: 120
cccggctggt ttctggactc tccagacaga ccttggaacc ctccaacctt ctctcccgct      60
ctgctggtgg ttaccgaggg cgacaatgcc accttcacct gttccttcag caacaccctc     120
gagtccttcg tgctgaactg gtacagaatg tccctagca accagaccga caagctggcc      180
gcctttcctg aggacagatc tcagccaggc caggactgtc ggttcagagt tacccagctg     240
cctaacggcc gggacttcca catgtctgtt gtgcgggcca gacggaacga ctctggcaca     300
tatctgtgcg cgccatctc tctggctccc aaggctcaga tcaaagagtc tctgcgggcc      360
gagctgagag tgacagaaag acgagctgag gtgcccaccg ctcatccctc accttctcca     420
agacctgct                                                             429

<210> SEQ ID NO 121
<211> LENGTH: 14
<212> TYPE: PRT
<213> ORGANISM: Artificial sequence
<220> FEATURE:
<223> OTHER INFORMATION: linker amino acid sequence

<400> SEQUENCE: 121

Gly Gly Gly Gly Ser Gly Gly Gly Ser Gly Gly Gly Gly
1               5                   10

<210> SEQ ID NO 122
<211> LENGTH: 9
<212> TYPE: PRT
<213> ORGANISM: Artificial sequence
<220> FEATURE:
<223> OTHER INFORMATION: linker amino acid sequence

<400> SEQUENCE: 122

Gly Gly Gly Gly Ser Gly Gly Gly Gly
1               5

<210> SEQ ID NO 123
<211> LENGTH: 184
<212> TYPE: PRT
<213> ORGANISM: Artificial sequence
<220> FEATURE:
<223> OTHER INFORMATION: 4-1BBL variant amino acid sequence

<400> SEQUENCE: 123

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
                20                  25                  30

Ile Asp Gly Pro Leu Ser Trp Tyr Ser Asp Pro Gly Leu Ala Gly Val
            35                  40                  45

Ser Leu Thr Gly Gly Leu Ser Tyr Lys Glu Asp Thr Lys Glu Leu Val
        50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
```

```
                100                 105                 110
Val Asp Leu Pro Pro Ala Ser Ser Glu Ala Arg Asn Ser Ala Phe Gly
            115                 120                 125

Phe Gln Gly Arg Leu Leu His Leu Ser Ala Gly Gln Arg Leu Gly Val
        130                 135                 140

His Leu His Thr Glu Ala Arg Ala Arg His Ala Trp Gln Leu Thr Gln
145                 150                 155                 160

Gly Ala Thr Val Leu Gly Leu Phe Arg Val Thr Pro Glu Ile Pro Ala
                165                 170                 175

Gly Leu Pro Ser Pro Arg Ser Glu
            180

<210> SEQ ID NO 124
<211> LENGTH: 552
<212> TYPE: DNA
<213> ORGANISM: Artificial sequence
<220> FEATURE:
<223> OTHER INFORMATION: 4-1BBL variant nucleic acid sequence

<400> SEQUENCE: 124
agagagggcc ctgagctgtc tcctgatgat cctgctggac tgctggacct gagacagggc     60
atgtttgctc agctggtggc ccagaacgtg ctgctgattg atggccctct gtcctggtac    120
tctgatcctg gattggctgg cgtgtccctg actggcggcc tgtcttacaa agaggacacc    180
aaagaactgg tggtcgccaa ggccggcgtg tactacgtgt ctttcagct ggaactgcgg     240
agagtggtgg ctggcgaagg atctggatct gtgtctctgg ccctgcatct gcagcctctg    300
agaagtgctg caggcgctgc tgcactggct ctgacagttg atctgcctcc tgcctcctcc    360
gaggccagaa actccgcctt tggcttccaa ggcagactgc tgcatctgtc tgccggacag    420
agactgggag tgcacctcca tacagaggcc agagctagac acgcttggca gttgacacag    480
ggcgctacag tgctgggcct gtttagagtg cacctgagaa tcccagccgg cctgccatct    540
ccaagatctg aa                                                        552

<210> SEQ ID NO 125
<211> LENGTH: 182
<212> TYPE: PRT
<213> ORGANISM: Artificial sequence
<220> FEATURE:
<223> OTHER INFORMATION: 4-1BBL variant amino acid sequence

<400> SEQUENCE: 125

Gly Pro Glu Leu Ser Pro Asp Asp Pro Ala Gly Leu Leu Asp Leu Arg
1               5                   10                  15

Gln Gly Met Phe Ala Gln Leu Val Ala Gln Asn Val Leu Leu Ile Asp
            20                  25                  30

Gly Pro Leu Ser Trp Tyr Ser Asp Pro Gly Leu Ala Gly Val Ser Leu
        35                  40                  45

Thr Gly Gly Leu Ser Tyr Lys Glu Asp Thr Lys Glu Leu Val Val Ala
    50                  55                  60

Lys Ala Gly Val Tyr Tyr Val Phe Phe Gln Leu Glu Leu Arg Arg Val
65                  70                  75                  80

Val Ala Gly Glu Gly Ser Gly Ser Val Ser Leu Ala Leu His Leu Gln
                85                  90                  95

Pro Leu Arg Ser Ala Ala Gly Ala Ala Ala Leu Ala Leu Thr Val Asp
            100                 105                 110

Leu Pro Pro Ala Ser Ser Glu Ala Arg Asn Ser Ala Phe Gly Phe Gln
```

```
                115                 120                 125
Gly Arg Leu Leu His Leu Ser Ala Gly Gln Arg Leu Gly Val His Leu
        130                 135                 140

His Thr Glu Ala Arg Ala Arg His Ala Trp Gln Leu Thr Gln Gly Ala
145                 150                 155                 160

Thr Val Leu Gly Leu Phe Arg Val Thr Pro Glu Ile Pro Ala Gly Leu
                165                 170                 175

Pro Ser Pro Arg Ser Glu
            180

<210> SEQ ID NO 126
<211> LENGTH: 546
<212> TYPE: DNA
<213> ORGANISM: Artificial sequence
<220> FEATURE:
<223> OTHER INFORMATION: 4-1BBL variant nucleic acid sequence

<400> SEQUENCE: 126
ggccctgagc tgtctcctga tgatcctgct ggactgctgg acctgagaca gggcatgttt      60
gctcagctgg tggcccagaa cgtgctgctg attgatggcc ctctgtcctg gtactctgat     120
cctggattgg ctggcgtgtc cctgactggc ggcctgtctt acaaagagga caccaaagaa     180
ctggtggtcg ccaaggccgg cgtgtactac gtgttctttc agctggaact gcggagagtg     240
gtggctggcg aaggatctgg atctgtgtct ctggccctgc atctgcagcc tctgagaagt     300
gctgcaggcg ctgctgcact ggctctgaca gttgatctgc ctcctgcctc ctccgaggcc     360
agaaactccg cctttggctt ccaaggcaga ctgctgcatc tgtctgccgg acagagactg     420
ggagtgcacc tccatacaga ggccagagct agacacgctt ggcagttgac acaggcgct      480 acagtgctgg gcctgtttag agtgacacct gagatcccag ccggcctgcc atctccaaga     540
tctgaa                                                                546

<210> SEQ ID NO 127
<211> LENGTH: 183
<212> TYPE: PRT
<213> ORGANISM: Artificial sequence
<220> FEATURE:
<223> OTHER INFORMATION: 4-1BBL variant amino acid sequence

<400> SEQUENCE: 127

Ser Ala Ala Ser Pro Arg Leu Arg Glu Gly Pro Glu Leu Ser Pro Asp
1               5                   10                  15

Asp Pro Ala Gly Leu Leu Asp Leu Arg Gln Gly Met Phe Ala Gln Leu
            20                  25                  30

Val Ala Gln Asn Val Leu Leu Ile Asp Gly Pro Leu Ser Trp Tyr Ser
        35                  40                  45

Asp Pro Gly Leu Ala Gly Val Ser Leu Thr Gly Gly Leu Ser Tyr Lys
    50                  55                  60

Glu Asp Thr Lys Glu Leu Val Val Ala Lys Ala Gly Val Tyr Tyr Val
65                  70                  75                  80

Phe Phe Gln Leu Glu Leu Arg Arg Val Val Ala Gly Glu Gly Ser Gly
                85                  90                  95

Ser Val Ser Leu Ala Leu His Leu Gln Pro Leu Arg Ser Ala Ala Gly
            100                 105                 110

Ala Ala Ala Leu Ala Leu Thr Val Asp Leu Pro Pro Ala Ser Ser Glu
        115                 120                 125

Ala Arg Asn Ser Ala Phe Gly Phe Gln Gly Arg Leu Leu His Leu Ser
```

```
                    130                 135                 140

Ala Gly Gln Arg Leu Gly Val His Leu His Thr Glu Ala Arg Ala Arg
145                 150                 155                 160

His Ala Trp Gln Leu Thr Gln Gly Ala Thr Val Leu Gly Leu Phe Arg
                165                 170                 175

Val Thr Pro Glu Ile Pro Ala
            180

<210> SEQ ID NO 128
<211> LENGTH: 551
<212> TYPE: DNA
<213> ORGANISM: Artificial sequence
<220> FEATURE:
<223> OTHER INFORMATION: 4-1BBL variant nucleic acid sequence

<400> SEQUENCE: 128
gatctgccgc ttctcctaga ctgagagagg gccctgagct gtctcctgat gatcctgctg      60
gactgctgga cctgagacag gcatgtttg ctcagctggt ggcccagaac gtgctgctga     120
ttgatggccc tctgtcctgg tactctgatc ctggattggc tggcgtgtcc ctgactggcg     180
gcctgtctta caaagaggac accaaagaac tggtggtcgc caaggccggc gtgtactacg     240
tgttctttca gctggaactg cggagagtgg tggctggcga aggatctgga tctgtgtctc     300
tggccctgca tctgcagcct ctgagaagtg ctgcaggcgc tgctgcactg gctctgacag     360
ttgatctgcc tcctgcctcc tccgaggcca gaaactccgc ctttggcttc caaggcagac     420
tgctgcatct gtctgccgga cagagactgg gagtgcacct ccatacagag gccagagcta     480
gacacgcttg gcagttgaca cagggcgcta cagtgctggg cctgtttaga gtgacacctg     540
agatcccagc c                                                          551

<210> SEQ ID NO 129
<211> LENGTH: 176
<212> TYPE: PRT
<213> ORGANISM: Artificial sequence
<220> FEATURE:
<223> OTHER INFORMATION: 4-1BBL variant amino acid sequence

<400> SEQUENCE: 129

Arg Glu Gly Pro Glu Leu Ser Pro Asp Asp Pro Ala Gly Leu Leu Asp
1               5                   10                  15

Leu Arg Gln Gly Met Phe Ala Gln Leu Val Ala Gln Asn Val Leu Leu
                20                  25                  30

Ile Asp Gly Pro Leu Ser Trp Tyr Ser Asp Pro Gly Leu Ala Gly Val
            35                  40                  45

Ser Leu Thr Gly Gly Leu Ser Tyr Lys Glu Asp Thr Lys Glu Leu Val
        50                  55                  60

Val Ala Lys Ala Gly Val Tyr Tyr Val Phe Phe Gln Leu Glu Leu Arg
65                  70                  75                  80

Arg Val Val Ala Gly Glu Gly Ser Gly Ser Val Ser Leu Ala Leu His
                85                  90                  95

Leu Gln Pro Leu Arg Ser Ala Ala Gly Ala Ala Ala Leu Ala Leu Thr
            100                 105                 110

Val Asp Leu Pro Pro Ala Ser Ser Glu Ala Arg Asn Ser Ala Phe Gly
        115                 120                 125

Phe Gln Gly Arg Leu Leu His Leu Ser Ala Gly Gln Arg Leu Gly Val
    130                 135                 140

His Leu His Thr Glu Ala Arg Ala Arg His Ala Trp Gln Leu Thr Gln
```

```
145                 150                 155                 160
Gly Ala Thr Val Leu Gly Leu Phe Arg Val Thr Pro Glu Ile Pro Ala
                165                 170                 175
```

<210> SEQ ID NO 130
<211> LENGTH: 528
<212> TYPE: DNA
<213> ORGANISM: Artificial sequence
<220> FEATURE:
<223> OTHER INFORMATION: 4-1BBL variant nucleic acid sequence

<400> SEQUENCE: 130

```
agagagggcc ctgagctgtc tcctgatgat cctgctggac tgctggacct gagacagggc    60
atgtttgctc agctggtggc ccagaacgtg ctgctgattg atggccctct gtcctggtac   120
tctgatcctg gattggctgg cgtgtccctg actggcggcc tgtcttacaa agaggacacc   180
aaagaactgg tggtcgccaa ggccggcgtg tactacgtgt ctttcagct ggaactgcgg   240
agagtggtgg ctggcgaagg atctggatct gtgtctctgg ccctgcatct gcagcctctg   300
agaagtgctg caggcgctgc tgcactggct ctgacagttg atctgcctcc tgcctcctcc   360
gaggccagaa actccgcctt tggcttccaa ggcagactgc tgcatctgtc tgccggacag   420
agactgggag tgcacctcca tacagaggcc agagctagac acgcttggca gttgacacag   480
ggcgctacag tgctgggcct gtttagagtg acacctgaga tcccagcc              528
```

<210> SEQ ID NO 131
<211> LENGTH: 601
<212> TYPE: PRT
<213> ORGANISM: Artificial sequence
<220> FEATURE:
<223> OTHER INFORMATION: sc3x4-1BBL -14-0 amino acis sequence

<400> SEQUENCE: 131

```
Ser Ala Ala Ser Pro Arg Leu Arg Glu Gly Pro Glu Leu Ser Pro Asp
1               5                  10                  15
Asp Pro Ala Gly Leu Leu Asp Leu Arg Gln Gly Met Phe Ala Gln Leu
            20                  25                  30
Val Ala Gln Asn Val Leu Leu Ile Asp Gly Pro Leu Ser Trp Tyr Ser
        35                  40                  45
Asp Pro Gly Leu Ala Gly Val Ser Leu Thr Gly Gly Leu Ser Tyr Lys
    50                  55                  60
Glu Asp Thr Lys Glu Leu Val Val Ala Lys Ala Gly Val Tyr Tyr Val
65                  70                  75                  80
Phe Phe Gln Leu Glu Leu Arg Arg Val Val Ala Gly Glu Gly Ser Gly
                85                  90                  95
Ser Val Ser Leu Ala Leu His Leu Gln Pro Leu Arg Ser Ala Ala Gly
            100                 105                 110
Ala Ala Ala Leu Ala Leu Thr Val Asp Leu Pro Pro Ala Ser Ser Glu
        115                 120                 125
Ala Arg Asn Ser Ala Phe Gly Phe Gln Gly Arg Leu Leu His Leu Ser
    130                 135                 140
Ala Gly Gln Arg Leu Gly Val His Leu His Thr Glu Ala Arg Ala Arg
145                 150                 155                 160
His Ala Trp Gln Leu Thr Gln Gly Ala Thr Val Leu Gly Leu Phe Arg
                165                 170                 175
Val Thr Pro Glu Ile Pro Ala Gly Leu Pro Ser Pro Arg Ser Glu Gly
            180                 185                 190
```

```
Gly Gly Gly Ser Gly Gly Gly Ser Gly Gly Gly Ser Ala Ala
        195             200             205
Ser Pro Arg Leu Arg Glu Gly Pro Glu Leu Ser Pro Asp Asp Pro Ala
210                 215                 220
Gly Leu Leu Asp Leu Arg Gln Gly Met Phe Ala Gln Leu Val Ala Gln
225                 230                 235                 240
Asn Val Leu Leu Ile Asp Gly Pro Leu Ser Trp Tyr Ser Asp Pro Gly
            245                 250                 255
Leu Ala Gly Val Ser Leu Thr Gly Gly Leu Ser Tyr Lys Glu Asp Thr
                260                 265                 270
Lys Glu Leu Val Val Ala Lys Ala Gly Val Tyr Tyr Val Phe Phe Gln
    275                 280                 285
Leu Glu Leu Arg Arg Val Val Ala Gly Glu Gly Ser Gly Ser Val Ser
    290                 295                 300
Leu Ala Leu His Leu Gln Pro Leu Arg Ser Ala Ala Gly Ala Ala Ala
305                 310                 315                 320
Leu Ala Leu Thr Val Asp Leu Pro Pro Ala Ser Ser Glu Ala Arg Asn
                325                 330                 335
Ser Ala Phe Gly Phe Gln Gly Arg Leu Leu His Leu Ser Ala Gly Gln
            340                 345                 350
Arg Leu Gly Val His Leu His Thr Glu Ala Arg Ala Arg His Ala Trp
        355                 360                 365
Gln Leu Thr Gln Gly Ala Thr Val Leu Gly Leu Phe Arg Val Thr Pro
    370                 375                 380
Glu Ile Pro Ala Gly Leu Pro Ser Pro Arg Ser Glu Gly Gly Gly Gly
385                 390                 395                 400
Ser Gly Gly Gly Ser Gly Gly Gly Ser Ala Ala Ser Pro Arg
            405                 410                 415
Leu Arg Glu Gly Pro Glu Leu Ser Pro Asp Asp Pro Ala Gly Leu Leu
                420                 425                 430
Asp Leu Arg Gln Gly Met Phe Ala Gln Leu Val Ala Gln Asn Val Leu
            435                 440                 445
Leu Ile Asp Gly Pro Leu Ser Trp Tyr Ser Asp Pro Gly Leu Ala Gly
450                 455                 460
Val Ser Leu Thr Gly Gly Leu Ser Tyr Lys Glu Asp Thr Lys Glu Leu
465                 470                 475                 480
Val Val Ala Lys Ala Gly Val Tyr Tyr Val Phe Phe Gln Leu Glu Leu
                485                 490                 495
Arg Arg Val Val Ala Gly Glu Gly Ser Gly Ser Val Ser Leu Ala Leu
            500                 505                 510
His Leu Gln Pro Leu Arg Ser Ala Ala Gly Ala Ala Ala Leu Ala Leu
        515                 520                 525
Thr Val Asp Leu Pro Pro Ala Ser Ser Glu Ala Arg Asn Ser Ala Phe
    530                 535                 540
Gly Phe Gln Gly Arg Leu Leu His Leu Ser Ala Gly Gln Arg Leu Gly
545                 550                 555                 560
Val His Leu His Thr Glu Ala Arg Ala Arg His Ala Trp Gln Leu Thr
                565                 570                 575
Gln Gly Ala Thr Val Leu Gly Leu Phe Arg Val Thr Pro Glu Ile Pro
            580                 585                 590
Ala Gly Leu Pro Ser Pro Arg Ser Glu
        595                 600
```

<210> SEQ ID NO 132
<211> LENGTH: 1803
<212> TYPE: DNA
<213> ORGANISM: Artificial sequence
<220> FEATURE:
<223> OTHER INFORMATION: sc3x4-1BBL -14-0 nucleic acis sequence

<400> SEQUENCE: 132

```
tctgccgcca gccctaggct gcgcgaggga cccgagctga gcccagacga tcccgccggc      60
ctgctggacc tgaggcaggg aatgttcgca cagctggtgg cccagaacgt gctgctgatc     120
gacggccctc tgtcctggta ctctgatcca ggcctggccg gcgtgtccct gacaggaggc     180
ctgtcttata aggaggatac caaggagctg gtggtggcaa aggcaggcgt gtactacgtg     240
ttcttccagc tggagctgag gagagtggtg gcaggagagg gcagcggctc cgtgtctctg     300
gccctgcacc tccagcctct gcggagcgcc gccggcgccg ccgccctggc cctgaccgtg     360
gatctgcctc cagccagctc cgaggccagg aatagcgcct tcggctttca gggccgcctg     420
ctgcacctgt ccgccggcca gcggctggga gtgcacctgc acacagaggc cagagcccgg     480
cacgcatggc agctgacaca gggagcaacc gtgctgggcc tgttccgcgt gacccctgag     540
atcccagccg gcctgccaag ccccccggtcc gagggcggcg gcggctctgg cggaggaggc     600
agcggaggcg gcggctctgc cgccagcccc aggctgcgcg agggacccga gctgtcccca     660
gacgatcctg ccgcctgct ggacctgcgc cagggaatgt tgcccagct ggtggctcaa     720
aacgtgctgt taatcgacgg ccctctgagc tggtactctg atcctggcct ggccggcgtg     780
agcctgaccg gcggcctgtc ctacaaagag gatactaaag agctggtggt cgccaaagcc     840
ggcgtgtact acgtgttctt ccaactggag ctgaggaggg tcgtcgccgg cgaaggcagc     900
ggctccgtgt ctctggccct gcacctccag ccgctgagga gcgccgccgg cgccgccgcc     960
ctggccctga cggtggacct gccacctgcc tctagcgagg caagaaattc tgccttcggc    1020
ttccagggca ggctgctgca cctgagcgcc ggccagcgcc tgggcgtcca cctgcatacc    1080
gaagccagag cccggcatgc ctggcagctg acccagggcg ccaccgtgct gggcctgttc    1140
agagtgaccc cagagatccc cgccggcctg cctagcccaa ggtccgaagg cggcggcggc    1200
tccggcggcg gaggctctgg aggaggggc tctgccgcca gccaaggct gcgcgaggga    1260
cccgagctgt cgcctgacga tccagccggc ctgctggacc tgcgtcaggg catgttcgcc    1320
cagctggtgg ctcagaacgt gctgttaatc gacggcccac tgtcttggta ttctgatccc    1380
ggcctggccg gcgtgtctct gacaggaggc ctgagctaca agaggatac aaaagagctg    1440
gtggtcgcta agctggcgt gtactacgtg ttcttccaac tggagctgcg cagggtcgtc    1500
gccggcgagg gcagcggctc cgtgtctctg gccctgcacc tccagccatt acggagcgcc    1560
gccggcgccg ccgccctggc cctgactgtg gacctgccac cagcctcctc tgaggcacgg    1620
aacagcgcct tcggcttcca aggcagactg ctgcacctgt ctgccggcca gaggctgggc    1680
gtccacctgc acaccgaagc cagagcccgg cacgcctggc agctgactca gggcgctacc    1740
gtgctgggcc tgttccgcgt aaccccagag atccctgccg gcctgccaag ccctcggtcc    1800
gag                                                                 1803
```

<210> SEQ ID NO 133
<211> LENGTH: 321
<212> TYPE: PRT
<213> ORGANISM: Artificial sequence
<220> FEATURE:
<223> OTHER INFORMATION: DSP105 variant amino acid sequence

<400> SEQUENCE: 133

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
                20                  25                  30

Asn Thr Ser Glu Ser Phe Val Leu Asn Trp Tyr Arg Met Ser Pro Ser
            35                  40                  45

Asn Gln Thr Asp Lys Leu Ala Ala Phe Pro Glu Asp Arg Ser Gln Pro
        50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Gly Arg Glu Gly Pro Glu Leu Ser
130                 135                 140

Pro Asp Asp Pro Ala Gly Leu Leu Asp Leu Arg Gln Gly Met Phe Ala
145                 150                 155                 160

Gln Leu Val Ala Gln Asn Val Leu Leu Ile Asp Gly Pro Leu Ser Trp
                165                 170                 175

Tyr Ser Asp Pro Gly Leu Ala Gly Val Ser Leu Thr Gly Gly Leu Ser
            180                 185                 190

Tyr Lys Glu Asp Thr Lys Glu Leu Val Val Ala Lys Ala Gly Val Tyr
        195                 200                 205

Tyr Val Phe Phe Gln Leu Glu Leu Arg Arg Val Val Ala Gly Glu Gly
210                 215                 220

Ser Gly Ser Val Ser Leu Ala Leu His Leu Gln Pro Leu Arg Ser Ala
225                 230                 235                 240

Ala Gly Ala Ala Ala Leu Ala Leu Thr Val Asp Leu Pro Pro Ala Ser
                245                 250                 255

Ser Glu Ala Arg Asn Ser Ala Phe Gly Phe Gln Gly Arg Leu Leu His
            260                 265                 270

Leu Ser Ala Gly Gln Arg Leu Gly Val His Leu His Thr Glu Ala Arg
        275                 280                 285

Ala Arg His Ala Trp Gln Leu Thr Gln Gly Ala Thr Val Leu Gly Leu
290                 295                 300

Phe Arg Val Thr Pro Glu Ile Pro Ala Gly Leu Pro Ser Pro Arg Ser
305                 310                 315                 320

Glu

<210> SEQ ID NO 134
<211> LENGTH: 963
<212> TYPE: DNA
<213> ORGANISM: Artificial sequence
<220> FEATURE:
<223> OTHER INFORMATION: DSP105 variant nucleic acid sequence

<400> SEQUENCE: 134
gactctccag acagaccttg gaaccctcca accttctctc ccgctctgct ggtggttacc    60
gagggcgaca atgccacctt cacctgttcc ttcagcaaca cctccgagtc cttcgtgctg   120
aactggtaca gaatgtcccc tagcaaccag accgacaagc tggccgcctt tcctgaggac   180

```
agatctcagc caggccagga ctgtcggttc agagttaccc agctgcctaa cggccgggac    240
ttccacatgt ctgttgtgcg ggccagacgg aacgactctg cacatatct gtgcggcgcc    300 atctctctgg ctcccaaggc tcagatcaaa gagtctctgc gggccgagct gagagtgaca    360
gaaagacgag ctgaggtgcc caccgctcat ccctcacctt ctccaagagg aagagagggc    420
cctgagctgt ctcctgatga tcctgctgga ctgctggacc tgagacaggg catgtttgct    480
cagctggtgg cccagaacgt gctgctgatt gatggccctc tgtcctggta ctctgatcct    540
ggattggctg gcgtgtccct gactggcggc ctgtcttaca agaggacac caaagaactg    600 gtggtcgcca aggccggcgt gtactacgtg ttctttcagc tggaactgcg agagtggtg    660 gctggcgaag atctggatc tgtgtctctg ccctgcatc tgcagcctct gagaagtgct    720
gcaggcgctg ctgcactggc tctgacagtt gatctgcctc ctgcctcctc cgaggccaga    780
aactccgcct ttggcttcca aggcagactg ctgcatctgt ctgccggaca gagactggga    840
gtgcacctcc atacagaggc cagagctaga cacgcttggc agttgacaca gggcgctaca    900
gtgctgggcc tgtttagagt gacacctgag atcccagccg gcctgccatc tccaagatct    960
gaa                                                                 963
```

<210> SEQ ID NO 135
<211> LENGTH: 319
<212> TYPE: PRT
<213> ORGANISM: Artificial sequence
<220> FEATURE:
<223> OTHER INFORMATION: DSP105 variant amino acid sequence

<400> SEQUENCE: 135

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Gly Gly Pro Glu Leu Ser Pro Asp
    130                 135                 140

Asp Pro Ala Gly Leu Leu Asp Leu Arg Gln Gly Met Phe Ala Gln Leu
145                 150                 155                 160

Val Ala Gln Asn Val Leu Leu Ile Asp Gly Pro Leu Ser Trp Tyr Ser
                165                 170                 175

Asp Pro Gly Leu Ala Gly Val Ser Leu Thr Gly Gly Leu Ser Tyr Lys
            180                 185                 190

Glu Asp Thr Lys Glu Leu Val Val Ala Lys Ala Gly Val Tyr Tyr Val
        195                 200                 205

Phe Phe Gln Leu Glu Leu Arg Arg Val Val Ala Gly Glu Gly Ser Gly

```
                210                 215                 220

Ser Val Ser Leu Ala Leu His Leu Gln Pro Leu Arg Ser Ala Ala Gly
225                 230                 235                 240

Ala Ala Ala Leu Ala Leu Thr Val Asp Leu Pro Pro Ala Ser Ser Glu
                245                 250                 255

Ala Arg Asn Ser Ala Phe Gly Phe Gln Gly Arg Leu Leu His Leu Ser
                260                 265                 270

Ala Gly Gln Arg Leu Gly Val His Leu His Thr Glu Ala Arg Ala Arg
                275                 280                 285

His Ala Trp Gln Leu Thr Gln Gly Ala Thr Val Leu Gly Leu Phe Arg
                290                 295                 300

Val Thr Pro Glu Ile Pro Ala Gly Leu Pro Ser Pro Arg Ser Glu
305                 310                 315

<210> SEQ ID NO 136
<211> LENGTH: 957
<212> TYPE: DNA
<213> ORGANISM: Artificial sequence
<220> FEATURE:
<223> OTHER INFORMATION: DSP105 variant nucleic acid sequence

<400> SEQUENCE: 136
gactctccag acagaccttg aaccctcca accttctctc ccgctctgct ggtggttacc      60
gagggcgaca atgccacctt cacctgttcc ttcagcaaca cctccgagtc cttcgtgctg     120
aactggtaca gaatgtcccc tagcaaccag accgacaagc tggccgcctt tcctgaggac     180
agatctcagc caggccagga ctgtcggttc agagttaccc agctgcctaa cggccgggac     240
ttccacatgt ctgttgtgcg ggccagacgg aacgactctg cacatatct gtgcggcgcc     300
atctctctgg ctcccaaggc tcagatcaaa gagtctctgc gggccgagct gagagtgaca     360
gaaagacgag ctgaggtgcc caccgctcat ccctcacctt ctccaagagg aggccctgag     420
ctgtctcctg atgatcctgc tggactgctg acctgagac agggcatgtt tgctcagctg     480
gtggcccaga acgtgctgct gattgatggc cctctgtcct ggtactctga tcctggattg     540
gctggcgtgt ccctgactgg cggcctgtct tacaaagagg acaccaaaga actggtggtc     600
gccaaggccg gcgtgtacta cgtgttcttt cagctggaac tgcggagagt ggtggctggc     660
gaaggatctg gatctgtgtc tctggccctg catctgcagc ctctgagaag tgctgcaggc     720
gctgctgcac tggctctgac agttgatctg cctcctgcct cctccgaggc cagaaactcc     780
gcctttggct ccaaggcag actgctgcat ctgtctgccg gacagagact gggagtgcac     840
ctccatacag aggccagagc tagacacgct tggcagttga cacagggcgc tacagtgctg     900
ggcctgttta gagtgacacc tgagatccca gccggcctgc atctccaag atctgaa       957

<210> SEQ ID NO 137
<211> LENGTH: 329
<212> TYPE: PRT
<213> ORGANISM: Artificial sequence
<220> FEATURE:
<223> OTHER INFORMATION: DSP105 variant amino acid sequence

<400> SEQUENCE: 137

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
```

```
                35                  40                  45
Arg Met Ser Pro Ser Asn Gln Thr Asp Lys Leu Ala Ala Phe Pro Glu
 50                  55                  60
Asp Arg Ser Gln Pro Gly Gln Asp Cys Arg Phe Arg Val Thr Gln Leu
65                  70                  75                  80
Pro Asn Gly Arg Asp Phe His Met Ser Val Val Arg Ala Arg Arg Asn
                85                  90                  95
Asp Ser Gly Thr Tyr Leu Cys Gly Ala Ile Ser Leu Ala Pro Lys Ala
            100                 105                 110
Gln Ile Lys Glu Ser Leu Arg Ala Glu Leu Arg Val Thr Glu Arg Arg
        115                 120                 125
Ala Glu Val Pro Thr Ala His Pro Ser Pro Ser Pro Arg Pro Ala Gly
130                 135                 140
Gln Gly Ser Ala Ala Ser Pro Arg Leu Arg Glu Gly Pro Glu Leu Ser
145                 150                 155                 160
Pro Asp Asp Pro Ala Gly Leu Leu Asp Leu Arg Gln Gly Met Phe Ala
                165                 170                 175
Gln Leu Val Ala Gln Asn Val Leu Leu Ile Asp Gly Pro Leu Ser Trp
            180                 185                 190
Tyr Ser Asp Pro Gly Leu Ala Gly Val Ser Leu Thr Gly Gly Leu Ser
        195                 200                 205
Tyr Lys Glu Asp Thr Lys Glu Leu Val Val Ala Lys Ala Gly Val Tyr
210                 215                 220
Tyr Val Phe Phe Gln Leu Glu Leu Arg Arg Val Val Ala Gly Glu Gly
225                 230                 235                 240
Ser Gly Ser Val Ser Leu Ala Leu His Leu Gln Pro Leu Arg Ser Ala
                245                 250                 255
Ala Gly Ala Ala Ala Leu Ala Leu Thr Val Asp Leu Pro Pro Ala Ser
            260                 265                 270
Ser Glu Ala Arg Asn Ser Ala Phe Gly Phe Gln Gly Arg Leu Leu His
        275                 280                 285
Leu Ser Ala Gly Gln Arg Leu Gly Val His Leu His Thr Glu Ala Arg
290                 295                 300
Ala Arg His Ala Trp Gln Leu Thr Gln Gly Ala Thr Val Leu Gly Leu
305                 310                 315                 320
Phe Arg Val Thr Pro Glu Ile Pro Ala
            325

<210> SEQ ID NO 138
<211> LENGTH: 987
<212> TYPE: DNA
<213> ORGANISM: Artificial sequence
<220> FEATURE:
<223> OTHER INFORMATION: DSP105 variant nucleic acid sequence

<400> SEQUENCE: 138
cccggctggt ttctggactc tccagacaga ccttggaacc ctccaacctt ctctcccgct     60
ctgctggtgg ttaccgaggg cgacaatgcc accttcacct gttccttcag caacacctcc    120
gagtccttcg tgctgaactg gtacagaatg tcccctagca accagaccga caagctggcc    180
gcctttcctg aggacagatc tcagccaggc caggactgtc ggttcagagt acccagctg    240 cctaacggcc gggacttcca catgtctgtt gtgcgggcca gacggaacga ctctggcaca    300
tatctgtgcg gcgccatctc tctggctccc aaggctcaga tcaaagagtc tctgcgggcc    360
gagctgagag tgacagaaag acgagctgag gtgcccaccg ctcatccctc accttctcca    420
```

```
agacctgctg gccagggatc tgccgcttct cctagactga gagagggccc tgagctgtct    480
cctgatgatc ctgctggact gctggacctg agacagggca tgtttgctca gctggtggcc    540
cagaacgtgc tgctgattga tggccctctg tcctggtact ctgatcctgg attggctggc    600
gtgtccctga ctggcggcct gtcttacaaa gaggacacca agaactggt ggtcgccaag    660 gccggcgtgt actacgtgtt ctttcagctg gaactgcgga gagtggtggc tggcgaagga    720
tctggatctg tgtctctggc cctgcatctg cagcctctga aagtgctgc aggcgctgct    780 gcactggctc tgacagttga tctgcctcct gcctcctccg aggccagaaa ctccgccttt    840
ggcttccaag cagactgct gcatctgtct gccggacaga gactgggagt gcacctccat    900
acagaggcca gagctagaca cgcttggcag ttgacacagg gcgctacagt gctgggcctg    960
tttagagtga cacctgagat cccagcc                                        987
```

<210> SEQ ID NO 139
<211> LENGTH: 320
<212> TYPE: PRT
<213> ORGANISM: Artificial sequence
<220> FEATURE:
<223> OTHER INFORMATION: DSP105 variant amino acid sequence

<400> SEQUENCE: 139

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Arg Glu Gly Pro Glu Leu Ser Pro Asp Asp Pro Ala Gly Leu Leu Asp
145                 150                 155                 160

Leu Arg Gln Gly Met Phe Ala Gln Leu Val Ala Gln Asn Val Leu Leu
                165                 170                 175

Ile Asp Gly Pro Leu Ser Trp Tyr Ser Asp Pro Gly Leu Ala Gly Val
            180                 185                 190

Ser Leu Thr Gly Gly Leu Ser Tyr Lys Glu Asp Thr Lys Glu Leu Val
        195                 200                 205

Val Ala Lys Ala Gly Val Tyr Tyr Val Phe Phe Gln Leu Glu Leu Arg
    210                 215                 220

Arg Val Val Ala Gly Glu Gly Ser Gly Ser Val Ser Leu Ala Leu His
225                 230                 235                 240

Leu Gln Pro Leu Arg Ser Ala Ala Gly Ala Ala Leu Ala Leu Thr
                245                 250                 255
```

Val Asp Leu Pro Pro Ala Ser Ser Glu Ala Arg Asn Ser Ala Phe Gly
              260                 265                 270

Phe Gln Gly Arg Leu Leu His Leu Ser Ala Gly Gln Arg Leu Gly Val
          275                 280                 285

His Leu His Thr Glu Ala Arg Ala Arg His Ala Trp Gln Leu Thr Gln
      290                 295                 300

Gly Ala Thr Val Leu Gly Leu Phe Arg Val Thr Pro Glu Ile Pro Ala
305                 310                 315                 320

<210> SEQ ID NO 140
<211> LENGTH: 960
<212> TYPE: DNA
<213> ORGANISM: Artificial sequence
<220> FEATURE:
<223> OTHER INFORMATION: DSP105 variant nucleic acid sequence

<400> SEQUENCE: 140
cccggctggt ttctggactc tccagacaga ccttggaacc ctccaacctt ctctcccgct      60
ctgctggtgg ttaccgaggg cgacaatgcc accttcacct gttccttcag caacacctcc     120
gagtccttcg tgctgaactg gtacagaatg tcccctagca accagaccga caagctggcc     180 gccttcctg aggacagatc tcagccaggc caggactgtc ggttcagagt acccagctg       240 cctaacggcc gggacttcca catgtctgtt gtgcgggcca gacggaacga ctctggcaca     300
tatctgtgcg cgccatctc tctggctccc aaggctcaga tcaaagagtc tctgcgggcc      360
gagctgagag tgacagaaag acgagctgag gtgcccaccg ctcatccctc accttctcca     420
agacctgctg aagagaggg ccctgagctg tctcctgatg atcctgctgg actgctggac      480
ctgagacagg gcatgtttgc tcagctggtg gcccagaacg tgctgctgat tgatggccct     540
ctgtcctggt actctgatcc tggattggct ggcgtgtccc tgactggcgg cctgtcttac     600
aaagaggaca ccaaagaact ggtggtcgcc aaggccggcg tgtactacgt gttctttcag     660
ctggaactgc ggagagtggt ggctggcgaa ggatctggat ctgtgtctct ggccctgcat     720
ctgcagcctc tgagaagtgc tgcaggcgct gctgcactgg ctctgacagt tgatctgcct     780
cctgcctcct ccgaggccag aaactccgcc tttggcttcc aaggcagact gctgcatctg     840
tctgccggac agagactggg agtgcacctc catacagagg ccagagctag acacgcttgg     900
cagttgacac agggcgctac agtgctgggc ctgtttagag tgacacctga tcccagcc      960

<210> SEQ ID NO 141
<211> LENGTH: 346
<212> TYPE: PRT
<213> ORGANISM: Artificial sequence
<220> FEATURE:
<223> OTHER INFORMATION: DSP105 variant amino acid sequence

<400> SEQUENCE: 141

Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
              20                  25                  30

Asn Thr Ser Glu Ser Phe Val Leu Asn Trp Tyr Arg Met Ser Pro Ser
          35                  40                  45

Asn Gln Thr Asp Lys Leu Ala Ala Phe Pro Glu Asp Arg Ser Gln Pro
      50                  55                  60

Gly Gln Asp Cys Arg Phe Arg Val Thr Gln Leu Pro Asn Gly Arg Asp
65                  70                  75                  80

```
Phe His Met Ser Val Val Arg Ala Arg Arg Asn Asp Ser Gly Thr Tyr
                 85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
            115                 120                 125

Ala His Pro Ser Pro Ser Pro Arg Pro Ala Gly Gln Gly Ala Cys Pro
        130                 135                 140

Trp Ala Val Ser Gly Ala Arg Ala Ser Pro Gly Ser Ala Ala Ser Pro
145                 150                 155                 160

Arg Leu Arg Glu Gly Pro Glu Leu Ser Pro Asp Asp Pro Ala Gly Leu
                165                 170                 175

Leu Asp Leu Arg Gln Gly Met Phe Ala Gln Leu Val Ala Gln Asn Val
            180                 185                 190

Leu Leu Ile Asp Gly Pro Leu Ser Trp Tyr Ser Asp Pro Gly Leu Ala
            195                 200                 205

Gly Val Ser Leu Thr Gly Gly Leu Ser Tyr Lys Glu Asp Thr Lys Glu
        210                 215                 220

Leu Val Val Ala Lys Ala Gly Val Tyr Tyr Val Phe Phe Gln Leu Glu
225                 230                 235                 240

Leu Arg Arg Val Val Ala Gly Glu Gly Ser Gly Ser Val Ser Leu Ala
                245                 250                 255

Leu His Leu Gln Pro Leu Arg Ser Ala Ala Gly Ala Ala Leu Ala
            260                 265                 270

Leu Thr Val Asp Leu Pro Pro Ala Ser Ser Glu Ala Arg Asn Ser Ala
            275                 280                 285

Phe Gly Phe Gln Gly Arg Leu Leu His Leu Ser Ala Gly Gln Arg Leu
        290                 295                 300

Gly Val His Leu His Thr Glu Ala Arg Ala Arg His Ala Trp Gln Leu
305                 310                 315                 320

Thr Gln Gly Ala Thr Val Leu Gly Leu Phe Arg Val Thr Pro Glu Ile
                325                 330                 335

Pro Ala Gly Leu Pro Ser Pro Arg Ser Glu
            340                 345

<210> SEQ ID NO 142
<211> LENGTH: 1038
<212> TYPE: DNA
<213> ORGANISM: Artificial sequence
<220> FEATURE:
<223> OTHER INFORMATION: DSP105 variant nucleic acid sequence

<400> SEQUENCE: 142
gactctccag acagaccttg gaaccctcca accttctctc ccgctctgct ggtggttacc      60
gagggcgaca atgccacctt cacctgttcc ttcagcaaca cctccgagtc cttcgtgctg     120
aactggtaca gaatgtcccc tagcaaccag accgacaagc tggccgcctt tcctgaggac     180
agatctcagc caggccagga ctgtcggttc agagttaccc agctgcctaa cggccgggac     240
ttccacatgt ctgttgtgcg ggccagacgg aacgactctg gcacatatct gtgcggcgcc     300
atctctctgg ctcccaaggc tcagatcaaa gagtctctgc gggccgagct gagagtgaca     360
gaaagacgag ctgaggtgcc caccgctcat ccctcacctt ctccaagacc tgctggccag     420
ggagcctgtc cttgggctgt gtctggcgct agagcatctc ctggctctgc tgcctctcct     480
agactgagag aggacctga  gctgtctcct gatgatcctg ctggcctgct ggatctgaga     540
```

```
cagggcatgt tgctcagct ggtggcccag aacgtgctgc tgattgatgg ccctctgtcc      600
tggtactctg atcctggatt ggctggcgtg tccctgactg gcggcctgtc ttacaaagag      660
gacaccaaag aactggtggt ggccaaggcc ggcgtgtact acgtgttctt tcagctggaa      720
ctgcggagag tggtggccgg cgaaggatct ggatctgtgt ctctggcact gcatctgcag      780
cccctgagat ctgctgcagg cgctgctgct ctggctctga cagttgatct gcctcctgcc      840
tcctccgagg ccagaaactc cgcctttggc ttccaaggca gactgctgca tctgtctgcc      900
ggccagagac tgggagtcca tctgcataca gaggctagag ccaggcacgc ctggcagttg      960
acacaaggtg ctacagtgct gggcctgttc agagtgaccc cagagattcc agccggcctg     1020
ccttctccaa gatccgag                                                   1038
```

<210> SEQ ID NO 143
<211> LENGTH: 350
<212> TYPE: PRT
<213> ORGANISM: Artificial sequence
<220> FEATURE:
<223> OTHER INFORMATION: DSP105 variant amino acid sequence

<400> SEQUENCE: 143

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Ser Gly Ala Arg Ala Ser Pro Gly Ser
145                 150                 155                 160

Ala Ala Ser Pro Arg Leu Arg Glu Gly Pro Glu Leu Ser Pro Asp Asp
                165                 170                 175

Pro Ala Gly Leu Leu Asp Leu Arg Gln Gly Met Phe Ala Gln Leu Val
            180                 185                 190

Ala Gln Asn Val Leu Leu Ile Asp Gly Pro Leu Ser Trp Tyr Ser Asp
        195                 200                 205

Pro Gly Leu Ala Gly Val Ser Leu Thr Gly Gly Leu Ser Tyr Lys Glu
    210                 215                 220

Asp Thr Lys Glu Leu Val Val Ala Lys Ala Gly Val Tyr Tyr Val Phe
225                 230                 235                 240

Phe Gln Leu Glu Leu Arg Arg Val Val Ala Gly Glu Gly Ser Gly Ser
                245                 250                 255

Val Ser Leu Ala Leu His Leu Gln Pro Leu Arg Ser Ala Ala Gly Ala
            260                 265                 270
```

```
Ala Ala Leu Ala Leu Thr Val Asp Leu Pro Pro Ala Ser Ser Glu Ala
            275                 280                 285

Arg Asn Ser Ala Phe Gly Phe Gln Gly Arg Leu Leu His Leu Ser Ala
        290                 295                 300

Gly Gln Arg Leu Gly Val His Leu His Thr Glu Ala Arg Ala Arg His
305                 310                 315                 320

Ala Trp Gln Leu Thr Gln Gly Ala Thr Val Leu Gly Leu Phe Arg Val
                325                 330                 335

Thr Pro Glu Ile Pro Ala Gly Leu Pro Ser Pro Arg Ser Glu
            340                 345                 350

<210> SEQ ID NO 144
<211> LENGTH: 1092
<212> TYPE: DNA
<213> ORGANISM: Artificial sequence
<220> FEATURE:
<223> OTHER INFORMATION: DSP105 variant nucleic acid sequence

<400> SEQUENCE: 144
cctggctggt ttctggacag ccccgacaga ccttggaacc ctcctacatt cagccccgct      60
ctgctggtgg ttaccgaggg cgataatgcc accttcacct gtagcttcag caacaccagc     120
gagagcttcg tgctgaactg gtacagaatg agccccagca ccagaccga caagctggcc      180 gcctttcctg aggatagatc tcagcccggc caggactgtc ggttcagagt tacacagctg     240
cccaacggcc gggacttcca catgtctgtc gtccgggcca agaaacga cagcggcaca      300 tatctgtgcg gcgccatttc tctggcccct aaggctcaga tcaaagagag cctgagagcc     360
gagctgagag tgacagaaag acgggccgaa gtgcccacag ctcacccttc accttctcca     420
agacctgccg ccagtttca gacactcgtg ggagcttgtc cttgggccgt ttctggcgct     480
agagcctctc ctggatctgg cgctagagcc tctcctggat ctgccgcttc tcccagactg     540
agagagggac ctgagctgag ccctgatgat cctgctggac tgctggatct gagacagggc     600
atgtttgccc agctggtggc ccagaatgtg ctgctgattg atggccctct gtcctggtac     660
agcgatcctg gacttgctgg cgttagcctg actggcggcc tgagctacaa agaggacacc     720
aaagaactgg tggtggccaa ggccggcgtg tactacgtgt tctttcagct ggaactgcgg     780
agagtggtgg ccggcgaagg atctggatct gtgtctctgg ctctgcatct gcagcctctg     840
agatctgctg ctggtgctgc tgctctggcc ctgacagttg atctgcctcc tgcctctagc     900
gaggccagaa actccgcctt tggcttccaa ggcagactgc tgcacctgag cgctggacag     960
agactgggag tccatctgca cacagaagcc agagctagac acgcctggca gctgacacaa    1020
ggcgctacag tgctgggcct gttcagagtg accctgaga ttccagccgg cctgccatct    1080
cctagatctg ag                                                        1092

<210> SEQ ID NO 145
<211> LENGTH: 365
<212> TYPE: PRT
<213> ORGANISM: Artificial sequence
<220> FEATURE:
<223> OTHER INFORMATION: DSP105 variant amino acid sequence

<400> SEQUENCE: 145

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30
```

| | | | | | | | | | | | | |
|---|---|---|---|---|---|---|---|---|---|---|---|---|
|Thr|Cys|Ser|Phe|Ser|Asn|Thr|Ser|Glu|Ser|Phe|Val|Leu|Asn|Trp|Tyr|
| |35| | | |40| | | |45| | | |

Thr Cys Ser Phe Ser Asn Thr Ser Glu Ser Phe Val Leu Asn Trp Tyr
          35                  40                  45

Arg Met Ser Pro Ser Asn Gln Thr Asp Lys Leu Ala Ala Phe Pro Glu
 50                  55                  60

Asp Arg Ser Gln Pro Gly Gln Asp Cys Arg Phe Arg Val Thr Gln Leu
 65                  70                  75                  80

Pro Asn Gly Arg Asp Phe His Met Ser Val Val Arg Ala Arg Asn
                 85                  90                  95

Asp Ser Gly Thr Tyr Leu Cys Gly Ala Ile Ser Leu Ala Pro Lys Ala
                100                 105                 110

Gln Ile Lys Glu Ser Leu Arg Ala Glu Leu Arg Val Thr Glu Arg Arg
                115                 120                 125

Ala Glu Val Pro Thr Ala His Pro Ser Pro Ser Pro Arg Pro Ala Gly
130                 135                 140

Gln Phe Gln Thr Leu Val Gly Gly Gly Ser Gly Gly Gly Gly Ser
145                 150                 155                 160

Ala Cys Pro Trp Ala Val Ser Gly Ala Arg Ala Ser Pro Gly Ser Ala
                165                 170                 175

Ala Ser Pro Arg Leu Arg Glu Gly Pro Glu Leu Ser Pro Asp Asp Pro
                180                 185                 190

Ala Gly Leu Leu Asp Leu Arg Gln Gly Met Phe Ala Gln Leu Val Ala
                195                 200                 205

Gln Asn Val Leu Leu Ile Asp Gly Pro Leu Ser Trp Tyr Ser Asp Pro
210                 215                 220

Gly Leu Ala Gly Val Ser Leu Thr Gly Gly Leu Ser Tyr Lys Glu Asp
225                 230                 235                 240

Thr Lys Glu Leu Val Val Ala Lys Ala Gly Val Tyr Tyr Val Phe Phe
                245                 250                 255

Gln Leu Glu Leu Arg Arg Val Val Ala Gly Glu Gly Ser Gly Ser Val
                260                 265                 270

Ser Leu Ala Leu His Leu Gln Pro Leu Arg Ser Ala Ala Gly Ala Ala
                275                 280                 285

Ala Leu Ala Leu Thr Val Asp Leu Pro Pro Ala Ser Ser Glu Ala Arg
290                 295                 300

Asn Ser Ala Phe Gly Phe Gln Gly Arg Leu Leu His Leu Ser Ala Gly
305                 310                 315                 320

Gln Arg Leu Gly Val His Leu His Thr Glu Ala Arg Ala Arg His Ala
                325                 330                 335

Trp Gln Leu Thr Gln Gly Ala Thr Val Leu Gly Leu Phe Arg Val Thr
                340                 345                 350

Pro Glu Ile Pro Ala Gly Leu Pro Ser Pro Arg Ser Glu
                355                 360                 365

<210> SEQ ID NO 146
<211> LENGTH: 1095
<212> TYPE: DNA
<213> ORGANISM: Artificial sequence
<220> FEATURE:
<223> OTHER INFORMATION: DSP105 variant nucleic acid sequence

<400> SEQUENCE: 146
cctggctggt ttctggacag ccccgacaga ccttggaacc ctcctacatt cagccccgct      60
ctgctggtgg ttaccgaggg cgataatgcc accttcacct gtagcttcag caacaccagc     120
gagagcttcg tgctgaactg gtacagaatg agccccagca accagaccga caagctggcc     180

```
gcctttcctg aggatagatc tcagcccggc caggactgtc ggttcagagt tacacagctg    240
cccaacggcc gggacttcca catgtctgtc gtccgggcca aagaaacga cagcggcaca    300 tatctgtgcg gcgccatttc tctggcccct aaggctcaga tcaaagagag cctgagagcc    360
gagctgagag tgacagaaag acgggccgaa gtgcccacag ctcacccttc accttctcca    420
agacctgccg ccagtttca  gacactcgtg ggaggaggag gatccggagg aggaggatcc    480
gcctgtcctt gggctgtgtc tggcgctaga gcatctcctg ctctgctgc ctctcctaga    540 ctgagagagg gacctgagct gtctcctgat gatcctgctg gcctgctgga tctgagacag    600
ggcatgtttg ctcagctggt ggcccagaac gtgctgctga ttgatggccc tctgtcctgg    660
tactctgatc ctggattggc tggcgtgtcc ctgactggcg gcctgtctta caaagaggac    720
accaaagaac tggtggtggc caaggccggc gtgtactacg tgttctttca gctgaactg     780 cggagagtgg tggccggcga aggatctgga tctgtgtctc tggcactgca tctgcagccc    840
ctgagatctg ctgcaggcgc tgctgctctg gctctgacag ttgatctgcc tcctgcctcc    900
tccgaggcca gaaactccgc ctttggcttc caaggcagac tgctgcatct gtctgccggc    960
cagagactgg gagtccatct gcatacagag gctagagcca ggcacgcctg cagttgaca    1020 caaggtgcta cagtgctggg cctgttcaga gtgaccccag agattccagc cggcctgcct   1080
tctccaagat ccgag                                                     1095
```

<210> SEQ ID NO 147
<211> LENGTH: 750
<212> TYPE: PRT
<213> ORGANISM: Artificial sequence
<220> FEATURE:
<223> OTHER INFORMATION: DSP105 variant amino acid sequence

<400> SEQUENCE: 147

```
Asp Ser Pro Asp Arg Pro Trp Asn Pro Pro Thr Phe Ser Pro Ala Leu
1               5                   10                  15

Leu Val Val Thr Glu Gly Asp Asn Ala Thr Phe Thr Cys Ser Phe Ser
            20                  25                  30

Asn Thr Ser Glu Ser Phe Val Leu Asn Trp Tyr Arg Met Ser Pro Ser
        35                  40                  45

Asn Gln Thr Asp Lys Leu Ala Ala Phe Pro Glu Asp Arg Ser Gln Pro
    50                  55                  60

Gly Gln Asp Cys Arg Phe Arg Val Thr Gln Leu Pro Asn Gly Arg Asp
65                  70                  75                  80

Phe His Met Ser Val Val Arg Ala Arg Arg Asn Asp Ser Gly Thr Tyr
                85                  90                  95

Leu Cys Gly Ala Ile Ser Leu Ala Pro Lys Ala Gln Ile Lys Glu Ser
            100                 105                 110

Leu Arg Ala Glu Leu Arg Val Thr Glu Arg Arg Ala Glu Val Pro Thr
        115                 120                 125

Ala His Pro Ser Pro Ser Pro Arg Pro Ala Gly Gln Gly Gly Gly Gly
    130                 135                 140

Ser Gly Gly Gly Gly Ser Ala Ala Ser Pro Arg Leu Arg Glu Gly Pro
145                 150                 155                 160

Glu Leu Ser Pro Asp Asp Pro Ala Gly Leu Leu Asp Leu Arg Gln Gly
                165                 170                 175

Met Phe Ala Gln Leu Val Ala Gln Asn Val Leu Leu Ile Asp Gly Pro
            180                 185                 190

Leu Ser Trp Tyr Ser Asp Pro Gly Leu Ala Gly Val Ser Leu Thr Gly
```

```
            195                 200                 205
Gly Leu Ser Tyr Lys Glu Asp Thr Lys Glu Leu Val Val Ala Lys Ala
210                 215                 220

Gly Val Tyr Tyr Val Phe Phe Gln Leu Glu Leu Arg Arg Val Val Ala
225                 230                 235                 240

Gly Glu Gly Ser Gly Ser Val Ser Leu Ala Leu His Leu Gln Pro Leu
                    245                 250                 255

Arg Ser Ala Ala Gly Ala Ala Ala Leu Ala Leu Thr Val Asp Leu Pro
                260                 265                 270

Pro Ala Ser Ser Glu Ala Arg Asn Ser Ala Phe Gly Phe Gln Gly Arg
                275                 280                 285

Leu Leu His Leu Ser Ala Gly Gln Arg Leu Gly Val His Leu His Thr
290                 295                 300

Glu Ala Arg Ala Arg His Ala Trp Gln Leu Thr Gln Gly Ala Thr Val
305                 310                 315                 320

Leu Gly Leu Phe Arg Val Thr Pro Glu Ile Pro Ala Gly Leu Pro Ser
                    325                 330                 335

Pro Arg Ser Glu Gly Gly Gly Ser Gly Gly Gly Ser Gly Gly
                340                 345                 350

Gly Gly Ser Ala Ala Ser Pro Arg Leu Arg Glu Gly Pro Glu Leu Ser
                355                 360                 365

Pro Asp Asp Pro Ala Gly Leu Leu Asp Leu Arg Gln Gly Met Phe Ala
370                 375                 380

Gln Leu Val Ala Gln Asn Val Leu Leu Ile Asp Gly Pro Leu Ser Trp
385                 390                 395                 400

Tyr Ser Asp Pro Gly Leu Ala Gly Val Ser Leu Thr Gly Gly Leu Ser
                    405                 410                 415

Tyr Lys Glu Asp Thr Lys Glu Leu Val Val Ala Lys Ala Gly Val Tyr
                420                 425                 430

Tyr Val Phe Phe Gln Leu Glu Leu Arg Arg Val Val Ala Gly Glu Gly
                435                 440                 445

Ser Gly Ser Val Ser Leu Ala Leu His Leu Gln Pro Leu Arg Ser Ala
    450                 455                 460

Ala Gly Ala Ala Ala Leu Ala Leu Thr Val Asp Leu Pro Pro Ala Ser
465                 470                 475                 480

Ser Glu Ala Arg Asn Ser Ala Phe Gly Phe Gln Gly Arg Leu Leu His
                    485                 490                 495

Leu Ser Ala Gly Gln Arg Leu Gly Val His Leu His Thr Glu Ala Arg
                500                 505                 510

Ala Arg His Ala Trp Gln Leu Thr Gln Gly Ala Thr Val Leu Gly Leu
    515                 520                 525

Phe Arg Val Thr Pro Glu Ile Pro Ala Gly Leu Pro Ser Pro Arg Ser
    530                 535                 540

Glu Gly Gly Gly Ser Gly Gly Gly Ser Gly Gly Gly Gly Ser
545                 550                 555                 560

Ala Ala Ser Pro Arg Leu Arg Glu Gly Pro Glu Leu Ser Pro Asp Asp
                565                 570                 575

Pro Ala Gly Leu Leu Asp Leu Arg Gln Gly Met Phe Ala Gln Leu Val
                580                 585                 590

Ala Gln Asn Val Leu Leu Ile Asp Gly Pro Leu Ser Trp Tyr Ser Asp
                595                 600                 605

Pro Gly Leu Ala Gly Val Ser Leu Thr Gly Gly Leu Ser Tyr Lys Glu
610                 615                 620
```

Asp Thr Lys Glu Leu Val Val Ala Lys Ala Gly Val Tyr Tyr Val Phe
625                 630                 635                 640

Phe Gln Leu Glu Leu Arg Arg Val Val Ala Gly Glu Gly Ser Gly Ser
                645                 650                 655

Val Ser Leu Ala Leu His Leu Gln Pro Leu Arg Ser Ala Ala Gly Ala
            660                 665                 670

Ala Ala Leu Ala Leu Thr Val Asp Leu Pro Pro Ala Ser Ser Glu Ala
        675                 680                 685

Arg Asn Ser Ala Phe Gly Phe Gln Gly Arg Leu Leu His Leu Ser Ala
    690                 695                 700

Gly Gln Arg Leu Gly Val His Leu His Thr Glu Ala Arg Ala Arg His
705                 710                 715                 720

Ala Trp Gln Leu Thr Gln Gly Ala Thr Val Leu Gly Leu Phe Arg Val
                725                 730                 735

Thr Pro Glu Ile Pro Ala Gly Leu Pro Ser Pro Arg Ser Glu
            740                 745                 750

<210> SEQ ID NO 148
<211> LENGTH: 2250
<212> TYPE: DNA
<213> ORGANISM: Artificial sequence
<220> FEATURE:
<223> OTHER INFORMATION: DSP105 variant nucleic acid sequence

<400> SEQUENCE: 148
gactctccag acagaccttg aaccctcca accttctctc ccgctctgct ggtggttacc     60
gagggcgaca atgccacctt cacctgttcc ttcagcaaca cctccgagtc cttcgtgctg    120
aactggtaca gaatgtcccc tagcaaccag accgacaagc tggccgcctt tcctgaggac    180
agatctcagc caggccagga ctgtcggttc agagttaccc agctgcctaa cggccgggac    240
ttccacatgt ctgttgtgcg ggccagacgg aacgactctg cacatatct gtgcggcgcc    300 atctctctgg ctcccaaggc tcagatcaaa gagtctctgc gggccgagct gagagtgaca    360
gaaagacgag ctgaggtgcc caccgctcat ccctcacctt ctccaagacc tgctggccag    420
ggcggcggcg gctccggagg aggaggatct gccgccagcc ctaggctgcg cgagggaccc    480
gagctgagcc agacgatcc cgccggcctg ctggacctga gcagggaat gttcgcacag    540 ctggtggccc agaacgtgct gctgatcgac ggccctctgt cctggtactc tgatccaggc    600
ctggccggcg tgtccctgac aggaggcctg tcttataagg aggataccaa ggagctggtg    660
gtggcaaagg caggcgtgta ctacgtgttc ttccagctgg agctgaggag agtggtggca    720
ggagagggca gcggctccgt gtctctggcc ctgcacctcc agcctctgcg gagcgccgcc    780
ggcgccgccg ccctggccct gaccgtggat ctgcctccag ccagtccga ggccaggaat    840 agcgccttcg gctttcaggg ccgcctgctg cacctgtccg ccggccagcg gctgggagtg    900
cacctgcaca cagaggccag agcccggcac gcatggcagc tgacacaggg agcaaccgtg    960
ctgggcctgt tccgcgtgac ccctgagatc ccagccggcc tgccaagccc ccggtccgag   1020
ggcggcggcg gctctggcgg aggaggcagc ggaggcggcg gctctgccgc cagccccagg   1080
ctgcgcgagg accccgagct gtccccagac gatcctgccg gctgctgga cctgcgccag   1140 ggaatgtttg cccagctggt ggctcaaaac gtgctgttaa tcgacggccc tctgagctgg   1200
tactctgatc ctggcctggc cggcgtgagc ctgaccggcg gcctgtccta caaagaggat   1260
actaaagagc tggtggtcgc caagccggc gtgtactacg tgttcttcca actggagctg   1320

```
aggagggtcg tcgccggcga aggcagcggc tccgtgtctc tggccctgca cctccagccg    1380
ctgaggagcg ccgccggcgc cgccgccctg gccctgacgg tggacctgcc acctgcctct    1440
agcgaggcaa gaaattctgc cttcggcttc cagggcaggc tgctgcacct gagcgccggc    1500
cagcgcctgg gcgtccacct gcataccgaa gccagagccc ggcatgcctg cagctgacc     1560 cagggcgcca ccgtgctggg cctgttcaga gtgacccag agatcccgc cggcctgcct      1620 agcccaaggt ccgaaggcgg cggcggctcc ggcggcggag gctctggagg aggggggctct   1680 gccgccagcc caaggctgcg cgagggaccc gagctgtcgc ctgacgatcc agccggcctg    1740
ctggacctgc gtcagggcat gttcgcccag ctggtggctc agaacgtgct gttaatcgac    1800
ggcccactgt cttggtattc tgatcccggc ctggccggcg tgtctctgac aggaggcctg    1860
agctacaaag aggatacaaa agagctggtg gtcgctaaag ctggcgtgta ctacgtgttc    1920
ttccaactgg agctgcgcag ggtcgtcgcc ggcgagggca gcggctccgt gtctctggcc    1980
ctgcacctcc agccattacg gagcgccgcc ggcgccgccg ccctggccct gactgtggac    2040
ctgccaccag cctcctctga ggcacggaac agcgccttcg gcttccaagg cagactgctg    2100
cacctgtctg ccggccagag gctgggcgtc cacctgcaca ccgaagccag agcccggcac    2160
gcctggcagc tgactcaggg cgctaccgtg ctgggcctgt ccgcgtaac cccagagatc     2220 cctgccggcc tgcccagccc tcggtccgag                                     2250
```

```
<210> SEQ ID NO 149
<211> LENGTH: 5
<212> TYPE: PRT
<213> ORGANISM: Artificial sequence
<220> FEATURE:
<223> OTHER INFORMATION: linker amino acid sequence
<220> FEATURE:
<221> NAME/KEY: REPEAT
<222> LOCATION: (1)..(5)
<223> OTHER INFORMATION: may repeat 1-4 times

<400> SEQUENCE: 149

Gly Gly Gly Gly Ser
1               5

<210> SEQ ID NO 150
<211> LENGTH: 5
<212> TYPE: PRT
<213> ORGANISM: Artificial sequence
<220> FEATURE:
<223> OTHER INFORMATION: linker amino acid sequence

<400> SEQUENCE: 150

Gly Gly Gly Gly Ser
1               5

<210> SEQ ID NO 151
<211> LENGTH: 10
<212> TYPE: PRT
<213> ORGANISM: Artificial sequence
<220> FEATURE:
<223> OTHER INFORMATION: linker amino acid sequence

<400> SEQUENCE: 151

Gly Gly Gly Gly Ser Gly Gly Gly Gly Ser
1               5                   10

<210> SEQ ID NO 152
<211> LENGTH: 5
<212> TYPE: PRT
```

```
<213> ORGANISM: Artificial sequence
<220> FEATURE:
<223> OTHER INFORMATION: linker amino acid sequence
<220> FEATURE:
<221> NAME/KEY: REPEAT
<222> LOCATION: (1)..(5)
<223> OTHER INFORMATION: may repeat 1-3 times

<400> SEQUENCE: 152

Glu Ala Ala Ala Lys
1               5

<210> SEQ ID NO 153
<211> LENGTH: 7
<212> TYPE: PRT
<213> ORGANISM: Artificial sequence
<220> FEATURE:
<223> OTHER INFORMATION: linker amino acid sequence
<220> FEATURE:
<221> NAME/KEY: REPEAT
<222> LOCATION: (2)..(6)
<223> OTHER INFORMATION: EAAAK
<220> FEATURE:
<221> NAME/KEY: REPEAT
<222> LOCATION: (2)..(6)
<223> OTHER INFORMATION: repeat 2-5 times

<400> SEQUENCE: 153

Ala Glu Ala Ala Ala Lys Ala
1               5

<210> SEQ ID NO 154
<211> LENGTH: 12
<212> TYPE: PRT
<213> ORGANISM: Artificial sequence
<220> FEATURE:
<223> OTHER INFORMATION: linker amino acid sequence

<400> SEQUENCE: 154

Ala Glu Ala Ala Ala Lys Glu Ala Ala Ala Lys Ala
1               5                   10

<210> SEQ ID NO 155
<211> LENGTH: 46
<212> TYPE: PRT
<213> ORGANISM: Artificial sequence
<220> FEATURE:
<223> OTHER INFORMATION: linker amino acid sequence

<400> SEQUENCE: 155

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
            35                  40                  45

<210> SEQ ID NO 156
<211> LENGTH: 5
<212> TYPE: PRT
<213> ORGANISM: Artificial sequence
<220> FEATURE:
<223> OTHER INFORMATION: linker amino acid sequence

<400> SEQUENCE: 156

Pro Ala Pro Ala Pro
1               5
```

-continued

<210> SEQ ID NO 157
<211> LENGTH: 18
<212> TYPE: PRT
<213> ORGANISM: Artificial sequence
<220> FEATURE:
<223> OTHER INFORMATION: linker amino acid sequence

<400> SEQUENCE: 157

Lys Glu Ser Gly Ser Val Ser Ser Glu Gln Leu Ala Gln Phe Arg Ser
1               5                   10                  15

Leu Asp

<210> SEQ ID NO 158
<211> LENGTH: 14
<212> TYPE: PRT
<213> ORGANISM: Artificial sequence
<220> FEATURE:
<223> OTHER INFORMATION: linker amino acid sequence

<400> SEQUENCE: 158

Glu Gly Lys Ser Ser Gly Ser Gly Ser Glu Ser Lys Ser Thr
1               5                   10

<210> SEQ ID NO 159
<211> LENGTH: 12
<212> TYPE: PRT
<213> ORGANISM: Artificial sequence
<220> FEATURE:
<223> OTHER INFORMATION: linker amino acid sequence

<400> SEQUENCE: 159

Gly Ser Ala Gly Ser Ala Ala Gly Ser Gly Glu Phe
1               5                   10

<210> SEQ ID NO 160
<211> LENGTH: 229
<212> TYPE: PRT
<213> ORGANISM: Artificial sequence
<220> FEATURE:
<223> OTHER INFORMATION: hIgG4 Fc linker

<400> SEQUENCE: 160

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
        50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
        130                 135                 140

Val Ser Leu Thr Cys Leu Val Lys Gly Phe Tyr Pro Ser Asp Ile Ala

```
145                 150                 155                 160
Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 161

<400> SEQUENCE: 161

000

<210> SEQ ID NO 162

<400> SEQUENCE: 162

000

<210> SEQ ID NO 163
<211> LENGTH: 232
<212> TYPE: PRT
<213> ORGANISM: Artificial sequence
<220> FEATURE:
<223> OTHER INFORMATION: hIgG4 Fc linker

<400> SEQUENCE: 163

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 164

<400> SEQUENCE: 164

000

<210> SEQ ID NO 165

<400> SEQUENCE: 165

000

<210> SEQ ID NO 166
<211> LENGTH: 8
<212> TYPE: PRT
<213> ORGANISM: Artificial sequence
<220> FEATURE:
<223> OTHER INFORMATION: Linker amino acid sequence

<400> SEQUENCE: 166

Gly Leu Pro Ser Pro Arg Ser Glu
1               5

<210> SEQ ID NO 167
<211> LENGTH: 23
<212> TYPE: PRT
<213> ORGANISM: Artificial sequence
<220> FEATURE:
<223> OTHER INFORMATION: Linker amino acid sequence

<400> SEQUENCE: 167

Ala Cys Pro Trp Ala Val Ser Gly Ala Arg Ala Ser Pro Gly Ser Ala
1               5                   10                  15

Ala Ser Pro Arg Leu Arg Glu
            20

<210> SEQ ID NO 168
<211> LENGTH: 331
<212> TYPE: PRT
<213> ORGANISM: Artificial sequence
<220> FEATURE:
<223> OTHER INFORMATION: DSP105_V32 (4-1BBL-PD1 FUSION) amino acid
      sequence

<400> SEQUENCE: 168

Ala Ala Ser Pro Arg Leu Arg Glu Gly Pro Glu Leu Ser Pro Asp Asp
1               5                   10                  15

Pro Ala Gly Leu Leu Asp Leu Arg Gln Gly Met Phe Ala Gln Leu Val
            20                  25                  30

Ala Gln Asn Val Leu Leu Ile Asp Gly Pro Leu Ser Trp Tyr Ser Asp
        35                  40                  45

Pro Gly Leu Ala Gly Val Ser Leu Thr Gly Gly Leu Ser Tyr Lys Glu
    50                  55                  60

Asp Thr Lys Glu Leu Val Val Ala Lys Ala Gly Val Tyr Tyr Val Phe
65                  70                  75                  80

Phe Gln Leu Glu Leu Arg Arg Val Val Ala Gly Glu Gly Ser Gly Ser
                85                  90                  95
```

Val Ser Leu Ala Leu His Leu Gln Pro Leu Arg Ser Ala Ala Gly Ala
            100                 105                 110

Ala Ala Leu Ala Leu Thr Val Asp Leu Pro Pro Ala Ser Ser Glu Ala
        115                 120                 125

Arg Asn Ser Ala Phe Gly Phe Gln Gly Arg Leu Leu His Leu Ser Ala
    130                 135                 140

Gly Gln Arg Leu Gly Val His Leu His Thr Glu Ala Arg Ala Arg His
145                 150                 155                 160

Ala Trp Gln Leu Thr Gln Gly Ala Thr Val Leu Gly Leu Phe Arg Val
                165                 170                 175

Thr Pro Glu Ile Pro Ala Gly Leu Pro Ser Pro Arg Ser Glu Gly Asp
            180                 185                 190

Ser Pro Asp Arg Pro Trp Asn Pro Pro Thr Phe Ser Pro Ala Leu Leu
        195                 200                 205

Val Val Thr Glu Gly Asp Asn Ala Thr Phe Thr Cys Ser Phe Ser Asn
    210                 215                 220

Thr Ser Glu Ser Phe Val Leu Asn Trp Tyr Arg Met Ser Pro Ser Asn
225                 230                 235                 240

Gln Thr Asp Lys Leu Ala Ala Phe Pro Glu Asp Arg Ser Gln Pro Gly
                245                 250                 255

Gln Asp Cys Arg Phe Arg Val Thr Gln Leu Pro Asn Gly Arg Asp Phe
            260                 265                 270

His Met Ser Val Val Arg Ala Arg Asn Asp Ser Gly Thr Tyr Leu
        275                 280                 285

Cys Gly Ala Ile Ser Leu Ala Pro Lys Ala Gln Ile Lys Glu Ser Leu
    290                 295                 300

Arg Ala Glu Leu Arg Val Thr Glu Arg Arg Ala Glu Val Pro Thr Ala
305                 310                 315                 320

His Pro Ser Pro Ser Pro Arg Pro Ala Gly Gln
                325                 330

<210> SEQ ID NO 169
<211> LENGTH: 996
<212> TYPE: DNA
<213> ORGANISM: Artificial sequence
<220> FEATURE:
<223> OTHER INFORMATION: DSP105_V32 (4-1BBL-PD1 FUSION) nucleic acid
      sequence

<400> SEQUENCE: 169
tctgccgctt ctcccagact gagagaagga cctgagctga gccctgatga tcctgctgga    60
ctgctggatc tgcggcaggg catgtttgct cagttggtgg cccagaacgt gctgctgatc    120
gatggccctc tgtcctggta ctctgatcca ggattggctg gcgtgtccct gactggcggc    180
ctgtcttaca agaggacac caaagaactg gtggtggcca aggccggcgt gtactacgtg    240
ttctttcagc tggaactgcg gagagtggtg gctggcgaag atctggatc tgtgtctctg    300 gccctgcatc tgcagcctct gagaagtgct gcaggcgctg ctgcactggc tctgacagtt    360
gatctgcctc ctgcctcctc cgaggccaga aactccgcct ttggcttcca aggcagactg    420
ctgcacctgt ccgctggaca gagactggga gtccatctgc acacagaggc cagagctaga    480
cacgcttggc agttgacaca gggcgctaca gtgctgggcc tgtttagagt gacccctgag    540
attccagccg gcctgccatc tcctagatct gagggcgact cccctgacag accttggaac    600
cctccaacct tctctcccgc tctgctggtg gttaccgagg gcgacaatgc cacctttacc    660
tgttccttca gcaacaccct cgagtccttc gtgctgaact ggtacagaat gtcccctagc    720

-continued

```
aaccagaccg acaagctggc cgcctttcct gaggacagat ctcagccagg ccaggactgc    780
cggttcagag ttacccagct gcctaacggc cgggacttcc acatgtctgt tgtgcgggcc    840
agacggaacg actctggcac atatctgtgc ggcgccatct ctctggctcc caaggctcag    900
atcaaagagt ctctgcgggc cgagctgaga gtgacagaaa gacgagctga ggtgcccacc    960
gctcatccct caccttctcc aagacctgcc ggccag                              996
```

<210> SEQ ID NO 170
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 170

Arg Pro Ala Gly
1

<210> SEQ ID NO 171
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 171

Arg Pro Ala Gly
1

<210> SEQ ID NO 172
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 172

Gly Gln Phe Gln
1

<210> SEQ ID NO 173
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 173

Thr Leu Val Gly
1

<210> SEQ ID NO 174
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 174

Arg Leu Arg Glu

```
<210> SEQ ID NO 175
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 175

Gln Phe Gln Thr
1

<210> SEQ ID NO 176
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 176

Gln Phe Gln Thr
1

<210> SEQ ID NO 177
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 177

Thr Leu Val Gly
1

<210> SEQ ID NO 178
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 178

Ala Cys Pro Trp
1

<210> SEQ ID NO 179
<211> LENGTH: 4
<212> TYPE: PRT
<213> ORGANISM: Artificial sequence
<220> FEATURE:
<223> OTHER INFORMATION: Predicted proteolytic sites in DSP105 PD1-4-
      1BBL fusion protein

<400> SEQUENCE: 179

Gly Pro Glu Leu
1
```

PD1-4-1BBL VARIANT FUSION PROTEIN AND METHODS OF USE THEREOF

RELATED APPLICATIONS

This application is a National Phase of PCT Patent Application No. PCT/IL2019/050782 having International filing date of Jul. 11, 2019, which claims the benefit of priority under 35 USC § 119 (c) of U.S. Provisional Patent Application No. 62/696,365 filed on Jul. 11, 2018 and U.S. Provisional Patent Application No. 62/786,599 filed on Dec. 31, 2018. The contents of the above applications are all incorporated by reference as if fully set forth herein in their entirety.

SEQUENCE LISTING STATEMENT

The ASCII file, entitled 85817ReplacementSequenceListing.txt, created on Dec. 4, 2024, comprising 267,589 bytes, submitted concurrently with the filing of this application is incorporated herein by reference.

BACKGROUND OF THE INVENTION

The present invention, in some embodiments thereof, relates to a PD1-4-1BBL variant fusion protein and methods of use thereof.

Dual Signaling Proteins (DSP), also known as Signal-Converting-Proteins (SCP), which are currently known in the art as bi-functional fusion proteins that link an extracellular portion of a type I membrane protein (extracellular amino-terminus), to an extracellular portion of a type II membrane protein (extracellular carboxyl-terminus), forming a fusion protein with two active sides (see e.g. U.S. Pat. Nos. 7,569,663 and 8,039,437).

PD1 is a surface co-inhibitory receptor of the immunoglobulin super family. PD1 is expressed on T cells, B cells, monocytes, natural killer cells, dendritic cells and many tumor-infiltrating lymphocytes (TILs). PD1 has two ligands: PDL1 (also named B7H1; CD274) and PDL2 (B7DC; CD273), that are both co-inhibitory. PDL1 is expressed on resting and activated T cells, B cells, dendritic cells, macrophage, vascular endothelial cells and pancreatic islet cells. PDL1 is also known to be expressed in various types of cancers, especially in NSCLC, melanoma, renal cell carcinoma, gastric cancer, hepatocellular as well as cutaneous and various leukemia cancers, multiple myeloma and others. PDL2 expression is seen on macrophages and dendritic cells alone and is far less prevalent than PDL1 across tumor types. The expression of PDL1 is induced by multiple proinflammatory molecules, including types I and II IFN-γ, TNF-α, LPS, GM-CSF and VEGF, as well as the cytokines IL-10 and IL-4, with IFN-γ being the most potent inducer. The tumor micro-environment upregulates PDL1 expression, thereby, promoting immune suppression. In response to immune attack, cancer cells overexpress PDL1, which binds to PD1 receptor on T cells, inhibiting the activation of T-cells, thus suppressing T-cell attack and inducing tumor immune escape. PD1/PDL1 pathway regulates immune suppression by several mechanisms:

Induces apoptosis of activated T cells;
Restrains cytotoxic T lymphocytes (CTL-CD8) activity;
Inhibits the proliferation of T cells;
Facilitates T cell anergy and exhaustion;
Enhances the function of regulatory T cells; and
Restrains impaired T cell activation and IL-2 production.

4-1BBL is the activating ligand of the 4-1BB receptor (CD137), a member of the TNF receptor superfamily and a potent activation-induced T cell costimulatory molecule. 4-1BBL naturally forms a homo-trimer but signaling via 4-1BB requires significant oligomerization of 4-1BBL. 4-1BBL is present on a variety of antigen presenting cells (APCs), including dendritic cells (DCs), B cells, and macrophages. The 4-1BB receptor is not detected (<3%) on resting T cells or T cell lines; however, 4-1BB is stably upregulated when T cells are activated. 4-1BB activation upregulates survival genes, enhances cell division, induces cytokine production and prevents activation induced cell death in T-cells.

Additional background art includes:
Maute et al. PNAS. 2015 Nov. 24; 112 (47):E6506-14;
International Patent Application Publication No. WO 2018053885;
International Patent Application Publication No. WO 2018032793;
International Patent Application Publication No. WO 2018006881;
International Patent Application Publication No. WO 2013144704;
International Patent Application Publication No. WO 2016022994;
International Patent Application Publication No. WO 2010027828;
International Patent Application Publication No. WO 2018085358;
Chinese Patent Application Publication No. CN 107857819;
International Patent Application Publication No. WO 2017194641;
International Patent Application Publication No. WO 2014180288;
International Patent Application Publication No. WO2017059168;
International Patent Application Publication No. WO2001/049318;
International Patent Application Publication No. WO2016/139668;
International Patent Application Publication No. WO2014/106839;
International Patent Application Publication No. WO2012/042480;
US Patent Application Publication No. 20150183881;
US Patent Application Publication No. US20070110746;
US Patent Application Publication No. US20070036783; and
US Patent No. U.S. Pat. No. 9,562,087.

SUMMARY OF THE INVENTION

According to an aspect of some embodiments of the present invention there is provided a PD1-4-1BBL fusion protein comprising a PD1 amino acid sequence and a 4-1BBL amino acid sequence, wherein the PD1 amino acid sequence:

(a) is 123-148 amino acids in length having at least 80% identity to an amino acid sequence selected from the group consisting of SEQ ID NO: 18-21, 85, 89, 93 and 115 and does not comprise any of amino acid segments P1-L5 and F146-V150 corresponding to SEQ ID NO: 2, or is 138-145 amino acids in length having at least 80% identity to an amino acid sequence selected from the group consisting of SEQ ID NO: 18, 117 and 119 and does not comprise an amino acid segment F146-V150 corresponding to SEQ ID NO: 2; and/or (b) comprises a C to S amino acid modification in a position corresponding to amino acid 73 of SEQ ID NO: 2; and/or wherein the 4-1BBL amino acid sequence:

(aa) is 185-202 amino acids in length having at least 95% identity to an amino acid sequence selected form the group consisting of SEQ ID NOs: 22-25, is 170-197 amino acids in length having at least 80% identity to an amino acid sequence selected from the group consisting of SEQ ID NO: 127 and 129 and does not comprise an amino acid segment G198-E205 corresponding to SEQ ID NO: 3, is 170-182 amino acids in length having at least 80% identity to SEQ ID NO: 125 and does not comprise an amino acid segment A1-E23 corresponding to SEQ ID NO: 3 or is 184 amino acids in length having at least 80% identity to SEQ ID NO: 123; and/or (bb) comprises three repeats of a 4-1BBL amino acid sequence;

and wherein the fusion protein is capable of at least one of:
(i) binding PDL1 and 4-1BB;
(ii) activating the 4-1BB signaling pathway in a cell expressing the 4-1BB; and/or
(iii) co-stimulating immune cells expressing the 4-1BB.

According to an aspect of some embodiments of the present invention there is provided a PD1-4-1BBL fusion protein comprising a PD1 amino acid sequence and a 4-1BBL amino acid sequence, wherein the PD1 amino acid sequence:

(a) is 123-148 amino acids in length having at least 80% identity to an amino acid sequence selected from the group consisting of SEQ ID NO: 18-21, 85, 89 and 93 and does not comprise any of amino acid segments P1-L5 and F146-V150 corresponding to SEQ ID NO: 2 and/or (b) comprises a C to S amino acid modification in a position corresponding to amino acid 73 of SEQ ID NO: 2; and/or wherein the 4-1BBL amino acid sequence is 185-202 amino acids in length having at least 95% identity to an amino acid sequence selected form the group consisting of SEQ ID NOs: 22-25; and wherein the fusion protein is capable of at least one of:
(i) binding PDL1 and 4-1BB;
(ii) activating the 4-1BB signaling pathway in a cell expressing the 4-1BB; and/or
(iii) co-stimulating immune cells expressing the 4-1BB.

According to an aspect of some embodiments of the present invention there is provided a PD1-4-1BBL fusion protein comprising a PD1 amino acid sequence and a 4-1BBL amino acid sequence, wherein the PD1 amino acid sequence is 123-148 amino acids in length having at least 80% identity to an amino acid sequence selected from the group consisting of SEQ ID NO: 18-21 and does not comprise any of amino acid segments P1-L5 and F146-V150 corresponding to SEQ ID NO: 2; and/or wherein the 4-1BBL amino acid sequence is 185-202 amino acids in length having at least 95% identity to an amino acid sequence selected form the group consisting of SEQ ID NOs: 22-25; and wherein the fusion protein is capable of at least one of:
(i) binding PDL1 and 4-1BB;
(ii) activating the 4-1BB signaling pathway in a cell expressing the 4-1BB; and/or
(iii) co-stimulating immune cells expressing the 4-1BB.

According to an aspect of some embodiments of the present invention there is provided a PD1-4-1BBL fusion protein comprising a (GGGGS), (n=1-4) linker between the PD1 and the 4-1BBL, wherein the fusion protein is capable of at least one of:
(i) binding PDL1 and 4-1BB;
(ii) activating the 4-1BB signaling pathway in a cell expressing the 4-1BB; and/or
(iii) co-stimulating immune cells expressing the 4-1BB.

According to some embodiments of the invention, the PD1-4-1BBL fusion protein amino acid sequence comprises an amino acid sequence having at least 80% identity to SEQ ID NO: 145.

According to some embodiments of the invention, the PD1-4-1BBL fusion protein amino acid sequence comprises SEQ ID NO: 145.

According to some embodiments of the invention, the PD1-4-1BBL fusion protein amino acid sequence consists of SEQ ID NO: 145.

According to an aspect of some embodiments of the present invention there is provided an isolated polypeptide comprising a PD1 amino acid sequence, wherein the PD1 amino acid sequence is 123-148 amino acids in length having at least 80% identity to an amino acid sequence selected from the group consisting of SEQ ID NO: 18-21, 85, 89, 93 and 115 and does not comprise any of amino acid segments P1-L5 and F146-V150 corresponding to SEQ ID NO: 2, or is 138-145 amino acids in length having at least 80% identity to an amino acid sequence selected from the group consisting of SEQ ID NO: 18, 117 and 119 and does not comprise an amino acid segment F146-V150 corresponding to SEQ ID NO: 2; and optionally comprises a C to S amino acid modification in a position corresponding to amino acid 73 of SEQ ID NO: 2; and wherein the polypeptide is capable of binding PDL1.

According to an aspect of some embodiments of the present invention there is provided an isolated polypeptide comprising a PD1 amino acid sequence, wherein the PD1 amino acid sequence is 123-148 amino acids in length having at least 80% identity to an amino acid sequence selected from the group consisting of SEQ ID NO: 18-21, 85, 89 and 93 and does not comprise any of amino acid segments P1-L5 and F146-V150 corresponding to SEQ ID NO: 2; and optionally comprises a C to S amino acid modification in a position corresponding to amino acid 73 of SEQ ID NO: 2; and wherein the polypeptide is capable of binding PDL1.

According to an aspect of some embodiments of the present invention there is provided an isolated polypeptide comprising a PD1 amino acid sequence, wherein the PD1 amino acid sequence is 123-148 amino acids in length having at least 80% identity to an amino acid sequence selected from the group consisting of SEQ ID NO: 18-21 and does not comprise any of amino acid segments P1-L5 and F146-V150 corresponding to SEQ ID NO: 2; and wherein the polypeptide is capable of binding PDL1.

According to an aspect of some embodiments of the present invention there is provided an isolated polypeptide comprising a 4-1BBL amino acid sequence, wherein the 4-1BBL amino acid sequence is 185-202 amino acids in length having at least 95% identity to an amino acid sequence selected form the group consisting of SEQ ID NOs: 22-25, is 170-197 amino acids in length having at least 80% identity to an amino acid sequence selected from the group consisting of SEQ ID NO: 127 and 129 and does not comprise an amino acid segment G198-E205 corresponding to SEQ ID NO: 3, or is 170-182 amino acids in length having at least 80% identity to SEQ ID NO: 125 and does not comprise an amino acid segment A1-E23 corresponding to SEQ ID NO: 3; and optionally comprises three repeats of the 4-1BBL amino acid sequence; and wherein the polypeptide is capable of at least one of:
  (i) binding 4-1BB.
  (ii) activating the 4-1BB signaling pathway in a cell expressing the 4-1BB; and/or
  (iii) co-stimulating immune cells expressing the 4-1BB.

According to an aspect of some embodiments of the present invention there is provided an isolated polypeptide comprising a 4-1BBL amino acid sequence, wherein the 4-1BBL amino acid sequence is 185-202 amino acids in length having at least 95% identity to an amino acid sequence selected from the group consisting of SEQ ID NOs: 22-25; and wherein the polypeptide is capable of at least one of:
  (i) binding 4-1BB,
  (ii) activating the 4-1BB signaling pathway in a cell expressing the 4-1BB; and/or
  (iii) co-stimulating immune cells expressing the 4-1BB.

According to some embodiments of the invention, the PD1 amino acid sequence is no more than 140 amino acids long.

According to some embodiments of the invention, the PD1 amino acid sequence is at least 126 amino acids long.

According to some embodiments of the invention, the PD1 amino acid sequence comprises the SEQ ID NO: 18, 19, 20 or 21.

According to some embodiments of the invention, the PD1 amino acid sequence comprises the SEQ ID NO: 18, 19, 20, 21, 85, 89 or 93.

According to some embodiments of the invention, the PD1 amino acid sequence comprises the SEQ ID NO: 18, 19, 20, 21, 85, 89, 93 or 115.

According to some embodiments of the invention, the PD1 amino acid sequence comprises the SEQ ID NO: 117 or 119.

According to some embodiments of the invention, the PD1 amino acid sequence comprises SEQ ID NO: 75, 79, 81, 83, 87, 91 or 95.

According to some embodiments of the invention, the PD1 amino acid sequence comprises SEQ ID NO: 75, 83, 87, 91 or 95.

According to some embodiments of the invention, the PD1 amino acid sequence comprises SEQ ID NO: 73.

According to some embodiments of the invention, the PD1 amino acid sequence comprises the SEQ ID NO: 18.

According to some embodiments of the invention, the PD1 amino acid sequence consists of the SEQ ID NO: 18, 19, 20 or 21.

According to some embodiments of the invention, the PD1 amino acid sequence consists of the SEQ ID NO: 18, 19, 20, 21, 85, 89 or 93.

According to some embodiments of the invention, the PD1 amino acid sequence consists of the SEQ ID NO: 18, 19, 20, 21, 85, 89, 93 or 115.

According to some embodiments of the invention, the PD1 amino acid sequence consists of the SEQ ID NO: 117 or 119.

According to some embodiments of the invention, the PD1 amino acid sequence consists of SEQ ID NO: 75, 79, 81, 83, 87, 91 or 95.

According to some embodiments of the invention, the PD1 amino acid sequence consists of SEQ ID NO: 75, 83, 87, 91 or 95.

According to some embodiments of the invention, the PD1 amino acid sequence consists of SEQ ID NO: 73.

According to some embodiments of the invention, the PD1 amino acid sequence consists of the SEQ ID NO: 18.

According to some embodiments of the invention, the 4-1BBL amino acid sequence has at least 95% identity to an amino acid sequence selected form the group consisting of SEQ ID NO: 22-24.

According to some embodiments of the invention, the 4-1BBL amino acid sequence does not comprise any of amino acid residues A1-V6 or A1-G14 corresponding to SEQ ID NO: 3.

According to some embodiments of the invention, the 4-1BBL amino acid sequence comprises the SEQ ID NO: 22, 23, 24 or 25.

According to some embodiments of the invention, the 4-1BBL amino acid sequence consists of the SEQ ID NO: 22, 23, 24 or 25.

According to some embodiments of the invention, the 4-1BBL amino acid sequence comprises the SEQ ID NO: 125, 127 or 129.

According to some embodiments of the invention, the 4-1BBL amino acid sequence consists of the SEQ ID NO: 125, 127 or 129.

According to some embodiments of the invention, the 4-1BBL amino acid sequence comprises the SEQ ID NO: 123.

According to some embodiments of the invention, the 4-1BBL amino acid sequence consists of the SEQ ID NO: 123.

According to some embodiments of the invention, the PD1-4-1BBL fusion protein comprises a linker between the PD1 and the 4-1BBL.

According to some embodiments of the invention, the PD1-4-1BBL fusion protein or the isolated polypeptide comprising a linker between each of the three repeats of the 4-1BBL amino acid sequence.

According to some embodiments of the invention, the linker has a length of one to six amino acids.

According to some embodiments of the invention, the linker is a single amino acid linker.

According to some embodiments of the invention, the linker is glycine.

According to some embodiments of the invention, the linker is not an Fc domain of an antibody or a fragment thereof.

According to some embodiments of the invention, the linker is an Fc domain of an antibody or a fragment thereof.

According to some embodiments of the invention, the linker is a $(GGGGS)_n$ (n=1-4) (SEQ ID NO: 149) linker.

According to some embodiments of the invention, the PD1-4-1BBL fusion protein being in a form of at least a homo-trimer.

According to some embodiments of the invention, the at least homo-trimer is at least 100 kD in molecular weight as determined by SEC-MALS.

According to some embodiments of the invention, the PD1-4-1BBL fusion protein or the isolated polypeptide being soluble.

According to some embodiments of the invention, the production yield of the fusion protein is at least 1.5 fold higher than the production yield of SEQ ID NO: 5 under the same production conditions, the production conditions comprise expression in a mammalian cell and culturing at 32-37° C. 5-10% $CO_2$ for 5-13 days.

According to some embodiments of the invention, the amount of aggregates of the fusion protein is at least 20% lower than the amount of aggregates of SEQ ID NO: 5 under the same production conditions, the aggregates are of at least 300 kDa in molecular weight and the production conditions comprise expression in a mammalian cell and culturing at 32-37° C., 5-10% $CO_2$ for 5-13 days.

According to some embodiments of the invention, the PD1-4-1BBL fusion protein amino acid sequence comprises an amino acid sequence having at least 80% identity to an amino acid sequence selected from the group consisting of SEQ ID NO: 12, 14, 16, 44-56, 97, 101, 103, 105, 107, 111, 113, 133, 135, 137, 139, 141, 143 and 147.

According to some embodiments of the invention, the PD1-4-1BBL fusion protein amino acid sequence comprises an amino acid sequence having at least 80% identity to an amino acid sequence selected from the group consisting of SEQ ID NO: 133, 135, 137, 139, 141, 143 and 147.

According to some embodiments of the invention, the PD1-4-1BBL fusion protein amino acid sequence comprises an amino acid sequence having at least 80% identity to an amino acid sequence selected from the group consisting of SEQ ID NO: 12, 14, 16, 44-56, 97, 101, 103, 105, 107 and 111.

According to some embodiments of the invention, the PD1-4-1BBL fusion protein amino acid sequence comprises an amino acid sequence having at least 80% identity to an amino acid sequence selected from the group consisting of SEQ ID NO: 97, 101, 103, 105, 107 and 111.

According to some embodiments of the invention, the PD1-4-1BBL fusion protein amino acid sequence comprises an amino acid sequence having at least 80% identity to an amino acid sequence selected from the group consisting of SEQ ID NO: 97, 101, 103, 105 and 107.

According to some embodiments of the invention, the PD1-4-1BBL fusion protein amino acid sequence comprises an amino acid sequence having at least 80% identity to an amino acid sequence selected from the group consisting of SEQ ID NO: 12, 14, 16 and 44-56.

According to some embodiments of the invention, the PD1-4-1BBL fusion protein amino acid sequence comprises an amino acid sequence having at least 80% identity to an amino acid sequence selected from the group consisting of SEQ ID NO: 12, 14 and 16.

According to some embodiments of the invention, the at least 80% identity comprises at least 90% identity.

According to some embodiments of the invention, the at least 80% identity comprises at least 95% identity.

According to some embodiments of the invention, the PD1-4-1BBL fusion protein amino acid sequence comprises an amino acid sequence selected from the group consisting of SEQ ID NO: 12, 14, 16, 44-56, 97, 101, 103, 105, 107, 111, 113, 133, 135, 137, 139, 141, 143 and 147.

According to some embodiments of the invention, the PD1-4-1BBL fusion protein amino acid sequence comprises an amino acid sequence selected from the group consisting of SEQ ID NO: 133, 135, 137, 139, 141, 143 and 147.

According to some embodiments of the invention, the PD1-4-1BBL fusion protein amino acid sequence comprises an amino acid sequence selected from the group consisting of SEQ ID NO: 12, 14, 16, 44-56, 97, 101, 103, 105, 107 and 111.

According to some embodiments of the invention, the PD1-4-1BBL fusion protein amino acid sequence comprises an amino acid sequence selected from the group consisting of SEQ ID NO: 97, 101, 103, 105, 107 and 111.

According to some embodiments of the invention, the PD1-4-1BBL fusion protein amino acid sequence comprises an amino acid sequence selected from the group consisting of SEQ ID NO: 97, 101, 103, 105 and 107.

According to some embodiments of the invention, the PD1-4-1BBL fusion protein amino acid sequence comprises an amino acid sequence selected from the group consisting of SEQ ID NO: 12, 14, 16 and 44-56.

According to some embodiments of the invention, the PD1-4-1BBL fusion protein amino acid sequence comprises an amino acid sequence selected from the group consisting of SEQ ID NO: 12, 14 and 16.

According to some embodiments of the invention, the PD1-4-1BBL fusion protein amino acid sequence consists of an amino acid sequence selected from the group consisting of SEQ ID NO: 12, 14, 16, 44-56, 97, 101, 103, 105, 107, 111, 113, 133, 135, 137, 139, 141, 143 and 147.

According to some embodiments of the invention, the PD1-4-1BBL fusion protein amino acid sequence consists of an amino acid sequence selected from the group consisting of SEQ ID NO: 133, 135, 137, 139, 141, 143 and 147.

According to some embodiments of the invention, the PD1-4-1BBL fusion protein amino acid sequence consists of an amino acid sequence selected from the group consisting of SEQ ID NO: 12, 14, 16, 44-56, 97, 101, 103, 105, 107 and 111.

According to some embodiments of the invention, the PD1-4-1BBL fusion protein amino acid sequence consists of an amino acid sequence selected from the group consisting of SEQ ID NO: 97, 101, 103, 105, 107 and 111.

According to some embodiments of the invention, the PD1-4-1BBL fusion protein amino acid sequence consists of an amino acid sequence selected from the group consisting of SEQ ID NO: 97, 101, 103, 105 and 107.

According to some embodiments of the invention, the PD1-4-1BBL fusion protein amino acid sequence consist of an amino acid sequence selected from the group consisting of SEQ ID NO: 12, 14, 16 and 44-56.

According to some embodiments of the invention, the PD1-4-1BBL fusion protein amino acid sequence consist of an amino acid sequence selected from the group consisting of SEQ ID NO: 12, 14 and 16.

According to an aspect of some embodiments of the present invention there is provided a polynucleotide encoding the PD1-4-1BBL fusion protein or the isolated polypeptide.

According to an aspect of some embodiments of the present invention there is provided a nucleic acid construct comprising the polynucleotide, and a regulatory element for directing expression of the polynucleotide in a host cell.

According to some embodiments of the invention, the polynucleotide comprises a nucleic acid sequence selected from the group consisting of SEQ ID NO: 57-72, 98, 102, 104, 106, 108, 112, 114, 134, 136, 138, 140, 142, 144 and 148.

According to some embodiments of the invention, the polynucleotide comprises a nucleic acid sequence selected from the group consisting of SEQ ID NO: 57-72, 98, 102, 104, 106, 108 and 112.

According to some embodiments of the invention, the polynucleotide comprises a nucleic acid sequence selected from the group consisting of SEQ ID NO: 98, 102, 104, 106, 108 and 112.

According to some embodiments of the invention, the polynucleotide comprises a nucleic acid sequence selected from the group consisting of SEQ ID NO: 98, 102, 104, 106 and 108.

According to some embodiments of the invention, the polynucleotide comprises a nucleic acid sequence selected from the group consisting of SEQ ID NO: 57-72.

According to some embodiments of the invention, the polynucleotide comprises a nucleic acid sequence selected from the group consisting of SEQ ID NO: 70-72.

According to some embodiments of the invention, the polynucleotide comprises a nucleic acid sequence selected from the group consisting of SEQ ID NO: 134, 136, 138, 140, 142, 144 and 148.

According to some embodiments of the invention, the polynucleotide comprises SEQ ID NO: 146.

According to an aspect of some embodiments of the present invention there is provided a host cell comprising the PD1-4-1BBL fusion protein or the polypeptide or the polynucleotide or the nucleic acid construct.

According to an aspect of some embodiments of the present invention there is provided a method of producing a PD1-4-1BBL fusion protein or a polypeptide, the method comprising expressing in a host cell the polynucleotide or the nucleic acid construct.

According to some embodiments of the invention, the method comprising isolating the fusion protein or the polypeptide.

According to an aspect of some embodiments of the present invention there is provided a method of treating a disease that can benefit from activating immune cells comprising administering to a subject in need thereof the PD1-4-1BBL fusion protein or the isolated polypeptide, the polynucleotide or the nucleic acid construct or the host cell.

According to some embodiments of the invention, the method further comprising administering to the subject a therapeutic agent for treating the disease.

According to an aspect of some embodiments of the present invention there is provided the PD1-4-1BBL fusion protein or the isolated polypeptide, the polynucleotide or the nucleic acid construct or the host cell, for use in treating a disease that can benefit from activating immune cells.

According to some embodiments of the invention, the composition further comprising a therapeutic agent for treating the disease.

According to an aspect of some embodiments of the present invention there is provided an article of manufacture comprising a packaging material packaging a therapeutic agent for treating a disease that can benefit from activating immune cells; and the PD1-4-1BBL fusion protein or the isolated polypeptide, the polynucleotide or the nucleic acid construct or the host cell.

According to some embodiments of the invention, cells of the disease express PDL1.

According to some embodiments of the invention, the disease comprises a hyper-proliferative disease.

According to some embodiments of the invention, the hyper-proliferative disease comprises sclerosis, fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to some embodiments of the invention, the hyper-proliferative disease comprises cancer.

According to some embodiments of the invention, the cancer is selected from the group consisting of lymphoma, leukemia and carcinoma.

According to some embodiments of the invention, the disease comprises a disease associated with immune suppression or medication induced immunosuppression.

According to some embodiments of the invention, the disease comprises HIV, Measles, influenza, LCCM, RSV, Human Rhinoviruses, EBV, CMV or Parvo viruses.

According to some embodiments of the invention, the disease comprises an infection.

According to an aspect of some embodiments of the present invention there is provided a method of activating immune cells, the method comprising in-vitro activating immune cells in the presence of the PD1-4-1BBL fusion protein or the isolated polypeptide, the polynucleotide or the nucleic acid construct or the host cell.

According to some embodiments of the invention, the activating is in the presence of cells expressing PDL1 or exogenous PDL1.

According to some embodiments of the invention, the cells expressing the PDL1 comprise pathologic cells.

According to some embodiments of the invention, the pathologic cells comprise cancer cells.

According to some embodiments of the invention, the activating is in the presence of an anti-cancer agent.

According to some embodiments of the invention, the therapeutic agent for treating the disease or the anti-cancer agent comprises an antibody.

According to some embodiments of the invention, the antibody is selected from the group consisting rituximab, cetuximab, trastuzumab, edrecolomab, almetuzumab, gemtuzumab, ibritumomab, panitumumab, Belimumab, Bevacizumab, Bivatuzumab mertansine, Blinatumomab, Blontuvetmab, Brentuximab vedotin, Catumaxomab, Cixutumumab, Daclizumab, Adalimumab, Bezlotoxumab, Certolizumab pegol, Citatuzumab bogatox, Daratumumab, Dinutuximab, Elotuzumab, Ertumaxomab, Etaracizumab, Gemtuzumab ozogamicin, Girentuximab, Necitumumab, Obinutuzumab, Ofatumumab, Pertuzumab, Ramucirumab, Siltuximab, Tositumomab, Trastuzumab and ipilimumab.

According to some embodiments of the invention, the antibody is selected from the group consisting of rituximab and cetuximab.

According to some embodiments of the invention, the therapeutic agent for treating the disease or the anti-cancer agent comprises an IMiD (e.g. Thalidomide, Lenalidomide, Pomalidomide).

According to some embodiments of the invention, the method comprising adoptively transferring the immune cells following the activating to a subject in need thereof.

According to some embodiments of the invention, the immune cells comprise T cells. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic representation of the PD1-4-1BBL fusion protein referred to herein as "DSP105" (SEQ ID NO: 5) comprising an N-terminal signal peptide and a His-tag (SEQ ID NO: 26). Shown the signal peptide (black underlined, SEQ ID NO: 4), the N-terminal His-tag (black bold), the PD1 domain (red. SEQ ID NO: 2), the glycine linker (black) and the 4-1BBL domain (blue, SEQ ID NO: 3) and FIGS. 2A, 2B, 2C and 2D demonstrate the predicted 3D structure of DSP105 (SEQ ID NO: 5). FIG. 2A is a schematic 3D model. PD1 is shown in grey ribbons, PDL1 (PD1 ligand) is shown in green ribbons, 4-1BBL is shown in blue ribbons and 2 additional copies of 4-1BBL (forming the trimer) are shown in light blue. FIG. 2B is a schematic, full atomic 3D model. FIGS. 2C-D are schematic 3D models. The X-ray resolved domains are represented by its surface and colored by a hydrophobicity scale-blue (most hydrophilic) to Brown (Hydrophobic).

FIG. 3 is a schematic representation of the domain and segments identified in DSP105 (SEQ ID NO: 5). An Ig-like V-type domain is highlighted in light blue (the underlined sequence was resolved in X-ray), An X-ray resolved part is highlighted in grey and flanking/unstructured regions are marked with red boxes.

FIG. 4 demonstrates the predicted 3D structure of PD1-4-1BBL variant fusion protein referred to herein as "DSP105_var1" (SEQ ID NO: 12). In the upper panel, the X-ray resolved domains are displayed in surface representation colored by hydrophobicity scale-Blue (most hydrophilic) to Brown (Hydrophobic). PDL1 (PD1 ligand) is presented in green ribbons. In the lower panel, 4-1BBL is presented in red ribbons, and PD1 in blue ribbons.

FIG. 5 demonstrates the predicted 3D structure of PD1-4-1BBL variant fusion protein referred to herein as "DSP105_var2" (SEQ ID NO: 14). The color code is the same as in FIG. 4.

FIG. 6 demonstrates the predicted 3D structure of PD1-4-1BBL variant fusion protein referred to herein as "DSP105_var3" (SEQ ID NO: 16). The color code is the same as in FIG. 4.

Figure 7:
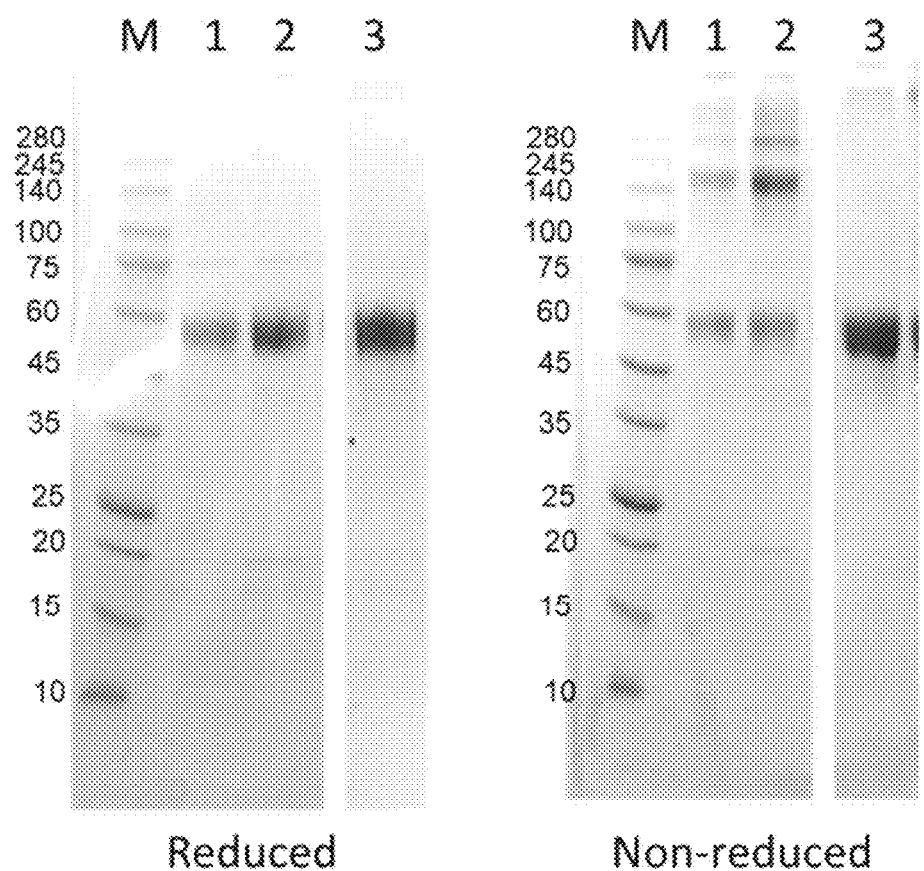
Figure 8A:
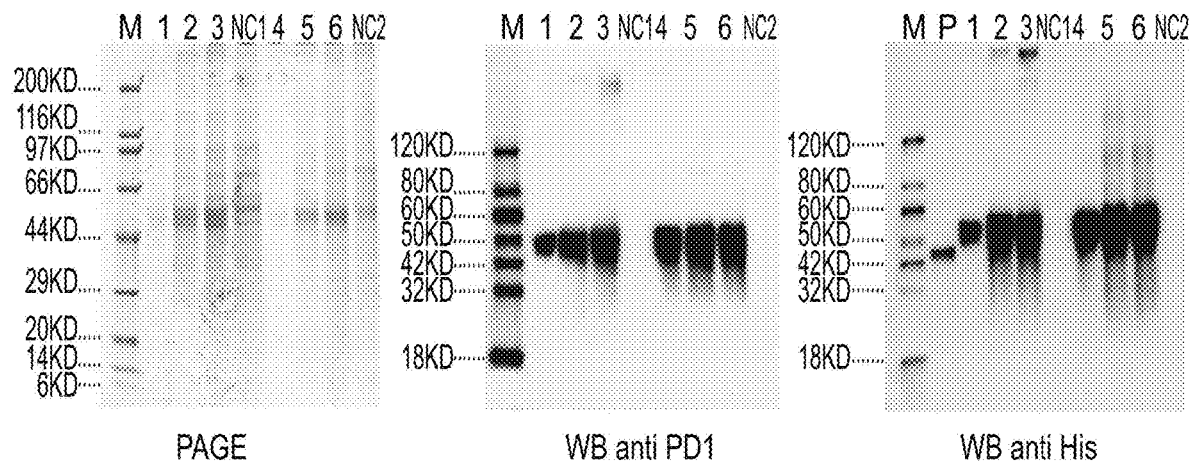
Figure 8B:
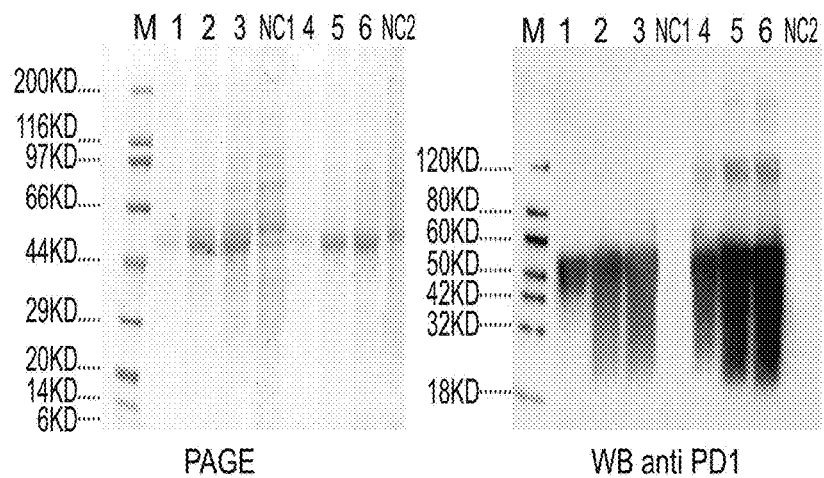
Figure 8C:
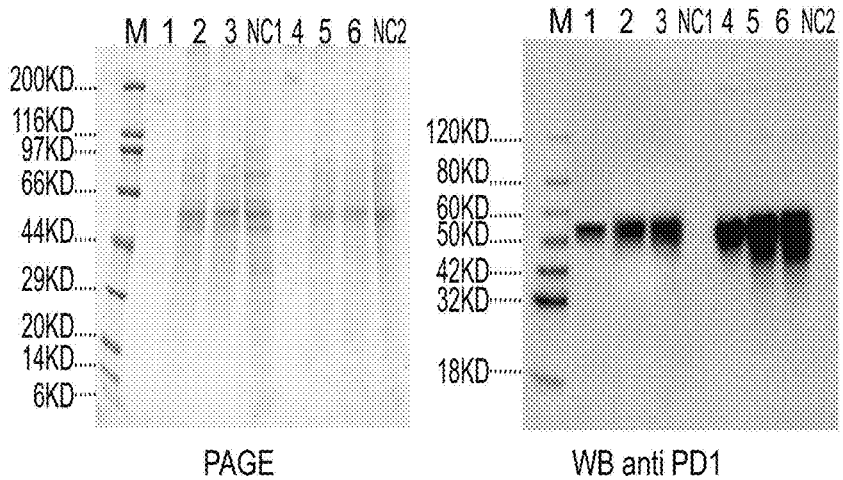
Figure 8D:
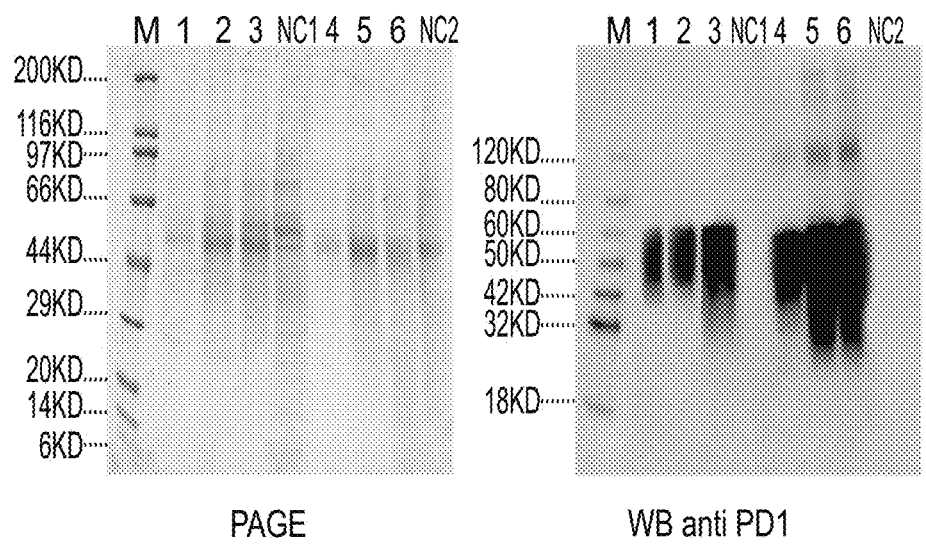
Figure 8E:
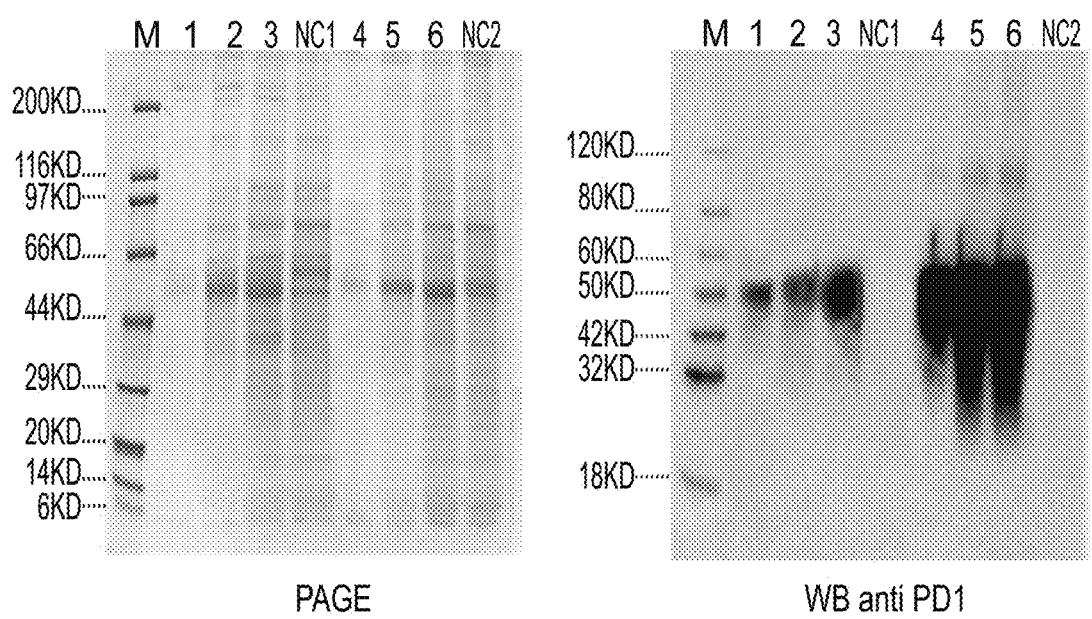

FIG. 7 presents images of SDS-PAGE analysis of N-terminal His-tagged DSP105 (SEQ ID NO: 1), expressed in Expi293 cells; and N-terminal His-tagged DSP105_var17 (SEQ ID NO: 99), expressed in CHO-3E7. Both fusion proteins were purified by a single step affinity purification on a Nickel column and separated under reducing and non-reducing conditions, as indicated. The samples presented in the images are as follows: Lane M-molecular weight marker; Lanes 1-2: Two separate preparations of N-terminal His-tagged DSP105 (SEQ ID NO: 1), Lane 3-N-terminal His-tagged DSP105_var17 (SEQ ID NO: 99).

FIGS. 8A, 8B, 8C, 8D AND 8E present images of SDS-PAGE analysis (marked as PAGE) and western blot (marked as WB) analysis using the indicated antibody of the PD1-4-1BBL variant fusion proteins produced in CHO-3E7 cells. Shown are PD1-4-1BBL variant fusion proteins referred to herein as "N-terminal His-tagged DSP105_var17" (SEQ ID NO: 99, FIG. 8A), "DSP105_var18" (SEQ ID NO: 101, FIG. 8B), "DSP105_var19" (SEQ ID NO: 103, FIG. 8C), "DSP105_var20" (SEQ ID NO: 105, FIG. 8D) and "DSP105_var23" (SEQ ID NO: 113, FIG. 8E) under reducing or non-reducing conditions. The samples presented in the images are as follows: Lane M—molecular weight marker; Lanes 1 to 3—cell culture supernatants collected on day 2, day 4 and day 5 post-transfection, respectively, under reducing conditions; Lane NC1—negative control under reducing conditions; Lanes 4 to 6—cell culture supernatants collected on day 2, day 4 and day 5 post-transfection, respectively, under non-reducing conditions; Lane NC2—negative control under non-reducing conditions; and lane P—multiple-tag (GenScript, Cat.No. M0101) as a positive control.

Figure 9A:
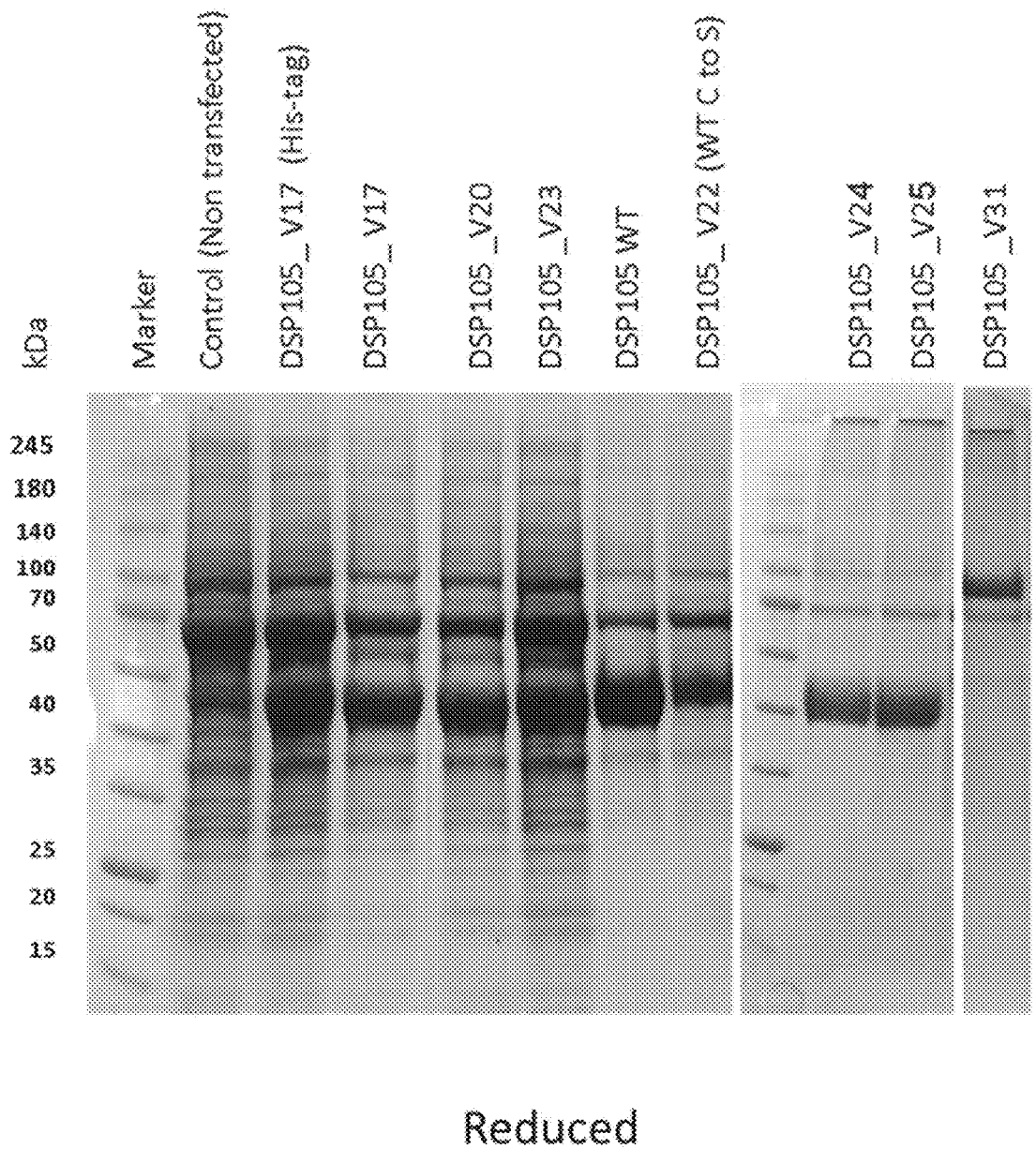

FIGS. 9A-B present images of SDS-PAGE analysis of the PD1-4-1BBL variant fusion proteins produced in Expi293F cells. Shown are PD1-4-1BBL variant fusion proteins referred to herein as "N-terminal His-tagged DSP105_var17" (SEQ ID NO: 99), "DSP105_var17" (SEQ ID NO: 97), "DSP105_var20" (SEQ ID NO: 105), "DSP105_var23" (SEQ ID NO: 113), "His-tagged DSP105_var22" (SEQ ID NO: 110), "His-tagged DSP105" (SEQ ID NO: 1), "DSP105_var24" (SEQ ID NO: 133), "DSP105_var25" (SEQ ID NO: 135) and "DSP105_var31" (SEQ ID NO: 147), under reducing (FIG. 9A) or non-reducing (FIG. 9B) conditions.

FIGS. 10A, 10B and 10C present flow cytometric analysis demonstrating DSP105_var17 (SEQ ID NO: 99) binding to PDL1 or 41BB expressing cells. FIG. 10A shows expression of the indicated receptors on DLD1-PDL1 or HT1080-41BB cell lines. The surface expression level of PDL1 or 41BB was determined by immuno-staining of each cell line with the corresponding antibodies, followed by flow cytometric analysis. FIGS. 10B-C demonstrate binding of N-terminal His-tagged DSP105_var17 (SEQ ID NO: 99) to DLD1-PD1 or to HT1080-41BB cell lines.

FIG. 11 presents flow cytometric analysis demonstrating expression of the 4-1BB receptor on HT1080-4-1BB cell line.

Figure 12:
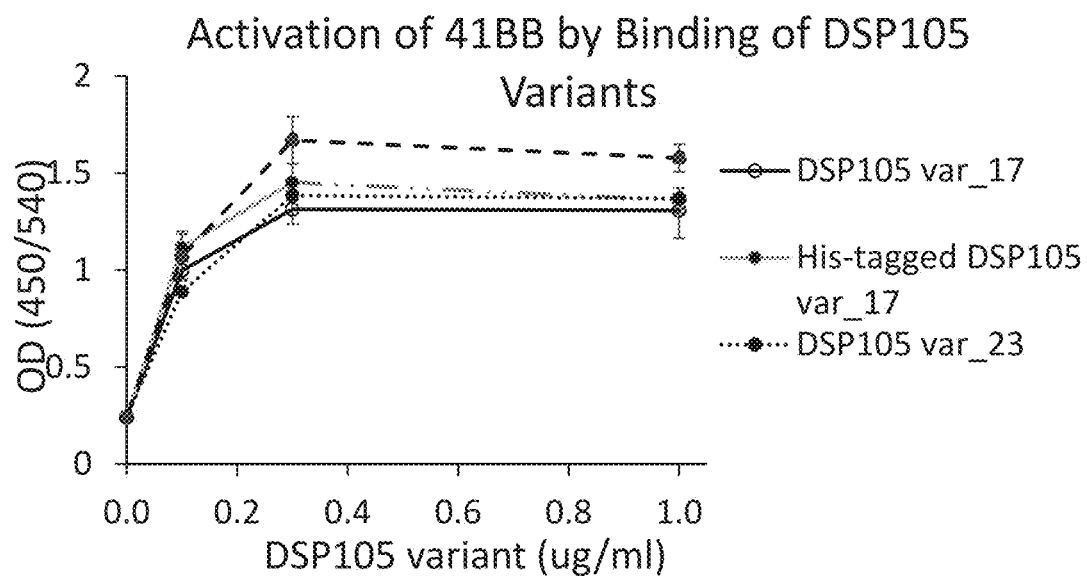

FIG. 12 presents a graph demonstrating that the N-terminal His-tagged DSP105_var17 protein (SEQ ID NO: 99), DSP105 var_17 protein (SEQ ID NO: 97), DSP105 var_21 protein (SEQ ID NO: 107) and His-tagged PD1-4-1BBL var_22 (SEQ ID NO: 110), promote 4-1BBL/4-1BB signaling as demonstrated by OD values indicating IL-8 secretion levels from HT1080-4-1BB cells, following binding of the DSP105 molecules.

Figure 13A:
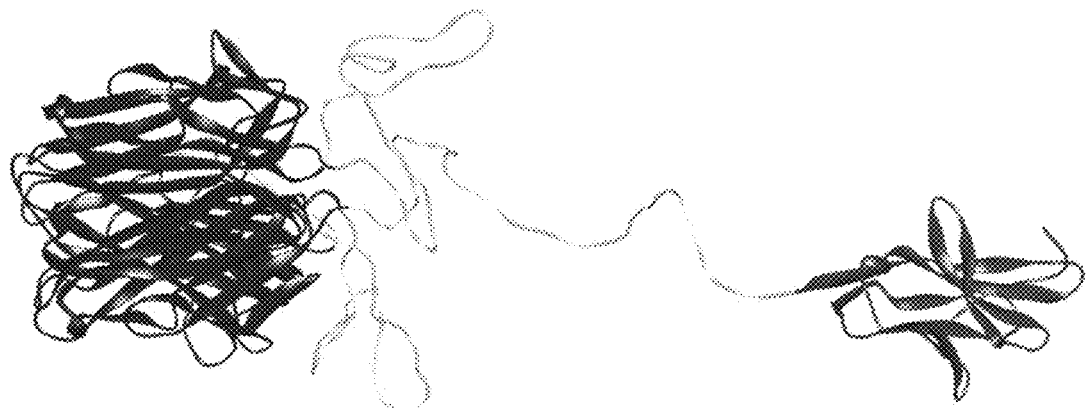
Figure 13B:
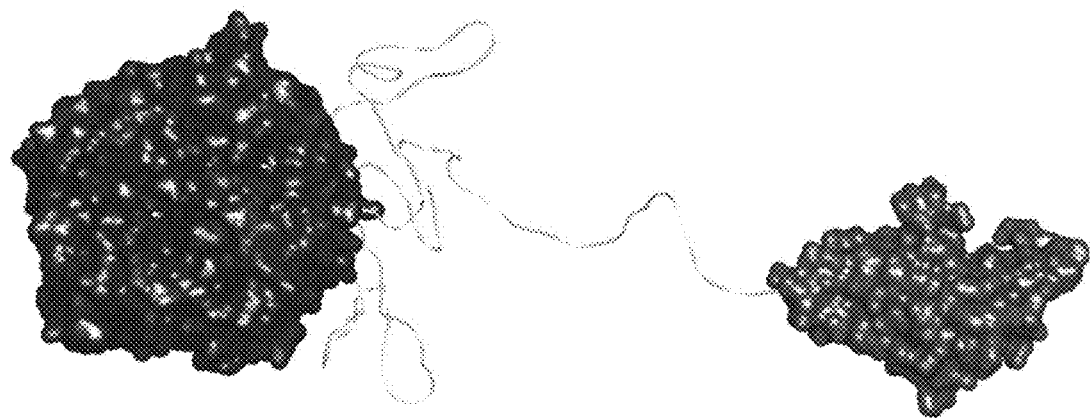
Figure 13C:
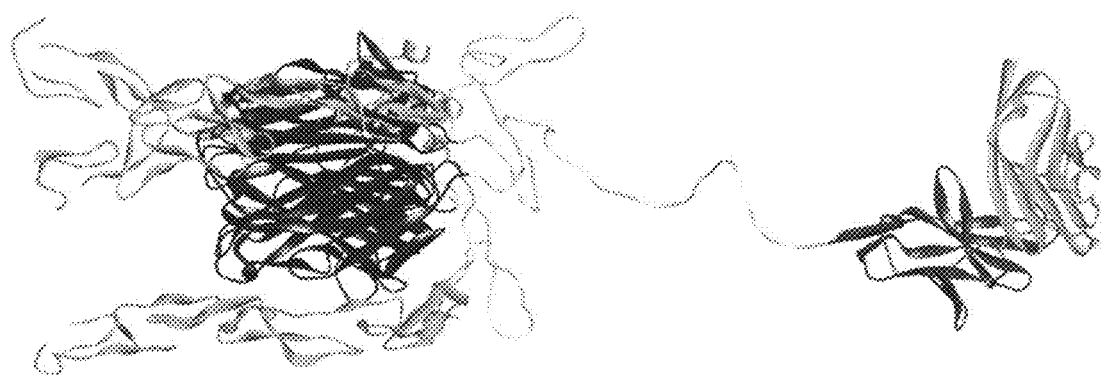
Figure 13D:
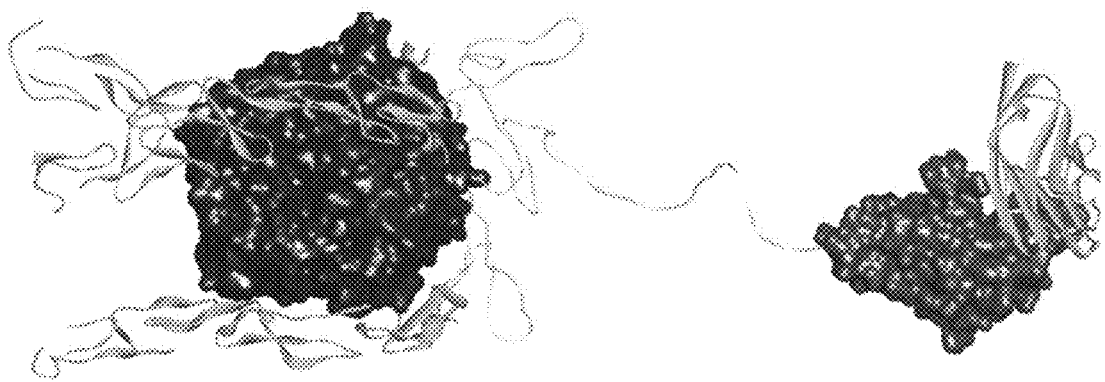

FIGS. 13A, 13B, 13C and 13D demonstrate the predicted 3D structure of the PD1-4-1BBL variant fusion referred to herein as "DSP105_V31" (SEQ ID NO: 147). FIG. 13A is a schematic 3D ribbon model. PD1 is represented in dark grey ribbons (right-hand side), 41BB-L is represented in black ribbons (left-hand side), linker segments are represented in white ribbons between the structural elements of PD1 and 41BB-L. FIG. 13B is a schematic 3D surface display model. PD1 is represented in a dark grey surface display (right-hand side), 41BB-L is represented in a black surface display (left-hand side), linker segments are represented in white ribbons between the structural elements of PD1 and 41BB-L. FIG. 13C is a schematic 3D ribbon model of the fusion protein and its binding counterparts. PD1 is represented in dark grey ribbons (right-hand side), 41BB-L is represented in black ribbons (left-hand side), linker segments are represented in white ribbons between the structural elements of PD1 and 41BB-L, PD-L1 bound to PD1 is represented in grey ribbons (right-hand side) and three 41BB receptors are represented in grey ribbons in complex with 41BB-L (left-hand side). FIG. 13D is a schematic 3D surface display model of the fusion protein and its binding counterparts. PD1 is represented in a dark grey surface display (right-hand side), 41BB-L is represented in a black surface display (left-hand side), 'linker segments are represented in white ribbons between the structural elements of PD1 and 41BB-L, PD-L1 bound to PD1 is represented in grey ribbons (right-hand side) and three 41BB receptors are represented in grey ribbons in complex with 41BB-L (left-hand side).

DESCRIPTION OF DETAILED EMBODIMENTS OF THE INVENTION

The present invention, in some embodiments thereof, relates to a PD1-4-1BBL variant fusion protein and methods of use thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Dual Signaling Proteins (DSP), also known as Signal-Converting-Proteins (SCP), which are currently known in the art as bi-functional fusion proteins that link an extracellular portion of a type I membrane protein (extracellular amino-terminus), to an extracellular portion of a type II membrane protein (extracellular carboxyl-terminus), forming a fusion protein with two active sides.

Employing structural-functional tools, the present inventors were able to generate PD1-4-1BBL fusion proteins comprising a PD1 variant and/or a 4-1BBL variant with improved production characteristics (e.g. higher yield, lower percentage of aggregates); and which can be advantageously used for activating immune cells (via co-stimulation) in general and treating diseases that can benefit from activating immune cells (e.g. cancer) in particular.

Without being bound by theory, the following is suggested by the inventors as a mode of action of the PD1-4-1BBL fusion protein of some embodiments of the invention in the treatment of cancer as an example:

Due to the relatively high expression of PDL1 on the surface of tumor cells and in the tumor micro-environment, the PD1 moiety of the PD1-4-1BBL chimera targets the molecule to tumor and metastasis sites, leading to binding of the fusion to PDL1 within the tumor micro-environment.

Targeting the fusion protein to the tumor cells or/and tumor micro-environment facilitates an increase in PD1-4-1BBL concentration in the tumor micro-environment and subsequent oligomerization of the 4-1BBL moiety of the fusion protein at the tumor site. Since oligomerization of 4-1BBL is a necessary step for 4-1BB signaling, this 4-1BBL binding and oligomerization delivers a 4-1BB co-stimulatory signal that promotes activation of T cells, B cells, NK cells, especially Tumor-Infiltrating Lymphocytes (TILs), and other immune cells at the tumor site, to kill cancer cells.

In addition to the 4-1BBL-4-1BB co-stimulatory signal, the binding of the fusion protein's PD1 moiety to PDL1 in the tumor site competes with the endogenous PD1 expressed on T cells; thus, removing the inhibition on T cells and further contributing to the activation of TILs in the tumor micro-environment.

The above activities of PD1-4-1BBL are expected to lead to a synergistic effect on the activation of TILs within the tumor micro-environment, which is expected to be a more specific and more robust effect as compared to the effect of each moiety separately, as well as when using the two different moieties thereof in combination.

Thus, according to an aspect of the present invention, there is provided a PD1-4-1BBL fusion protein comprising a PD1 amino acid sequence and a 4-1BBL amino acid sequence, wherein said PD1 amino acid sequence:
  (a) is 123-148 amino acids in length having at least 80% identity to an amino acid sequence selected from the group consisting of SEQ ID NO: 18-21, 85, 89, 93 and 115 and does not comprise any of amino acid segments P1-L5 and F146-V150 corresponding to SEQ ID NO: 2, or is 138-145 amino acids in length having at least 80% identity to an amino acid sequence selected from the group consisting of SEQ ID NO: 18, 117 and 119 and does not comprise an amino acid segment F146-V150 corresponding to SEQ ID NO: 2; and/or
  (b) comprises a C to S amino acid modification in a position corresponding to amino acid 73 of SEQ ID NO: 2; and/or
wherein said 4-1BBL amino acid sequence:
  (aa) is 185-202 amino acids in length having at least 95% identity to an amino acid sequence selected form the group consisting of SEQ ID NOs: 22-25, is 170-197 amino acids in length having at least 80% identity to an amino acid sequence selected from the group consisting of SEQ ID NO: 127 and 129 and does not comprise an amino acid segment G198-E205 corresponding to SEQ ID NO: 3, is 170-182 amino acids in length having at least 80% identity to SEQ ID NO: 125 and does not comprise an amino acid segment A1-E23 corresponding to SEQ ID NO: 3 or is 184 amino acids in length having at least 80% identity to SEQ ID NO: 123; and/or
  (bb) comprises three repeats of a 4-1BBL amino acid sequence;
and wherein said fusion protein is capable of at least one of:
  (i) binding PDL1 and 4-1BB;
  (ii) activating said 4-1BB signaling pathway in a cell expressing said 4-1BB; and/or
  (iii) co-stimulating immune cells expressing said 4-1BB.

According to an alternative or an additional aspect of the present invention, there is provided a PD1-4-1BBL fusion protein comprising a PD1 amino acid sequence and a 4-1BBL amino acid sequence, wherein said PD1 amino acid sequence:
  (a) is 123-148 amino acids in length having at least 80% identity to an amino acid sequence selected from the group consisting of SEQ ID NO: 18-21, 85, 89 and 93 and does not comprise any of amino acid segments P1-L5 and F146-V150 corresponding to SEQ ID NO: 2 and/or
  (b) comprises a C to S amino acid modification in a position corresponding to amino acid 73 of SEQ ID NO: 2; and/or
wherein said 4-1BBL amino acid sequence is 185-202 amino acids in length having at least 95% identity to an amino acid sequence selected form the group consisting of SEQ ID NOs: 22-25; and wherein said fusion protein is capable of at least one of:
  (i) binding PDL1 and 4-1BB;
  (ii) activating said 4-1BB signaling pathway in a cell expressing said 4-1BB; and/or
  (iii) co-stimulating immune cells expressing said 4-1BB.

According to an alternative or an additional aspect of the present invention, there is provided a PD1-4-1BBL fusion protein comprising a PD1 amino acid sequence and a 4-1BBL amino acid sequence, wherein said PD1 amino acid sequence is 123-148 amino acids in length having at least 80% identity to an amino acid sequence selected from the group consisting of SEQ ID NO: 18-21 and does not comprise any of amino acid segments P1-L5 and F146-V150 corresponding to SEQ ID NO: 2 and/or wherein said 4-1BBL amino acid sequence is 185-202 amino acids in length having at least 95% identity to an amino acid sequence selected form the group consisting of SEQ ID NOs: 22-25; and wherein said fusion protein is capable of at least one of:
(i) binding PDL1 and 4-1BB;
(ii) activating said 4-1BB signaling pathway in a cell expressing said 4-1BB; and/or
(iii) co-stimulating immune cells expressing said 4-1BB.

According to an alternative or an additional aspect of the present invention, there is provided a PD1-4-1BBL fusion protein comprising a (GGGGS)$_n$(n=1-4) (SEQ ID NO: 149) linker between said PD1 and said 4-1BBL, wherein said fusion protein is capable of at least one of:
(i) binding PDL1 and 4-1BB;
(ii) activating said 4-1BB signaling pathway in a cell expressing said 4-1BB; and/or
(iii) co-stimulating immune cells expressing said 4-1BB.

According to an alternative or an additional aspect of the present invention, there is provided an isolated polypeptide comprising a PD1 amino acid sequence, wherein said PD1 amino acid sequence is 123-148 amino acids in length having at least 80% identity to an amino acid sequence selected from the group consisting of SEQ ID NO: 18-21, 85, 89, 93 and 115 and does not comprise any of amino acid segments P1-L5 and F146-V150 corresponding to SEQ ID NO: 2, or is 138-145 amino acids in length having at least 80% identity to an amino acid sequence selected from the group consisting of SEQ ID NO: 18, 117 and 119 and does not comprise an amino acid segment F146-V150 corresponding to SEQ ID NO: 2; and optionally comprises a C to S amino acid modification in a position corresponding to amino acid 73 of SEQ ID NO: 2; and wherein said polypeptide is capable of binding PDL1.

According to an alternative or an additional aspect of the present invention, there is provided an isolated polypeptide comprising a PD1 amino acid sequence, wherein said PD1 amino acid sequence is 123-148 amino acids in length having at least 80% identity to an amino acid sequence selected from the group consisting of SEQ ID NO: 18-21, 85, 89 and 93 and does not comprise any of amino acid segments P1-L5 and F146-V150 corresponding to SEQ ID NO: 2; and optionally comprises a C to S amino acid modification in a position corresponding to amino acid 73 of SEQ ID NO: 2; and wherein said polypeptide is capable of binding PDL1.

According to an alternative or an additional aspect of the present invention, there is provided an isolated polypeptide comprising a PD1 amino acid sequence, wherein said PD1 amino acid sequence is 123-148 amino acids in length having at least 80% identity to an amino acid sequence selected from the group consisting of SEQ ID NO: 18-21 and does not comprise any of amino acid segments P1-L5 and F146-V150 corresponding to SEQ ID NO: 2; and wherein said polypeptide is capable of binding PDL1.

According to an alternative or an additional aspect of the present invention, there is provided an isolated polypeptide comprising a 4-1BBL amino acid sequence, wherein said 4-1BBL amino acid sequence is 185-202 amino acids in length having at least 95% identity to an amino acid sequence selected form the group consisting of SEQ ID NOs: 22-25, is 170-197 amino acids in length having at least 80% identity to an amino acid sequence selected from the group consisting of SEQ ID NO: 127 and 129 and does not comprise an amino acid segment G198-E205 corresponding to SEQ ID NO: 3, or is 170-182 amino acids in length having at least 80% identity to SEQ ID NO: 125 and does not comprise an amino acid segment A1-E23 corresponding to SEQ ID NO: 3; and optionally comprises three repeats of said 4-1BBL amino acid sequence; and wherein said polypeptide is capable of at least one of:
(i) binding 4-1BB,
(ii) activating said 4-1BB signaling pathway in a cell expressing said 4-1BB; and/or
(iii) co-stimulating immune cells expressing said 4-1BB.

According to an alternative or an additional aspect of the present invention, there is provided an isolated polypeptide comprising a 4-1BBL amino acid sequence, wherein said 4-1BBL amino acid sequence is 185-202 amino acids in length having at least 95% identity to an amino acid sequence selected from the group consisting of SEQ ID NOs: 22-25; and wherein said polypeptide is capable of at least one of:
(i) binding 4-1BB,
(ii) activating said 4-1BB signaling pathway in a cell expressing said 4-1BB; and/or
(iii) co-stimulating immune cells expressing said 4-1BB.

As used herein the term "PD1 (Programmed Death 1, also known as CD279)" refers to the polypeptide of the PDCD1 gene (Gene ID 5133) or a functional homolog e.g., functional fragment thereof. According to specific embodiments, the term "PD1" refers to a functional homolog of PD1 polypeptide. According to specific embodiments, PD1 is human PD1. According to a specific embodiment, the PD1 protein refers to the human protein, such as provided in the following GenBank Number NP_005009.

Two ligands for PD-1 have been identified so far, PDL1 and PDL2 (also known as B7-DC). According to a specific embodiment, the PDL1 protein refers to the human protein, such as provided in the following GenBank Number NP_001254635 and NP_054862. According to a specific embodiment, the PDL2 protein refers to the human protein, such as provided in the following GenBank Number NP_079515.

As use herein, the phrase "functional homolog" or "functional fragment" when related to PD1 refers to a portion of the polypeptide which maintains the activity of the full length PD1 e.g., PD-L1 binding.

Assays for testing binding are well known in the art and include, but not limited to flow cytometry, BiaCore, bio-layer interferometry Blitz® assay, HPLC.

According to specific embodiments, the PD1 binds PD-L1 with a Kd of 1 nM-100 µM, 10-nM-10 µM, 100 nM-100 µM, 200 nM-10 µM, as determined by SPR analysis, each possibility represents a separate embodiment of the present invention.

According to specific embodiments, the PD1 binds PDL1 with a Kd of about 270 nM as determined by SPR analysis.

According to specific embodiments, the PD1 binds PDL1 with a Kd of about 8-9 µM as determined by SPR analysis, According to specific embodiments, the PD1 comprises an extracellular domain of said PD1 or a functional fragment thereof.

According to specific embodiments, PD1 amino acid sequence comprises SEQ ID NO: 27.

According to specific embodiments, PD1 amino acid sequence consists of SEQ ID NO: 27.

According to specific embodiments, PD1 nucleic acid sequence comprises SEQ ID NO: 28.

According to specific embodiments, PD1 nucleic acid sequence consists of SEQ ID NO: 28.

According to specific embodiments, PD1 amino acid sequence comprises SEQ ID NO: 2.

According to specific embodiments, PD1 amino acid sequence consists of SEQ ID NO: 2.

According to specific embodiments, PD1 nucleic acid sequence comprises SEQ ID NO: 29.

According to specific embodiments, PD1 nucleic acid sequence consists of SEQ ID NO: 29.

According to specific embodiments, PD1 amino acid sequence comprises SEQ ID NO: 30 or SEQ ID NO: 31.

According to specific embodiments, PD1 amino acid sequence consists of SEQ ID NO: 30 or SEQ ID NO: 31.

The term "PD1" also encompasses functional homologues (naturally occurring or synthetically/recombinantly produced), which exhibit the desired activity (i.e., binding PD-L1 and/or PD-L2). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 2, 27, 30 or 31; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

According to specific embodiments the PD1 functional homologues are at least 95%, at least 96%, at least 97%, at least 98%, at least 99% or 100% identical or homologous to the polypeptide SEQ ID NO: 2, 27, 30 or 31; or at least 95%, at least 96%, at least 97%, at least 98%, at least 99% or 100% identical to the polynucleotide sequence encoding same (as further described hereinbelow).

As used herein, "identity" or "sequence identity" refers to global identity, i.e., an identity over the entire amino acid or nucleic acid sequences disclosed herein and not over portions thereof.

Sequence identity or homology can be determined using any protein or nucleic acid sequence alignment algorithm such as Blast, ClustalW, and MUSCLE.

The homolog may also refer to an ortholog, a deletion, insertion, or substitution variant, including an amino acid substitution, as further described hereinbelow.

According to specific embodiments, the PD1 polypeptide may comprise conservative and non-conservative amino acid substitutions (also referred to herein as mutations). Such substitution are known in the art and disclosed e.g. in Maute et al. PNAS, 2015 Nov. 24; 112 (47):E6506-14; Ju Yeon et al. Nature Communications 2016 volume 7, Article number: 13354 (DOI: 10.1038/ncomms13354); and Zack K M et al. Structure. 2015 23 (12): 2341-2348 (DOI: 10.1016/j.str.2015.09.010), the contents of which are fully incorporated herein by reference.

When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Henikoff S and Henikoff J G. [Amino acid substitution matrices from protein blocks. Proc. Natl. Acad. Sci. U.S.A. 1992, 89 (22): 10915-9].

According to specific embodiments, one or more amino acid mutations are located at an amino acid residue selected from: V39, L40, N41, Y43, R44, M45, S48, N49, Q50, T51, D52, K53, A56, Q63, G65, Q66, V72, H82, M83, R90, Y96, L97, A100, S102, L103, A104, P105, K106, and A107 corresponding to the PD1 amino acid sequence set forth in SEQ ID NO: 31. According to specific embodiments, one or more amino acid mutations are located at an amino acid residue selected from: V39, L40, N41, Y43, R44, M45, S48, N49, Q50, T51, D52, K53, A56, Q63, G65, Q66, C68, V72, H82, M83, R90, Y96, L97, A100, S102, L103, A104, P105, K106, and A107 corresponding to the PD1 amino acid sequence set forth in SEQ ID NO: 31.

According to specific embodiments, one or more amino acid changes are selected from the group consisting of: (1) V39H or V39R; (2) L40V or L40I; (3) N41I or N41V; (4) Y43F or Y43H; (5) R44Y or R44L; (6) M45Q, M45E, M45L, or M45D; (7) S48D, S48L, S48N, S48G, or S48V; (8) N49C, N49G, N49Y, or N49S; (9) Q50K, Q50E, or Q50H; (10) T51V. T51L, or T51A; (11) D52F. D52R, D52Y, or D52V; (12) K53T or K53L; (13) A56S or A56L; (14) Q63T, Q63I, Q63E, Q63L, or Q63P; (15) G65N, G65R, G65I, G65L, G65F, or G65V; (16) Q66P; (17) V72I; (18) H82Q; (19) M83L or M83F; (20) R90K; (21) Y96F; (22) L97Y, L97V, or L97I; (23) A100I or A100V; (24) S102T or S102A; (25) L103I, L103Y, or L103F; (26) A104S, A104H, or A104D; (27) P105A; (28) K106G, K106E, K106I, K106V, K106R, or K106T; and (29) A107P, A107I, or A107V corresponding to the PD1 amino acid sequence set forth in SEQ ID NO: 31.

According to specific embodiments, one or more amino acid changes are selected from the group consisting of: (1) V39H or V39R; (2) L40V or L40I; (3) N41I or N41V; (4) Y43F or Y43H; (5) R44Y or R44L; (6) M45Q, M45E, M45L, or M45D; (7) S48D, S48L, S48N, S48G, or S48V; (8) N49C, N49G, N49Y, or N49S; (9) Q50K, Q50E, or Q50H; (10) T51V. T51L, or T51A; (11) D52F. D52R, D52Y, or D52V; (12) K53T or K53L; (13) A56S or A56L; (14) Q63T, Q63I, Q63E, Q63L, or Q63P; (15) G65N, G65R, G65I, G65L, G65F, or G65V; (16) Q66P; (17) C68S (18). V72I; (19) H82Q; (20) M83L or M83F; (21) R90K; (22) Y96F; (23) L97Y, L97V, or L97I; (24) A100I or A100V; (25) S102T or S102A; (26) L103I, L103Y, or L103F; (27) A104S, A104H, or A104D; (28) P105A; (29) K106G, K106E, K106I, K106V, K106R, or K106T; and (30) A107P, A107I, or A107V corresponding to the PD1 amino acid sequence set forth in SEQ ID NO: 31.

According to specific embodiments, an amino acid mutation is located at an amino acid residue C73 corresponding to the PD1 amino acid sequence set forth in SEQ ID NO: 2 (e.g. equivalent to an amino acid residue C68 corresponding to the PD1 amino acid sequence set forth in SEQ ID NO: 31).

According to specific embodiments, the PD1 polypeptide may comprise a C to S amino acid modification in a position corresponding to amino acid residue 73 of the PD1 amino acid sequence set forth in SEQ ID NO: 2 (e.g. equivalent to amino acid residue 68 of the PD1 amino acid sequence set forth in SEQ ID NO: 31).

Thus, according to specific embodiments, the PD1 amino acid sequence comprises SEQ ID NO: 73.

According to specific embodiments, PD1 amino acid sequence consists of SEQ ID NO: 73.

According to specific embodiments, the PD1 nucleic acid sequence comprises SEQ ID NO: 74.

According to specific embodiments, the PD1 nucleic acid sequence consists of SEQ ID NO: 74.

As used herein, the phrase "corresponding to PD1 amino acid sequence as set forth in SEQ ID NO: 31", "corresponding to SEQ ID NO: 31", "corresponding to PD1 amino acid sequence as set forth in SEQ ID NO: 2" or "corresponding to SEQ ID NO: 2", intends to include the corresponding amino acid residue relative to any other PD1 amino acid sequence.

Additional description on conservative amino acid and non-conservative amino acid substitutions is further provided hereinbelow.

The PD1 of some embodiments of the present invention is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 18-21; or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow), each possibility represents a separate embodiment of the present invention.

According to specific embodiments, the PD1 amino acid sequence has at least 80% identity to an amino acid sequence selected from the group consisting of SEQ ID NO: 18, 19, 20, 21, 85, 89, 93 and 115.

According to specific embodiments, the PD1 amino acid sequence has at least 80% identity to an amino acid sequence selected from the group consisting of SEQ ID NO: 18, 117 and 119.

According to specific embodiments, the PD1 amino acid sequence has at least 80% identity to an amino acid sequence selected from the group consisting of SEQ ID NO: 117 and 119.

According to specific embodiments, the PD1 amino acid sequence has at least 80% identity to an amino acid sequence selected from the group consisting of SEQ ID NO: 18-21, 85, 89 and 93.

According to specific embodiments, the PD1 amino acid sequence has at least 80% identity to an amino acid sequence selected from the group consisting of SEQ ID NO: 18-21.

According to specific embodiments, the PD1 amino acid sequence has at least 80% identity to SEQ ID NO: 18.

According to specific embodiments, the PD1 amino acid sequence has at least 80% identity to SEQ ID NO: 19.

According to specific embodiments, the PD1 amino acid sequence has at least 80% identity to SEQ ID NO: 20.

According to specific embodiments, the PD1 amino acid sequence has at least 80% identity to SEQ ID NO: 21.

According to specific embodiments, the PD1 amino acid sequence has at least 80% identity to SEQ ID NO: 85.

According to specific embodiments, the PD1 amino acid sequence has at least 80% identity to SEQ ID NO: 89.

According to specific embodiments, the PD1 amino acid sequence has at least 80% identity to SEQ ID NO: 93.

According to specific embodiments, the PD1 amino acid sequence has at least 80% identity to SEQ ID NO: 115.

According to specific embodiments, the PD1 amino acid sequence has at least 80% identity to SEQ ID NO: 117.

According to specific embodiments, the PD1 amino acid sequence has at least 80% identity to SEQ ID NO: 119.

According to specific embodiments, the PD1 amino acid sequence has at least 85% identity to an amino acid sequence selected from the group consisting of SEQ ID NO: 18, 19, 20, 21, 85, 89, 93 and 115.

According to specific embodiments, the PD1 amino acid sequence has at least 85% identity to an amino acid sequence selected from the group consisting of SEQ ID NO: 18, 117 and 119.

According to specific embodiments, the PD1 amino acid sequence has at least 85% identity to an amino acid sequence selected from the group consisting of SEQ ID NO: 117 and 119.

According to specific embodiments, the PD1 amino acid sequence has at least 85% identity to an amino acid sequence selected from the group consisting of SEQ ID NO: 18-21, 85, 89 and 93.

According to specific embodiments, the PD1 amino acid sequence has at least 85% identity to an amino acid sequence selected from the group consisting of SEQ ID NO: 18-21.

According to specific embodiments, the PD1 amino acid sequence has at least 85% identity to SEQ ID NO: 18.

According to specific embodiments, the PD1 amino acid sequence has at least 85% identity to SEQ ID NO: 19.

According to specific embodiments, the PD1 amino acid sequence has at least 85% identity to SEQ ID NO: 20.

According to specific embodiments, the PD1 amino acid sequence has at least 85% identity to SEQ ID NO: 21.

According to specific embodiments, the PD1 amino acid sequence has at least 85% identity to SEQ ID NO: 85.

According to specific embodiments, the PD1 amino acid sequence has at least 85% identity to SEQ ID NO: 89.

According to specific embodiments, the PD1 amino acid sequence has at least 85% identity to SEQ ID NO: 93.

According to specific embodiments, the PD1 amino acid sequence has at least 85% identity to SEQ ID NO: 115.

According to specific embodiments, the PD1 amino acid sequence has at least 85% identity to SEQ ID NO: 117.

According to specific embodiments, the PD1 amino acid sequence has at least 85% identity to SEQ ID NO: 119.

According to specific embodiments, the PD1 amino acid sequence has at least 90% identity to an amino acid sequence selected from the group consisting of SEQ ID NO: 18, 19, 20, 21, 85, 89, 93 and 115.

According to specific embodiments, the PD1 amino acid sequence has at least 90% identity to an amino acid sequence selected from the group consisting of SEQ ID NO: 18, 117 and 119.

According to specific embodiments, the PD1 amino acid sequence has at least 90% identity to an amino acid sequence selected from the group consisting of SEQ ID NO: 117 and 119.

According to specific embodiments, the PD1 amino acid sequence has at least 90% identity to an amino acid sequence selected from the group consisting of SEQ ID NO: 18-21, 85, 89 and 93.

According to specific embodiments, the PD1 amino acid sequence has at least 90% identity to an amino acid sequence selected from the group consisting of SEQ ID NO: 18-21.

According to specific embodiments, the PD1 amino acid sequence has at least 90% identity to SEQ ID NO: 18.

According to specific embodiments, the PD1 amino acid sequence has at least 90% identity to SEQ ID NO: 19.

According to specific embodiments, the PD1 amino acid sequence has at least 90% identity to SEQ ID NO: 20.

According to specific embodiments, the PD1 amino acid sequence has at least 90% identity to SEQ ID NO: 21.

According to specific embodiments, the PD1 amino acid sequence has at least 90% identity to SEQ ID NO: 85.

According to specific embodiments, the PD1 amino acid sequence has at least 90% identity to SEQ ID NO: 89.

According to specific embodiments, the PD1 amino acid sequence has at least 90% identity to SEQ ID NO: 93.

According to specific embodiments, the PD1 amino acid sequence has at least 90% identity to SEQ ID NO: 115.

According to specific embodiments, the PD1 amino acid sequence has at least 90% identity to SEQ ID NO: 117.

According to specific embodiments, the PD1 amino acid sequence has at least 90% identity to SEQ ID NO: 119.

According to specific embodiments, the PD1 amino acid sequence has at least 91%, at least 92%, at least 93%, at least 94%, at least 95%, at least 96%, at least 97%, at least 98%, at least 99% or 100% identity to an amino acid sequence selected from the group consisting of SEQ ID NO: 18, 19, 20, 21, 85, 89, 93 and 115.

According to specific embodiments, the PD1 amino acid sequence has at least 91%, at least 92%, at least 93%, at least 94%, at least 95%, at least 96%, at least 97%, at least 98%, at least 99% or 100% identity to an amino acid sequence selected from the group consisting of SEQ ID NO: 18, 117 and 119.

According to specific embodiments, the PD1 amino acid sequence has at least 91%, at least 92%, at least 93%, at least 94%, at least 95%, at least 96%, at least 97%, at least 98%, at least 99% or 100% identity to an amino acid sequence selected from the group consisting of SEQ ID NO: 117 and 119.

According to specific embodiments, the PD1 amino acid sequence has at least 91%, at least 92%, at least 93%, at least 94%, at least 95%, at least 96%, at least 97%, at least 98%, at least 99% or 100% identity to an amino acid sequence selected from the group consisting of SEQ ID NO: 18-21, 85, 89 and 93, each possibility represents a separate embodiment of the present invention.

According to specific embodiments, the PD1 amino acid sequence has at least 91%, at least 92%, at least 93%, at least 94%, at least 95%, at least 96%, at least 97%, at least 98%, at least 99% or 100% identity to an amino acid sequence selected from the group consisting of SEQ ID NO: 18-21, each possibility represents a separate embodiment of the present invention.

According to specific embodiments, the PD1 amino acid sequence has at least 95% identity to an amino acid sequence selected from the group consisting of SEQ ID NO: 18-21.

According to specific embodiments, the PD1 amino acid sequence has at least 95% identity to SEQ ID NO: 18.

According to specific embodiments, the PD1 amino acid sequence has at least 95% identity to SEQ ID NO: 19.

According to specific embodiments, the PD1 amino acid sequence has at least 95% identity to SEQ ID NO: 20.

According to specific embodiments, the PD1 amino acid sequence has at least 95% identity to SEQ ID NO: 21.

According to specific embodiments, the PD1 amino acid sequence has at least 95% identity to SEQ ID NO: 85.

According to specific embodiments, the PD1 amino acid sequence has at least 95% identity to SEQ ID NO: 89.

According to specific embodiments, the PD1 amino acid sequence has at least 95% identity to SEQ ID NO: 93.

According to specific embodiments, the PD1 amino acid sequence has at least 95% identity to SEQ ID NO: 115.

According to specific embodiments, the PD1 amino acid sequence has at least 95% identity to SEQ ID NO: 117.

According to specific embodiments, the PD1 amino acid sequence has at least 95% identity to SEQ ID NO: 119.

According to specific embodiments, the PD1 amino acid sequence has at least 96%, at least 97%, at least 98%, at least 99% or 100% identity to an amino acid sequence selected from the group consisting of SEQ ID NO: 18-21, 85, 89, 93 and 115, each possibility represents a separate embodiment of the present invention.

According to specific embodiments, the PD1 amino acid sequence has at least 96%, at least 97%, at least 98%, at least 99% or 100% identity to an amino acid sequence selected from the group consisting of SEQ ID NO: 18, 117 and 119, each possibility represents a separate embodiment of the present invention.

According to specific embodiments, the PD1 amino acid sequence has at least 96%, at least 97%, at least 98%, at least 99% or 100% identity to an amino acid sequence selected from the group consisting of SEQ ID NO: 117 and 119, each possibility represents a separate embodiment of the present invention.

According to specific embodiments, the PD1 amino acid sequence has at least 96%, at least 97%, at least 98%, at least 99% or 100% identity to an amino acid sequence selected from the group consisting of SEQ ID NO: 18-21, 85, 89 and 93, each possibility represents a separate embodiment of the present invention.

According to specific embodiments, the PD1 amino acid sequence has at least 96%, at least 97%, at least 98%, at least 99% or 100% identity to an amino acid sequence selected from the group consisting of SEQ ID NO: 18-21, each possibility represents a separate embodiment of the present invention.

According to specific embodiments, the PD1 amino acid sequence has at least 96%, at least 97%, at least 98%, at least 99% or 100% identity to SEQ ID NO: 18.

According to specific embodiments, the PD1 amino acid sequence has at least 96%, at least 97%, at least 98%, at least 99% or 100% identity to SEQ ID NO: 19.

According to specific embodiments, the PD1 amino acid sequence has at least 96%, at least 97%, at least 98%, at least 99% or 100% identity to SEQ ID NO: 20.

According to specific embodiments, the PD1 amino acid sequence has at least 96%, at least 97%, at least 98%, at least 99% or 100% identity to SEQ ID NO: 21.

According to specific embodiments, the PD1 amino acid sequence has at least 96%, at least 97%, at least 98%, at least 99% or 100% identity to SEQ ID NO: 85.

According to specific embodiments, the PD1 amino acid sequence has at least 96%, at least 97%, at least 98%, at least 99% or 100% identity to SEQ ID NO: 89.

According to specific embodiments, the PD1 amino acid sequence has at least 96%, at least 97%, at least 98%, at least 99% or 100% identity to SEQ ID NO: 93.

According to specific embodiments, the PD1 amino acid sequence has at least 96%, at least 97%, at least 98%, at least 99% or 100% identity to SEQ ID NO: 115.

According to specific embodiments, the PD1 amino acid sequence has at least 96%, at least 97%, at least 98%, at least 99% or 100% identity to SEQ ID NO: 117.

According to specific embodiments, the PD1 amino acid sequence has at least 96%, at least 97%, at least 98%, at least 99% or 100% identity to SEQ ID NO: 119.

According to specific embodiments, the PD1 amino acid sequence does not comprise amino acid segment P1-L5 corresponding to SEQ ID NO: 2.

According to specific embodiments, the PD1 amino acid sequence does not comprise amino acid segment F146-V150 corresponding to SEQ ID NO: 2.

According to specific embodiments, the PD1 amino acid sequence does not comprise any of amino acid segments P1-L5 and F146-V150 corresponding to SEQ ID NO: 2.

According to specific embodiments, the PD1 amino acid sequence does not comprise any of amino acid residues P1-L5 corresponding to SEQ ID NO: 2.

According to specific embodiments, the PD1 amino acid sequence does not comprise any of amino acid residues F146-V150 corresponding to SEQ ID NO: 2.

According to specific embodiments, the PD1 amino acid sequence does not comprise any of amino acid residues P1-L5 and F146-V150 corresponding to SEQ ID NO: 2.

According to specific embodiments, the PD1 amino acid sequence does not comprise SEQ ID NO: 8 or any fragment thereof.

According to specific embodiments, the PD1 amino acid sequence does not comprise SEQ ID NO: 8.

According to specific embodiments, the PD1 amino acid sequence does not comprise SEQ ID NO: 9 or any fragment thereof.

According to specific embodiments, the PD1 amino acid sequence does not comprise SEQ ID NO: 9.

According to specific embodiments, the PD1 amino acid sequence does not comprise SEQ ID NO: 8 and 9 or any fragment thereof.

According to specific embodiments, the PD1 amino acid sequence does not comprise SEQ ID NO: 8 and 9.

According to specific embodiments, the PD1 amino acid sequence comprises SEQ ID NO: 18, 19, 20, 21, 85, 89, 93 or 115.

According to specific embodiments, the PD1 amino acid sequence comprises SEQ ID NO: 18, 117 or 119.

According to specific embodiments, the PD1 amino acid sequence comprises SEQ ID NO: 117 or 119.

According to specific embodiments, the PD1 amino acid sequence comprises SEQ ID NO: 18, 19, 20, 21, 85, 89 or 93.

According to specific embodiments, the PD1 amino acid sequence comprises SEQ ID NO: 75, 79, 81, 83, 87, 91 or 95.

According to specific embodiments, the PD1 amino acid sequence comprises SEQ ID NO: 75, 83, 87, 91 or 95.

According to specific embodiments, the PD1 amino acid sequence comprises SEQ ID NO: 18, 19, 20 or 21.

According to specific embodiments, the PD1 amino acid sequence comprises SEQ ID NO: 18 or 21.

According to specific embodiments, the PD1 amino acid sequence comprises SEQ ID NO: 18.

According to specific embodiments, the PD1 amino acid sequence comprises SEQ ID NO: 19.

According to specific embodiments, the PD1 amino acid sequence comprises SEQ ID NO: 20.

According to specific embodiments, the PD1 amino acid sequence comprises SEQ ID NO: 21.

According to specific embodiments, the PD1 amino acid sequence comprises SEQ ID NO: 85.

According to specific embodiments, the PD1 amino acid sequence comprises SEQ ID NO: 89.

According to specific embodiments, the PD1 amino acid sequence comprises SEQ ID NO: 93.

According to specific embodiments, the PD1 amino acid sequence comprises SEQ ID NO: 75.

According to specific embodiments, the PD1 amino acid sequence comprises SEQ ID NO: 79.

According to specific embodiments, the PD1 amino acid sequence comprises SEQ ID NO: 81.

According to specific embodiments, the PD1 amino acid sequence comprises SEQ ID NO: 83.

According to specific embodiments, the PD1 amino acid sequence comprises SEQ ID NO: 87.

According to specific embodiments, the PD1 amino acid sequence comprises SEQ ID NO: 91.

According to specific embodiments, the PD1 amino acid sequence comprises SEQ ID NO: 95.

According to specific embodiments, the PD1 amino acid sequence comprises SEQ ID NO: 115.

According to specific embodiments, the PD1 amino acid sequence comprises SEQ ID NO: 117.

According to specific embodiments, the PD1 amino acid sequence comprises SEQ ID NO: 119.

According to specific embodiments, the PD1 amino acid sequence consists of SEQ ID NO: 18, 19, 20, 21, 85, 89, 93 or 115.

According to specific embodiments, the PD1 amino acid sequence consists of SEQ ID NO: 18, 117 or 119.

According to specific embodiments, the PD1 amino acid sequence consists of SEQ ID NO: 117 or 119.

According to specific embodiments, the PD1 amino acid sequence consists of SEQ ID NO: 18, 19, 20, 21, 85, 89 or 93.

According to specific embodiments, the PD1 amino acid sequence consists of SEQ ID NO: 75, 79, 81, 83, 87, 91 or 95.

According to specific embodiments, the PD1 amino acid sequence consists of SEQ ID NO: 75, 83, 87, 91 or 95.

According to specific embodiments, the PD1 amino acid sequence consists of SEQ ID NO: 18, 19, 20 or 21.

According to specific embodiments, the PD1 amino acid sequence consists of SEQ ID NO: 18 or 21.

According to specific embodiments, the PD1 amino acid sequence consists of SEQ ID NO: 18.

According to specific embodiments, the PD1 amino acid sequence consists of SEQ ID NO: 19.

According to specific embodiments, the PD1 amino acid sequence consists of SEQ ID NO: 20.

According to specific embodiments, the PD1 amino acid sequence consists of SEQ ID NO: 21.

According to specific embodiments, the PD1 amino acid sequence consists of SEQ ID NO: 85.

According to specific embodiments, the PD1 amino acid sequence consists of SEQ ID NO: 89.

According to specific embodiments, the PD1 amino acid sequence consists of SEQ ID NO: 93.

According to specific embodiments, the PD1 amino acid sequence consists of SEQ ID NO: 75.

According to specific embodiments, the PD1 amino acid sequence consists of SEQ ID NO: 79.

According to specific embodiments, the PD1 amino acid sequence consists of SEQ ID NO: 81.

According to specific embodiments, the PD1 amino acid sequence consists of SEQ ID NO: 83.

According to specific embodiments, the PD1 amino acid sequence consists of SEQ ID NO: 87.

According to specific embodiments, the PD1 amino acid sequence consists of SEQ ID NO: 91.

According to specific embodiments, the PD1 amino acid sequence consists of SEQ ID NO: 95.

According to specific embodiments, the PD1 amino acid sequence consists of SEQ ID NO: 115.

According to specific embodiments, the PD1 amino acid sequence consists of SEQ ID NO: 117.

According to specific embodiments, the PD1 amino acid sequence consists of SEQ ID NO: 119.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 32, 33, 34, 35, 76, 80, 82, 84, 86, 88, 90, 92, 94, 96, 116, 118 and/or 120, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 32, 33, 34, 35, 76, 80, 82, 84, 86, 88, 90, 92, 94 and/or 96, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 76, 80, 82, 84, 86, 88, 90, 92, 94 and/or 96, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 76, 80, 82, 84, 88, 92 and/or 96, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 32, 33, 34 and/or 35, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 32, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 33, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 34, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 35, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 76, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 80, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 82, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 84, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 86, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 88, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 90, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 92, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 94, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 96, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 116, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 118, each possibility represents a separate embodiment of the present invention.

According to specific embodiments, the PD1 nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 120, each possibility represents a separate embodiment of the present invention.

According to specific embodiments, the PD1 nucleic acid sequence has at least 80% identity to SEQ ID NO: 32, 33, 34, 35, 76, 80, 82, 84, 86, 88, 90, 92, 94, 94, 96, 116, 118 and/or 120.

According to specific embodiments, the PD1 nucleic acid sequence has at least 80% identity to SEQ ID NO: 32, 33, 34, 35, 76, 80, 82, 84, 86, 88, 90, 92 and/or 96.

According to specific embodiments, the PD1 nucleic acid sequence has at least 80% identity to SEQ ID NO: 32, 33, 34 and/or 35.

According to specific embodiments, the PD1 nucleic acid sequence has at least 80% identity to SEQ ID NO: 32.

According to specific embodiments, the PD1 nucleic acid sequence has at least 80% identity to SEQ ID NO: 33.

According to specific embodiments, the PD1 nucleic acid sequence has at least 80% identity to SEQ ID NO: 34.

According to specific embodiments, the PD1 nucleic acid sequence has at least 80% identity to SEQ ID NO: 35.

According to specific embodiments, the PD1 nucleic acid sequence has at least 80% identity to SEQ ID NO: 76.

According to specific embodiments, the PD1 nucleic acid sequence has at least 80% identity to SEQ ID NO: 80.

According to specific embodiments, the PD1 nucleic acid sequence has at least 80% identity to SEQ ID NO: 82.

According to specific embodiments, the PD1 nucleic acid sequence has at least 80% identity to SEQ ID NO: 84.

According to specific embodiments, the PD1 nucleic acid sequence has at least 80% identity to SEQ ID NO: 86.

According to specific embodiments, the PD1 nucleic acid sequence has at least 80% identity to SEQ ID NO: 88.

According to specific embodiments, the PD1 nucleic acid sequence has at least 80% identity to SEQ ID NO: 90.

According to specific embodiments, the PD1 nucleic acid sequence has at least 80% identity to SEQ ID NO: 92.

According to specific embodiments, the PD1 nucleic acid sequence has at least 80% identity to SEQ ID NO: 94.

According to specific embodiments, the PD1 nucleic acid sequence has at least 80% identity to SEQ ID NO: 96.

According to specific embodiments, the PD1 nucleic acid sequence has at least 80% identity to SEQ ID NO: 116.

According to specific embodiments, the PD1 nucleic acid sequence has at least 80% identity to SEQ ID NO: 118.

According to specific embodiments, the PD1 nucleic acid sequence has at least 80% identity to SEQ ID NO: 120.

According to specific embodiments, the PD1 nucleic acid sequence has at least 85% identity to SEQ ID NO: 32, 33, 34, 35, 76, 80, 82, 84, 86, 88, 90, 92, 94, 96, 116, 118 and/or 120.

According to specific embodiments, the PD1 nucleic acid sequence has at least 85% identity to SEQ ID NO: 32, 33, 34, 35, 76, 80, 82, 84, 86, 88, 90, 92, 94 and/or 96.

According to specific embodiments, the PD1 nucleic acid sequence has at least 85% identity to SEQ ID NO: 32, 33, 34 and/or 35.

According to specific embodiments, the PD1 nucleic acid sequence has at least 90% identity to SEQ ID NO: 32, 33, 34, 35, 76, 80, 82, 84, 86, 88, 90, 92, 94, 96, 116, 118 and/or 120.

According to specific embodiments, the PD1 nucleic acid sequence has at least 90% identity to SEQ ID NO: 32, 33, 34, 35, 76, 80, 82, 84, 86, 88, 90, 92, 94 and/or 96.

According to specific embodiments, the PD1 nucleic acid sequence has at least 90% identity to SEQ ID NO: 32, 33, 34 and/or 35.

According to specific embodiments, the PD1 nucleic acid sequence has at least 95% identity to SEQ ID NO: 32, 33, 34, 35, 76, 80, 82, 84, 86, 88, 90, 92, 94, 96, 116, 118 and/or 120.

According to specific embodiments, the PD1 nucleic acid sequence has at least 95% identity to SEQ ID NO: 32, 33, 34, 35, 76, 80, 82, 84, 86, 88, 90, 92, 94 and/or 96.

According to specific embodiments, the PD1 nucleic acid sequence has at least 95% identity to SEQ ID NO: 32, 33, 34 and/or 35.

According to specific embodiments, the PD1 nucleic acid sequence has at least 96%, at least 97%, at least 98%, at least 99% or 100% identity to SEQ ID NO: 32, 33, 34, 35, 76, 80, 82, 84, 86, 88, 90, 92, 94, 96, 116, 118 and/or 120, each possibility represents a separate embodiment of the present invention.

According to specific embodiments, the PD1 nucleic acid sequence has at least 96%, at least 97%, at least 98%, at least 99% or 100% identity to SEQ ID NO: 32, 33, 34, 35, 76, 80, 82, 84, 86, 88, 90, 92, 94 and/or 96, each possibility represents a separate embodiment of the present invention.

According to specific embodiments, the PD1 nucleic acid sequence has at least 96%, at least 97%, at least 98%, at least 99% or 100% identity to SEQ ID NO: 32, 33, 34 and/or 35, each possibility represents a separate embodiment of the present invention.

According to specific embodiments, the PD1 nucleic acid sequence comprises SEQ ID NO: 32, 33, 34, 35, 76, 80, 82, 84, 86, 88, 90, 92, 94, 96, 116, 118 or 120.

According to specific embodiments, the PD1 nucleic acid sequence comprises SEQ ID NO: 32, 33, 34, 35, 76, 80, 82, 84, 86, 88, 90, 92, 94 or 96.

According to specific embodiments, the PD1 nucleic acid sequence comprises SEQ ID NO: 32, 33, 34 or 35.

According to specific embodiments, the PD1 nucleic acid sequence comprises SEQ ID NO: 32.

According to specific embodiments, the PD1 nucleic acid sequence comprises SEQ ID NO: 33.

According to specific embodiments, the PD1 nucleic acid sequence comprises SEQ ID NO: 34.

According to specific embodiments, the PD1 nucleic acid sequence comprises SEQ ID NO: 35.

According to specific embodiments, the PD1 nucleic acid sequence comprises SEQ ID NO: 76.

According to specific embodiments, the PD1 nucleic acid sequence comprises SEQ ID NO: 80.

According to specific embodiments, the PD1 nucleic acid sequence comprises SEQ ID NO: 82.

According to specific embodiments, the PD1 nucleic acid sequence comprises SEQ ID NO: 84.

According to specific embodiments, the PD1 nucleic acid sequence comprises SEQ ID NO: 86.

According to specific embodiments, the PD1 nucleic acid sequence comprises SEQ ID NO: 88.

According to specific embodiments, the PD1 nucleic acid sequence comprises SEQ ID NO: 90.

According to specific embodiments, the PD1 nucleic acid sequence comprises SEQ ID NO: 92.

According to specific embodiments, the PD1 nucleic acid sequence comprises SEQ ID NO: 94.

According to specific embodiments, the PD1 nucleic acid sequence comprises SEQ ID NO: 96.

According to specific embodiments, the PD1 nucleic acid sequence comprises SEQ ID NO: 116.

According to specific embodiments, the PD1 nucleic acid sequence comprises SEQ ID NO: 118.

According to specific embodiments, the PD1 nucleic acid sequence comprises SEQ ID NO: 120.

According to specific embodiments, the PD1 nucleic acid sequence consists of SEQ ID NO: 32, 33, 34, 35, 76, 80, 82, 84, 86, 88, 90, 92, 94, 96, 116, 180 or 120.

According to specific embodiments, the PD1 nucleic acid sequence consists of SEQ ID NO: 32, 33, 34, 35, 76, 80, 82, 84, 86, 88, 90, 92, 94 or 96.

According to specific embodiments, the PD1 nucleic acid sequence consists of SEQ ID NO: 32, 33, 34 and/or 35.

According to specific embodiments, the PD1 nucleic acid sequence consists of SEQ ID NO: 32.

According to specific embodiments, the PD1 nucleic acid sequence consists of SEQ ID NO: 33.

According to specific embodiments, the PD1 nucleic acid sequence consists of SEQ ID NO: 34.

According to specific embodiments, the PD1 nucleic acid sequence consists of SEQ ID NO: 35.

According to specific embodiments, the PD1 nucleic acid sequence consists of SEQ ID NO: 76.

According to specific embodiments, the PD1 nucleic acid sequence consists of SEQ ID NO: 80.

According to specific embodiments, the PD1 nucleic acid sequence consists of SEQ ID NO: 82.

According to specific embodiments, the PD1 nucleic acid sequence consists of SEQ ID NO: 84.

According to specific embodiments, the PD1 nucleic acid sequence consists of SEQ ID NO: 86.

According to specific embodiments, the PD1 nucleic acid sequence consists of SEQ ID NO: 88.

According to specific embodiments, the PD1 nucleic acid sequence consists of SEQ ID NO: 90.

According to specific embodiments, the PD1 nucleic acid sequence consists of SEQ ID NO: 92.

According to specific embodiments, the PD1 nucleic acid sequence consists of SEQ ID NO: 94.

According to specific embodiments, the PD1 nucleic acid sequence consists of SEQ ID NO: 96.

According to specific embodiments, the PD1 nucleic acid sequence consists of SEQ ID NO: 116.

According to specific embodiments, the PD1 nucleic acid sequence consists of SEQ ID NO: 118.

According to specific embodiments, the PD1 nucleic acid sequence consists of SEQ ID NO: 120.

According to specific embodiments, PD1 amino acid sequence comprises 100-200 amino acids, 120-180 amino acids, 120-160, 130-170 amino acids, 130-160, 130-150, 140-160 amino acids, 145-155 amino acids, each possibility represents a separate embodiment of the present invention.

According to specific embodiments, PD1 amino acid sequence is 123-166 amino acids in length.

According to specific embodiment, PD1 amino acid sequence is 156 amino acids in length.

According to specific embodiments, PD1 amino acid sequence is 145-155 amino acids in length.

According to specific embodiments, PD1 amino acid sequence is 150 amino acids in length.

According to specific embodiment, PD1 amino acid sequence comprises less than 150 amino acids in length.

According to specific embodiments, PD1 amino acid sequence comprises less than 149 amino acids in length.

According to specific embodiments, PD1 amino acid sequence comprises less than 148, less than 147, less than 146, less than 145, less than 144, less than 143, less than 142, less than 141 amino acids in length, each possibility represents a separate embodiment of the present invention.

According to specific embodiments, PD1 amino acid sequence is 138-145 amino acids in length.

According to specific embodiments, PD1 amino acid sequence is 145 amino acids in length.

According to specific embodiments, PD1 amino acid sequence is 143 amino acids in length.

According to specific embodiments, the PD1 amino acid sequence in no more than 140 amino acids in length.

According to specific embodiments, PD1 amino acid sequence is at least 123, at least, 124, at least 125, at least 126, at least 127, at least 128, at least 129, at least 130, at least 133, at least 137, at least 138 amino acids in length, each possibility represents a separate embodiments of the present invention.

According to specific embodiments, PD1 amino acid sequence is at least 123, at least, 124, at least 125, at least 126, at least 127, at least 128, at least 129, at least 130 amino acids in length, each possibility represents a separate embodiments of the present invention.

According to specific embodiments, PD1 amino acid sequence comprises 123-148 amino acids in length.

According to specific embodiments, PD1 amino acid sequence is at least 126 amino acids in length.

According to specific embodiments, PD1 amino acid sequence is 126-148 amino acids in length.

According to specific embodiments, PD1 amino acid sequence is 123-140 amino acids in length.

According to specific embodiments, PD1 amino acid sequence is 126-140 amino acids in length.

According to specific embodiments, PD1 amino acid sequence is 127-140 amino acids in length.

According to specific embodiments, PD1 amino acid sequence is 128-140 amino acids in length.

According to specific embodiments, PD1 amino acid sequence is 130-140 amino acids in length.

According to specific embodiments, PD1 amino acid sequence is 130-135 amino acids in length.

According to specific embodiments, PD1 amino acid sequence comprises 135-140 amino acids in length.

According to specific embodiments, PD1 amino acid sequence comprises 126-130 amino acids in length.

According to specific embodiments, PD1 amino acid sequence is 127 amino acids in length.

According to specific embodiments, PD1 amino acid sequence is 128 amino acids in length.

According to specific embodiments, PD1 amino acid sequence is 133 amino acids in length.

According to specific embodiments, PD1 amino acid sequence is 135 amino acids in length.

According to specific embodiments, PD1 amino acid sequence is 136 amino acids in length.

According to specific embodiments, PD1 amino acid sequence is 137 amino acids in length.

According to specific embodiments, PD1 amino acid sequence is 138 amino acids in length.

According to specific embodiments, PD1 amino acid sequence is 140 amino acids in length.

As used herein the term "4-1BBL (also known as CD137L and TNFSF9)" refers to the polypeptide of the TNFSF9 gene (Gene ID 8744) or a functional homolog e.g., functional fragment thereof. According to specific embodiments, the term "4-1BBL" refers to a functional homolog of 4-1BBL polypeptide. According to specific embodiments, 4-1BBL is human 4-1BBL. According to a specific embodiment, the 4-1BBL protein refers to the human protein, such as provided in the following GenBank Number NP_003802.

As use herein, the phrase "functional homolog" or "functional fragment" when related to 4-1BBL, refers to a portion of the polypeptide which maintains the activity of the full length 4-1BBL e.g., (i) binding 4-1BB, (ii) activating 4-1BB signaling pathway, (iii) activating immune cells expressing 4-1BB, (iv) forming a homotrimer.

According to specific embodiments, the functional homolog when related to 4-1BBL is capable of (i), (ii), (iii), (i)+ (ii), (i)+ (iii), (ii)+ (iii).

According to specific embodiments, the functional homolog when related to 4-1BBL is capable of (i)+ (ii)+ (iii).

According to specific embodiments, the functional homolog when related to 4-1BBL is capable of (iv), (i)+ (iv), (ii)+ (iv), (iii)+ (iv), (i)+ (ii)+ (iv), (i)+ (iii)+ (iv), (ii)+ (iii)+ (iv).

According to specific embodiments, the functional homolog when related to 4-1BBL is capable of (i)+ (ii)+ (iii)+ (iv).

According to a specific embodiment, the 4-1BB protein refers to the human protein, such as provided in the following GenBank Number NP_001552.

Assays for testing binding are well known in the art and are further described hereinabove and below.

According to specific embodiments, the 4-1BBL binds 4-1BB with a Kd of about 0.1-1000 nM, 0.1-100 nM. 1-100 nM, or 55.2 nM as determined by SPR, each possibility represents a separate embodiment of the claimed invention.

Assays for testing trimerization are well known in the art and include, but not limited to NATIVE-PAGE, SEC-HPLC 2D gels, gel filtration, SEC-MALS, Analytical ultracentrifugation (AUC) Mass spectrometry (MS), capillary gel electrophoresis (CGE).

As used herein the terms "activating" or "activation" refer to the process of stimulating an immune cell (e.g. T cell, B cell, NK cell, phagocytic cell) that results in cellular proliferation, maturation, cytokine production, phagocytosis and/or induction of regulatory or effector functions.

According to specific embodiments, activating comprises co-stimulating.

As used herein the term "co-stimulating" or "co-stimulation" refers to transmitting a secondary antigen independent stimulatory signal (e.g. 4-1BB signal) resulting in activation of the immune cell.

According to specific embodiments, activating comprises suppressing an inhibitory signal (e.g. PDL1 signal) resulting in activation of the immune cell.

Methods of determining signaling of a stimulatory or inhibitory signal are well known in the art and also disclosed in the Examples section which follows, and include, but are not limited to, binding assay using e.g. BiaCore, HPLC or flow cytometry, enzymatic activity assays such as kinase activity assays, and expression of molecules involved in the signaling cascade using e.g. PCR, Western blot, immunoprecipitation and immunohistochemistry. Additionally or alternatively, determining transmission of a signal (co-stimulatory or inhibitory) can be effected by evaluating immune cell activation or function. Methods of evaluating immune cell activation or function are well known in the art and include, but are not limited to, proliferation assays such as CFSE staining, MTS, Alamar blue, BRDU and thymidine incorporation, cytotoxicity assays such as CFSE staining, chromium release, Calcin AM, cytokine secretion assays such as intracellular cytokine staining, ELISPOT and ELISA, expression of activation markers such as CD25, CD69, CD137, CD107a, PD1, and CD62L using flow cytometry.

According to specific embodiments, determining the signaling activity or activation is effected in-vitro or ex-vivo e.g. in a mixed lymphocyte reaction (MLR), as further described hereinbelow.

For the same culture conditions the signaling activity or the immune cell activation or function are generally expressed in comparison to the signaling, activation or function in a cell of the same species but not contacted with the PF1-4-1BBL fusion protein, a polynucleotide encoding same or a host cell encoding same; or contacted with a vehicle control, also referred to as control.

According to specific embodiments, the 4-1BBL comprises an extracellular domain of said 4-1BBL or a functional fragment thereof.

According to specific embodiments, 4-1BBL amino acid sequence comprises SEQ ID NO: 36.

According to specific embodiments, 4-1BBL amino acid sequence consists of SEQ ID NO: 36.

According to specific embodiments, 4-1BBL nucleic acid sequence comprises SEQ ID NO: 37.

According to specific embodiments, 4-1BBL nucleic acid sequence consists of SEQ ID NO: 37.

According to specific embodiments, 4-1BBL amino acid sequence comprises SEQ ID NO: 3.

According to specific embodiments, 4-1BBL amino acid sequence consists of SEQ ID NO: 3.

According to specific embodiments, 4-1BBL nucleic acid sequence comprises SEQ ID NO: 38.

According to specific embodiments, 4-1BBL nucleic acid sequence consists of SEQ ID NO: 38.

The term "4-1BBL" also encompasses functional homologues (naturally occurring or synthetically/recombinantly produced), which exhibit the desired activity (as defined hereinabove). Such homologues can be, for example, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical or homologous to the polypeptide SEQ ID NO: 3, 36; or at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to the polynucleotide sequence encoding same (as further described hereinbelow).

According to specific embodiments the 4-1BBL functional homologues are at least 95%, at least 96%, at least 97%, at least 98%, at least 99% or 100% identical or homologous to the polypeptide SEQ ID NO: 3, 36; or at least 95%, at least 96%, at least 97%, at least 98%, at least 99% or 100% identical to the polynucleotide sequence encoding same (as further described hereinbelow).

According to specific embodiments, the 4-1BBL polypeptide may comprise conservative amino acid substitutions, as further described hereinabove and below.

The 4-1BBL of some embodiments of the present invention is at least 95%, at least 96%, at least 97%, at least 98%, at least 99% or 100% identical or homologous to the polypeptide SEQ ID NO: 22, 23, 24 and/or 25; or at least 95%, at least 96%, at least 97%, at least 98%, at least 99% or 100% identical to the polynucleotide sequence encoding same (as further described hereinbelow), each possibility represents a separate embodiment of the present invention.

According to specific embodiments, the 4-1BBL amino acid sequence has at least 95% identity to an amino acid sequence selected from the group consisting of SEQ ID NOs: 22-25, each possibility represents a separate embodiment of the present invention.

According to specific embodiments, the 4-1BBL amino acid sequence has at least 96%, at least 97%, at least 98%, at least 99% or 100% identity to SEQ ID NO: 22, 23, 24 and/or 25, each possibility represents a separate embodiment of the present invention.

According to specific embodiments, the 4-1BBL amino acid sequence has at least 95%, at least 96%, at least 97%, at least 98%, at least 99% or 100% identity to SEQ ID NO: 22, 23 and/or 24.

According to specific embodiments, the 4-1BBL amino acid sequence has at least 95%, at least 96%, at least 97%, at least 98%, at least 99% or 100% identity to SEQ ID NO: 22.

According to specific embodiments, the 4-1BBL amino acid sequence has at least 95%, at least 96%, at least 97%, at least 98%, at least 99% or 100% identity to SEQ ID NO: 23.

According to specific embodiments, the 4-1BBL amino acid sequence has at least 95%, at least 96%, at least 97%, at least 98%, at least 99% or 100% identity to SEQ ID NO: 24.

According to specific embodiments, the 4-1BBL amino acid sequence has at least 95%, at least 96%, at least 97%, at least 98%, at least 99% or 100% identity to SEQ ID NO: 25.

According to specific embodiments, the 4-1BBL amino acid sequence does not comprise the amino acid segment A1-V6 corresponding to SEQ ID NO: 3.

According to specific embodiments, the 4-1BBL amino acid sequence does not comprise the amino acid segment A1-G14 corresponding to SEQ ID NO: 3.

According to specific embodiments, the 4-1BBL amino acid sequence does not comprise any of amino acid residues A1-V6 or A1-G14 corresponding to SEQ ID NO: 3.

As used herein, the phrase "corresponding to SEQ ID NO: 3" intends to include the corresponding amino acid residue relative to any other 4-1BBL amino acid sequence.

According to specific embodiments, the 4-1BBL amino acid sequence does not comprise SEQ ID NO: 6 or 7 or any fragment thereof.

According to specific embodiments, the 4-1BBL amino acid sequence does not comprise SEQ ID NO: 6 or 7.

According to specific embodiments, the 4-1BBL amino acid sequence comprises SEQ ID NO: 22, 23, 24 or 25.

According to specific embodiments, the 4-1BBL amino acid sequence comprises SEQ ID NO: 22, 23 or 24.

According to specific embodiments, the 4-1BBL amino acid sequence comprises SEQ ID NO: 22 or 23.

According to specific embodiments, the 4-1BBL amino acid sequence comprises SEQ ID NO: 22.

According to specific embodiments, the 4-1BBL amino acid sequence comprises SEQ ID NO: 23.

According to specific embodiments, the 4-1BBLα amino acid sequence comprises SEQ ID NO: 24.

According to specific embodiments, the 4-1BBL amino acid sequence comprises SEQ ID NO: 25.

According to specific embodiments, the 4-1BBL amino acid sequence consists of SEQ ID NO: 22, 23, 24 or 25.

According to specific embodiments, the 4-1BBL amino acid sequence consists of SEQ ID NO: 22, 23 or 24.

According to specific embodiments, the 4-1BBL amino acid sequence consists of SEQ ID NO: 22 or 23.

According to specific embodiments, the 4-1BBL amino acid sequence consists of SEQ ID NO: 22.

According to specific embodiments, the 4-1BBL amino acid sequence consists of SEQ ID NO: 23.

According to specific embodiments, the 4-1BBLα amino acid sequence consists of SEQ ID NO: 24.

According to specific embodiments, the 4-1BBL amino acid sequence consists of SEQ ID NO: 25.

According to specific embodiments, the 4-1BBL amino acid sequence has at least 80% identity to an amino acid sequence selected from the group consisting of SEQ ID NOs: 127 and 129, each possibility represents a separate embodiment of the present invention.

According to specific embodiments, the 4-1BBL amino acid sequence has at least 85% identity to an amino acid sequence selected from the group consisting of SEQ ID NOs: 127 and 129, each possibility represents a separate embodiment of the present invention.

According to specific embodiments, the 4-1BBL amino acid sequence has at least 90% identity to an amino acid sequence selected from the group consisting of SEQ ID NOs: 127 and 129, each possibility represents a separate embodiment of the present invention.

According to specific embodiments, the 4-1BBL amino acid sequence has at least 91%, at least 92%, at least 93%, at least 94%, at least 95%, at least 96%, at least 97%, at least 98%, at least 99% or 100% identity to an amino acid sequence selected from the group consisting of SEQ ID NOs: 127 and 129, each possibility represents a separate embodiment of the present invention.

According to specific embodiments, the 4-1BBL amino acid sequence has at least 95% identity to an amino acid sequence selected from the group consisting of SEQ ID NOs: 127 and 129, each possibility represents a separate embodiment of the present invention.

According to specific embodiments, the 4-1BBL amino acid sequence has at least 96%, at least 97%, at least 98%, at least 99% or 100% identity to an amino acid sequence selected from the group consisting of SEQ ID NOs: 127 and 129, each possibility represents a separate embodiment of the present invention.

According to specific embodiments, the 4-1BBL amino acid sequence does not comprise the amino acid segment G198-E205 corresponding to SEQ ID NO: 3.

According to specific embodiments, the 4-1BBL amino acid sequence does not comprise any of amino acid residues G198-E205 corresponding to SEQ ID NO: 3.

According to specific embodiments, the 4-1BBL amino acid sequence does not comprise SEQ ID NO: 166 or any fragment thereof.

According to specific embodiments, the 4-1BBL amino acid sequence does not comprise SEQ ID NO: 166.

According to specific embodiments, the 4-1BBL amino acid sequence comprises SEQ ID NOs: 127 or 129.

According to specific embodiments, the 4-1BBL amino acid sequence consists of SEQ ID NOs: 127 or 129.

According to specific embodiments, the 4-1BBL amino acid sequence has at least 80% identity to SEQ ID NO: 125.

According to specific embodiments, the 4-1BBL amino acid sequence has at least 85% identity SEQ ID NO: 125.

According to specific embodiments, the 4-1BBL amino acid sequence has at least 90% identity to SEQ ID NO: 125.

According to specific embodiments, the 4-1BBL amino acid sequence has at least 91%, at least 92%, at least 93%, at least 94%, at least 95%, at least 96%, at least 97%, at least 98%, at least 99% or 100% identity to SEQ ID NO: 125.

According to specific embodiments, the 4-1BBL amino acid sequence has at least 95% identity to SEQ ID NO: 125.

According to specific embodiments, the 4-1BBL amino acid sequence has at least 96%, at least 97%, at least 98%, at least 99% or 100% identity to SEQ ID NO: 125.

According to specific embodiments, the 4-1BBL amino acid sequence does not comprise the amino acid segment A1-E23 corresponding to SEQ ID NO: 3.

According to specific embodiments, the 4-1BBL amino acid sequence does not comprise any of amino acid residues A1-E23 corresponding to SEQ ID NO: 3.

According to specific embodiments, the 4-1BBL amino acid sequence does not comprise SEQ ID NO: 167 or any fragment thereof.

According to specific embodiments, the 4-1BBL amino acid sequence does not comprise SEQ ID NO: 167.

According to specific embodiments, the 4-1BBL amino acid sequence comprises SEQ ID NO: 125.

According to specific embodiments, the 4-1BBL amino acid sequence consists of SEQ ID NO: 125.

According to specific embodiments, the 4-1BBL amino acid sequence has at least 80% identity to SEQ ID NO: 123.

According to specific embodiments, the 4-1BBL amino acid sequence has at least 85% identity SEQ ID NO: 123.

According to specific embodiments, the 4-1BBL amino acid sequence has at least 90% identity to SEQ ID NO: 123.

According to specific embodiments, the 4-1BBL amino acid sequence has at least 91%, at least 92%, at least 93%, at least 94%, at least 95%, at least 96%, at least 97%, at least 98%, at least 99% or 100% identity to SEQ ID NO: 123.

According to specific embodiments, the 4-1BBL amino acid sequence has at least 95% identity to SEQ ID NO: 123.

According to specific embodiments, the 4-1BBL amino acid sequence has at least 96%, at least 97%, at least 98%, at least 99% or 100% identity to SEQ ID NO: 123.

According to specific embodiments, the 4-1BBL amino acid sequence comprises SEQ ID NO: 123.

According to specific embodiments, the 4-1BBL amino acid sequence consists of SEQ ID NO: 123.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 39, 40, 41 and/or 42, each possibility represents a separate embodiment of the present invention.

According to specific embodiments, the 4-1BBL nucleic acid sequence has at least 95% identity to SEQ ID NO: 39, 40, 41 and/or 42.

According to specific embodiments, the 4-1BBL nucleic acid sequence has at least 96%, at least 97%, at least 98%, at least 99% or 100% identity to SEQ ID NO: 39, 40, 41 and/or 42.

According to specific embodiments, the 4-1BBL nucleic acid sequence has at least 95%, at least 96%, at least 97%, at least 98%, at least 99% or 100% identity to SEQ ID NO: 39 and/or 40.

According to specific embodiments, the 4-1BBL nucleic acid sequence comprises SEQ ID NO: 39, 40, 41 or 42.

According to specific embodiments, the 4-1BBL nucleic acid sequence comprises SEQ ID NO: 39, 40 or 41.

According to specific embodiments, the 4-1BBL nucleic acid sequence comprises SEQ ID NO: 39 or 40.

According to specific embodiments, the 4-1BBL nucleic acid sequence comprises SEQ ID NO: 39.

According to specific embodiments, the 4-1BBL nucleic acid sequence comprises SEQ ID NO: 40.

According to specific embodiments, the 4-1BBLα nucleic acid sequence comprises SEQ ID NO: 41.

According to specific embodiments, the 4-1BBL nucleic acid sequence comprises SEQ ID NO: 42.

According to specific embodiments, the 4-1BBL nucleic acid sequence consists of SEQ ID NO: 39, 40, 41 or 42.

According to specific embodiments, the 4-1BBL nucleic acid sequence consists of SEQ ID NO: 39, 40 or 41.

According to specific embodiments, the 4-1BBL nucleic acid sequence consists of SEQ ID NO: 39 or 40.

According to specific embodiments, the 4-1BBL nucleic acid sequence consists of SEQ ID NO: 39.

According to specific embodiments, the 4-1BBL nucleic acid sequence consists of SEQ ID NO: 40.

According to specific embodiments, the 4-1BBL nucleic acid sequence consists of SEQ ID NO: 41.

According to specific embodiments, the 4-1BBL nucleic acid sequence consists of SEQ ID NO: 42.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 128 and/or 130, each possibility represents a separate embodiment of the present invention.

According to specific embodiments, the 4-1BBL nucleic acid sequence has at least 95% identity to SEQ ID NO: 128 and/or 130.

According to specific embodiments, the 4-1BBL nucleic acid sequence has at least 96%, at least 97%, at least 98%, at least 99% or 100% identity to SEQ ID NO: 128 and/or 130.

According to specific embodiments, the 4-1BBL nucleic acid sequence comprises SEQ ID NO: 128 or 130.

According to specific embodiments, the 4-1BBL nucleic acid sequence consists of SEQ ID NO: 128 or 130.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 126.

According to specific embodiments, the 4-1BBL nucleic acid sequence has at least 95% identity to SEQ ID NO: 126.

According to specific embodiments, the 4-1BBL nucleic acid sequence has at least 96%, at least 97%, at least 98%, at least 99% or 100% identity to SEQ ID NO: 126.

According to specific embodiments, the 4-1BBL nucleic acid sequence comprises SEQ ID NO: 126.

According to specific embodiments, the 4-1BBL nucleic acid sequence consists of SEQ ID NO: 126.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 124.

According to specific embodiments, the 4-1BBL nucleic acid sequence has at least 95% identity to SEQ ID NO: 124.

According to specific embodiments, the 4-1BBL nucleic acid sequence has at least 96%, at least 97%, at least 98%, at least 99% or 100% identity to SEQ ID NO: 124.

According to specific embodiments, the 4-1BBL nucleic acid sequence comprises SEQ ID NO: 124.

According to specific embodiments, the 4-1BBL nucleic acid sequence consists of SEQ ID NO: 124.

According to specific embodiments, 4-1BBL amino acid sequence comprises 100-300 amino acids, 150-250 amino acids, 100-250 amino acids, 150-220 amino acids, 180-220 amino acids, 180-210 amino acids, 185-205 amino acids, 190-210 amino acids, each possibility represents a separate embodiment of the present invention.

According to specific embodiments, 4-1BBL amino acid sequence is 190-210 amino acids in length.

According to specific embodiments, 4-1BBL amino acid sequence is 204 amino acids in length.

According to specific embodiments, 4-1BBL amino acid sequence is 185-202 amino acids in length.

According to specific embodiments, 4-1BBL amino acid sequence is 185-200 amino acids in length.

According to specific embodiments, 4-1BBL amino acid sequence is 185-199 amino acids in length.

According to specific embodiments, 4-1BBL amino acid sequence is 170-197 amino acids in length.

According to specific embodiments, 4-1BBL amino acid sequence is 170-182 amino acids in length.

According to specific embodiments, 4-1BBL amino acid sequence is 184 amino acids in length.

According to specific embodiments, 4-1BBL amino acid sequence is 185, 191, 197 or 199 amino acids in length, each possibility represents a separate embodiment of the present invention.

According to specific embodiments, 4-1BBL amino acid sequence is 184 amino acids in length.

According to specific embodiments, 4-1BBL amino acid sequence is 183 amino acids in length.

According to specific embodiments, 4-1BBL amino acid sequence is 182 amino acids in length.

According to specific embodiments, 4-1BBL amino acid sequence is 176 amino acids in length.

According to specific embodiments, the 4-1BBL amino acid sequence comprised in the PD1-4-1BBL fusion protein or the 4-1BBL polypeptide disclosed herein comprises three repeats of a 4-1BBL amino acid sequence.

According to specific embodiments, each of the three repeats is capable of at least one of: (i) binding 4-1BB, (ii) activating 4-1BB signaling pathway, (iii) activating immune cells expressing 4-1BB, (iv) forming a homotrimer.

According to specific embodiments, the 4-1BBL amino acid sequence does not comprise a linker between each of said three repeats of said 4-1BBL amino acid sequence.

According to other specific embodiments, the 4-1BBL amino acid sequence comprises a linker between each of said three repeats of said 4-1BBL amino acid sequence. Any linker known in the art can be used with specific embodiments of the invention. Non-limiting examples of linkers that can be used are described in details hereinbelow.

According to a specific embodiment, the linker is a (GGGGS)x2+GGGG (SEQ ID NO: 121) linker.

According to specific embodiments, the repeated sequence can be any of the 4-1BBL as defined herein.

According to specific embodiments, the three repeats have an identical 4-1BBL amino acid sequence.

According to other specific embodiments, the three repeats are distinct, i.e. have different 4-1BBL amino acid sequences.

According to other specific embodiments, two of the three repeats have an identical 4-1BBL amino acid sequence.

According to specific embodiments, at least one of the repeats comprises a 4-1BBL amino acid sequence disclosed herein.

According to specific embodiments, at least one of the repeats consists of a 4-1BBL amino acid sequence disclosed herein.

According to specific embodiments, the 4-1BBL amino acid sequence comprises three repeats of an amino acid sequence comprising SEQ ID NO: 22.

According to specific embodiments, the 4-1BBL amino acid sequence comprises three repeats of an amino acid sequence consisting of SEQ ID NO: 22.

Thus, according to specific embodiments, the 4-1BBL amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 131.

According to specific embodiments, the 4-1BBL amino acid sequence comprises an amino acid sequence having at least 80% identify to SEQ ID NO: 131.

According to specific embodiments, the 4-1BBL amino acid sequence comprises an amino acid sequence having at least 85% identify to SEQ ID NO: 131.

According to specific embodiments, the 4-1BBL amino acid sequence comprises an amino acid sequence having at least 90% identify to SEQ ID NO: 131.

According to specific embodiments, the 4-1BBL amino acid sequence comprises an amino acid sequence having at least 95% identify to SEQ ID NO: 131.

According to specific embodiments, the 4-1BBL amino acid sequence comprises SEQ ID NO: 131.

According to specific embodiments, the 4-1BBL amino acid sequence consists of SEQ ID NO: 131.

According to specific embodiments, the 4-1BBL nucleic acid sequence has at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 132.

According to specific embodiments, the 4-1BBL nucleic acid sequence has at least 95% identity to SEQ ID NO: 132.

According to specific embodiments, the 4-1BBL nucleic acid sequence has at least 96%, at least 97%, at least 98%, at least 99% or 100% identity to SEQ ID NO: 132.

According to specific embodiments, the 4-1BBL nucleic acid sequence comprises SEQ ID NO: 132.

According to specific embodiments, the 4-1BBL nucleic acid sequence consists of SEQ ID NO: 132.

The terms "DSP" and "fusion protein", "chimeric protein" or "chimera" are used herein interchangeably, and refer to an amino acid sequence having two or more parts which are not found together in a single amino acid sequence in nature.

The fusion protein of some embodiments of the present invention comprises a PD1 amino acid sequence and a 4-1BBL amino acid sequence (referred to herein as PD1-4-1BBL fusion protein).

According to specific embodiments, the PD1 is N-terminal to the 4-1BBL.

According to other specific embodiments, the PD1 is C-terminal to the 4-1BBL.

The PD1-4-1BBL fusion protein of some embodiments of the present invention can comprise any PD1 as defined herein; and any 4-1BBL amino acid sequence:
(aa) being 185-202 amino acids in length and having at least 95% identity to an amino acid sequence selected form the group consisting of SEQ ID NOs: 22-25, being 170-197 amino acids in length having at least 80% identity to an amino acid sequence selected from the group consisting of SEQ ID NO: 127 and 129 and not comprising an amino acid segment G198-E205 corresponding to SEQ ID NO: 3, being 170-182 amino acids in length having at least 80% identity to SEQ ID NO: 125 and not comprising an amino acid segment A1-E23 corresponding to SEQ ID NO: 3 or being 184 amino acids in length having at least 80% identity to SEQ ID NO: 123; and/or
(bb) comprising three repeats of a 4-1BBL amino acid sequence; such as e.g. disclosed herein, each possibility represents a separate embodiment of the present invention.

The PD1-4-1BBL fusion protein of some embodiments of the present invention can comprise any PD1 amino acid sequence:
(a) being 123-148 amino acids in length having at least 80% identity to an amino acid sequence selected from the group consisting of SEQ ID NO: 18-21, 85, 89, 93 and 115 and not comprising any of amino acid segments P1-L5 and F146-V150 corresponding to SEQ ID NO: 2, or being 138-145 amino acids in length having at least 80% identity to an amino acid sequence selected from the group consisting of SEQ ID NO: 18, 117 and 119 and not comprising an amino acid segment F146-V150 corresponding to SEQ ID NO: 2; and/or
(b) comprising a C to S amino acid modification in a position corresponding to amino acid 73 of SEQ ID NO: 2; such as e.g. disclosed herein; and any 4-1BBL as defined herein, each possibility represents a separate embodiment of the present invention.

The PD1-4-1BBL fusion protein of some embodiments of the present invention can comprise any PD1 amino acid sequence:
(a) being 123-148 amino acids in length having at least 80% identity to an amino acid sequence selected from the group consisting of SEQ ID NO: 18-21, 85, 89, 93 and 115 and not comprising any of amino acid segments P1-L5 and F146-V150 corresponding to SEQ ID NO: 2, or being 138-145 amino acids in length having at least 80% identity to an amino acid sequence selected from the group consisting of SEQ ID NO: 18, 117 and 119 and not comprising an amino acid segment F146-V150 corresponding to SEQ ID NO: 2; and/or
(b) comprising a C to S amino acid modification in a position corresponding to amino acid 73 of SEQ ID NO: 2; such as e.g. disclosed herein;
and any 4-1BBL amino acid sequence:
(aa) being 185-202 amino acids in length and having at least 95% identity to an amino acid sequence selected form the group consisting of SEQ ID NOs: 22-25, being 170-197 amino acids in length having at least 80% identity to an amino acid sequence selected from the group consisting of SEQ ID NO: 127 and 129 and not comprising an amino acid segment G198-E205 corresponding to SEQ ID NO: 3, being 170-182 amino acids in length having at least 80% identity to SEQ ID NO: 125 and not comprising an amino acid segment A1-E23 corresponding to SEQ ID NO: 3 or being 184 amino acids in length having at least 80% identity to SEQ ID NO: 123; and/or
(bb) comprising three repeats of a 4-1BBL amino acid sequence; such as e.g. disclosed herein, each possibility represents a separate embodiment of the present invention.

The PD1-4-1BBL fusion protein of some embodiments of the present invention can comprise any PD1 as defined herein; and any 4-1BBL amino acid sequence being 185-202 amino acids in length and having at least 95% identity to an amino acid sequence selected from the group consisting of SEQ ID NOs: 22-25 such as e.g. disclosed herein, each possibility represents a separate embodiment of the present invention.

The PD1-4-1BBL fusion protein of some embodiments of the present invention can comprise any PD1 amino acid sequence:
(a) being 123-148 amino acids in length having at least 80% identity to an amino acid sequence selected from the group consisting of SEQ ID NO: 18-21, 85, 89 and 93 and not comprising any of amino acid segments P1-L5 and F146-V150 corresponding to SEQ ID NO: 2 and/or
(b) comprising a C to S amino acid modification in a position corresponding to amino acid 73 of SEQ ID NO: 2; such as e.g. disclosed herein; and any 4-1BBL as defined herein, each possibility represents a separate embodiment of the present invention.

The PD1-4-1BBL fusion protein of some embodiments of the present invention can comprise any PD1 amino acid sequence being 123-148 amino acids in length having at least 80% identity to an amino acid sequence selected from the group consisting of SEQ ID NO: 18-21 and not comprising any of amino acid segments P1-L5 and F146-V150 corresponding to SEQ ID NO: 2 such as e.g. disclosed herein; and any 4-1BBL as defined herein, each possibility represents a separate embodiment of the present invention.

The PD1-4-1BBL fusion protein of some embodiments of the present invention can comprise any PD1 amino acid sequence:
(a) being 123-148 amino acids in length having at least 80% identity to an amino acid sequence selected from the group consisting of SEQ ID NO: 18-21, 85, 89 and 93 and not comprising any of amino acid segments P1-L5 and F146-V150 corresponding to SEQ ID NO: 2 and/or
(b) comprising a C to S amino acid modification in a position corresponding to amino acid 73 of SEQ ID NO: 2; such as e.g. disclosed herein; and any 4-1BBL amino acid sequence being 185-202 amino acids in length and having at least 95% identity to an amino acid sequence selected from the group consisting of SEQ ID NOs: 22-25 such as e.g. disclosed herein, each possibility represents a separate embodiment of the present invention.

The PD1-4-1BBL fusion protein of some embodiments of the present invention can comprise any PD1 amino acid sequence being 123-148 amino acids in length having at least 80% identity to an amino acid sequence selected from the group consisting of SEQ ID NO: 18-21 and not comprising any of amino acid segments P1-L5 and F146-V150 corresponding to SEQ ID NO: 2 such as e.g. disclosed herein; and any 4-1BBL amino acid sequence being 185-202 amino acids in length and having at least 95% identity to an amino acid sequence selected from the group consisting of SEQ ID NOs: 22-25 such as e.g. disclosed herein, each possibility represents a separate embodiment of the present invention.

According to specific embodiments, the PD1 amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 2, 18-21, 85, 89, 93, 27, 30 and/or 31; and the 4-1BBL amino acid sequence is 185-202 amino acids in length having at least 95%, at least 96%, at least 97%, at least 98%, at least 99% or 100% identity to SEQ ID NO: 22, 23, 24 or 25, each possibility represents a separate embodiment of the present invention.

According to specific embodiments, the PD1 amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 73, 75, 79, 81, 83, 87, 91 and/or 95; and the 4-1BBL amino acid sequence is 185-202 amino acids in length having at least 95%, at least 96%, at least 97%, at least 98%, at least 99% or 100% identity to SEQ ID NO: 22, 23, 24 or 25, each possibility represents a separate embodiment of the present invention.

According to specific embodiments, the PD1 amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 2, 18-21, 27, 30 and/or 31; and the 4-1BBL amino acid sequence is 185-202 amino acids in length having at least 95%, at least 96%, at least 97%, at least 98%, at least 99% or 100% identity to SEQ ID NO: 22, 23, 24 or 25, each possibility represents a separate embodiment of the present invention.

According to specific embodiments, the PD1 amino acid sequence comprises SEQ ID NO: 2, 18-21, 85, 89, 93, 27, 30 or 31; and the 4-1BBL amino acid sequence is 185-202 amino acids in length comprising SEQ ID NO: 22, 23, 24 or 25, each possibility represents a separate embodiment of the present invention.

According to specific embodiments, the PD1 amino acid sequence comprises SEQ ID NO: 73, 75, 79, 81, 83, 87, 91 or 95; and the 4-1BBL amino acid sequence is 185-202 amino acids in length comprising SEQ ID NO: 22, 23, 24 or 25, each possibility represents a separate embodiment of the present invention.

According to specific embodiments, the PD1 amino acid sequence comprises SEQ ID NO: 73; and the 4-1BBL amino acid sequence is 185-202 amino acids in length comprising SEQ ID NO: 22, 23, 24 or 25, each possibility represents a separate embodiment of the present invention.

According to specific embodiments, the PD1 amino acid sequence comprises SEQ ID NO: 75, 79, 81, 83, 87, 91 or 95; and the 4-1BBL amino acid sequence is 185-202 amino acids in length comprising SEQ ID NO: 22, 23, 24 or 25, each possibility represents a separate embodiment of the present invention.

According to specific embodiments, the PD1 amino acid sequence comprises SEQ ID NO: 75, 83, 87, 91 or 95; and the 4-1BBL amino acid sequence is 185-202 amino acids in length comprising SEQ ID NO: 22, 23, 24 or 25, each possibility represents a separate embodiment of the present invention.

According to specific embodiments, the PD1 amino acid sequence comprises SEQ ID NO: 73, 75, 83, 87, 91 or 95; and the 4-1BBL amino acid sequence is 185-202 amino acids in length comprising SEQ ID NO: 22, 23, 24 or 25, each possibility represents a separate embodiment of the present invention.

According to specific embodiments, the PD1 amino acid sequence comprises SEQ ID NO: 2, 18-21, 27, 30 or 31; and the 4-1BBL amino acid sequence is 185-202 amino acids in length comprising SEQ ID NO: 22, 23, 24 or 25, each possibility represents a separate embodiment of the present invention.

According to specific embodiments, the PD1 amino acid sequence is as set forth in SEQ ID NO: 2, 18-21, 85, 89, 93, 27, 30 or 31; and the 4-1BBL amino acid sequence is as set forth in SEQ ID NO: 22, 23, 24 or 25, each possibility represents a separate embodiment of the present invention.

According to specific embodiments, the PD1 amino acid sequence is as set forth in SEQ ID NO: 73, 75, 79, 81, 83, 87, 91 or 95; and the 4-1BBL amino acid sequence is as set forth in SEQ ID NO: 22, 23, 24 or 25, each possibility represents a separate embodiment of the present invention.

According to specific embodiments, the PD1 amino acid sequence is as set forth in SEQ ID NO: 73; and the 4-1BBL amino acid sequence is as set forth in SEQ ID NO: 22, 23, 24 or 25, each possibility represents a separate embodiment of the present invention.

According to specific embodiments, the PD1 amino acid sequence is as set forth in SEQ ID NO: 75, 79, 81, 83, 87, 91 or 95; and the 4-1BBL amino acid sequence is as set forth in SEQ ID NO: 22, 23, 24 or 25, each possibility represents a separate embodiment of the present invention.

According to specific embodiments, the PD1 amino acid sequence is as set forth in SEQ ID NO: 75, 83, 87, 91 or 95; and the 4-1BBL amino acid sequence is as set forth in SEQ ID NO: 22, 23, 24 or 25, each possibility represents a separate embodiment of the present invention.

According to specific embodiments, the PD1 amino acid sequence is as set forth in SEQ ID NO: 73, 75, 83, 87, 91 or 95; and the 4-1BBL amino acid sequence is as set forth in SEQ ID NO: 22, 23, 24 or 25, each possibility represents a separate embodiment of the present invention.

According to specific embodiments, the PD1 amino acid sequence is as set forth in SEQ ID NO: 2, 18-21, 27, 30 or 31; and the 4-1BBL amino acid sequence is as set forth in SEQ ID NO: 22, 23, 24 or 25, each possibility represents a separate embodiment of the present invention.

According to specific embodiments, the PD1 amino acid sequence:
(a) is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18-21, 85, 89 and/or 93; and/or
(b) comprises a C to S amino acid modification in a position corresponding to amino acid 73 of SEQ ID NO: 2; and the 4-1BBL amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 3, 22-25 and/or 36, each possibility represents a separate embodiment of the present invention.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18, 19, 20 and/or 21; and the 4-1BBL amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 3, 22-25 and/or 36, each possibility represents a separate embodiment of the present invention.

According to specific embodiments, the PD1 amino acid sequence:
(a) is 123-148 amino acids in length comprising SEQ ID NO: 18-21, 85, 89 and/or 93; and/or
(b) comprises a C to S amino acid modification in a position corresponding to amino acid 73 of SEQ ID NO: 2; and the 4-1BBL amino acid sequence comprises SEQ ID NO: 3, 22-25 or 36, each possibility represents a separate embodiment of the present invention.

According to specific embodiments, the PD1 amino acid sequence comprises SEQ ID NO: 18-21, 85, 89 or 93; and the 4-1BBL amino acid sequence comprises SEQ ID NO: 3, 22-25 or 36, each possibility represents a separate embodiment of the present invention.

According to specific embodiments, the PD1 amino acid sequence comprises SEQ ID NO: 73, 75, 79, 81, 83, 87, 91 or 95; and the 4-1BBL amino acid sequence comprises SEQ ID NO: 3, 22-25 or 36, each possibility represents a separate embodiment of the present invention.

According to specific embodiments, the PD1 amino acid sequence comprises SEQ ID NO: 73; and the 4-1BBL amino acid sequence comprises SEQ ID NO: 3, 22-25 or 36, each possibility represents a separate embodiment of the present invention.

According to specific embodiments, the PD1 amino acid sequence comprises SEQ ID NO: 75, 79, 81, 83, 87, 91 or 95; and the 4-1BBL amino acid sequence comprises SEQ ID NO: 3, 22-25 or 36, each possibility represents a separate embodiment of the present invention.

According to specific embodiments, the PD1 amino acid sequence comprises SEQ ID NO: 75, 83, 87, 91 or 95; and the 4-1BBL amino acid sequence comprises SEQ ID NO: 3, 22-25 or 36, each possibility represents a separate embodiment of the present invention.

According to specific embodiments, the PD1 amino acid sequence comprises SEQ ID NO: 73, 75, 83, 87, 91 or 95; and the 4-1BBL amino acid sequence comprises SEQ ID NO: 3, 22-25 or 36, each possibility represents a separate embodiment of the present invention.

According to specific embodiments, the PD1 amino acid sequence is 123-148 amino acids in length comprising SEQ ID NO: 18, 19, 20 or 21; and the 4-1BBL amino acid sequence comprises SEQ ID NO: 3, 22-25 or 36, each possibility represents a separate embodiment of the present invention.

According to specific embodiments, the PD1 amino acid sequence is as set forth in SEQ ID NO: 18, 19, 20 or 21; and the 4-1BBL amino acid sequence is as set forth in SEQ ID NO: 3, 22-25 or 36, each possibility represents a separate embodiment of the present invention.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18; and the 4-1BBL amino acid sequence is 185-202 amino acids in length having at least 95%, at least 96%, at least 97%, at least 98%, at least 99% or 100% identity to SEQ ID NO: 22, 23, 24 or 25, each possibility represents a separate embodiment of the present invention.

According to specific embodiments, the PD1 amino acid sequence is 123-148 amino acids in length comprising SEQ ID NO: 18; and the 4-1BBL amino acid sequence is 185-202 amino acids in length and comprising SEQ ID NO: 22, 23, 24 or 25.

According to specific embodiments, the PD1 amino acid sequence is as set forth in SEQ ID NO: 18; and the 4-1BBL amino acid sequence is as set forth in SEQ ID NO: 22, 23, 24 or 25.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18; and the 4-1BBL amino acid sequence is 185-202 amino acids in length having at least 95%, at least 96%, at least 97%, at least 98%, at least 99% or 100% identity to SEQ ID NO: 22, 23 or 24.

According to specific embodiments, the PD1 amino acid sequence is 123-148 amino acids in length comprising SEQ ID NO: 18; and the 4-1BBL amino acid sequence is 185-202 amino acids in length comprising SEQ ID NO: 22, 23 or 24.

According to specific embodiments, the PD1 amino acid sequence is as set forth in SEQ ID NO: 18; and the 4-1BBL amino acid sequence is as set forth in SEQ ID NO: 22, 23 or 24.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18; and the 4-1BBL amino acid sequence is 185-202 amino acids in length having at least 95%, at least 96%, at least 97%, at least 98%, at least 99% or 100% identity to SEQ ID NO: 22.

According to specific embodiments, the PD1 amino acid sequence is 123-148 amino acids in length comprising SEQ ID NO: 18; and the 4-1BBL amino acid sequence is 185-202 amino acids in length comprising SEQ ID NO: 22.

According to specific embodiments, the PD1 amino acid sequence is as set forth in SEQ ID NO: 18; and the 4-1BBL amino acid sequence is as set forth in SEQ ID NO: 22.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18; and the 4-1BBL amino acid sequence is 185-202 amino acids in length having at least 95%, at least 96%, at least 97%, at least 98%, at least 99% or 100% identity to SEQ ID NO: 23.

According to specific embodiments, the PD1 amino acid sequence is 123-148 amino acids in length comprising SEQ ID NO: 18; and the 4-1BBL amino acid sequence is 185-202 amino acids in length comprising SEQ ID NO: 23.

According to specific embodiments, the PD1 amino acid sequence is as set forth in SEQ ID NO: 18; and the 4-1BBL amino acid sequence is as set forth in SEQ ID NO: 23.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18; and the 4-1BBL amino acid sequence is 185-202 amino acids in length having at least 95%, at least 96%, at least 97%, at least 98%, at least 99% or 100% identity to SEQ ID NO: 24.

According to specific embodiments, the PD1 amino acid sequence is 123-148 amino acids in length comprising SEQ ID NO: 18; and the 4-1BBL amino acid sequence is 185-202 amino acids in length comprising SEQ ID NO: 24.

According to specific embodiments, the PD1 amino acid sequence is as set forth in SEQ ID NO: 18; and the 4-1BBL amino acid sequence is as set forth in SEQ ID NO: 24.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 19; and the 4-1BBL amino acid sequence is 185-202 amino acids in length having at least 95%, at least 96%, at least 97%, at least 98%, at least 99% or 100% identity to SEQ ID NO: 22, 23, 24 or 25, each possibility represents a separate embodiment of the present invention.

According to specific embodiments, the PD1 amino acid sequence is 123-148 amino acids in length comprising SEQ ID NO: 19; and the 4-1BBL amino acid sequence is 185-202 amino acids in length comprising SEQ ID NO: 22, 23, 24 or 25.

According to specific embodiments, the PD1 amino acid sequence is as set forth in SEQ ID NO: 19; and the 4-1BBL amino acid sequence is as set forth in SEQ ID NO: 22, 23, 24 or 25.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 20; and the 4-1BBL amino acid sequence is 185-202 amino acids in length having at least 95%, at least 96%, at least 97%, at least 98%, at least 99% or 100% identity to SEQ ID NO: 22, 23, 24 or 25, each possibility represents a separate embodiment of the present invention.

According to specific embodiments, the PD1 amino acid sequence is 123-148 amino acids in length comprising SEQ ID NO: 20; and the 4-1BBL amino acid sequence is 185-202 amino acids in length comprising embodiments, the PD1 amino acid sequence is as set forth in SEQ ID NO: 20; and the 4-1BBL amino acid sequence is as set forth in SEQ ID NO: 22, 23, 24 or 25.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 21; and the 4-1BBL amino acid sequence is 185-202 amino acids in length having at least 95%, at least 96%, at least 97%, at least 98%, at least 99% or 100% identity to SEQ ID NO: 22, 23, 24 or 25, each possibility represents a separate embodiment of the present invention.

According to specific embodiments, the PD1 amino acid sequence is 123-148 amino acids in length comprising SEQ ID NO: 21; and the 4-1BBL amino acid sequence is 185-202 amino acids in length comprising SEQ ID NO: 22, 23, 24 or 25.

According to specific embodiments, the PD1 amino acid sequence is as set forth in SEQ ID NO: 21; and the 4-1BBL amino acid sequence is as set forth in SEQ ID NO: 22, 23, 24 or 25.

According to specific embodiments, the PD1 amino acid sequence:
(a) is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18-21, 85, 89 or 93 and/or
(b) comprises a C to S amino acid modification in a position corresponding to amino acid 73 of SEQ ID NO: 2; and the 4-1BBL amino acid sequence is 185-202 amino acids in length having at least 95%, at least 96%, at least 97%, at least 98%, at least 99% or 100% identity to SEQ ID NO: 22, each possibility represents a separate embodiment of the present invention.

According to specific embodiments, the PD1 amino acid sequence is 123-148 amino acids in length comprising SEQ ID NO: 85, 89 or 93; and the 4-1BBL amino acid sequence is 185-202 amino acids in length and comprising SEQ ID NO: 22.

According to specific embodiments, the PD1 amino acid sequence is as set forth in SEQ ID NO: 85, 89 or 93; and the 4-1BBL amino acid sequence is as set forth in SEQ ID NO: 22, 23, 24 or 25. According to specific embodiments, the PD1 amino acid sequence is 123-148 amino acids in length comprising SEQ ID NO: 75, 79, 81, 83, 87, 91 or 95; and the 4-1BBL amino acid sequence is 185-202 amino acids in length and comprising SEQ ID NO: 22.

According to specific embodiments, the PD1 amino acid sequence is as set forth in SEQ ID NO: 75, 79, 81, 83, 87, 91 or 95; and the 4-1BBL amino acid sequence is as set forth in SEQ ID NO: 22, 23, 24 or 25.

According to specific embodiments, the PD1 amino acid sequence is 123-148 amino acids in length comprising SEQ ID NO: 75, 83, 87, 91 or 95; and the 4-1BBL amino acid sequence is 185-202 amino acids in length and comprising SEQ ID NO: 22.

According to specific embodiments, the PD1 amino acid sequence is as set forth in SEQ ID NO: 75, 83, 87, 91 or 95; and the 4-1BBL amino acid sequence is as set forth in SEQ ID NO: 22, 23, 24 or 25.

According to specific embodiments, the PD1 amino acid sequence is 123-148 amino acids in length comprising SEQ ID NO: 75; and the 4-1BBL amino acid sequence is 185-202 amino acids in length and comprising SEQ ID NO: 22.

According to specific embodiments, the PD1 amino acid sequence is as set forth in SEQ ID NO: 75; and the 4-1BBL amino acid sequence is as set forth in SEQ ID NO: 22, 23, 24 or 25.

According to specific embodiments, the PD1 amino acid sequence is 123-148 amino acids in length comprising SEQ ID NO: 83; and the 4-1BBL amino acid sequence is 185-202 amino acids in length and comprising SEQ ID NO: 22.

According to specific embodiments, the PD1 amino acid sequence is as set forth in SEQ ID NO: 783; and the 4-1BBL amino acid sequence is as set forth in SEQ ID NO: 22, 23, 24 or 25.

According to specific embodiments, the PD1 amino acid sequence comprises SEQ ID NO: 73 and the 4-1BBL amino acid sequence comprises SEQ ID NO: 3.

According to specific embodiments, the PD1 amino acid sequence is as set forth in SEQ ID NO: 73; and the 4-1BBL amino acid sequence is as set forth in SEQ ID NO: 3.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 115 and not comprising any of amino acid segments P1-L5 and F146-V150 corresponding to SEQ ID NO: 2; and the 4-1BBL amino acid sequence is any 4-1BBL as defined herein, each possibility represents a separate embodiment of the present invention.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 115 and not comprising any of amino acid segments P1-L5 and F146-V150 corresponding to SEQ ID NO: 2; and the 4-1BBL amino acid sequence:
(aa) is 185-202 amino acids in length having at least 95% identity to an amino acid sequence selected form the group consisting of SEQ ID NOs: 22-25, is 170-197 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 127 and 129 and not comprising an amino acid segment G198-E205 corresponding to SEQ ID NO: 3, is 170-182 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 125 and not comprising an amino acid segment A1-E23 corresponding to SEQ ID NO: 3 or is 184 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 123; and/or
(bb) comprises three repeats of a 4-1BBL amino acid sequence, each possibility represents a separate embodiment of the present invention.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 115 and not comprising any of amino acid segments P1-L5 and F146-V150 corresponding to SEQ ID NO: 2; and the 4-1BBL amino acid sequence is 170-182 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 125 and not comprising an amino acid segment A1-E23 corresponding to SEQ ID NO: 3.

According to specific embodiments, the PD1 amino acid sequence is 123-148 amino acids in length comprising SEQ ID NO: 115; and the 4-1BBL amino acid sequence is 170-182 amino acids in length comprising SEQ ID NO: 125.

According to specific embodiments, the PD1 amino acid sequence is as set forth in SEQ ID NO: 115; and the 4-1BBL amino acid sequence is as set forth in SEQ ID NO: 125.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 115 and not comprising any of amino acid segments P1-L5 and F146-V150 corresponding to SEQ ID NO: 2; and the 4-1BBL amino acid sequence is 184 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 123.

According to specific embodiments, the PD1 amino acid sequence is 123-148 amino acids in length comprising SEQ ID NO: 115; and the 4-1BBL amino acid sequence is 184 amino acids in length comprising SEQ ID NO: 123.

According to specific embodiments, the PD1 amino acid sequence is as set forth in SEQ ID NO: 115; and the 4-1BBL amino acid sequence is as set forth in SEQ ID NO: 123.

According to specific embodiments, the PD1 amino acid sequence is 138-145 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 117 and 119 and not comprising an amino acid segment F146-V150 corresponding to SEQ ID NO: 2; and the 4-1BBL amino acid sequence is any 4-1BBL as defined herein, each possibility represents a separate embodiment of the present invention.

According to specific embodiments, the PD1 amino acid sequence is 138-145 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 117 and 119 and not comprising an amino acid segment F146-V150 corresponding to SEQ ID NO: 2; and the 4-1BBL amino acid sequence:
- (aa) is 185-202 amino acids in length having at least 95% identity to an amino acid sequence selected form the group consisting of SEQ ID NOs: 22-25, is 170-197 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 127 and 129 and not comprising an amino acid segment G198-E205 corresponding to SEQ ID NO: 3, is 170-182 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 125 and not comprising an amino acid segment A1-E23 corresponding to SEQ ID NO: 3 or is 184 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 123; and/or
- (bb) comprises three repeats of a 4-1BBL amino acid sequence, each possibility represents a separate embodiment of the present invention.

According to specific embodiments, the PD1 amino acid sequence is 138-145 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 117 and 119 and not comprise an amino acid segment F146-V150 corresponding to SEQ ID NO: 2; and the 4-1BBL amino acid sequence is 170-197 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 127 and 129 and not comprising an amino acid segment G198-E205 corresponding to SEQ ID NO: 3.

According to specific embodiments, the PD1 amino acid sequence is 138-145 amino acids in length comprising an amino acid sequence selected from the group consisting of SEQ ID NO: 117 and 119; and the 4-1BBL amino acid sequence is 170-197 amino acids in length comprising an amino acid sequence selected from the group consisting of SEQ ID NO: 127 and 129.

According to specific embodiments, the PD1 amino acid sequence is as set forth in SEQ ID NO: 117 or 119; and the 4-1BBL amino acid sequence is as set forth in SEQ ID NO: 127 or 129.

According to specific embodiments, the PD1 amino acid sequence is 138-145 amino acids in length comprising SEQ ID NO: 117; and the 4-1BBL amino acid sequence is 170-197 amino acids in length comprising SEQ ID NO: 127.

According to specific embodiments, the PD1 amino acid sequence is as set forth in SEQ ID NO: 117; and the 4-1BBL amino acid sequence is as set forth in SEQ ID NO: 127.

According to specific embodiments, the PD1 amino acid sequence is 138-145 amino acids in length comprising SEQ ID NO: 119; and the 4-1BBL amino acid sequence is 170-197 amino acids in length comprising SEQ ID NO: 129.

According to specific embodiments, the PD1 amino acid sequence is as set forth in SEQ ID NO: 119; and the 4-1BBL amino acid sequence is as set forth in SEQ ID NO: 129.

According to specific embodiments, the PD1 amino acid sequence is 123-148 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 115 and not comprising any of amino acid segments P1-L5 and F146-V150 corresponding to SEQ ID NO: 2; and the 4-1BBL amino acid sequence is 184 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 123.

According to specific embodiments, the PD1 amino acid sequence is 123-148 amino acids in length comprising SEQ ID NO: 115; and the 4-1BBL amino acid sequence is 184 amino acids in length having comprising SEQ ID NO: 123.

According to specific embodiments, the PD1 amino acid sequence is as set forth in SEQ ID NO: 115; and the 4-1BBL amino acid sequence is as set forth in SEQ ID NO: 123.

According to specific embodiments, the PD1 amino acid sequence is 123-148 amino acids in length or 138-145 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18; and the 4-1BBL amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 3.

According to specific embodiments, the PD1 amino acid sequence is 123-148 amino acids in length or 138-145 amino acids in length comprising SEQ ID NO: 18; and the 4-1BBL amino acid sequence comprises SEQ ID NO: 3.

According to specific embodiments, the PD1 amino acid sequence is as set forth in SEQ ID NO: 18; and the 4-1BBL amino acid sequence is as set forth in SEQ ID NO: 3.

According to specific embodiments, the PD1 amino acid sequence is 123-148 amino acids in length or 138-145 amino acids in length having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 18; and the 4-1BBL amino acid sequence has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to SEQ ID NO: 131.

According to specific embodiments, the PD1 amino acid sequence is 123-148 amino acids in length or 138-145 amino acids in length comprising SEQ ID NO: 18; and the 4-1BBL amino acid sequence comprises SEQ ID NO: 131.

According to specific embodiments, the PD1 amino acid sequence is as set forth in SEQ ID NO: 18; and the 4-1BBL amino acid sequence is as set forth in SEQ ID NO: 131.

Non-limiting examples of specific combinations of PD1 amino acid sequence and 4-1BBL amino acid sequence which can be used with specific embodiments of the present invention are provided in Table 4 of the Examples section which follows, which serves as an integral part of the specification.

According to specific embodiments, the isolated polypeptide comprising the PD1 amino acid sequence or the isolated polypeptide comprising the 4-1BBL amino acid sequence is soluble (i.e., not immobilized to a synthetic or a naturally occurring surface).

According to specific embodiments, the isolated polypeptide comprising the PD1 amino acid sequence or the isolated polypeptide comprising the 4-1BBL amino acid sequence is immobilized to a synthetic or a naturally occurring surface.

According to specific embodiments, the PD1-4-1BBL fusion protein is soluble (i.e., not immobilized to a synthetic or a naturally occurring surface).

According to specific embodiments, the PD1-4-1BBL fusion protein is immobilized to a synthetic or a naturally occurring surface.

According to specific embodiments the PD1-4-1BBL fusion protein is in a form of at least a homo-trimer.

According to specific embodiments, at least 10%, at least 20%, at least 30%, at least 40%, at least 50%, at least 60%, at least 70%, at least 80%, at least 90%, at least 95% of the PD1-4-1BBL fusion protein is in a form of at least a homo-trimer, each possibility represents a separate embodiment of the present invention.

According to specific embodiments, the at least homo-trimer comprises a homo-trimer.

According to specific embodiments, the at least homo-trimer comprises a homo-tetramer.

According to specific embodiments, the at least homo-trimer comprises a homo-pentamer.

According to specific embodiments, the at least homo-trimer comprises a homo-hexamer.

Methods of determining trimerization are well known in the art and include, but are not limited to NATIVE-PAGE, SEC-HPLC 2D gels, gel filtration, SEC-MALS, Analytical ultracentrifugation (AUC) Mass spectrometry (MS), capillary gel electrophoresis (CGE).

According to specific embodiments the at least homo-trimer is at least 100 kD, at least 120 kD, at least 140 kD, at least 160 kD, at least 180 kD in molecular weight as determined by SEC-MALLS.

According to specific embodiments the at least homo-trimer is at least 100 kD in molecular weight as determined by SEC-MALS.

According to specific embodiments the at least homo-trimer is at least 140 kD in molecular weight as determined by SEC-MALS.

According to specific embodiments the at least homo-trimer is at least 200 kD in molecular weight as determined by SEC-MALS.

According to specific embodiments, the PD1-4-1BBL does not comprise a linker between the PD1 and the 4-1BBL.

In some embodiments, the PD1-4-1BBL comprises a linker which may be at any length.

Hence, according to specific embodiments the PD1-4-1BBL fusion protein comprises a linker between said PD1 and said 4-1BBL.

Any linker known in the art can be used with specific embodiments of the invention.

According to specific embodiments, the linker may be derived from naturally-occurring multi-domain proteins or is an empirical linker as described, for example, in Chichili et al., (2013), Protein Sci. 22 (2): 153-167, Chen et al.

(2013), Adv Drug Deliv Rev. 65 (10): 1357-1369, the entire contents of which are hereby incorporated by reference. In some embodiments, the linker may be designed using linker designing databases and computer programs such as those described in Chen et al., (2013), Adv Drug Deliv Rev. 65 (10): 1357-1369 and Crasto et al., (2000), Protein Eng. 13 (5): 309-312, the entire contents of which are hereby incorporated by reference.

According to specific embodiments, the linker is a synthetic linker such as PEG.

According to specific embodiments, the linker is an Fc domain or the hinge region of an antibody (e.g., of IgG, IgA, IgD or IgE) or a fragment thereof.

According to specific embodiments, the linker is an Fc domain or the hinge region of human IgG4.

According to specific embodiments, the Fc domain linker comprises SEQ ID NO: 160.

According to specific embodiments, the linker is an Fc domain or the hinge region of human IgG1.

According to specific embodiments, the Fc domain linker comprises SEQ ID NO: 163.

According to specific embodiments, the Fc domain or the hinge region linker may comprise conservative and non-conservative amino acid substitutions (also referred to herein as mutations). Such substitution are known in the art.

According to other specific embodiments, the linker is not an Fc domain or a hinge region of an antibody or a fragment thereof.

According to specific embodiments, the linker may be functional. For example, without limitation, the linker may function to improve the folding and/or stability, improve the expression, improve the pharmacokinetics, and/or improve the bioactivity of the PD1-4-1BBL fusion protein. In another example, the linker may function to target the PD1-4-1BBL fusion protein to a particular cell type or location.

According to specific embodiments, the linker is a polypeptide.

Non-limiting examples of polypeptide linkers include linkers having the sequence LE, GGGGS (SEQ ID NO: 150), (GGGGS)$_n$ (n=1-4) (SEQ ID NO: 149), GGGGSGGGG (SEQ ID NO: 122), (GGGGS)x2 (SEQ ID NO: 151), (GGGGS)x2+GGGG (SEQ ID NO: 121), (Gly)$_8$, (Gly)$_6$, (EAAAK)$_n$ (n=1-3) (SEQ ID NO: 152), A(EAAAK)$_n$ A (n=2-5) (SEQ ID NO: 153), AEAAAKEAAAKA (SEQ ID NO: 154), A(EAAAK)$_4$ ALEA(EAAAK)4A (SEQ ID NO: 155), PAPAP (SEQ ID NO: 156), K ESGSVSS EQ LAQ FRS LD (SEQ ID NO: 157), EGKSSGSGSESKST (SEQ ID NO: 158), GSAGSAAGSGEF (SEQ ID NO: 159), and (XP)$_n$, with X designating any amino acid, e.g., Ala, Lys, or Glu.

According to specific embodiments, the linker is selected from the group consisting of GGGGS (SEQ ID NO: 150), (GGGGS)$_n$ (n=1-4) (SEQ ID NO: 149), GGGGSGGGG (SEQ ID NO: 122), (GGGGS)x2 (SEQ ID NO: 151), (GGGGS)x2+GGGG (SEQ ID NO: 121).

According to specific embodiments, the linker is a (GGGGS)$_n$(n=1-4) (SEQ ID NO: 149) linker.

According to specific embodiments, the linker is GGGGSx2 (SEQ ID NO: 151) linker.

Thus, according to specific embodiments, the PD1-4-1BBL fusion protein amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 145.

According to specific embodiments, the PD1-4-1BBL fusion protein amino acid sequence comprises an amino acid sequence having at least 80% identity to SEQ ID NO: 145.

According to specific embodiments, the PD1-4-1BBL fusion protein amino acid sequence comprises an amino acid sequence having at least 85% identity to SEQ ID NO: 145.

According to specific embodiments, the PD1-4-1BBL fusion protein amino acid sequence comprises an amino acid sequence having at least 90% identity to SEQ ID NO: 145.

According to specific embodiments, the PD1-4-1BBL fusion protein amino acid sequence comprises an amino acid sequence having at least 95% identity to SEQ ID NO: 145.

According to specific embodiments, the PD1-4-1BBL fusion protein amino acid sequence comprises an amino acid sequence having at least 96%, at least 97%, at least 98%, at least 99% or 100% identity to SEQ ID NO: 145.

According to specific embodiments, the PD1-4-1BBL fusion protein amino acid sequence comprises SEQ ID NO: 145.

According to specific embodiments, the PD1-4-1BBL fusion protein amino acid sequence consists of SEQ ID NO: 145.

According to specific embodiments, the linker is a GGGGSGGGG (SEQ ID NO: 122) linker.

According to specific embodiments, the linker is a (GGGGS)x2+GGGG (SEQ ID NO: 121) linker.

Thus, according to specific embodiments, the PD1-4-1BBL fusion protein amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 147.

According to specific embodiments, the PD1-4-1BBL fusion protein amino acid sequence comprises an amino acid sequence having at least 80% identity to SEQ ID NO: 147.

According to specific embodiments, the PD1-4-1BBL fusion protein amino acid sequence comprises an amino acid sequence having at least 85% identity to SEQ ID NO: 147.

According to specific embodiments, the PD1-4-1BBL fusion protein amino acid sequence comprises an amino acid sequence having at least 90% identity to SEQ ID NO: 147.

According to specific embodiments, the PD1-4-1BBL fusion protein amino acid sequence comprises an amino acid sequence having at least 95% identity to SEQ ID NO: 147.

According to specific embodiments, the PD1-4-1BBL fusion protein amino acid sequence comprises an amino acid sequence having at least 96%, at least 97%, at least 98%, at least 99% or 100% identity to SEQ ID NO: 147.

According to specific embodiments, the PD1-4-1BBL fusion protein amino acid sequence comprises SEQ ID NO: 147.

According to specific embodiments, the PD1-4-1BBL fusion protein amino acid sequence consists of SEQ ID NO: 147.

In some embodiments, the PD1-4-1BBL fusion protein comprises a linker at a length of one to six amino acids.

According to specific embodiments, the linker is substantially comprised of glycine and/or serine residues (e.g. about 30%, or about 40%, or about 50%, or about 60%, or about 70%, or about 80%, or about 90%, or about 95%, or about 97% or 100% glycines and serines).

According to specific embodiments, the linker is a single amino acid linker.

In some embodiments of the invention, the one amino acid which links PD1 and 4-1BBL is glycine, also referred to herein as PD1-G-4-1BBL fusion protein.

According to specific embodiments, the PD1-4-1BBL fusion protein amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 12, 14, 16, 44-56, 97, 101, 103, 105, 107, 111, 113, 133, 135, 137, 139, 141, 143 and 147, each possibility represents a separate embodiment of the present invention.

According to specific embodiments, the PD1-4-1BBL fusion protein amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 133, 135, 137, 139, 141, 143 and 147, each possibility represents a separate embodiment of the present invention.

According to specific embodiments, the PD1-4-1BBL fusion protein amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 12, 14, 16, 44-56, 97, 101, 103, 105, 107 and 111, each possibility represents a separate embodiment of the present invention.

According to specific embodiments, the PD1-4-1BBL fusion protein amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 97, 101, 103, 105, 107 and 111, each possibility represents a separate embodiment of the present invention.

According to specific embodiments, the PD1-4-1BBL fusion protein amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 97, 101, 103, 105 and 107, each possibility represents a separate embodiment of the present invention.

According to specific embodiments, the PD1-4-1BBL fusion protein amino acid sequence comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identity to an amino acid sequence selected from the group consisting of SEQ ID NO: 12, 14 and 16, each possibility represents a separate embodiment of the present invention.

According to specific embodiments, the PD1-4-1BBL fusion protein amino acid sequence comprises an amino acid sequence having at least 80% identity to an amino acid sequence selected from the group consisting of SEQ ID NO: 12, 14, 16, 44-56, 97, 101, 103, 105, 107, 111, 113, 133, 135, 137, 139, 141, 143 and 147, each possibility represents a separate embodiment of the present invention.

According to specific embodiments, the PD1-4-1BBL fusion protein amino acid sequence comprises an amino acid sequence having at least 80% identity to an amino acid sequence selected from the group consisting of SEQ ID NO: 133, 135, 137, 139, 141, 143 and 147, each possibility represents a separate embodiment of the present invention.

According to specific embodiments, the PD1-4-1BBL fusion protein amino acid sequence comprises an amino acid sequence having at least 80% identity to an amino acid sequence selected from the group consisting of SEQ ID NO: 97, 101, 103, 105, 107 and 111, each possibility represents a separate embodiment of the present invention.

According to specific embodiments, the PD1-4-1BBL fusion protein amino acid sequence comprises an amino acid sequence having at least 80% identity to an amino acid sequence selected from the group consisting of SEQ ID NO: 97, 101, 103, 105 and 107, each possibility represents a separate embodiment of the present invention.

According to specific embodiments, the PD1-4-1BBL fusion protein amino acid sequence comprises an amino acid sequence having at least 80% identity to an amino acid sequence selected from the group consisting of SEQ ID NO: 12, 14 and 16, each possibility represents a separate embodiment of the present invention.

According to specific embodiments, the PD1-4-1BBL fusion protein amino acid sequence comprises an amino acid sequence having at least 85% identity to an amino acid sequence selected from the group consisting of SEQ ID NO: 12, 14, 16, 44-56, 97, 101, 103, 105, 107, 111, 113, 133, 135, 137, 139, 141, 143 and 147, each possibility represents a separate embodiment of the present invention.

According to specific embodiments, the PD1-4-1BBL fusion protein amino acid sequence comprises an amino acid sequence having at least 85% identity to an amino acid sequence selected from the group consisting of SEQ ID NO: 133, 135, 137, 139, 141, 143 and 147, each possibility represents a separate embodiment of the present invention.

According to specific embodiments, the PD1-4-1BBL fusion protein amino acid sequence comprises an amino acid sequence having at least 85% identity to an amino acid sequence selected from the group consisting of SEQ ID NO: 97, 101, 103, 105, 107 and 111, each possibility represents a separate embodiment of the present invention.

According to specific embodiments, the PD1-4-1BBL fusion protein amino acid sequence comprises an amino acid sequence having at least 85% identity to an amino acid sequence selected from the group consisting of SEQ ID NO: 97, 101, 103, 105 and 107, each possibility represents a separate embodiment of the present invention.

According to specific embodiments, the PD1-4-1BBL fusion protein amino acid sequence comprises an amino acid sequence having at least 85% identity to an amino acid sequence selected from the group consisting of SEQ ID NO: 12, 14 and 16, each possibility represents a separate embodiment of the present invention.

According to specific embodiments, the PD1-4-1BBL fusion protein amino acid sequence comprises an amino acid sequence having at least 90% identity to an amino acid sequence selected from the group consisting of SEQ ID NO: 12, 14, 16, 44-56, 97, 101, 103, 105, 107, 111, 113, 133, 135, 137, 139, 141, 143 and 147, each possibility represents a separate embodiment of the present invention.

According to specific embodiments, the PD1-4-1BBL fusion protein amino acid sequence comprises an amino acid sequence having at least 90% identity to an amino acid sequence selected from the group consisting of SEQ ID NO: 133, 135, 137, 139, 141, 143 and 147, each possibility represents a separate embodiment of the present invention.

According to specific embodiments, the PD1-4-1BBL fusion protein amino acid sequence comprises an amino acid sequence having at least 90% identity to an amino acid sequence selected from the group consisting of SEQ ID NO: 97, 101, 103, 105, 107 and 111, each possibility represents a separate embodiment of the present invention.

According to specific embodiments, the PD1-4-1BBL fusion protein amino acid sequence comprises an amino acid sequence having at least 90% identity to an amino acid sequence selected from the group consisting of SEQ ID NO: 97, 101, 103, 105 and 107, each possibility represents a separate embodiment of the present invention.

According to specific embodiments, the PD1-4-1BBL fusion protein amino acid sequence comprises an amino acid sequence having at least 90% identity to an amino acid sequence selected from the group consisting of SEQ ID NO: 12, 14 and 16, each possibility represents a separate embodiment of the present invention.

According to specific embodiments, the PD1-4-1BBL fusion protein amino acid sequence comprises an amino acid sequence having at least 95% identity to an amino acid sequence selected from the group consisting of SEQ ID NO: 12, 14, 16, 44-56, 97, 101, 103, 105, 107, 111, 113, 133, 135, 137, 139, 141, 143 and 147, each possibility represents a separate embodiment of the present invention.

According to specific embodiments, the PD1-4-1BBL fusion protein amino acid sequence comprises an amino acid sequence having at least 95% identity to an amino acid sequence selected from the group consisting of SEQ ID NO: 133, 135, 137, 139, 141, 143 and 147, each possibility represents a separate embodiment of the present invention.

According to specific embodiments, the PD1-4-1BBL fusion protein amino acid sequence comprises an amino acid sequence having at least 95% identity to an amino acid sequence selected from the group consisting of SEQ ID NO: 97, 101, 103, 105, 107 and 111, each possibility represents a separate embodiment of the present invention.

According to specific embodiments, the PD1-4-1BBL fusion protein amino acid sequence comprises an amino acid sequence having at least 95% identity to an amino acid sequence selected from the group consisting of SEQ ID NO: 97, 101, 103, 105 and 107, each possibility represents a separate embodiment of the present invention.

According to specific embodiments, the PD1-4-1BBL fusion protein amino acid sequence comprises an amino acid sequence having at least 95% identity to an amino acid sequence selected from the group consisting of SEQ ID NO: 12, 14 and 16, each possibility represents a separate embodiment of the present invention.

According to specific embodiments, the PD1-4-1BBL fusion protein amino acid sequence comprises an amino acid sequence having at least 95% identity to SEQ ID NO: 97.

According to specific embodiments, the PD1-4-1BBL fusion protein amino acid sequence comprises an amino acid sequence having at least 95% identity to SEQ ID NO: 101.

According to specific embodiments, the PD1-4-1BBL fusion protein amino acid sequence comprises an amino acid sequence having at least 95% identity to SEQ ID NO: 103.

According to specific embodiments, the PD1-4-1BBL fusion protein amino acid sequence comprises an amino acid sequence having at least 95% identity to SEQ ID NO: 105.

According to specific embodiments, the PD1-4-1BBL fusion protein amino acid sequence comprises an amino acid sequence having at least 95% identity to SEQ ID NO: 107.

According to specific embodiments, the PD1-4-1BBL fusion protein amino acid sequence comprises an amino acid sequence having at least 95% identity to SEQ ID NO: 111.

According to specific embodiments, the PD1-4-1BBL fusion protein amino acid sequence comprises an amino acid sequence having at least 95% identity to SEQ ID NO: 12.

According to specific embodiments, the PD1-4-1BBL fusion protein amino acid sequence comprises an amino acid sequence having at least 95% identity to SEQ ID NO: 14.

According to specific embodiments, the PD1-4-1BBL fusion protein amino acid sequence comprises an amino acid sequence having at least 95% identity to SEQ ID NO: 16.

According to specific embodiments, the PD1-4-1BBL fusion protein amino acid sequence comprises an amino acid sequence having at least 95% identity to SEQ ID NO: 113.

According to specific embodiments, the PD1-4-1BBL fusion protein amino acid sequence comprises an amino acid sequence having at least 95% identity to SEQ ID NO: 133.

According to specific embodiments, the PD1-4-1BBL fusion protein amino acid sequence comprises an amino acid sequence having at least 95% identity to SEQ ID NO: 135.

According to specific embodiments, the PD1-4-1BBL fusion protein amino acid sequence comprises an amino acid sequence having at least 95% identity to SEQ ID NO: 137.

According to specific embodiments, the PD1-4-1BBL fusion protein amino acid sequence comprises an amino acid sequence having at least 95% identity to SEQ ID NO: 139.

According to specific embodiments, the PD1-4-1BBL fusion protein amino acid sequence comprises an amino acid sequence having at least 95% identity to SEQ ID NO: 141.

According to specific embodiments, the PD1-4-1BBL fusion protein amino acid sequence comprises an amino acid sequence having at least 95% identity to SEQ ID NO: 143.

According to specific embodiments, the PD1-4-1BBL fusion protein amino acid sequence comprises an amino acid sequence having at least 95% identity to SEQ ID NO: 147.

According to specific embodiments, the PD1-4-1BBL fusion protein amino acid sequence comprises an amino acid sequence having at least 96%, at least 97%, at least 98%, at least 99% or 100% identity to an amino acid sequence selected from the group consisting of SEQ ID NO: 12, 14, 16, 44-56, 97, 101, 103, 105, 107, 111, 113, 133, 135, 137, 139, 141, 143 and 147, each possibility represents a separate embodiment of the present invention.

According to specific embodiments, the PD1-4-1BBL fusion protein amino acid sequence comprises an amino acid sequence having at least 96%, at least 97%, at least 98%, at least 99% or 100% identity to an amino acid sequence selected from the group consisting of SEQ ID NO: 133, 135, 137, 139, 141, 143 and 147, each possibility represents a separate embodiment of the present invention.

According to specific embodiments, the PD1-4-1BBL fusion protein amino acid sequence comprises an amino acid sequence having at least 96%, at least 97%, at least 98%, at least 99% or 100% identity to an amino acid sequence selected from the group consisting of SEQ ID NO: 97, 101, 103, 105, 107 and 111, each possibility represents a separate embodiment of the present invention.

According to specific embodiments, the PD1-4-1BBL fusion protein amino acid sequence comprises an amino acid sequence an amino acid sequence having at least 96%, at least 97%, at least 98%, at least 99% or 100% identity to an amino acid sequence selected from the group consisting of SEQ ID NO: 97, 101, 103, 105 and 107, each possibility represents a separate embodiment of the present invention.

According to specific embodiments, the PD1-4-1BBL fusion protein amino acid sequence comprises an amino acid sequence having at least 96%, at least 97%, at least 98%, at least 99% or 100% identity to an amino acid sequence selected from the group consisting of SEQ ID NO: 12, 14 and 16, each possibility represents a separate embodiment of the present invention.

According to specific embodiments, the PD1-4-1BBL fusion protein amino acid sequence comprises an amino acid sequence selected from the group consisting of SEQ ID NO: 12, 14, 16, 44-56, 97, 101, 103, 105, 107, 111, 113, 133, 135, 137, 139, 141, 143 and 147.

According to specific embodiments, the PD1-4-1BBL fusion protein amino acid sequence comprises an amino acid sequence selected from the group consisting of SEQ ID NO: 133, 135, 137, 139, 141, 143 and 147.

According to specific embodiments, the PD1-4-1BBL fusion protein amino acid sequence comprises an amino acid sequence selected from the group consisting of SEQ ID NO: 12, 14, 16, 44-56, 97, 101, 103, 105, 107 and 111.

According to specific embodiments, the PD1-4-1BBL fusion protein amino acid sequence comprises an amino acid sequence selected from the group consisting of SEQ ID NO: 97, 101, 103, 105, 107 and 111.

According to specific embodiments, the PD1-4-1BBL fusion protein amino acid sequence comprises an amino acid sequence selected from the group consisting of SEQ ID NO: 97, 101, 103, 105 and 107, each possibility represents a separate embodiment of the present invention.

According to specific embodiments, the PD1-4-1BBL fusion protein amino acid sequence comprises an amino acid sequence selected from the group consisting of SEQ ID NO: 12, 14, 16 and 44-56.

According to specific embodiments, the PD1-4-1BBL fusion protein amino acid sequence comprises an amino acid sequence selected from the group consisting of SEQ ID NO: 12, 14 and 16.

According to specific embodiments, the PD1-4-1BBL fusion protein amino acid sequence comprises SEQ ID NO: 97.

According to specific embodiments, the PD1-4-1BBL fusion protein amino acid sequence comprises SEQ ID NO: 101.

According to specific embodiments, the PD1-4-1BBL fusion protein amino acid sequence comprises SEQ ID NO: 103.

According to specific embodiments, the PD1-4-1BBL fusion protein amino acid sequence comprises SEQ ID NO: 105.

According to specific embodiments, the PD1-4-1BBL fusion protein amino acid sequence comprises SEQ ID NO: 107.

According to specific embodiments, the PD1-4-1BBL fusion protein amino acid sequence comprises SEQ ID NO: 111.

According to specific embodiments, the PD1-4-1BBL fusion protein amino acid sequence comprises SEQ ID NO: 12.

According to specific embodiments, the PD1-4-1BBL fusion protein amino acid sequence comprises SEQ ID NO: 14.

According to specific embodiments, the PD1-4-1BBL fusion protein amino acid sequence comprises SEQ ID NO: 16.

According to specific embodiments, the PD1-4-1BBL fusion protein amino acid sequence comprises SEQ ID NO: 113.

According to specific embodiments, the PD1-4-1BBL fusion protein amino acid sequence comprises SEQ ID NO: 133.

According to specific embodiments, the PD1-4-1BBL fusion protein amino acid sequence comprises SEQ ID NO: 135.

According to specific embodiments, the PD1-4-1BBL fusion protein amino acid sequence comprises SEQ ID NO: 137.

According to specific embodiments, the PD1-4-1BBL fusion protein amino acid sequence comprises SEQ ID NO: 139.

According to specific embodiments, the PD1-4-1BBL fusion protein amino acid sequence comprises SEQ ID NO: 141.

According to specific embodiments, the PD1-4-1BBL fusion protein amino acid sequence comprises SEQ ID NO: 143.

According to specific embodiments, the PD1-4-1BBL fusion protein amino acid sequence comprises SEQ ID NO: 147.

According to specific embodiments, the PD1-4-1BBL fusion protein amino acid sequence consists of an amino acid sequence selected from the group consisting of SEQ ID NO: 12, 14, 16, 44-56, 97, 101, 103, 105, 107, 111, 113, 133, 135, 137, 139, 141, 143 and 147.

According to specific embodiments, the PD1-4-1BBL fusion protein amino acid sequence consists of an amino acid sequence selected from the group consisting of SEQ ID NO: 133, 135, 137, 139, 141, 143 and 147.

According to specific embodiments, the PD1-4-1BBL fusion protein amino acid sequence consists of an amino acid sequence selected from the group consisting of SEQ ID NO: 12, 14, 16, 44-56, 97, 101, 103, 105, 107 and 111.

According to specific embodiments, the PD1-4-1BBL fusion protein amino acid sequence consists of an amino acid sequence selected from the group consisting of SEQ ID NO: 97, 101, 103, 105, 107 and 111.

According to specific embodiments, the PD1-4-1BBL fusion protein amino acid sequence consists of an amino acid sequence an amino acid sequence selected from the group consisting of SEQ ID NO: 97, 101, 103, 105 and 107, each possibility represents a separate embodiment of the present invention.

According to specific embodiments, the PD1-4-1BBL fusion protein amino acid sequence consists of an amino acid sequence selected from the group consisting of SEQ ID NO: 12, 14, 16 and 44-56.

According to specific embodiments, the PD1-4-1BBL fusion protein amino acid sequence consists of an amino acid sequence selected from the group consisting of SEQ ID NO: 12, 14 and 16.

According to specific embodiments, the PD1-4-1BBL fusion protein amino acid sequence consists of SEQ ID NO: 97.

According to specific embodiments, the PD1-4-1BBL fusion protein amino acid sequence consists of SEQ ID NO: 101.

According to specific embodiments, the PD1-4-1BBL fusion protein amino acid sequence consists of SEQ ID NO: 103.

According to specific embodiments, the PD1-4-1BBL fusion protein amino acid sequence consists of SEQ ID NO: 105.

According to specific embodiments, the PD1-4-1BBL fusion protein amino acid sequence consists of SEQ ID NO: 107.

According to specific embodiments, the PD1-4-1BBL fusion protein amino acid sequence consists of SEQ ID NO: 111.

According to specific embodiments, the PD1-4-1BBL fusion protein amino acid sequence consists of SEQ ID NO: 12.

According to specific embodiments, the PD1-4-1BBL fusion protein amino acid sequence consists of SEQ ID NO: 14.

According to specific embodiments, the PD1-4-1BBL fusion protein amino acid sequence consists of SEQ ID NO: 16.

According to specific embodiments, the PD1-4-1BBL fusion protein amino acid sequence consists of SEQ ID NO: 113.

According to specific embodiments, the PD1-4-1BBL fusion protein amino acid sequence consists of SEQ ID NO: 133.

According to specific embodiments, the PD1-4-1BBL fusion protein amino acid sequence consists of SEQ ID NO: 135.

According to specific embodiments, the PD1-4-1BBL fusion protein amino acid sequence consists of SEQ ID NO: 137.

According to specific embodiments, the PD1-4-1BBL fusion protein amino acid sequence consists of SEQ ID NO: 139.

According to specific embodiments, the PD1-4-1BBL fusion protein amino acid sequence consists of SEQ ID NO: 141.

According to specific embodiments, the PD1-4-1BBL fusion protein amino acid sequence consists of SEQ ID NO: 143.

According to specific embodiments, the PD1-4-1BBL fusion protein amino acid sequence consists of SEQ ID NO: 147.

According to specific embodiments, the PD1-4-1BBL fusion protein amino acid sequence is 300-900 amino acids, 300-800 amino acids, 300-600 amino acids, 300-550 amino acids, 300-500 amino acids in length, each possibility represents a separate embodiment of the present invention.

According to specific embodiments, the PD1-4-1BBL fusion protein amino acid sequence is 300-750 amino acids in length.

According to specific embodiments, the PD1-4-1BBL fusion protein amino acid sequence is 308-750 amino acids in length.

According to specific embodiments, the PD1-4-1BBL fusion protein amino acid sequence is 308-400 amino acids in length.

According to specific embodiments, the PD1-4-1BBL fusion protein amino acid sequence is 308-350 amino acids in length.

According to specific embodiments, the PD1-4-1BBL fusion protein amino acid sequence is 308-448, 308-362, 308-351, 313-351, 313-339, 318-351, 318-362, 318-340, 318-332 amino acids in length, each possibility represents a separate embodiment of the present invention.

According to specific embodiments, the PD1-4-1BBL fusion protein amino acid sequence is 308-488 amino acids in length.

According to specific embodiments, the PD1-4-1BBL fusion protein amino acid sequence is 308-351 amino acids in length.

According to specific embodiments, the PD1-4-1BBL fusion protein amino acid sequence is 318-351 amino acids in length.

Non-limiting examples of specific PD1-4-1BBL fusion proteins which can be used with specific embodiments of the present invention are provided in Table 4 of the Examples section which follows, which serves as an integral part of the specification.

According to specific embodiments, the production yield of the PD1-4-1BBL fusion protein of some embodiments of the present invention is at least 1.5 fold, at least 2 fold, at least 2.5 fold, at least 3 fold, at least 5 fold higher than the production yield of a PD1-4-1BBL fusion protein comprising a PD1 amino acid sequence as set forth in SEQ ID NO: 2 and a 4-1BBL amino acid sequence as set forth in SEQ ID NO: 3, under the same production conditions, each possibility represents a separate embodiment of the present invention.

According to specific embodiments, the production yield of the PD1-4-1BBL fusion protein of some embodiments of the present invention is at least 1.5 fold higher than the production yield of a PD1-4-1BBL fusion protein comprising a PD1 amino acid sequence as set forth in SEQ ID NO: 2 and a 4-1BBL amino acid sequence as set forth in SEQ ID NO: 3, under the same production conditions.

According to specific embodiments, the production yield of the PD1-4-1BBL fusion protein of some embodiments of the present invention is at least 2 fold higher than the production yield of a PD1-4-1BBL fusion protein comprising a PD1 amino acid sequence as set forth in SEQ ID NO: 2 and a 4-1BBL amino acid sequence as set forth in SEQ ID NO: 3, under the same production conditions.

According to specific embodiments, the production yield of the PD1-4-1BBL fusion protein of some embodiments of the present invention is at least 1.5 fold, at least 2 fold, at least 2.5 fold, at least 3 fold, at least 5 fold higher than the production yield of a SEQ ID NO: 5, under the same production conditions each possibility represents a separate embodiment of the present invention.

According to specific embodiments, the production yield of the PD1-4-1BBL fusion protein of some embodiments of the present invention is at least 1.5 fold higher than the production yield of SEQ ID NO: 5 under the same production conditions.

According to specific embodiments, the production yield of the PD1-4-1BBL fusion protein of some embodiments of the present invention is at least 2 fold higher than the production yield of a SEQ ID NO: 5 under the same production conditions.

According to specific embodiments, the production yield of the isolated polypeptide comprising the PD1 amino acid sequence of some embodiments of the present invention is at least 1.5 fold, at least 2 fold, at least 2.5 fold, at least 3 fold, at least 5 fold higher than the production yield of SEQ ID NO: 2, under the same production conditions, each possibility represents a separate embodiment of the present invention.

According to specific embodiments, the production yield of the isolated polypeptide comprising the 4-1BBL amino acid sequence of some embodiments of the present invention is at least 1.5 fold, at least 2 fold, at least 2.5 fold, at least 3 fold, at least 5 fold higher than the production yield of SEQ ID NO: 3, under the same production conditions, each possibility represents a separate embodiment of the present invention.

According to specific embodiments, the amount of aggregates of the PD1-4-1BBL fusion protein of some embodiments of the present invention is at least 20%, at least 30%, at least 40%, at least 50%, at least 60%, at least 70%, at least 80%, at least 90% or at least 95% lower than the amount of aggregates of SEQ ID NO: 5 under the same production conditions, said aggregates are of at least 300 kDa in molecular weight as may be determined by e.g. SDS-PAGE or SEC-MALS.

According to specific embodiments, the amount of aggregates of the PD1-4-1BBL fusion protein of some embodiments of the present invention is at least 20% lower than the amount of aggregates of SEQ ID NO: 5 under the same production conditions.

According to specific embodiments, the amount of aggregates of the PD1-4-1BBL fusion protein of some embodiments of the present invention is at least 50% lower than amount of aggregates of a SEQ ID NO: 5 under the same production conditions.

According to specific embodiments, the activity of the PD1-4-1BBL fusion protein of some embodiments of the present invention is at least 1.5 fold, at least 2 fold, at least 2.5 fold, at least 3 fold, at least 5 fold higher than the activity of a PD1-4-1BBL fusion protein comprising a PD1 amino acid sequence as set forth in SEQ ID NO: 2 and a 4-1BBL amino acid sequence as set forth in SEQ ID NO: 3, e.g. under the same production conditions, each possibility represents a separate embodiment of the present invention.

According to specific embodiments, the activity of the PD1-4-1BBL fusion protein of some embodiments of the present invention is at least 1.5 fold, at least 2 fold, at least 2.5 fold, at least 3 fold, at least 5 fold higher than the activity of a SEQ ID NO: 5, e.g. under the same production conditions, each possibility represents a separate embodiment of the present invention.

According to specific embodiments, the activity of the isolated polypeptide comprising the PD1 amino acid sequence of some embodiments of the present invention is at least 1.5 fold, at least 2 fold, at least 2.5 fold, at least 3 fold, at least 5 fold higher than the activity of SEQ ID NO: 2, e.g. under the same production conditions, each possibility represents a separate embodiment of the present invention.

According to specific embodiments, the activity of the isolated polypeptide comprising the 4-1BBL amino acid sequence of some embodiments of the present invention is at least 1.5 fold, at least 2 fold, at least 2.5 fold, at least 3 fold, at least 5 fold higher than the activity of SEQ ID NO: 3, e.g. under the same production conditions, each possibility represents a separate embodiment of the present invention.

According to specific embodiments, the stability of the PD1-4-1BBL fusion protein of some embodiments of the present invention is at least 1.5 fold, at least 2 fold, at least 2.5 fold, at least 3 fold, at least 5 fold higher than the stability of a PD1-4-1BBL fusion protein comprising a PD1 amino acid sequence as set forth in SEQ ID NO: 2 and a 4-1BBL amino acid sequence as set forth in SEQ ID NO: 3, under the same production conditions, each possibility represents a separate embodiment of the present invention.

According to specific embodiments, the stability of the PD1-4-1BBL fusion protein of some embodiments of the present invention is at least 1.5 fold, at least 2 fold, at least 2.5 fold, at least 3 fold, at least 5 fold higher than the stability of a SEQ ID NO: 5, under the same production conditions each possibility represents a separate embodiment of the present invention.

According to specific embodiments, the stability of the isolated polypeptide comprising the PD1 amino acid sequence of some embodiments of the present invention is at least 1.5 fold, at least 2 fold, at least 2.5 fold, at least 3 fold, at least 5 fold higher than the stability of SEQ ID NO: 2, under the same production conditions, each possibility represents a separate embodiment of the present invention.

According to specific embodiments, the stability of the isolated polypeptide comprising the 4-1BBL amino acid sequence of some embodiments of the present invention is at least 1.5 fold, at least 2 fold, at least 2.5 fold, at least 3 fold, at least 5 fold higher than the stability of SEQ ID NO: 3, under the same production conditions, each possibility represents a separate embodiment of the present invention.

According to specific embodiments, the safety of the PD1-4-1BBL fusion protein of some embodiments of the present invention is at least 1.5 fold, at least 2 fold, at least 2.5 fold, at least 3 fold, at least 5 fold higher than the safety of a PD1-4-1BBL fusion protein comprising a PD1 amino acid sequence as set forth in SEQ ID NO: 2 and a 4-1BBL amino acid sequence as set forth in SEQ ID NO: 3, under the same production conditions, each possibility represents a separate embodiment of the present invention.

According to specific embodiments, the safety of the PD1-4-1BBL fusion protein of some embodiments of the present invention is at least 1.5 fold, at least 2 fold, at least 2.5 fold, at least 3 fold, at least 5 fold higher than the safety of a SEQ ID NO: 5, under the same production conditions each possibility represents a separate embodiment of the present invention.

According to specific embodiments, the safety of the isolated polypeptide comprising the PD1 amino acid sequence of some embodiments of the present invention is at least 1.5 fold, at least 2 fold, at least 2.5 fold, at least 3 fold, at least 5 fold higher than the safety of SEQ ID NO: 2, under the same production conditions, each possibility represents a separate embodiment of the present invention.

According to specific embodiments, the safety of the isolated polypeptide comprising the 4-1BBL amino acid sequence of some embodiments of the present invention is at least 1.5 fold, at least 2 fold, at least 2.5 fold, at least 3 fold, at least 5 fold higher than the safety of SEQ ID NO: 3, under the same production conditions, each possibility represents a separate embodiment of the present invention.

According to specific embodiments, the production conditions comprise expression in a mammalian cell and culturing at 32-37° C., 5-10% $CO_2$ for 5-13 days.

Non-limiting examples of production conditions that can be used with specific embodiments of the invention are disclosed in the Examples section which follows.

Thus, for example an expression vector encoding the fusion protein, the isolated polypeptide comprising the PD1 amino acid sequence or the isolated polypeptide comprising the 4-1BBL amino acid sequence including an artificial signal peptide (e.g. SEQ ID NO: 4) in the N terminus and His-tag and a stop codon in the C terminus, is expressed in mammalian cells such as Expi293F or ExpiCHO cells. The transduced cells are then cultured at 32-37° C. 5-10% $CO_2$ in cell-specific culture medium according to the Expi293F or ExpiCHO cells manufacturer instructions (Thermo) and following at least 5 days in culture the proteins are collected from the supernatant and purified.

According to specific embodiments the culture is operated in a batch, split-batch, fed-batch, or perfusion mode.

According to specific embodiments, the culture is operated under fed-batch conditions.

According to specific embodiments, the culturing is effected at 37° C.

According to specific embodiments, the culturing it effected at 37° C. with a temperature shift to 32° C. This temperature shift can be effected to slow down cells metabolism prior to reaching a stationary phase.

According to specific embodiments, the isolated polypeptide comprising the PD1 amino acid sequence is capable of binding PDL1.

According to specific embodiments, the isolated polypeptide comprising the PD1 amino acid sequence of some embodiments of the present invention has an enhanced activity as disclosed herein compared to SEQ ID NO: 2.

According to specific embodiments, the isolated polypeptide comprising the 4-1BBL amino acid sequence is capable of at least one of:
(i) binding 4-1BB,
(ii) activating said 4-1BB signaling pathway in a cell expressing said 4-1BB; and/or
(iii) co-stimulating immune cells expressing said 4-1BB.

According to specific embodiments, the isolated polypeptide comprising the 4-1BBL amino acid sequence of some embodiments of the present invention has an enhanced activity as disclosed herein compared to SEQ ID NO: 3.

According to specific embodiments, the isolated polypeptide comprising the 4-1BBL amino acid sequence is capable of (i), (ii), (iii), (i)+(ii), (i)+(iii), (ii)+(iii), (i)+(ii)+(iii).

According to specific embodiments, the PD1-4-1BBL fusion protein is capable of least one of:
(i) binding PDL1 and 4-1BB,
(ii) activating 4-1BB signaling pathway in an immune cell (e.g. T cell) expressing 4-1BB; and/or
(iii) activating immune cells (e.g. T cells) expressing said 4-1BB.

According to specific embodiments, the PD1-4-1BBL fusion protein of some embodiments of the present invention has an enhanced activity as disclosed herein compared to a fusion protein comprising a PD1 amino acid sequence as set forth in SEQ ID NO: 2 and a 4-1BBL amino acid sequence as set forth in SEQ ID NO: 3.

According to specific embodiments, the PD1-4-1BBL fusion protein of some embodiments of the present invention has an enhanced activity as disclosed herein compared to SEQ ID NO: 5.

According to specific embodiments, the PD1-4-1BBL fusion protein is capable of (i), (ii), (iii), (i)+(ii), (i)+(iii), (ii)+(iii).

According to specific embodiments, the PD1-4-1BBL fusion protein is capable of (i)+(ii)+(iii).

Methods of determining binding, activating 4-1BB signaling pathway and activating immune cells are well known in the art and are further described hereinabove and in the Examples section which follows.

As the compositions of some embodiments of present invention (e.g. the fusion protein, the isolated polypeptide comprising the PD1 amino acid sequence, the isolated polypeptide comprising the 4-1BBL amino acid sequence, a polynucleotide or nucleic acid encoding same or a host cell expressing same) are capable of activating immune cells, they can be used in method of activating immune cells, in-vitro, ex-vivo and/or in-vivo.

Thus, according to an aspect of the present invention, there is provided a method of activating immune cells, the method comprising in-vitro or ex-vivo activating immune cells in the presence of the PD1-4-1BBL fusion protein, the isolated polypeptide comprising the PD1 amino acid sequence and/or the isolated polypeptide comprising the 4-1BBL amino acid sequence disclosed herein, a polynucleotide encoding same, a nucleic acid construct encoding same or a host cell expressing same.

According to another aspect of the present invention, there is provided a method of activating T cells, the method comprising in-vitro or ex-vivo activating T cells in the presence of the PD1-4-1BBL fusion protein the isolated polypeptide comprising the PD1 amino acid sequence and/or the isolated polypeptide comprising the 4-1BBL amino acid sequence disclosed herein and cells expressing PDL1.

According to specific embodiments, the activating is in the presence of the PD1-4-1BBL fusion protein, a polynucleotide encoding same, a nucleic acid construct encoding same or a host cell expressing same.

According to specific embodiments, the activating is in the presence of the isolated polypeptide comprising the PD1 amino acid sequence, a polynucleotide encoding same, a nucleic acid construct encoding same or a host cell expressing same.

According to specific embodiments, the activating is in the presence of the isolated polypeptide comprising the 4-1BBL amino acid sequence, a polynucleotide encoding same, a nucleic acid construct encoding same or a host cell expressing same.

According to specific embodiments, the activating is in the presence of the isolated polypeptide comprising the PD1 amino acid sequence, a polynucleotide encoding same, a nucleic acid construct encoding same or a host cell expressing same; and the 4-1BBL amino acid sequence, a polynucleotide encoding same, a nucleic acid construct encoding same or a host cell expressing same.

According to specific embodiments, the immune cells express 4-1BB.

According to specific embodiments, the immune cells comprise peripheral mononuclear blood cells (PBMCs).

As used herein the term "peripheral mononuclear blood cells (PBMCs)" refers to a blood cell having a single nucleus and includes lymphocytes, monocytes and dendritic cells (DCs).

According to specific embodiments, the PBMCs are selected from the group consisting of dendritic cells (DCs), T cells, B cells, NK cells and NKT cells.

According to specific embodiments, the PBMCs comprise T cells, B cells, NK cells and NKT cells.

Methods of obtaining PBMCs are well known in the art, such as drawing whole blood from a subject and collection in a container containing an anti-coagulant (e.g. heparin or citrate); and apheresis. Following, according to specific embodiments, at least one type of PBMCs is purified from the peripheral blood. There are several methods and reagents known to those skilled in the art for purifying PBMCs from whole blood such as leukapheresis, sedimentation, density gradient centrifugation (e.g. ficoll), centrifugal elutriation, fractionation, chemical lysis of e.g. red blood cells (e.g. by ACK), selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cells comprise tumor infiltrating lymphocytes.

As used herein the term "tumor infiltrating lymphocytes (TILs) refers to mononuclear white blood cells that have lest the bloodstream and migrated into a tumor.

According to specific embodiments, the TILs are selected from the group consisting of T cells, B cells, NK cells and monocytes.

Methods of obtaining TILs are well known in the art, such as obtaining tumor samples from a subject by e.g. biopsy or necropsy and preparing a single cell suspension thereof. The single cell suspension can be obtained in any suitable manner, e.g., mechanically (disaggregating the tumor using, e.g., a GentleMACS™ Dissociator, Miltenyi Biotec, Auburn, Calif.) or enzymatically (e.g., collagenase or DNase). Following, the at least one type of TILs can be purified from the cell suspension. There are several methods and reagents known to those skilled in the art for purifying the desired type of TILs, such as selection of specific cell types using cell surface markers (using e.g. FACS sorter or magnetic cell separation techniques such as are commercially available e.g. from Invitrogen, Stemcell Technologies, Cellpro, Advanced Magnetics, or Miltenyi Biotec.), and depletion of specific cell types by methods such as eradication (e.g. killing) with specific antibodies or by affinity based purification based on negative selection (using e.g. magnetic cell separation techniques, FACS sorter and/or capture ELISA labeling). Such methods are described for example in THE HANDBOOK OF EXPERIMENTAL IMMUNOLOGY, Volumes 1 to 4, (D. N. Weir, editor) and FLOW CYTOMETRY AND CELL SORTING (A. Radbruch, editor, Springer Verlag, 2000).

According to specific embodiments, the immune cells comprise phagocytic cells.

As used herein, the term "phagocytic cells" refer to a cell that is capable of phagocytosis and include both professional and non-professional phagocytic cells. Methods of analyzing phagocytosis are well known in the art and include for examples killing assays, flow cytometry and/or microscopic evaluation (live cell imaging, fluorescence microscopy, confocal microscopy, electron microscopy). According to specific embodiments, the phagocytic cells are selected from the group consisting of monocytes, dendritic cells (DCs) and granulocytes.

According to specific embodiments, the immune cells comprise monocytes.

According to specific embodiments, the term "monocytes" refers to both circulating monocytes and to macrophages (also referred to as mononuclear phagocytes) present in a tissue.

According to specific embodiments, the monocytes comprise macrophages. Typically, cell surface phenotype of macrophages include CD14, CD40, CD11b, CD64, F4/80 (mice)/EMR1 (human), lysozyme M, MAC-1/MAC-3 and CD68.

According to specific embodiments, the monocytes comprise circulating monocytes. Typically, cell surface phenotypes of circulating monocytes include CD14 and CD16 (e.g. CD14++CD16−, CD14+CD16++, CD14++CD16+).

According to specific embodiments, the immune cells comprise DCs.

As used herein the term "dendritic cells (DCs)" refers to any member of a diverse population of morphologically similar cell types found in lymphoid or non-lymphoid tissues. DCs are a class of professional antigen presenting cells, and have a high capacity for sensitizing HLA-restricted T cells. DCs include, for example, plasmacytoid dendritic cells, myeloid dendritic cells (including immature and mature dendritic cells), Langerhans cells, interdigitating cells, follicular dendritic cells. Dendritic cells may be recognized by function, or by phenotype, particularly by cell surface phenotype. These cells are characterized by their distinctive morphology having veil-like projections on the cell surface, intermediate to high levels of surface HLA-class II expression and ability to present antigen to T cells, particularly to naive T cells (See Steinman R, et al., Ann. Rev. Immunol. 1991; 9:271-196). Typically, cell surface phenotype of DCs include CD1a+, CD4+, CD86+, or HLA-DR. The term DCs encompasses both immature and mature DCs.

According to specific embodiments, the immune cells comprise granulocytes.

As used herein, the term "granulocytes" refer to polymorphonuclear leukocytes characterized by the presence of granules in their cytoplasm.

According to specific embodiments, the granulocytes comprise neutrophils.

According to specific embodiments, the granulocytes comprise mast-cells.

According to specific embodiments the immune cells comprise T cells.

As used herein, the term "T cells" refers to a differentiated lymphocyte with a CD3+, T cell receptor (TCR)+ having either CD4+ or CD8+ phenotype. The T cell may be either an effector or a regulatory T cell.

As used herein, the term "effector T cells" refers to a T cell that activates or directs other immune cells e.g. by producing cytokines or has a cytotoxic activity e.g., CD4+, Th1/Th2, CD8+ cytotoxic T lymphocyte.

As used herein, the term "regulatory T cell" or "Treg" refers to a T cell that negatively regulates the activation of other T cells, including effector T cells, as well as innate immune system cells. Treg cells are characterized by sustained suppression of effector T cell responses. According to a specific embodiment, the Treg is a CD4+CD25+Foxp3+ T cell.

According to specific embodiments, the T cells are CD4+ T cells.

According to other specific embodiments, the T cells are CD8+ T cells.

According to specific embodiments, the T cells are memory T cells. Non-limiting examples of memory T cells include effector memory CD4+ T cells with a CD3+/CD4+/

CD45RA−/CCR7− phenotype, central memory CD4+ T cells with a CD3+/CD4+/CD45RA−/CCR7+ phenotype, effector memory CD8+ T cells with a CD3+/CD8+ CD45RA−/CCR7− phenotype and central memory CD8+ T cells with a CD3+/CD8+CD45RA−/CCR7+ phenotype.

According to specific embodiments, the T cells comprise engineered T cells transduced with a nucleic acid sequence encoding an expression product of interest.

According to specific embodiments, the expression product of interest is a T cell receptor (TCR) or a chimeric antigen receptor (CAR).

As used herein the phrase "transduced with a nucleic acid sequence encoding a TCR" or "transducing with a nucleic acid sequence encoding a TCR" refers to cloning of variable α- and β-chains from T cells with specificity against a desired antigen presented in the context of MHC. Methods of transducing with a TCR are known in the art and are disclosed e.g. in Nicholson et al. Adv Hematol. 2012; 2012:404081; Wang and Rivière Cancer Gene Ther. 2015 March; 22 (2): 85-94); and Lamers et al, Cancer Gene Therapy (2002) 9, 613-623.

As used herein, the phrase "transduced with a nucleic acid sequence encoding a CAR" or "transducing with a nucleic acid sequence encoding a CAR" refers to cloning of a nucleic acid sequence encoding a chimeric antigen receptor (CAR), wherein the CAR comprises an antigen recognition moiety and a T-cell activation moiety. A chimeric antigen receptor (CAR) is an artificially constructed hybrid protein or polypeptide containing an antigen binding domain of an antibody (e.g., a single chain variable fragment (scFv)) linked to T-cell signaling or T-cell activation domains. Method of transducing with a CAR are known in the art and are disclosed e.g. in Davila et al. Oncoimmunology. 2012 Dec. 1; 1 (9): 1577-1583; Wang and Rivière Cancer Gene Ther. 2015 March; 22 (2): 85-94); Maus et al. Blood. 2014 Apr. 24; 123 (17): 2625-35; Porter DL The New England journal of medicine. 2011, 365 (8): 725-733; Jackson H J, Nat Rev Clin Oncol. 2016; 13 (6): 370-383; and Globerson-Levin et al. Mol Ther. 2014; 22 (5): 1029-1038.

According to specific embodiments, the immune cells comprise B cells.

As used herein the term "B cells" refers to a lymphocyte with a B cell receptor (BCR)+, CD19+ and or B220+ phenotype. B cells are characterized by their ability to bind a specific antigen and elicit a humoral response.

According to specific embodiments, the immune cells comprise NK cells.

As used herein the term "NK cells" refers to differentiated lymphocytes with a CD16+CD56+ and/or CD57+ TCR− phenotype. NK are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

According to specific embodiments, the immune cells comprise NKT cells.

As used herein the term "NKT cells" refers to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD1d. NKT cells can have either protective or deleterious effects due to their abilities to produce cytokines that promote either inflammation or immune tolerance.

According to specific embodiments, the immune cells are obtained from a healthy subject.

According to specific embodiments, the immune cells are obtained from a subject suffering from a pathology.

According to specific embodiments, the activating is in the presence of cells expressing PDL1 or exogenous PDL1.

According to specific embodiments, the activating is in the presence of exogenous PDL1.

According to specific embodiments, the exogenous PDL1 is soluble.

According to other specific embodiments, the exogenous PDL1 is immobilized to a solid support.

According to specific embodiments, the activating is in the presence of cells expressing PDL1.

According to specific embodiments, the cells expressing the PDL1 comprise pathologic (diseased) cells.

According to specific embodiments, the cells expressing the PDL1 comprise cancer cells.

According to specific embodiments, the activating is in the presence of a stimulatory agent capable of at least transmitting a primary activating signal [e.g. ligation of the T-Cell Receptor (TCR) with the Major Histocompatibility Complex (MHC)/peptide complex on the Antigen Presenting Cell (APC)] resulting in cellular proliferation, maturation, cytokine production, phagocytosis and/or induction of regulatory or effector functions of the immune cell. According to specific embodiments, the stimulator agent can also transmit a secondary co-stimulatory signal.

Methods of determining the amount of the stimulatory agent and the ratio between the stimulatory agent and the immune cells are well within the capabilities of the skilled in the art and thus are not specified herein.

The stimulatory agent can activate the immune cells in an antigen-dependent or -independent (i.e. polyclonal) manner.

According to specific embodiments, stimulatory agent comprises an antigen non-specific stimulator.

Non-specific stimulators are known to the skilled in the art. Thus, as a non-limiting example, when the immune cells comprise T cells, antigen non-specific stimulator can be an agent capable of binding to a T cell surface structure and induce the polyclonal stimulation of the T cell, such as but not limited to anti-CD3 antibody in combination with a co-stimulatory protein such as anti-CD28 antibody. Other non-limiting examples include anti-CD2, anti-CD137, anti-CD134, Notch-ligands, e.g. Delta-like 1/4, Jagged1/2 either alone or in various combinations with anti-CD3. Other agents that can induce polyclonal stimulation of T cells include, but not limited to mitogens, PHA, PMA-ionomycin, CEB and CytoStim (Miltenyi Biotech). According to specific embodiments, the antigen non-specific stimulator comprises anti-CD3 and anti-CD28 antibodies. According to specific embodiments, the T cell stimulator comprises anti-CD3 and anti-CD28 coated beads, such as the CD3CD28 MACSiBeads obtained from Miltenyi Biotec.

According to specific embodiments, the stimulatory agent comprises an antigen-specific stimulator.

Non-limiting examples of antigen specific T cell stimulators include an antigen-loaded antigen presenting cell [APC, e.g. dendritic cell] and peptide loaded recombinant MHC. Thus, for example, a T cells stimulator can be a dendritic cell preloaded with a desired antigen (e.g. a tumor antigen) or transfected with mRNA coding for the desired antigen.

According to specific embodiments, the antigen is a cancer antigen.

As used herein, the term "cancer antigen" refers to an antigen overexpressed or solely expressed by a cancerous cell as compared to a non-cancerous cell. A cancer antigen may be a known cancer antigen or a new specific antigen that develops in a cancer cell (i.e. neoantigens).

Non-limiting examples for known cancer antigens include MAGE-AI, MAGE-A2, MAGE-A3, MAGE-A4, MAGE-AS, MAGE-A6, MAGE-A7, MAGE-AS, MAGE-A9, MAGE-AIO, MAGE-All, MAGE-A12, GAGE-I, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), MAGE-CI/CT7, MAGE-C2, NY-ES0-1, LAGE-1, SSX-1. SSX-2 (HOM-MEL-40), SSX-3, SSX-4, SSX-5, SCP-1 and XAGE, melanocyte differentiation antigens, p53, ras, CEA, MUCI, PMSA, PSA, tyrosinase, Melan-A, MART-I, gplOO, gp75, alphaactinin-4, Bcr-Abl fusion protein, Casp-8, beta-catenin, cdc27, cdk4, cdkn2a, coa-l, dek-can fusion protein, EF2, ETV6-AML1 fusion protein, LDLR-fucosyltransferaseAS fusion protein, HLA-A2, HLA-All, hsp70-2, KIAA0205, Mart2, Mum-2, and 3, neo-PAP, myosin class I, OS-9, pml-RAR alpha fusion protein, PTPRK, K-ras, N-ras, Triosephosphate isomerase, GnTV, Herv-K-mel, NA-88, SP17, and TRP2-Int2, (MART-I), E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, plSOcrbB-3, c-met, nm-23HI, PSA, TAG-72-4, CA 19-9, CA 72-4, CAM 17.1, NuMa, K-ras, alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, 0250, Ga733 (EpCAM), HTgp-175, M344, MA-50, MG7-Ag, MOV18, NB\170K, NYCO-I, RCASI, SDCCAG16, TA-90 (Mac-2 binding protein\cyclophilin C-associated protein), TAAL6, TAG72, TLP. TPS, tyrosinase related proteins, TRP-1, or TRP-2.

Other tumor antigens that may be expressed are well-known in the art (see for example WO00/20581; Cancer Vaccines and Immunotherapy (2000) Eds Stern, Beverley and Carroll, Cambridge University Press, Cambridge). The sequences of these tumor antigens are readily available from public databases but are also found in WO 1992/020356 AI, WO 1994/005304 AI, WO 1994/023031 AI, WO 1995/020974 AI, WO 1995/023874 AI & WO 1996/026214 AI.

Alternatively, or additionally, a tumor antigen may be identified using cancer cells obtained from the subject by e.g. biopsy.

Thus, according to specific embodiments, the stimulatory agent comprises a cancer cell.

According to specific embodiments, the activating is in the presence of an anti-cancer agent.

According to specific embodiments, the immune cells are purified following the activation.

Thus, the present invention also contemplated isolated immune cells obtainable according to the methods of the present invention.

According to specific embodiments, the immune cells used and/or obtained according to the present invention can be freshly isolated, stored e.g., cryopreserved (i.e. frozen) at e.g. liquid nitrogen temperature at any stage for long periods of time (e.g., months, years) for future use; and cell lines.

Methods of cryopreservation are commonly known by one of ordinary skill in the art and are disclosed e.g. in International Patent Application Publication Nos. WO2007054160 and WO 2001039594 and US Patent Application Publication No. US20120149108.

According to specific embodiments, the cells obtained according to the present invention can be stored in a cell bank or a depository or storage facility.

Consequently, the present teachings further suggest the use of the isolated immune cells and the methods of the present invention as, but not limited to, a source for adoptive immune cells therapies for diseases that can benefit from activating immune cells e.g. a hyper-proliferative disease; a disease associated with immune suppression and infections.

Thus, according to specific embodiments, method of the present invention comprises adoptively transferring the immune cells following said activating to a subject in need thereof.

According to specific embodiments, there is provided the immune cells obtainable according to the methods of the present invention for use in adoptive cell therapy.

The cells used according to specific embodiments of the present invention may be autologous or non-autologous; they can be syngeneic or non-syngeneic: allogeneic or xenogeneic to the subject; each possibility represents a separate embodiment of the present invention.

The present teachings also contemplate the use of the compositions of the present invention (e.g. the fusion protein, the isolated polypeptide comprising the PD1 amino acid sequence, the isolated polypeptide comprising the 4-1BBL amino acid sequence, a polynucleotide or nucleic acid construct encoding same or a host cell expressing same) in methods of treating a disease that can benefit from activating immune cells.

Thus, according to another aspect of the present invention, there is provided a method of treating a disease that can benefit from activating immune cells comprising administering to a subject in need thereof the PD1-4-1BBL fusion protein, the isolated polypeptide comprising the PD1 amino acid sequence and/or the isolated polypeptide comprising the 4-1BBL amino acid sequence disclosed herein, a polynucleotide or nucleic acid construct encoding same or a host cell encoding same.

According to another aspect of the present invention, there is provided the PD1-4-1BBL fusion protein, the isolated polypeptide comprising the PD1 amino acid sequence and/or the isolated polypeptide comprising the 4-1BBL amino acid sequence disclosed herein, a polynucleotide or nucleic acid construct encoding same or a host cell encoding same for use in the treatment of a disease that can benefit from activating immune cells.

According to specific embodiments, the treating or the treatment is with the PD1-4-1BBL fusion protein, a polynucleotide encoding same, a nucleic acid construct encoding same or a host cell expressing same.

According to specific embodiments, the treating or the treatment is with the isolated polypeptide comprising the PD1 amino acid sequence, a polynucleotide encoding same, a nucleic acid construct encoding same or a host cell expressing same.

According to specific embodiments, the treating or the treatment is with the isolated polypeptide comprising the 4-1BBL amino acid sequence, a polynucleotide encoding same, a nucleic acid construct encoding same or a host cell expressing same.

According to specific embodiments, the treating or the treatment is with the isolated polypeptide comprising the PD1 amino acid sequence, a polynucleotide encoding same, a nucleic acid construct encoding same or a host cell expressing same; and the 4-1BBL amino acid sequence, a polynucleotide encoding same, a nucleic acid construct encoding same or a host cell expressing same.

The term "treating" or "treatment" refers to inhibiting, preventing or arresting the development of a pathology (disease, disorder or medical condition) and/or causing the reduction, remission, or regression of a pathology or a symptom of a pathology. Those of skill in the art will understand that various methodologies and assays can be used to assess the development of a pathology, and similarly, various methodologies and assays may be used to assess the reduction, remission or regression of a pathology.

As used herein, the term "subject" includes mammals, e.g., human beings at any age and of any gender. According to specific embodiments, the term "subject" refers to a subject who suffers from the pathology (disease, disorder or medical condition). According to specific embodiments, this term encompasses individuals who are at risk to develop the pathology.

According to specific embodiments, the subject is afflicted with a disease associated with cells expressing PDL1.

According to specific embodiments, diseased cells of the subject express PDL1.

As used herein the phrase "a disease that can benefit from activating immune cells" refers to diseases in which the subject's immune response activity may be sufficient to at least ameliorate symptoms of the disease or delay onset of symptoms, however for any reason the activity of the subject's immune response in doing so is less than optimal.

Non-limiting examples of diseases that can benefit from activating immune cells include hyper-proliferative diseases, diseases associated with immune suppression, immunosuppression caused by medication (e.g. mTOR inhibitors, calcineurin inhibitor, steroids) and infections.

According to specific embodiments, the disease comprises a hyper-proliferative disease. According to specific embodiments, the hyper-proliferative disease comprises sclerosis, fibrosis, Idiopathic pulmonary fibrosis, psoriasis, systemic sclerosis/scleroderma, primary biliary cholangitis, primary sclerosing cholangitis, liver fibrosis, prevention of radiation-induced pulmonary fibrosis, myelofibrosis or retroperitoneal fibrosis.

According to other specific embodiments, the hyper-proliferative disease comprises cancer.

Thus, according to another aspect of the present invention, there is provided a method of treating cancer comprising administering the PD1-4-1BBL fusion protein, the isolated polypeptide comprising the PD1 amino acid sequence and/or the isolated polypeptide comprising the 4-1BBL amino acid sequence disclosed herein to a subject in need thereof.

As used herein, the term cancer encompasses both malignant and pre-malignant cancers.

With regard to pre-malignant or benign forms of cancer, optionally the compositions and methods thereof may be applied for halting the progression of the pre-malignant cancer to a malignant form.

Cancers which can be treated by the methods of some embodiments of the invention can be any solid or non-solid cancer and/or cancer metastasis.

According to specific embodiments, the cancer comprises malignant cancer.

Cancers which can be treated by the methods of some embodiments of the invention can be any solid or non-solid cancer and/or cancer metastasis. Examples of cancer include but are not limited to, carcinoma, lymphoma, blastoma, sarcoma, and leukemia. More particular examples of such cancers include squamous cell cancer, lung cancer (including small-cell lung cancer, non-small-cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; Burkitt lymphoma, Diffused large B cell lymphoma (DLBCL), high grade lymphoblastic NHL; high-grade small non-cleaved cell NHL; bulky disease NHL; mantle cell lymphoma; AIDS-related lymphoma; and Waldenstrom's Macroglobulinemia); T cell lymphoma, Hodgkin lymphoma, chronic lymphocytic leukemia (CLL); acute lymphoblastic leukemia (ALL); Acute myeloid leukemia (AML), Acute promyelocytic leukemia (APL), Hairy cell leukemia; chronic myeloblastic leukemia (CML); and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of breast cancer, colorectal cancer, rectal cancer, non-small cell lung cancer, non-Hodgkins lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. The cancerous conditions amenable for treatment of the invention include metastatic cancers.

According to specific embodiments, the cancer comprises pre-malignant cancer.

Pre-malignant cancers (or pre-cancers) are well characterized and known in the art (refer, for example, to Berman J J. and Henson D E., 2003. Classifying the precancers: a metadata approach. BMC Med Inform Decis Mak. 3:8). Classes of pre-malignant cancers amenable to treatment via the method of the invention include acquired small or microscopic pre-malignant cancers, acquired large lesions with nuclear atypia, precursor lesions occurring with inherited hyperplastic syndromes that progress to cancer, and acquired diffuse hyperplasias and diffuse metaplasias. Examples of small or microscopic pre-malignant cancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

According to specific embodiments, the cancer is Acute Myeloid Leukemia, Anal Cancer, Basal Cell Carcinoma, B-Cell Non-Hodgkin Lymphoma, Bile Duct Cancer, Bladder Cancer, Breast Cancer, Cervical Cancer, Chronic Lymphocytic Leukemia (CLL), Chronic Myelocytic Leukemia (CML), Colorectal Cancer, Cutaneous T-Cell Lymphoma, Diffuse Large B-Cell Lymphoma, Endometrial Cancer, Esophageal Cancer, Fallopian Tube Cancer, Follicular Lymphoma, Gastric Cancer, Gastroesophageal (GE) Junction Carcinomas, Germ Cell Tumors, Germinomatous (Seminomatous), Germ Cell Tumors, Glioblastoma Multiforme (GBM), Gliosarcoma, Head And Neck Cancer, Hepatocellular Carcinoma, Hodgkin Lymphoma, Hypopharyngeal Cancer, Laryngeal Cancer, Leiomyosarcoma, Mantle Cell Lymphoma, Melanoma, Merkel Cell Carcinoma, Multiple Myeloma, Neuroendocrine Tumors, Non-Hodgkin Lymphoma, Non-Small Cell Lung Cancer, Oral Cavity (Mouth) Cancer, Oropharyngeal Cancer, Osteosarcoma, Ovarian Cancer, Pancreatic Cancer, Peripheral Nerve Sheath Tumor (Neurofibrosarcoma), Peripheral T-Cell Lymphomas (PTCL), Peritoneal Cancer, Prostate Cancer, Renal Cell Carcinoma, Salivary Gland Cancer, Skin Cancer, Small-Cell Lung Cancer, Soft Tissue Sarcoma, Squamous Cell Carcinoma, Synovial Sarcoma, Testicular Cancer, Thymic Carcinoma, Thyroid Cancer, Ureter Cancer, Urethral Cancer, Uterine Cancer, Vaginal Cancer or Vulvar Cancer.

According to specific embodiments, the cancer is Acute myeloid leukemia, Bladder Cancer, Breast Cancer, chronic lymphocytic leukemia, Chronic myelogenous leukemia, Colorectal cancer, Diffuse large B-cell lymphoma, Epithelial Ovarian Cancer, Epithelial Tumor, Fallopian Tube Cancer, Follicular Lymphoma, Glioblastoma multiform, Hepatocellular carcinoma, Head and Neck Cancer, Leukemia, Lymphoma, Mantle Cell Lymphoma, Melanoma, Mesothelioma, Multiple Myeloma, Nasopharyngeal Cancer, Non Hodgkin lymphoma, Non-small-cell lung carcinoma, Ovarian Cancer, Prostate Cancer or Renal cell carcinoma.

According to specific embodiments, the cancer is selected from the group consisting of lymphoma, leukemia and carcinoma.

According to specific embodiments, the cancer is selected from the group consisting of lymphoma, leukemia, colon cancer, pancreatic cancer, ovarian cancer, lung cancer and squamous cell carcinoma.

According to specific embodiments, the cancer is colon carcinoma.

According to specific embodiments, the cancer is ovarian carcinoma.

According to specific embodiments, the cancer is lung carcinoma.

According to specific embodiments, the cancer is head and neck carcinoma.

According to specific embodiments, the cancer is leukemia.

According to specific embodiments, the leukemia is selected from the group consisting of acute nonlymphocytic leukemia, chronic lymphocytic leukemia, acute granulocytic leukemia, chronic granulocytic leukemia, acute promyelocytic leukemia, adult T-cellleukemia, aleukemic leukemia, a leukocythemic leukemia, basophylic leukemia, blast cell leukemia, bovine leukemia, chronic myelocytic leukemia, leukemia cutis, embryonal leukemia, cosinophilic leukemia, ( )ross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

According to specific embodiments, the leukemia is promyelocytic leukemia, acute myeloid leukemia or chronic myelogenous leukemia.

According to specific embodiments, the cancer is lymphoma.

According to specific embodiments, the lymphoma is B cell lymphoma

According to specific embodiments, the lymphoma is T cell lymphoma.

According to other specific embodiments, the lymphoma is Hodgkins lymphoma.

According to specific embodiments, the lymphoma is non-Hodgkins lymphoma.

According to specific embodiments, the non-Hodgkin's Lymphoma is a selected from the group consisting of aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, diffuse large B—cell lymphoma, acute lymphoblastic lymphoma, and cutaneous T cell cancer, including mycosis fungoides/Sezary syndrome.

According to specific embodiments, the cancer is multiple myeloma.

According to at least some embodiments, the multiple myeloma is selected from the group consisting of multiple myeloma cancers which produce light chains of kappa-type and/or light chains of lambda-type; aggressive multiple myeloma, including primary plasma cell leukemia (PCL); benign plasma cell disorders such as MGUS (monoclonal gammopathy of undetermined significance), Waldenstrom's macroglobulinemia (WM, also known as lymphoplasmacytic lymphoma) which may proceed to multiple myeloma; smoldering multiple myeloma (SMM), indolent multiple myeloma, premalignant forms of multiple myeloma which may also proceed to multiple myeloma; primary amyloidosis.

According to specific embodiments, the cancer is defined by the presence of tumors that have tumor-infiltrating lymphocytes (TILs) in the tumor micro-environment and/or tumors with a relatively high expression of PDL1 in the tumor micro-environment.

According to specific embodiments, cells of the cancer express PDL1.

According to specific embodiments, the disease comprises a disease associated with immune suppression or immunosuppression caused by medication (e.g. mTOR inhibitors, calcineurin inhibitor, steroids).

According to specific embodiments, the disease comprises HIV, Measles, influenza, LCCM, RSV. Human Rhinoviruses, EBV, CMV or Parvo viruses.

According to specific embodiments, the disease comprises an infection.

As used herein, the term "infection" or "infectious disease" refers to a disease induced by a pathogen. Specific examples of pathogens include, viral pathogens, bacterial pathogens e.g., intracellular mycobacterial pathogens (such as, for example, *Mycobacterium tuberculosis*), intracellular bacterial pathogens (such as, for example, *Listeria monocy-*

*togenes*), or intracellular protozoan pathogens (such as, for example, *Leishmania* and *Trypanosoma*).

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, pox viruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

According to specific embodiments, the compositions disclosed herein (e.g. PD1-4-1BBL fusion protein, polypeptide comprising a PD1 amino acid sequence, polypeptide comprising a 4-1BBL amino acid sequence, polynucleotide or nucleic acid construct encoding same and/or host-cell expressing same) can be administered to a subject in combination with other established or experimental therapeutic regimen to treat a disease that can benefit from activating immune cells (e.g. cancer) including, but not limited to analgesics, chemotherapeutic agents, radiotherapeutic agents, cytotoxic therapies (conditioning), hormonal therapy, antibodies and other treatment regimens (e.g., surgery) which are well known in the art.

According to specific embodiments, the compositions disclosed herein (e.g. PD1-4-1BBL fusion protein, polypeptide comprising a PD1 amino acid sequence, polypeptide comprising a 4-1BBL amino acid sequence, polynucleotide or nucleic acid construct encoding same and/or host-cell expressing same) can be administered to a subject in combination with adoptive cell transplantation such as, but not limited to transplantation of bone marrow cells, hematopoietic stem cells, PBMCs, cord blood stem cells and/or induced pluripotent stem cells.

According to specific embodiments, the therapeutic agent administered in combination with the composition of some embodiments of the invention comprises an anti-cancer agent.

Thus, according to another aspect of the present invention, there is provided a method of treating cancer comprising administering to a subject in need thereof an anti-cancer agent; and the PD1-4-1BBL fusion protein, the polypeptide comprising the PD1 amino acid sequence and/or the polypeptide comprising the 4-1BBL amino acid sequence disclosed herein, a polynucleotide encoding same, a nucleic acid construct encoding same or a host cell expressing same.

Anti-cancer agent that can be use with specific embodiments of the invention include, but are not limited to the anti-cancer drugs Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriccin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

According to specific embodiments, the anti-cancer agent comprises an antibody.

According to specific embodiments, the antibody is selected from the group consisting rituximab, cetuximab, trastuzumab, edrecolomab, alemtuzumab, gemtuzumab, ibritumomab, panitumumab Belimumab, Bivatuzumab Bevacizumab, mertansine, Blinatumomab, Blontuvetmab, Brentuximab vedotin, Catumaxomab, Cixutumumab, Daclizumab, Adalimumab, Bezlotoxumab, Certolizumab pegol, Citatuzumab bogatox, Daratumumab, Dinutuximab, Elotuzumab, Ertumaxomab, Etaracizumab, Gemtuzumab ozogamicin. Girentuximab, Necitumumab, Obinutuzumab, Ofatumumab, Pertuzumab, Ramucirumab, Siltuximab, Tositumomab, Nivolumab, Pembrolizumab, Durvalumab, Atezolizumab, Avelumab Trastuzumab and ipilimumab.

According to specific embodiments, the antibody is selected from the group consisting of rituximab and cetuximab.

According to specific embodiments, the therapeutic agent or the anti-cancer agent comprises an IMiD (e.g. Thalidomide, Lenalidomic, Pomalidomide).

According to specific embodiments, the IMiD is selected from the group consisting of Thalidomide, Lenalidomie and Pomalidomide.

According to specific embodiments, the therapeutic agent administered in combination with the composition of some embodiments of the invention comprises an anti-infection agent (e.g. antibiotics and anti-viral agents)

According to specific embodiments, the therapeutic agent administered in combination with the composition of some embodiments of the invention comprises an immune suppressor agent (e.g. GCSF and other bone marrow stimulators, steroids).

According to specific embodiments the combination therapy has an additive effect.

According to specific embodiments, the combination therapy has a synergistic effect.

According to another aspect of the present invention there is provided an article of manufacture comprising a packaging material packaging a therapeutic agent for treating a disease that can benefit from activating immune cell; and the PD1-4-1BBL fusion protein, the polypeptide comprising the PD1 amino acid sequence and/or the polypeptide comprising the 4-1BBL amino acid sequence disclosed herein, a polynucleotide encoding same, a nucleic acid construct encoding same or a host cell expressing same.

According to specific embodiments, the article of manufacture is identified for the treatment of a disease that can benefit from activating immune cells.

According to specific embodiments, the therapeutic agent for treating said disease; and the PD1-4-1BBL fusion protein, the polypeptide comprising the PD1 amino acid sequence and/or the polypeptide comprising the 4-1BBL amino acid sequence, the polynucleotide encoding same, the nucleic acid construct encoding same or the host cell expressing same are packaged in separate containers.

According to specific embodiments, the therapeutic agent for treating said disease; and the PD1-4-1BBL fusion protein, the polypeptide comprising the PD1 amino acid sequence and/or the polypeptide comprising the 4-1BBL amino acid sequence, the polynucleotide or the nucleic acid encoding same, the nucleic acid construct encoding same or the host cell expressing same are packaged in a co-formulation.

According to specific embodiments, the article of manufacture comprises the PD1-4-1BBL fusion protein, a polynucleotide encoding same, a nucleic acid construct encoding same or a host cell expressing same.

According to specific embodiments, the article of manufacture comprises the isolated polypeptide comprising the PD1 amino acid sequence, a polynucleotide encoding same, a nucleic acid construct encoding same or a host cell expressing same.

According to specific embodiments, the article of manufacture comprises the isolated polypeptide comprising the 4-1BBL amino acid sequence, a polynucleotide encoding same, a nucleic acid construct encoding same or a host cell expressing same.

According to specific embodiments, the article of manufacture comprises the PD1 amino acid sequence, a polynucleotide encoding same, a nucleic acid construct encoding same or a host cell expressing same; and the 4-1BBL amino acid sequence, a polynucleotide encoding same, a nucleic acid construct encoding same or a host cell expressing same.

Thus, according to another aspect of the present invention there is provided an article of manufacture comprising a packaging material packaging the isolated polypeptide comprising the PD1 amino acid sequence disclosed herein, a polynucleotide encoding same, a nucleic acid construct encoding same or a host cell expressing same; and the isolated polypeptide comprising the 4-1BBL amino acid sequence disclosed herein, a polynucleotide encoding same, a nucleic acid construct encoding same or a host cell expressing same.

According to specific embodiments, the isolated polypeptide comprising the PD1 amino acid sequence disclosed herein, a polynucleotide encoding same, a nucleic acid construct encoding same or a host cell expressing same; and the isolated polypeptide comprising the 4-1BBL amino acid sequence disclosed herein, a polynucleotide encoding same, a nucleic acid construct encoding same or a host cell expressing same are packaged in separate containers.

According to specific embodiments, the isolated polypeptide comprising the PD1 amino acid sequence disclosed herein, a polynucleotide encoding same, a nucleic acid construct encoding same or a host cell expressing same; and the isolated polypeptide comprising the 4-1BBL amino acid sequence disclosed herein, a polynucleotide encoding same, a nucleic construct encoding same or a host cell expressing same are packaged in a co-formulation.

According to specific embodiments, the isolated polypeptide comprising the PD1 amino acid sequence; and/or the isolated polypeptide comprising the 4-1BBL amino acid sequence is attached to or comprises a heterologous therapeutic moiety. The therapeutic moiety may be any molecule, including small molecule chemical compounds and polypeptides.

Non-limiting examples of therapeutic moieties which can be used with specific embodiments of the invention include a cytotoxic moiety, a toxic moiety, a cytokine moiety, an immunomodultory moiety, a polypeptide, an antibody, a drug, a chemical and/or a radioisotope.

According to some embodiments of the invention, the therapeutic moiety is conjugated by translationally fusing the polynucleotide encoding the polypeptide of some embodiments of the invention with the nucleic acid sequence encoding the therapeutic moiety.

Additionally or alternatively, the therapeutic moiety can be chemically conjugated (coupled) to the polypeptide of some embodiments of the invention, using any conjugation method known to one skilled in the art. For example, a peptide can be conjugated to an agent of interest, using a 3-(2-pyridyldithio) propionic acid Nhydroxysuccinimide ester (also called N-succinimidyl 3-(2-pyridyldithio) propionate) ("SDPD") (Sigma, Cat. No. P-3415; see e.g., Cumber et al. 1985, Methods of Enzymology 112:207-224), a glutaraldehyde conjugation procedure (see e.g., G. T. Hermanson 1996, "Antibody Modification and Conjugation, in Bioconjugate Techniques, Academic Press, San Diego) or a carbodiimide conjugation procedure [see e.g., J. March, Advanced Organic Chemistry: Reaction's, Mechanism, and Structure, pp. 349-50 & 372-74 (3d ed.), 1985; B. Neises et al. 1978, Angew Chem., Int. Ed. Engl. 17:522; A. Hassner et al. 1978, Tetrahedron Lett. 4475; E. P. Boden et al. 1986, J. Org. Chem. 50:2394 and L. J. Mathias 1979, Synthesis 561].

A therapeutic moiety can be attached, for example, to the polypeptide of some embodiments of the invention using standard chemical synthesis techniques widely practiced in the art [see e.g., hypertexttransferprotocol://worldwideweb (dot) chemistry (dot) org/portal/Chemistry)], such as using any suitable chemical linkage, direct or indirect, as via a peptide bond (when the functional moiety is a polypeptide), or via covalent bonding to an intervening linker element, such as a linker peptide or other chemical moiety, such as an organic polymer. Chimeric peptides may be linked via bonding at the carboxy (C) or amino (N) termini of the peptides, or via bonding to internal chemical groups such as straight, branched or cyclic side chains, internal carbon or nitrogen atoms, and the like.

As used herein, the terms "protein", "peptide" and "polypeptide", which are interchangeably used herein, encompass native peptides (either degradation products, synthetically synthesized peptides or recombinant peptides) and peptidomimetics (typically, synthetically synthesized peptides), as well as peptoids and semipeptoids which are peptide analogs, which may have, for example, modifications rendering the peptides more stable while in a body or more capable of penetrating into cells. Such modifications include, but are not limited to N terminus modification, C terminus modification, peptide bond modification, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

Peptide bonds (—CO—NH—) within the peptide may be substituted, for example, by N-methylated amide bonds (—N(CH3)-CO—), ester bonds (—C(=O)—O—), ketomethylene bonds (—CO—CH2-), sulfinylmethylene bonds (—S(=O)—CH2-), α-aza bonds (—NH—N(R)—CO—), wherein R is any alkyl (e.g., methyl), amine bonds (—CH2-NH—), sulfide bonds (—CH2-S—), ethylene bonds (—CH2-CH2-), hydroxyethylene bonds (—CH(OH)—CH2-), thioamide bonds (—CS—NH—), olefinic double bonds (—CH=CH—), fluorinated olefinic double bonds (—CF=CH—), retro amide bonds (—NH—CO—), peptide derivatives (—N(R)—CH2-CO—), wherein R is the "normal" side chain, naturally present on the carbon atom.

These modifications can occur at any of the bonds along the peptide chain and even at several (2-3) bonds at the same time.

Natural aromatic amino acids, Trp, Tyr and Phe, may be substituted by non-natural aromatic amino acids such as 1,2,3,4-tetrahydroisoquinoline-3-carboxylic acid (Tic), naphthylalanine, ring-methylated derivatives of Phe, halogenated derivatives of Phe or O-methyl-Tyr.

The peptides of some embodiments of the invention may also include one or more modified amino acids or one or more non-amino acid monomers (e.g. fatty acids, complex carbohydrates etc).

The term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

Tables 1 and 2 below list naturally occurring amino acids (Table 1), and non-conventional or modified amino acids (e.g., synthetic, Table 2) which can be used with some embodiments of the invention.

TABLE 1

| Amino Acid | Three-Letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| ornithine | Orn | hydroxyproline | Hyp |
| α-aminobutyric acid | Abu | aminonorbornyl-carboxylate | Norb |
| D-alanine | Dala | aminocyclopropane-carboxylate | Cpro |
| D-arginine | Darg | N-(3-guanidinopropyl)glycine | Narg |
| D-asparagine | Dasn | N-(carbamylmethyl)glycine | Nasn |
| D-aspartic acid | Dasp | N-(carboxymethyl)glycine | Nasp |
| D-cysteine | Dcys | N-(thiomethyl)glycine | Ncys |
| D-glutamine | Dgln | N-(2-carbamylethyl)glycine | Ngln |
| D-glutamic acid | Dglu | N-(2-carboxyethyl)glycine | Nglu |
| D-histidine | Dhis | N-(imidazolylethyl)glycine | Nhis |
| D-isoleucine | Dile | N-(1-methylpropyl)glycine | Nile |
| D-leucine | Dleu | N-(2-methylpropyl)glycine | Nleu |
| D-lysine | Dlys | N-(4-aminobutyl)glycine | Nlys |
| D-methionine | Dmet | N-(2-methylthioethyl)glycine | Nmet |
| D-ornithine | Dorn | N-(3-aminopropyl)glycine | Norn |
| D-phenylalanine | Dphe | N-benzylglycine | Nphe |
| D-proline | Dpro | N-(hydroxymethyl)glycine | Nser |

TABLE 2-continued

| Non-conventional amino acid | Code | Non-conventional amino acid | Code |
|---|---|---|---|
| D-serine | Dser | N-(1-hydroxyethyl)glycine | Nthr |
| D-threonine | Dthr | N-(3-indolylethyl) glycine | Nhtrp |
| D-tryptophan | Dtrp | N-(p-hydroxyphenyl)glycine | Ntyr |
| D-tyrosine | Dtyr | N-(1-methylethyl)glycine | Nval |
| D-valine | Dval | N-methylglycine | Nmgly |
| D-N-methylalanine | Dnmala | L-N-methylalanine | Nmala |
| D-N-methylarginine | Dnmarg | L-N-methylarginine | Nmarg |
| D-N-methylasparagine | Dnmasn | L-N-methylasparagine | Nmasn |
| D-N-methylasparatate | Dnmasp | L-N-methylaspartic acid | Nmasp |
| D-N-methylcysteine | Dnmcys | L-N-methylcysteine | Nmcys |
| D-N-methylglutamine | Dnmgln | L-N-methylglutamine | Nmgln |
| D-N-methylglutamate | Dnmglu | L-N-methylglutamic acid | Nmglu |
| D-N-methylhistidine | Dnmhis | L-N-methylhistidine | Nmhis |
| D-N-methylisoleucine | Dnmile | L-N-methylisolleucine | Nmile |
| D-N-methylleucine | Dnmleu | L-N-methylleucine | Nmleu |
| D-N-methyllysine | Dnmlys | L-N-methyllysine | Nmlys |
| D-N-methylmethionine | Dnmmet | L-N-methylmethionine | Nmmet |
| D-N-methylornithine | Dnmorn | L-N-methylornithine | Nmorn |
| D-N-methylphenylalanine | Dnmphe | L-N-methylphenylalanine | Nmphe |
| D-N-methylproline | Dnmpro | L-N-methylproline | Nmpro |
| D-N-methylserine | Dnmser | L-N-methylserine | Nmser |
| D-N-methylthreonine | Dnmthr | L-N-methylthreonine | Nmthr |
| D-N-methyltryptophan | Dnmtrp | L-N-methyltryptophan | Nmtrp |
| D-N-methyltyrosine | Dnmtyr | L-N-methyltyrosine | Nmtyr |
| D-N-methylvaline | Dnmval | L-N-methylvaline | Nmval |
| L-norleucine | Nle | L-N-methylnorleucine | Nmnle |
| L-norvaline | Nva | L-N-methylnorvaline | Nmnva |
| L-ethylglycine | Etg | L-N-methyl-ethylglycine | Nmetg |
| L-t-butylglycine | Tbug | L-N-methyl-t-butylglycine | Nmtbug |
| L-homophenylalanine | Hphe | L-N-methyl-homophenylalanine | Nmhphe |
| α-naphthylalanine | Anap | N-methyl-α-naphthylalanine | Nmanap |
| penicillamine | Pen | N-methylpenicillamine | Nmpen |
| γ-aminobutyric acid | Gabu | N-methyl-γ-aminobutyrate | Nmgabu |
| cyclohexylalanine | Chexa | N-methyl-cyclohexylalanine | Nmchexa |
| cyclopentylalanine | Cpen | N-methyl-cyclopentylalanine | Nmcpen |
| α-amino-α-methylbutyrate | Aabu | N-methyl-α-amino-α-methylbutyrate | Nmaabu |
| α-aminoisobutyric acid | Aib | N-methyl-α-aminoisobutyrate | Nmaib |
| D-α-methylarginine | Dmarg | L-α-methylarginine | Marg |
| D-α-methylasparagine | Dmasn | L-α-methylasparagine | Masn |
| D-α-methylaspartate | Dmasp | L-α-methylaspartate | Masp |
| D-α-methylcysteine | Dmcys | L-α-methylcysteine | Mcys |
| D-α-methylglutamine | Dmgln | L-α-methylglutamine | Mgln |
| D-α-methyl glutamic acid | Dmglu | L-α-methylglutamate | Mglu |
| D-α-methylhistidine | Dmhis | L-α-methylhistidine | Mhis |
| D-α-methylisoleucine | Dmile | L-α-methylisoleucine | Mile |
| D-α-methylleucine | Dmleu | L-α-methylleucine | Mleu |
| D-α-methyllysine | Dmlys | L-α-methyllysine | Mlys |
| D-α-methylmethionine | Dmmet | L-α-methylmethionine | Mmet |
| D-α-methylornithine | Dmorn | L-α-methylornithine | Morn |
| D-α-methylphenylalanine | Dmphe | L-α-methylphenylalanine | Mphe |
| D-α-methylproline | Dmpro | L-α-methylproline | Mpro |
| D-α-methylserine | Dmser | L-α-methylserine | Mser |
| D-α-methylthreonine | Dmthr | L-α-methylthreonine | Mthr |
| D-α-methyltryptophan | Dmtrp | L-α-methyltryptophan | Mtrp |
| D-α-methyltyrosine | Dmtyr | L-α-methyltyrosine | Mtyr |
| D-α-methylvaline | Dmval | L-α-methylvaline | Mval |
| N-cyclobutylglycine | Ncbut | L-α-methylnorvaline | Mnva |
| N-cycloheptylglycine | Nchep | L-α-methylethylglycine | Metg |
| N-cyclohexylglycine | Nchex | L-α-methyl-t-butylglycine | Mtbug |
| N-cyclodecylglycine | Ncdec | L-α-methyl-homophenylalanine | Mhphe |
| N-cyclododecylglycine | Ncdod | α-methyl-α-naphthylalanine | Manap |
| N-cyclooctylglycine | Ncoct | α-methylpenicillamine | Mpen |
| N-cyclopropylglycine | Ncpro | α-methyl-γ-aminobutyrate | Mgabu |
| N-cycloundecylglycine | Ncund | α-methyl-cyclohexylalanine | Mchexa |
| N-(2-aminoethyl)glycine | Naeg | α-methyl-cyclopentylalanine | Mcpen |
| N-(2,2-diphenylethyl)glycine | Nbhm | N-(N-(2,2-diphenylethyl) carbamylmethyl-glycine | Nnbhm |
| N-(3,3-diphenylpropyl)glycine | Nbhe | N-(N-(3,3-diphenylpropyl) carbamylmethyl-glycine | Nnbhe |
| 1-carboxy-1-(2,2-diphenyl ethylamino)cyclopropane | Nmbc | 1,2,3,4-tetrahydroisoquinoline-3-carboxylic acid | Tic |

TABLE 2-continued

| Non-conventional amino acid | Code | Non-conventional amino acid | Code |
| --- | --- | --- | --- |
| phosphoserine | pSer | phosphothreonine | pThr |
| phosphotyrosine | pTyr | O-methyl-tyrosine | |
| 2-aminoadipic acid | | hydroxylysine | |

The peptides of some embodiments of the invention are preferably utilized in a linear form, although it will be appreciated that in cases where cyclicization does not severely interfere with peptide characteristics, cyclic forms of the peptide can also be utilized.

Since the present peptides are preferably utilized in therapeutics which require the peptides to be in soluble form, the peptides of some embodiments of the invention preferably include one or more non-natural or natural polar amino acids, including but not limited to serine and threonine which are capable of increasing peptide solubility due to their hydroxyl-containing side chain.

The amino acids of the peptides of the present invention may be substituted either conservatively or non-conservatively.

The term "conservative substitution" as used herein, refers to the replacement of an amino acid present in the native sequence in the peptide with a naturally or non-naturally occurring amino or a peptidomimetics having similar steric properties. Where the side-chain of the native amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid).

As naturally occurring amino acids are typically grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

When affecting conservative substitutions, the substituting amino acid should have the same or a similar functional group in the side chain as the original amino acid.

Conservative substitution tables providing functionally similar amino acids are well known in the art. Guidance concerning which amino acid changes are likely to be phenotypically silent can also be found in Bowie et al., 1990, Science 247:1306 1310. Such conservatively modified variants are in addition to and do not exclude polymorphic variants, interspecies homologs, and alleles. Typical conservative substitutions include but are not limited to: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine(S), Threonine (T); and 8) Cysteine (C), Methionine (M) (see, e.g., Creighton, Proteins (1984)). Amino acids can be substituted based upon properties associated with side chains, for example, amino acids with polar side chains may be substituted, for example, Serine(S) and Threonine (T); amino acids based on the electrical charge of a side chains, for example, Arginine (R) and Histidine (H); and amino acids that have hydrophobic side chains, for example, Valine (V) and Leucine (L). As indicated, changes are typically of a minor nature, such as conservative amino acid substitutions that do not significantly affect the folding or activity of the protein.

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted. Examples of non-conservative substitutions of this type include the substitution of phenylalanine or cycohexylmethyl glycine for alanine, isoleucine for glycine, or —NH—CH [(—CH$_2$)$_5$—COOH]—CO— for aspartic acid. Those non-conservative substitutions which fall under the scope of the present invention are those which still constitute a peptide having anti-bacterial properties.

The N and C termini of the peptides of the present invention may be protected by function groups. Suitable functional groups are described in Green and Wuts, "Protecting Groups in Organic Synthesis", John Wiley and Sons, Chapters 5 and 7, 1991, the teachings of which are incorporated herein by reference. Preferred protecting groups are those that facilitate transport of the compound attached thereto into a cell, for example, by reducing the hydrophilicity and increasing the lipophilicity of the compounds.

According to specific embodiments, one or more of the amino acids may be modified by the addition of a functional group, for example (conceptually views as "chemically modified"). For example, the side amino acid residues appearing in the native sequence may optionally be modified, although as described below alternatively other parts of the protein may optionally be modified, in addition to or in place of the side amino acid residues. The modification may optionally be performed during synthesis of the molecule if a chemical synthetic process is followed, for example by adding a chemically modified amino acid. However, chemical modification of an amino acid when it is already present in the molecule ("in situ" modification) is also possible. Modifications to the peptide or protein can be introduced by gene synthesis, site-directed (e.g., PCR based) or random mutagenesis (e.g., EMS) by exonuclease deletion, by chemical modification, or by fusion of polynucleotide sequences encoding a heterologous domain or binding protein, for example.

As used herein the term "chemical modification", when referring to a peptide, refers to a peptide where at least one of its amino acid residues is modified either by natural processes, such as processing or other post-translational modifications, or by chemical modification techniques which are well known in the art. Non-limiting exemplary types of modification include carboxymethylation, acetylation, acylation, phosphorylation, glycosylation, amidation, ADP-ribosylation, fatty acylation, addition of farnesyl group, an isofarnesyl group, a carbohydrate group, a fatty acid group, a linker for conjugation, functionalization, GPI anchor formation, covalent attachment of a lipid or lipid derivative, methylation, myristylation, pegylation, prenylation, phosphorylation, ubiquitination, or any similar process and known protecting/blocking groups. Ether bonds can optionally be used to join the serine or threonine hydroxyl to the hydroxyl of a sugar. Amide bonds can optionally be used to join the glutamate or aspartate carboxyl groups to an amino group on a sugar (Garg and Jeanloz, Advances in Carbohydrate Chemistry and Biochemistry, Vol. 43, Academic Press (1985); Kunz, Ang. Chem. Int. Ed. English 26:294-308 (1987)). Acetal and ketal bonds can also optionally be formed between amino acids and carbohydrates. Fatty acid acyl derivatives can optionally be made, for example, by acylation of a free amino group (e.g., lysine) (Toth et al., Peptides: Chemistry, Structure and Biology, Rivier and Marshal, eds., ESCOM Publ., Leiden, 1078-1079 (1990)).

According to specific embodiments, the modifications include the addition of a cycloalkane moiety to the peptide, as described in PCT Application No. WO 2006/050262, hereby incorporated by reference as if fully set forth herein. These moieties are designed for use with biomolecules and may optionally be used to impart various properties to proteins.

Furthermore, optionally any point on the peptide may be modified. For example, pegylation of a glycosylation moiety on a protein may optionally be performed, as described in PCT Application No. WO 2006/050247, hereby incorporated by reference as if fully set forth herein. One or more polyethylene glycol (PEG) groups may optionally be added to O-linked and/or N-linked glycosylation. The PEG group may optionally be branched or linear. Optionally any type of water-soluble polymer may be attached to a glycosylation site on a protein through a glycosyl linker.

By "PEGylated protein" is meant a protein, or a fragment thereof having biological activity, having a polyethylene glycol (PEG) moiety covalently bound to an amino acid residue of the protein.

By "polyethylene glycol" or "PEG" is meant a polyalkylene glycol compound or a derivative thereof, with or without coupling agents or derivatization with coupling or activating moieties (e.g., with thiol, triflate, tresylate, azirdine, oxirane, or preferably with a maleimide moiety). Compounds such as maleimido monomethoxy PEG are exemplary or activated PEG compounds of the invention. Other polyalkylene glycol compounds, such as polypropylene glycol, may be used in the present invention. Other appropriate polyalkylene glycol compounds include, but are not limited to, charged or neutral polymers of the following types: dextran, colominic acids or other carbohydrate-based polymers, polymers of amino acids, and biotin derivatives.

According to specific embodiments, the peptide is modified to have an altered glycosylation pattern (i.e., altered from the original or native glycosylation pattern). As used herein, "altered" means having one or more carbohydrate moieties deleted, and/or having at least one glycosylation site added to the original protein.

Glycosylation of proteins is typically either N-linked or O-linked. N-linked refers to the attachment of the carbohydrate moiety to the side chain of an asparagine residue. The tripeptide sequences, asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to a peptide is conveniently accomplished by altering the amino acid sequence of the peptide such that it contains one or more of the above-described tripeptide sequences (for N-linked glycosylation sites). The alteration may also be made by the addition of, or substitution by, one or more serine or threonine residues in the sequence of the original peptide (for O-linked glycosylation sites). The peptide's amino acid sequence may also be altered by introducing changes at the DNA level.

Another means of increasing the number of carbohydrate moieties on peptides is by chemical or enzymatic coupling of glycosides to the amino acid residues of the peptide. Depending on the coupling mode used, the sugars may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described e.g. in WO 87/05330, and in Aplin and Wriston, CRC Crit. Rev. Biochem., 22:259-306 (1981).

Removal of any carbohydrate moieties present on a peptide may be accomplished chemically, enzymatically or by introducing changes at the DNA level. Chemical deglycosylation requires exposure of the peptide to trifluoromethanesulfonic acid, or an equivalent compound. This treatment results in the cleavage of most or all sugars except the linking sugar (N-acetylglucosamine or N-acetylgalactosamine), leaving the amino acid sequence intact.

Chemical deglycosylation is described by Hakimuddin et al., Arch. Biochem. Biophys., 259:52 (1987); and Edge et al., Anal. Biochem., 118:131 (1981). Enzymatic cleavage of carbohydrate moieties on peptides can be achieved by the use of a variety of endo- and exo-glycosidases as described by Thotakura et al., Meth. Enzymol., 138:350 (1987).

According to specific embodiments, the peptide comprises a detectable tag. As used herein, in one embodiment the term "detectable tag" refers to any moiety that can be detected by a skilled practitioner using art known techniques. Detectable tags may be peptide sequences. Optionally the detectable tag may be removable by chemical agents or by enzymatic means, such as proteolysis. Detectable tags of some embodiments of the present invention can be used for purification of the peptide. For example the term "detectable tag" includes chitin binding protein (CBP)-tag, maltose binding protein (MBP)-tag, glutathione-S-transferase (GST)-tag, poly(His)-tag. FLAG tag, Epitope tags, such as, V5-tag, c-myc-tag, and HA-tag, and fluorescence tags such as green fluorescent protein (GFP), red fluorescent protein (RFP), yellow fluorescent protein (YFP), blue fluorescent protein (BFP), and cyan fluorescent protein (CFP); as well as derivatives of these tags, or any tag known in the art. The term "detectable tag" also includes the term "detectable marker".

According to specific embodiment, the peptide comprises a detectable tag attached to its N-terminal (e.g. poly(His)-tag).

According to specific embodiment, the peptide comprises a detectable tag attached to its C-terminal (e.g. poly(His)-tag).

According to specific embodiments, the N-terminal of the peptide does not comprise a detectable tag (e.g. poly(His)-tag).

According to specific embodiments, the C-terminal of the peptide does not comprise a detectable tag (e.g. poly(His)-tag).

According to specific embodiments the peptide is fused to a cleavable moiety. Thus, for example, to facilitate recovery, the expressed coding sequence can be engineered to encode the peptide of some embodiments of the present invention and fused cleavable moiety. In one embodiment, the peptide is designed such that it is readily isolated by affinity chromatography; e.g., by immobilization on a column specific for the cleavable moiety. In one embodiment, a cleavage site is engineered between the peptide and the cleavable moiety and the peptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)]. According to specific embodiments, the peptide is an isolated peptide.

The peptides of some embodiments of the invention may be synthesized and purified by any techniques that are known to those skilled in the art of peptide synthesis, such as, but not limited to, solid phase and recombinant techniques.

For solid phase peptide synthesis, a summary of the many techniques may be found in J. M. Stewart and J. D. Young, Solid Phase Peptide Synthesis, W. H. Freeman Co. (San Francisco), 1963 and J. Meienhofer, Hormonal Proteins and Peptides, vol. 2, p. 46, Academic Press (New York), 1973. For classical solution synthesis see G. Schroder and K. Lupke, The Peptides, vol. 1. Academic Press (New York), 1965.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide and so forth. Further description of peptide synthesis is disclosed in U.S. Pat. No. 6,472,505.

A preferred method of preparing the peptide compounds of some embodiments of the invention involves solid phase peptide synthesis.

Large scale peptide synthesis is described by Andersson Biopolymers 2000; 55 (3): 227-50.

According to specific embodiments, the peptide is synthesized using in vitro expression systems. Such in vitro synthesis methods are well known in the art and the components of the system are commercially available.

According to specific embodiments, the peptide is produced by recombinant DNA technology. A "recombinant" peptide, or protein refers to a peptide, or protein produced by recombinant DNA techniques; i.e., produced from cells transformed by an exogenous DNA construct encoding the desired peptide or protein.

Thus, according to another aspect of the present invention, there is provided an isolated polynucleotide comprising a nucleic acid sequence encoding any of the above described polypeptides and fusion proteins.

According to specific embodiments, the polynucleotide is at least about 70%, 75%, 80%, 85%, 90%, 95%, 96%, 97%, 98% or 99% homologous to the nucleic acid sequence as set forth in SEQ ID NO: 57-72, 98, 102, 104, 106, 108, 112, 114, 134, 136, 138, 140, 142, 144 and 148, each possibility represents a separate embodiment of the present invention.

According to specific embodiments, the polynucleotide is at least about 70%, 75%, 80%, 85%, 90%, 95%, 96%, 97%, 98% or 99% homologous to the nucleic acid sequence as set forth in SEQ ID NO: 134, 136, 138, 140, 142, 144 and 148, each possibility represents a separate embodiment of the present invention.

According to specific embodiments, the polynucleotide is at least about 70%, 75%, 80%, 85%, 90%, 95%, 96%, 97%, 98% or 99% homologous to the nucleic acid sequence as set forth in SEQ ID NO: 57-72, 98, 102, 104, 106, 108 or 112, each possibility represents a separate embodiment of the present invention.

According to specific embodiments, the polynucleotide is at least about 70%, 75%, 80%, 85%, 90%, 95%, 96%, 97%, 98% or 99% homologous to the nucleic acid sequence as set forth in SEQ ID NO: 98, 102, 104, 106, 108 or 112, each possibility represents a separate embodiment of the present invention.

According to specific embodiments, the polynucleotide is at least about 70%, 75%, 80%, 85%, 90%, 95%, 96%, 97%, 98% or 99% homologous to the nucleic acid sequence as set forth in SEQ ID NO: 98, 102, 104, 106 or 108, each possibility represents a separate embodiment of the present invention.

According to specific embodiments, the polynucleotide is at least about 70%, 75%, 80%, 85%, 90%, 95%, 96%, 97%, 98% or 99% homologous to the nucleic acid sequence as set forth in SEQ ID No. 57-72, each possibility represents a separate embodiment of the present invention.

According to specific embodiments, the polynucleotide is at least about 70%, 75%, 80%, 85%, 90%, 95%, 96%, 97%, 98% or 99% homologous to the nucleic acid sequence as set forth in SEQ ID NO: 146.

According to specific embodiments, the polynucleotide comprises a nucleic acid sequence selected from the group consisting of SEQ ID NO: 57-72, 98, 102, 104, 106, 108, 112, 114, 134, 136, 138, 140, 142, 144 and 148, each possibility represents a separate embodiment of the present invention.

According to specific embodiments, the polynucleotide comprises a nucleic acid sequence selected from the group consisting of SEQ ID NO: 134, 136, 138, 140, 142, 144 and 148, each possibility represents a separate embodiment of the present invention.

According to specific embodiments, the polynucleotide comprises a nucleic acid sequence selected from the group consisting of SEQ ID NO: 57-72, 98, 102, 104, 106, 108 or 112, each possibility represents a separate embodiment of the present invention.

According to specific embodiments, the polynucleotide comprises a nucleic acid sequence selected from the group consisting of SEQ ID NO: 98, 102, 104, 106, 108 or 112, each possibility represents a separate embodiment of the present invention.

According to specific embodiments the polynucleotide comprises a nucleic acid sequence selected from the group consisting of SEQ ID NO: 98, 102, 104, 106 or 108, each possibility represents a separate embodiment of the present invention.

According to specific embodiments, the polynucleotide comprises a nucleic acid sequence selected from the group consisting of SEQ ID NO: 57-72, each possibility represents a separate embodiment of the present invention.

According to specific embodiments, the polynucleotide comprises a nucleic acid sequence as set forth in SEQ ID NO: 146.

According to specific embodiments, the polynucleotide consists of a nucleic acid sequence selected from the group consisting of SEQ ID NO: 57-72, 98, 102, 104, 106, 108, 112, 114, 134, 136, 138, 140, 142, 144 and 148, each possibility represents a separate embodiment of the present invention.

According to specific embodiments, the polynucleotide consists of a nucleic acid sequence selected from the group consisting of SEQ ID NO: 134, 136, 138, 140, 142, 144 and 148, each possibility represents a separate embodiment of the present invention.

According to specific embodiments, the polynucleotide consists of a nucleic acid sequence selected from the group consisting of SEQ ID NO: 57-72, 98, 102, 104, 106, 108 or 112, each possibility represents a separate embodiment of the present invention.

According to specific embodiments, the polynucleotide consists of a nucleic acid sequence selected from the group consisting of SEQ ID NO: 98, 102, 104, 106, 108 or 112, each possibility represents a separate embodiment of the present invention.

According to specific embodiments the polynucleotide consists of a nucleic acid sequence selected from the group consisting of SEQ ID NO: 98, 102, 104, 106 or 108, each possibility represents a separate embodiment of the present invention.

According to specific embodiments, the polynucleotide consists of a nucleic acid sequence selected from the group consisting of SEQ ID NO: 57-72, each possibility represents a separate embodiment of the present invention.

According to specific embodiments, the polynucleotide is least about 70%, 75%, 80%, 85%, 90%, 95%, 96%, 97%, 98% or 99% homologous to the nucleic sequence as set forth in SEQ ID No. 70-72.

According to specific embodiments, the polynucleotide comprises a nucleic acid sequence selected from the group consisting of SEQ ID NO: 70-72

According to specific embodiments, the polynucleotide consists of a nucleic acid sequence selected from the group consisting of SEQ ID NO: 70-72.

According to specific embodiments, the polynucleotide consists of SEQ ID NO: 146.

According to another aspect of the present invention, there is provided an isolated polynucleotide comprising a nucleic acid sequence encoding any of the above described PD1 amino acid sequence being 123-148 amino acids in length having at least 80% identity to an amino acid sequence selected from the group consisting of SEQ ID NO: 18-21, 85, 89, 93 and 115 and not comprising any of amino acid segments P1-L5 and F146-V150 corresponding to SEQ ID NO: 2, or being 138-145 amino acids in length having at least 80% identity to an amino acid sequence selected from the group consisting of SEQ ID NO: 18, 117 and 119 and not comprising an amino acid segment F146-V150 corresponding to SEQ ID NO: 2; and optionally comprising a C to S amino acid modification in a position corresponding to amino acid 73 of SEQ ID NO: 2; or any of the above described 4-1BBL amino acid sequence being 185-202 amino acids in length having at least 95% identity to an amino acid sequence selected form the group consisting of SEQ ID NOs: 22-25, being 170-197 amino acids in length having at least 80% identity to an amino acid sequence selected from the group consisting of SEQ ID NO: 127 and 129 and not comprising an amino acid segment G198-E205 corresponding to SEQ ID NO: 3, or being 170-182 amino acids in length having at least 80% identity to SEQ ID NO: 125 and not comprising an amino acid segment A1-E23 corresponding to SEQ ID NO: 3; and optionally comprising three repeats of the 4-1BBL amino acid sequence.

According to another aspect of the present invention, there is provided an isolated polynucleotide comprising a nucleic acid sequence encoding any of the above described PD1 amino acid sequence being 123-148 amino acids in length having at least 80% identity to an amino acid sequence selected from the group consisting of SEQ ID NO: 18-21 and not comprising any of amino acid segments P1-L5 and F146-V150 corresponding to SEQ ID NO: 2; and optionally comprising a C to S amino acid modification in a position corresponding to amino acid 73 of SEQ ID NO: 2; or any of the above described 4-1BBL amino acid sequence being 185-202 amino acids in length and having at least 95% identity to an amino acid sequence selected from the group consisting of SEQ ID NOs: 22-25.

According to additional or an alternative aspect of the present invention, there is provided an isolated polynucleotide comprising a nucleic acid sequence encoding any of the above described PD1 amino acid sequence being 123-148 amino acids in length having at least 80% identity to an amino acid sequence selected from the group consisting of SEQ ID NO: 18-21 and not comprising any of amino acid segments P1-L5 and F146-V150 corresponding to SEQ ID NO: 2; or any of the above described 4-1BBL amino acid sequence being 185-202 amino acids in length and having at least 95% identity to an amino acid sequence selected from the group consisting of SEQ ID NOs: 22-25.

According to specific embodiments, the polynucleotide is at least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic acid sequence as set forth in SEQ ID NO: 32, 33, 34, 35, 74, 76, 80, 82, 84, 86, 88, 90, 92, 94, 96, 116, 118 or 120, each possibility represents a separate embodiment of the present invention.

According to specific embodiments, the polynucleotide is at least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic sequence as set forth in SEQ ID NO: 32, 33, 34, 35, 74, 76, 80, 82, 84, 86, 88, 90, 92, 94 or 96, each possibility represents a separate embodiment of the present invention.

According to specific embodiments, the polynucleotide is at least about 95%, 96%, 97%, 98% or 99% homologous to the nucleic acid sequence as set forth in SEQ ID NO: 32, 33, 34, 35, 74, 76, 80, 82, 84, 86, 88, 90, 92, 94, 96, 116, 118 or 120, each possibility represents a separate embodiment of the present invention.

According to specific embodiments, the polynucleotide is at least about 95%, 96%, 97%, 98% or 99% homologous to the nucleic sequence as set forth in SEQ ID NO: 32, 33, 34, 35, 74, 76, 80, 82, 84, 86, 88, 90, 92, 94 or 96.

According to specific embodiments, the polynucleotide comprises SEQ ID NO: 32, 33, 34, 35, 74, 76, 80, 82, 84, 86, 88, 90, 92, 94, 96, 116, 118 or 120. According to specific embodiments, the polynucleotide comprises SEQ ID NO: 32, 33, 34, 35, 74, 76, 80, 82, 84, 86, 88, 90, 92, 94 or 96.

According to specific embodiments, the polynucleotide consists of SEQ ID NO: 32, 33, 34, 35, 74, 76, 80, 82, 84, 86, 88, 90, 92, 94, 96, 116, 118 or 120.

According to specific embodiments, the polynucleotide consists of SEQ ID NO: 32, 33, 34, 35, 74, 76, 80, 82, 84, 86, 88, 90, 92, 94 or 96.

According to specific embodiments, the polynucleotide is least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic sequence as set forth in SEQ ID NO: 74, 76, 80, 82, 84, 86, 88, 90, 92, 94 or 96, each possibility represents a separate embodiment of the present invention.

According to specific embodiments, the polynucleotide is least about 95%, 96%, 97%, 98% or 99% homologous to the nucleic sequence as set forth in SEQ ID NO: 74, 76, 80, 82, 84, 86, 88, 90, 92, 94 or 96.

According to specific embodiments, the polynucleotide comprises SEQ ID NO: 74, 76, 80, 82, 84, 86, 88, 90, 92, 94 or 96.

According to specific embodiments, the polynucleotide consists of SEQ ID NO: 74, 76, 80, 82, 84, 86, 88, 90, 92, 94 or 96.

According to specific embodiments, the polynucleotide is least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic sequence as set forth in SEQ ID NO: 32, 33, 34 or 35, each possibility represents a separate embodiment of the present invention.

According to specific embodiments, the polynucleotide is least about 95%, 96%, 97%, 98% or 99% homologous to the nucleic sequence as set forth in SEQ ID NO: 32, 33, 34 or 35.

According to specific embodiments, the polynucleotide comprises SEQ ID NO: 32, 33, 34 or 35.

According to specific embodiments, the polynucleotide consists of SEQ ID NO: 32, 33, 34 or 35.

According to specific embodiments, the polynucleotide is at least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic acid sequence as set forth in SEQ ID NO: 39, 40, 41, 42, 126, 128, 130 or 132 each possibility represents a separate embodiment of the present invention.

According to specific embodiments, the polynucleotide is at least 70%, 75%, 80%, 81%, 82%, 83%, 84%, 85%, 86%, 87%, 88%, 88%, 90%, 91%, 92%, 93%, 94%, 95%, 96%, 97%, 98% or 99% homologous to the nucleic sequence as set forth in SEQ ID NO: 39, 40, 41 or 42, each possibility represents a separate embodiment of the present invention.

According to specific embodiments, the polynucleotide is at least about 95%, 96%, 97%, 98% or 99% homologous to the nucleic sequence as set forth in SEQ ID NO: 39, 40, 41, 42, 126, 128, 130 or 132.

According to specific embodiments, the polynucleotide is at least about 95%, 96%, 97%, 98% or 99% homologous to the nucleic sequence as set forth in SEQ ID NO: 39, 40, 41 or 42.

According to specific embodiments, the polynucleotide comprises SEQ ID NO: 39, 40, 41, 42, 126, 128, 130 or 132.

According to specific embodiments, the polynucleotide comprises SEQ ID NO: 39, 40, 41 or 42.

According to specific embodiments, the polynucleotide consists of SEQ ID NO: 39, 40, 41, 42, 126, 128, 130 or 132.

According to specific embodiments, the polynucleotide consists of SEQ ID NO: 39, 40, 41 or 42.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

According to specific embodiments, any of the polynucleotides and nucleic acid sequences disclosed herein may comprise conservative nucleic acid substitutions. Conservatively modified polynucleotides refer to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations", which are one species of conservatively modified polynucleotides. According to specific embodiments, any polynucleotide and nucleic acid sequence described herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a polynucleotide which encodes a polypeptide is implicit in a described sequence with respect to the expression product.

To express an exogenous polypeptide in mammalian cells, a polynucleotide sequence encoding the polypeptide is preferably ligated into a nucleic acid construct suitable for mammalian cell expression. Such a nucleic acid construct includes a promoter sequence for directing transcription of the polynucleotide sequence in the cell in a constitutive or inducible manner.

Hence, according to specific embodiments, there is provided nucleic acid construct comprising the polynucleotide and a regulatory element for directing expression of said polynucleotide in a host cell.

According to specific embodiments, the regulatory element is a heterologous regulatory element.

The nucleic acid construct (also referred to herein as an "expression vector") of some embodiments of the invention includes additional sequences which render this vector suitable for replication and integration in prokaryotes, eukaryotes, or preferably both (e.g., shuttle vectors). In addition, a typical cloning vector may also contain a transcription and translation initiation sequence, transcription and translation terminator and a polyadenylation signal. By way of example, such constructs will typically include a 5' LTR, a tRNA binding site, a packaging signal, an origin of second-strand DNA synthesis, and a 3' LTR or a portion thereof.

The nucleic acid construct of some embodiments of the invention typically includes a signal sequence for secretion of the peptide from a host cell in which it is placed. Preferably the signal sequence for this purpose is a mammalian signal sequence or the signal sequence of the polypeptide variants of some embodiments of the invention.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264,166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of PD1-4-1BBL, PD1 or 4-1BBL mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for some embodiments of the invention include those derived from SV40.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of some embodiments of the invention can further include additional polynucleotide sequences that allow, for example, the translation of several proteins from a single mRNA such as an internal ribosome entry site (IRES) and sequences for genomic integration of the promoter-chimeric polypeptide.

It will be appreciated that the individual elements comprised in the expression vector can be arranged in a variety of configurations. For example, enhancer elements, promoters and the like, and even the polynucleotide sequence(s) encoding a PD1-4-1BBL, a polypeptide comprising a PD1 amino acid sequence or a polypeptide comprising a 4-1BBL amino acid sequence can be arranged in a "head-to-tail" configuration, may be present as an inverted complement, or in a complementary configuration, as an anti-parallel strand. While such variety of configuration is more likely to occur with non-coding elements of the expression vector, alternative configurations of the coding sequence within the expression vector are also envisioned.

Examples for mammalian expression vectors include, but are not limited to, pcDNA3, pcDNA3.1 (+/−), pGL3, pZcoSV2 (+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149:51-60).

Recombinant viral vectors are useful for in vivo expression of PD1-4-1BBL, PD1 or 4-1BBL since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of some embodiments of the invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14 (1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. In addition, such a construct typically includes a signal sequence for secretion of the peptide from a host cell in which it is placed. Preferably the signal sequence for this purpose is a mammalian signal sequence or the signal sequence of the polypeptide variants of some embodiments of the invention. Optionally, the construct may also include a signal that directs polyadenylation, as well as one or more restriction sites and a translation termination sequence. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

As mentioned, other than containing the necessary elements for the transcription and translation of the inserted coding sequence, the expression construct of some embodiments of the invention can also include sequences engineered to enhance stability, production, purification, yield or toxicity of the expressed peptide. For example, the expression of a fusion protein or a cleavable fusion protein comprising the PD1-4-1BBL protein or the polypeptide of some embodiments of the invention and a heterologous protein can be engineered. Such a fusion protein can be designed so that the fusion protein can be readily isolated by affinity chromatography; e.g., by immobilization on a column specific for the heterologous protein. Where a cleavage site is engineered between the PD1-4-1BBL protein or the polypeptide of some embodiments of the present invention and the heterologous protein, the PD1-4-1BBL protein or the polypeptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

The present invention also contemplates cells comprising the composition described herein.

Thus, according to specific embodiments, there is provided a host cell comprising the PD1-4-1BBL fusion protein, the polypeptide comprising the PD1 amino acid sequence and/or the polypeptide comprising the 4-1BBL amino acid sequence disclosed herein, the polynucleotide encoding same or the nucleic acid construct encoding same.

As mentioned hereinabove, a variety of prokaryotic or eukaryotic cells can be used as host-expression systems to express the polypeptides of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the polypeptides of some embodiments of the invention.

Examples of bacterial constructs include the pET series of *E. coli* expression vectors [Studier et al. (1990) Methods in Enzymol. 185:60-89).

Examples of eukaryotic cells which may be used along with the teachings of the invention include but are not limited to, mammalian cells, fungal cells, yeast cells, insect cells, algal cells or plant cells.

In yeast, a number of vectors containing constitutive or inducible promoters can be used, as disclosed in U.S. Pat. Application No: 5,932,447. Alternatively, vectors can be used which promote integration of foreign DNA sequences into the yeast chromosome.

In cases where plant expression vectors are used, the expression of the coding sequence can be driven by a number of promoters. For example, viral promoters such as the 35S RNA and 19S RNA promoters of CaMV [Brisson et al. (1984) Nature 310:511-514], or the coat protein promoter to TMV [Takamatsu et al. (1987) EMBO J. 6:307-311] can be used. Alternatively, plant promoters such as the small subunit of RUBISCO [Coruzzi et al. (1984) EMBO J. 3:1671-1680 and Brogli et al., (1984) Science 224:838-843] or heat shock promoters, e.g., soybean hsp17.5-E or hsp17.3-B [Gurley et al. (1986) Mol. Cell. Biol. 6:559-565] can be used. These constructs can be introduced into plant cells using Ti plasmid, Ri plasmid, plant viral vectors, direct DNA transformation, microinjection, electroporation and other techniques well known to the skilled artisan. See, for example, Weissbach & Weissbach, 1988, Methods for Plant Molecular Biology, Academic Press, NY, Section VIII, pp 421-463.

Other expression systems such as insects and mammalian host cell systems which are well known in the art can also be used by some embodiments of the invention.

According to specific embodiments the cell is a mammalian cell.

According to specific embodiment, the cell is a human cell.

According to a specific embodiment, the cell is a cell line.

According to another specific embodiment, the cell is a primary cell.

The cell may be derived from a suitable tissue including but not limited to blood, muscle, nerve, brain, heart, lung, liver, pancreas, spleen, thymus, esophagus, stomach, intestine, kidney, testis, ovary, hair, skin, bone, breast, uterus, bladder, spinal cord, or various kinds of body fluids. The cells may be derived from any developmental stage including embryo, fetal and adult stages, as well as developmental origin i.e., ectodermal, mesodermal, and endodermal origin.

Non limiting examples of mammalian cells include monkey kidney CV1 line transformed by SV40 (COS, e.g. COS-7, ATCC CRL 1651); human embryonic kidney line (HEK293 or HEK293 cells subcloned for growth in suspension culture, Graham et al., J. Gen Virol., 36:59 1977); baby hamster kidney cells (BHK, ATCC CCL 10); mouse sertoli cells (TM4, Mather, Biol. Reprod., 23:243-251 1980); monkey kidney cells (CV1 ATCC CCL 70); African green monkey kidney cells (VERO-76, ATCC CRL-1587); human cervical carcinoma cells (HeLa, ATCC CCL 2); NIH3T3, Jurkat, canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 1982); MRC 5 cells; FS4 cells; and a human hepatoma line (Hep G2), PER.C6, K562, and Chinese hamster ovary cells (CHO).

According to some embodiments of the invention, the mammalian cell is selected from the group consisting of a Chinese Hamster Ovary (CHO), HEK293, PER.C6, HT1080, NSO, Sp2/0, BHK, Namalwa, COS, HeLa and Vero cell.

According to some embodiments of the invention, the host cell comprises a Chinese Hamster Ovary (CHO), PER.C6 or a 293 (e.g. Expi293F) cell.

According to another aspect of the present invention, there is provided a method of producing a PD1-4-1BBL fusion protein, a polypeptide comprising a PD1 amino acid sequence or a polypeptide comprising a 4-1BBL amino acid sequence, the method comprising expressing in a host cell the polynucleotide or the nucleic acid construct described herein.

According to specific embodiments, the methods comprising isolating the fusion protein or the polypeptide.

According to specific embodiments, recovery of the recombinant polypeptide is effected following an appropriate time in culture. The phrase "recovering the recombinant polypeptide" refers to collecting the whole fermentation medium containing the polypeptide and need not imply additional steps of separation or purification. Notwithstanding the above, polypeptides of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, mix mode chromatography, metal affinity chromatography, Lectins affinity chromatography chromatofocusing and differential solubilization.

According to specific embodiments, following synthesis and purification, the therapeutic efficacy of the peptide can be assayed either in vivo or in vitro. Such methods are known in the art and include for example cell viability, survival of transgenic mice, and expression of activation markers.

The compositions (e.g. the PD1-4-1BBL fusion protein, the polypeptide comprising the PD1 amino acid sequence or the polypeptide comprising the 4-1BBL amino acid sequence disclosed herein, polynucleotide encoding same, nucleic acid construct encoding same and/or cells) of some embodiments of the invention can be administered to an organism per se, or in a pharmaceutical composition where it is mixed with suitable carriers or excipients.

Thus, the present invention, in some embodiments, features a pharmaceutical composition comprising a therapeutically effective amount of the composition disclosed herein.

Herein the term "active ingredient" refers to the composition (e.g. PD1-4-1BBL fusion protein, polypeptide comprising a PD1 amino acid sequence, polypeptide comprising a 4-1BBL amino acid sequence, polynucleotide, nucleic acid construct and/or cells described herein) accountable for the biological effect.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., a polypeptide, a polynucleotide, a nucleic acid construct and/ or cell as described herein, may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include a pharmaceutically acceptable anti-oxidants. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. A pharmaceutical composition according to at least some embodiments of the present invention also may include additives such as detergents and solubilizing agents (e.g., TWEEN 20 (polysorbate-20), TWEEN 80 (polysorbate-80)) and preservatives (e.g., Thimersol, benzyl alcohol) and bulking substances (e.g., lactose, mannitol).

Examples of suitable aqueous and nonaqueous carriers that may be employed in the pharmaceutical compositions according to at least some embodiments of the present invention include water, buffered saline of various buffer content (e.g., Tris-HCl, acetate, phosphate), pH and ionic strength, ethanol, polyols (such as glycerol, propylene glycol, polyethylene glycol, and the like), and suitable mixtures thereof, vegetable oils, such as olive oil, and injectable organic esters, such as ethyl oleate.

Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Techniques for formulation and administration of drugs may be found in "Remington's Pharmaceutical Sciences," Mack Publishing Co., Easton, PA, latest edition, which is incorporated herein by reference.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the present invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intraperitoneal, intravenous (IV) and intradermal), transdermal (either passively or using iontophoresis or electroporation), transmucosal (e.g., sublingual administration, nasal, vaginal, rectal, or sublingual), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion or using biocrodible inserts, and can be formulated in dosage forms appropriate for each route of administration. In a specific embodiment, a protein, a therapeutic agent or a pharmaceutical composition according to at least some embodiments of the present invention can be administered intraperitoneally or intravenously.

According to specific embodiments, the compositions disclosed herein are administered in an aqueous solution, by parenteral injection. The formulation may also be in the form of a suspension or emulsion. In general, pharmaceutical compositions for parenteral injection are provided including effective amounts of the compositions described herein, and optionally include pharmaceutically acceptable diluents, preservatives, solubilizers, emulsifiers, adjuvants and/or carriers. Such compositions optionally include one or more for the following: diluents, sterile water, buffered saline of various buffer content (e.g., Tris-HCl, acetate, phosphate), pH and ionic strength; and additives such as detergents and solubilizing agents (e.g., TWEEN 20 (polysorbate-20), TWEEN 80 (polysorbate-80)), anti-oxidants (e.g., water soluble antioxidants such as ascorbic acid, sodium metabisulfite, cysteine hydrochloride, sodium bisulfate, sodium metabisulfite, sodium sulfite; oil-soluble antioxidants, such as ascorbyl palmitate, butylated hydroxyanisole (BHA), butylated hydroxytoluene (BHT), lecithin, propyl gallate, alpha-tocopherol; and metal chelating agents, such as citric acid, ethylenediamine tetraacetic acid (EDTA), sorbitol, tartaric acid, phosphoric acid), and preservatives (e.g., Thimersol, benzyl alcohol) and bulking substances (e.g., lactose, mannitol). Examples of non-aqueous solvents or vehicles are ethanol, propylene glycol, polyethylene glycol, vegetable oils, such as olive oil and corn oil, gelatin, and injectable organic esters such as ethyl oleate. The formulations may be freeze dried (lyophilized) or vacuum dried and redissolved/resuspended immediately before use. The formulation may be sterilized by, for example, filtration through a bacteria retaining filter, by incorporating sterilizing agents into the compositions, by irradiating the compositions, or by heating the compositions.

Various compositions (e.g., polypeptides) disclosed herein can be applied topically. Topical administration does not work well for most peptide formulations, although it can be effective especially if applied to the lungs, nasal, oral (sublingual, buccal), vaginal, or rectal mucosa.

Compositions of the present invention can be delivered to the lungs while inhaling and traverse across the lung epithelial lining to the blood stream when delivered either as an aerosol or spray dried particles having an aerodynamic diameter of less than about 5 microns. A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent nebulizer (Mallinckrodt Inc., St. Louis, Mo.); the Acorn II nebulizer (Marquest Medical Products, Englewood, Colo.); the Ventolin metered dose inhaler (Glaxo Inc., Research Triangle Park, N.C.); and the Spinhaler powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, sprays, or patches, all of which can be prepared using standard technology. Transdermal formulations will require the inclusion of penetration enhancers. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

According to specific embodiments, the compositions disclosed herein are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected. For the polypeptide compositions disclosed herein, the polynucleotides and nucleic acids constructs encoding same and the cells described herein, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. For polypeptide compositions, generally dosage levels of 0.0001 to 100 mg/kg of body weight daily are administered to mammals and more usually 0.001 to 20 mg/kg. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration 5 times per week, 4 times per week, 3 times per week, 2 times per week, once per week, once every two weeks, once every three weeks, once every four weeks, once a month, once every 3 months or once every three to 6 months. Generally, for intravenous injection or infusion, dosage may be lower. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for case of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

Optionally the polypeptide formulation may be administered in an amount between 0.0001 to 100 mg/kg weight of the patient/day, preferably between 0.001 to 20.0 mg/kg/day, according to any suitable timing regimen. A therapeutic composition according to at least some embodiments according to at least some embodiments of the present invention can be administered, for example, three times a day, twice a day, once a day, three times weekly, twice weekly or once weekly, once every two weeks or 3, 4, 5, 6, 7 or 8 weeks. Moreover, the composition can be administered over a short or long period of time (e.g., 1 week, 1 month, 1 year, 5 years).

Alternatively, the compositions disclosed herein can be administered as a sustained release formulation, in which case less frequent administration is required. Dosage and frequency vary depending on the half-life of the therapeutic agent in the patient. In general, human antibodies show the longest half-life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In certain embodiments, the polypeptide, polynucleotide, nucleic acid construct or cells compositions are administered locally, for example by injection directly into a site to be treated. Typically, the injection causes an increased localized concentration of the composition which is greater than that which can be achieved by systemic administration. The polypeptide compositions can be combined with a matrix as described above to assist in creating an increased localized concentration of the polypeptide compositions by reducing the passive diffusion of the polypeptides out of the site to be treated.

Pharmaceutical compositions of the present invention may be administered with medical devices known in the art. For example, in an optional embodiment, a pharmaceutical composition according to at least some embodiments of the present invention can be administered with a needles hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. Sec, e.g., Sustained and Controlled Release Drug Delivery Systems, J. R. Robinson, ed., Marcel Dekker, Inc., New York, 1978.

Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is of a different material than the polymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of the active agents disclosed herein, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although in others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release, 5:13-22 (1987); Mathiowitz, et al., Reactive Polymers, 6:275-283 (1987); and Mathiowitz, et al., J. Appl Polymer ScL, 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

In certain embodiments, to ensure that the therapeutic compounds according to at least some embodiments of the present invention cross the BBB (if desired), they can be formulated, for example, in liposomes. For methods of manufacturing liposomes, see, e.g., U.S. Pat. Nos. 4,522, 811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

Compositions of some embodiments of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to +10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells-A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press. (1986); "A Practical Guide to Molecular Cloning" Perbal. B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization-A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Selection of PD1-4-1BBL Variants

A structural analysis of a PD1-4-1BBL fusion protein referred to herein as "DSP105" comprising an N-terminal signal peptide and a his-tag (SEQ ID NO: 26, FIG. 1) was effected in order to optimize the following parameters:
Folding-proper folding to allow binding to targets, minimize potential di-sulfide scrambling
Integrity-no exposed proteolytic sites;
Multimerization-explore potential multimerization of the two domains.
Specifically, optimize trimerization of C-terminal domain formation;
High expression in mammalian expression system; and
Low immunogenicity.

Specifically, for the PD1 domain (corresponding to amino acids 21-170 of UniProt ID Q15116 Extracellular domain, SEQ ID NO: 2):
1. A PD1 comprehensive model was generated based on PDB structures: 3RRQ, 5GGR, 5GGS, 5IUS, 5JXE, 4ZQK, 5B8C, 5WT9 and one NMR structure 2M2D. The C-terminal part of PD1 which is missing in the above mentioned PDB structures (starting from GLU150, i.e. EVPTAHPSPSPRPAGQFQTLV. SEQ ID NO: 6) includes a Pro-rich segment which is expected to be folded onto itself (according to peptide modelling algorithms).
2. The fusion protein was analyzed for proteolytic sites using the PROSPER server.

For 4-1BBL (corresponding to amino acids 50-254 of UniProt ID P41273 EM domain, SEQ ID NO: 3):
1. A 4-1BBL extracellular (EC) domain model was generated based on PDB structure: 2X29. Since the N-terminal part of the 4-1BBL is missing in this PDB structure and was not resolved in the seems that X-ray, it this segment (ACPWAVSGARASPGSAASPRL-REGPELSPD, SEQ ID NO: 7) exposes hydrophobic residues to the solvent and attempts to predict its structure indicated an unstructured region. This might lower the stability of the fusion DSP105 and also might interfere with the proper orientation for trimerization via 4-1BBL.
2. The fusion protein was analyzed for proteolytic sites using the PROSPER server.
3. A loop within the 4-1BBL resolved domain was detected which is facing outwards toward the solvent, implying it could be a region which undergoes processing.

FIGS. 2A-3 and Table 3 below demonstrate the 3D models generated, the domains and segments identified, and the predicted proteolytic sites detected in the analysis of DSP105 fusion protein.

Taken together, the structural analysis indicated the following:
1. Removing a segment of five residues at the N-terminal of PD1 (PGWFL, SEQ ID NO: 8) is recommended since these are mainly hydrophobic by nature, they are not required for recognizing PDL1 and they span outside of the structured domain.
2. Removing a segment of five residues at the C-terminal of PD1 it is also recommended (FQTLV, SEQ ID NO: 9) due to similar apparent behavior as explained in point 1 above (i.e. these are mainly hydrophobic by nature, they are not required for recognizing PDL1 and they span outside of the structured domain).
3. There are 4 predicted cleavage sites found (focusing only on unstructured segments), on the C-terminal of PD1 and on the N-terminal of 4-1BBL.
4. Removing an N-terminal segment of the 4-1BBL domain (ACPWAVSGARASPG, SEQ ID NO: 10/ACPWAV, SEQ ID NO: 11) is expected to lower flexibility and hydrophobicity of DSP105.
5. In this removed N-terminal segment there is a free Cys residue which might prevent proper folding/rearrangement due to incorrect disulphide bonds.

Table 3: Predicted proteolytic sites in DSP105 PD1-4-1BBL fusion protein (SEQ ID NO: 1)

TABLE 3

Predicted proteolytic sites in DSP105 PD1-4-1BBL fusion protein (SEQ ID NO: 1)

| Merops ID | Protease Name | Position | P4-P4' site (SEQ ID Nos) | N-fragment (kDa) | C-fragment (kDa) | Cleavage score |
|---|---|---|---|---|---|---|
| M10.003 | matrix metallopeptidase-2 | 144 | RPAG\|QFQT (170\|171) | 19.03 | 24.84 | 0.99 |
| M10.004 | matrix metallopeptidase-9 | 144 | RPAG\|QFQT (172\|173) | 19.03 | 24.84 | 0.96 |
| C01.036 | cathepsin K | 147 | GQFQ\|TLVG (174\|175) | 19.44 | 24.44 | 1.1 |
| C02.001 | calpain-1 | 151 | TLVG\|ACPW (176\|177) | 19.92 | 23.95 | 0.94 |
| S01.269 | glutamyl peptidase I | 174 | RLRE\|GPEL (178\|179) | 22.43 | 21.44 | 1.04 |

Based on the structural analysis several PD1 variants were designed having an amino acid sequence of SEQ ID NO: 18, 19, 20, 21, 73, 75, 79, 81, 83, 85, 87, 89, 91, 93, 95, 115, 117 or 119 which can be fused to 4-1BBL or any variant thereof.

In addition, based on the structural analysis several 4-1BBL variants were designed having an amino acid sequence of SEQ ID NO: 22, 23, 24, 25, 123, 125, 127 or 129 which can be fused to PD1 or any variant thereof.

Moreover, to avoid the need of trimerization of the fusion protein to induce activity of the 4-1BBL moiety, 4-1BBL variants comprising 3 repeats of 4-1BBL amino acid sequence were designed, which can be fused to PD1 or any variant thereof. An exemplary sequence of such a 4-1BBL variant comprises three repeats of SEQ ID NO: 23 having a (GGGGS)×2+GGGG (SEQ ID NO: 121) linker between the repeats has an amino acid sequence of SEQ ID NO: 131.

As an example for DSP105 comprising such a 3 repeats 4-1BBL amino acid sequence, models of DSP105_V31 (SEQ ID NO: 147) were generated using homology modeling followed by side chains and loop refinement. Homology modeling was performed for each part based on a homologue X-ray structure. For PD1-PDB IDs: 3RRQ, 5GGR, 5GGS, 5JXE and 4ZQK were used as templates. For hIgG4-PDB IDs: 4C54, 4C55, 5W5M and 5W5N were used as templates. For 41BB-L-PDB IDs: 6CPR, 6A3V and 6CU0 were used as templates. Linker segments were modeled using loop modeling in CHARMM primarily in order to remove structural violations and to enable a plausible estimation for a possible 'spacer'. These models analysis predicted possible binding to the ligands and no interference between the different domains (FIGS. 13A-D).

Furthermore, a PD1-4-1BBL fusion protein comprising a (GGGGS)×2 (SEQ ID NO: 149) linker has been designed, to allow longer distance between PD1 moieties of distinct PD1-4-1BBL fusion proteins following trimerization.

Following, several PD1-4-1BBL variants were designed. Their sequences including the rational for their selection and their 3D model are demonstrated in Table 4 hereinbelow and FIGS. 4-6.

| Variant | Sequence | | description |
|---|---|---|---|
| DSP105 | PGWFLDSPDRPWNPPTFSPALLVVTEGDNATFTCSFSN TSESFVLNWYRMSPSNQTDKLAAFPEDRSQPGQDCRF RVTQLPNGRDFHMSVVRARRNDSGTYLCGAISLAPKA QIKESLRAELRVTERRAEVPTAHPSPSPRPAGQFQTLVG ACPWAVSGARASPGSAASPRLREGPELSPDDPAGLLDL RQGMFAQLVAQNVLLIDGPLSWYSDPGLAGVSLTGGL SYKEDTKELVVAKAGVYYVFFQLELRRVVAGEGSGSV SLALHLQPLRSAAGAAALALTVDLPPASSEARNSAFGF QGRLLHLSAGQRLGVHLHTEARARHAWQLTQGATVL GLFRVTPEIPAGLPSPRSE (SEQ ID NO: 5) | PD1 SEQ ID NO: 2 (150 amino acids), glycine linker, 4-1BBL SEQ ID NO: 3 (205 amino acids) | |
| DSP105_var1 | DSPDRPWNPPTFSPALLVVTEGDNATFTCSFSNTSESFV LNWYRMSPSNQTDKLAAFPEDRSQPGQDCRFRVTQLP NGRDFHMSVVRARRNDSGTYLCGAISLAPKAQIKESL RAELRVTERRAEVPTAHPSPSPRPAGQGSAASPRLREG PELSPDDPAGLLDLRQGMFAQLVAQNVLLIDGPLSWY SDPGLAGVSLTGGLSYKEDTKELVVAKAGVYYVFFQL ELRRVVAGEGSGSVSLALHLQPLRSAAGAAALALTVD LPPASSEARNSAFGFQGRLLHLSAGQRLGVHLHTEARA RHAWQLTQGATVLGLFRVTPEIPAGLPSPRSE (SEQ ID NO: 12) | PD1 SEQ ID NO: 18 (140 amino acids), glycine linker, 4-1BBL SEQ ID NO: 22 (191 amino acids) | Deletion of the 5AA from the N-ter of PD1 + 5AA from the C-ter of PD1 + 14AA from the N-ter of 4-1BBL (keeping the Gly linker) |
| DSP105_var2 | DSPDRPWNPPTFSPALLVVTEGDNATFTCSFSNTSESFV LNWYRMSPSNQTDKLAAFPEDRSQPGQDCRFRVTQLP NGRDFHMSVVRARRNDSGTYLCGAISLAPKAQIKESL RAELRVTERRAEVPTAHPSPSPRPAGQGARASPGSAAS PRLREGPELSPDDPAGLLDLRQGMFAQLVAQNVLLID GPLSWYSDPGLAGVSLTGGLSYKEDTKELVVAKAGV | PD1 SEQ ID NO: 18 (140 amino acids), glycine linker, 4-1BBL SEQ ID NO: 23 (197 amino acids) | Deletion of the 5AA from the N-ter of PD1 + 5AA from the C-ter of PD1 + 8AA from the N-ter of 4-1BBL (keeping the Gly linker) |

| Variant | Sequence | | description | |
|---|---|---|---|---|
| | YYVFFQLELRRVVAGEGSGSVSLALHLQPLRSAAGAA<br>ALALTVDLPPASSEARNSAFGFQGRLLHLSAGQRLGV<br>HLHTEARARHAWQLTQGATVLGLFRVTPEIPAGLPSPR<br>SE (SEQ ID NO: 14) | | | |
| DSP105_<br>var3 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPSPRPAGQGLREGPELSPD<br>DPAGLLDLRQGMFAQLVAQNVLLIDGPLSWYSDPGLA<br>GVSLTGGLSYKEDTKELVVAKAGVYYVFFQLELRRVV<br>AGEGSGSVSLALHLQPLRSAAGAAALALTVDLPPASSE<br>ARNSAFGFQGRLLHLSAGQRLGVHLHTEARARHAWQ<br>LTQGATVLGLFRVTPEIPAGLPSPRSE (SEQ ID NO: 16) | PD1 SEQ ID NO:<br>18 (140 amino<br>acids), glycine<br>linker, 4-1BBL<br>SEQ ID NO: 24<br>(185 amino acids) | Deletion of the 5AA<br>from the N-ter of PD1 +<br>5AA from the C-ter of<br>PD1 + 20AA from the<br>N-ter of 4-1BBL (keep-<br>ing the Gly linker) | |
| DSP105_<br>var4 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPSPRPAGQGSGARASPGSA<br>ASPRLREGPELSPDDPAGLLDLRQGMFAQLVAQNVLLI<br>DGPLSWYSDPGLAGVSLTGGLSYKEDTKELVVAKAG<br>VYYVFFQLELRRVVAGEGSGSVSLALHLQPLRSAAGA<br>AALALTVDLPPASSEARNSAFGFQGRLLHLSAGQRLG<br>VHLHTEARARHAWQLTQGATVLGLFRVTPEIPAGLPSP<br>RSE (SEQ ID NO: 44) | PD1 SEQ ID NO:<br>18 (140 amino<br>acids), glycine<br>linker, 4-1BBL<br>SEQ ID NO: 25<br>(199 amino acids) | Deletion of the 5AA<br>from the N-ter of PD1 +<br>5AA from the C-ter of<br>PD1+ Deletion of 6<br>amino acids from the N-<br>terminal of 4-1BBL | |
| DSP105_<br>var5 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPGSGARASPGSAASPRLRE<br>GPELSPDDPAGLLDLRQGMFAQLVAQNVLLIDGPLSW<br>YSDPGLAGVSLTGGLSYKEDTKELVVAKAGVYYVFFQ<br>LELRRVVAGEGSGSVSLALHLQPLRSAAGAAALALTV<br>DLPPASSEARNSAFGFQGRLLHLSAGQRLGVHLHTEAR<br>ARHAWQLTQGATVLGLFRVTPEIPAGLPSPRSE (SEQ<br>ID NO: 45) | PD1 SEQ ID NO:<br>21 (133 aa),<br>glycine linker, 4-<br>1BBL SEQ ID<br>NO: 25 (199<br>amino acids) | Deletion of the 5AA<br>from the N-ter of PD1 +<br>12AA from the C-ter of<br>PD1 + Deletion of 6<br>amino acids from the N-<br>terminal of 4-1BBL | |
| DSP105_<br>var6 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPGSAASPRLREGPELSPDD<br>PAGLLDLRQGMFAQLVAQNVLLIDGPLSWYSDPGLAG<br>VSLTGGLSYKEDTKELVVAKAGVYYVFFQLELRRVVA<br>GEGSGSVSLALHLQPLRSAAGAAALALTVDLPPASSEA<br>RNSAFGFQGRLLHLSAGQRLGVHLHTEARARHAWQL<br>TQGATVLGLFRVTPEIPAGLPSPRSE (SEQ ID NO: 46) | PD1 SEQ ID NO:<br>21 (133 aa),<br>glycine linker, 4-<br>1BBL SEQ ID<br>NO: 22 (191<br>amino acids) | Deletion of the 5AA<br>from the N-ter of PD1 +<br>12AA from the C-ter of<br>PD1 + Deletion of 14<br>amino acids from the N-<br>terminal of 4-1BBL | |
| DSP105_<br>var7 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPGARASPGSAASPRLREGP<br>ELSPDDPAGLLDLRQGMFAQLVAQNVLLIDGPLSWYS<br>DPGLAGVSLTGGLSYKEDTKELVVAKAGVYYVFFQLE<br>LRRVVAGEGSGSVSLALHLQPLRSAAGAAALALTVDL<br>PPASSEARNSAFGFQGRLLHLSAGQRLGVHLHTEARA<br>RHAWQLTQGATVLGLFRVTPEIPAGLPSPRSE (SEQ ID<br>NO: 47) | PD1 SEQ ID NO:<br>21 (133 aa),<br>glycine linker, 4-<br>1BBL SEQ ID<br>NO: 23 (197<br>amino acids) | Deletion of the 5AA<br>from the N-ter of PD1 +<br>12AA from the C-ter of<br>PD1 + Deletion of 8<br>amino acids from the N-<br>terminal of 4-1BBL | |
| DSP105_<br>var8 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPGLREGPELSPDDPAGLLD<br>LRQGMFAQLVAQNVLLIDGPLSWYSDPGLAGVSLTGG<br>LSYKEDTKELVVAKAGVYYVFFQLELRRVVAGEGSGS<br>VSLALHLQPLRSAAGAAALALTVDLPPASSEARNSAFG<br>FQGRLLHLSAGQRLGVHLHTEARARHAWQLTQGATV<br>LGLFRVTPEIPAGLPSPRSE (SEQ ID NO: 48) | PD1 SEQ ID NO:<br>21 (133 aa),<br>glycine linker, 4-<br>1BBL SEQ ID<br>NO: 24 (185<br>amino acids) | Deletion of the 5AA<br>from the N-ter of PD1 +<br>12AA from the C-ter of<br>PD1 +20AA from the N-<br>ter of 4-1BBL (keeping<br>the Gly linker) | |
| DSP105_<br>var9 | PWNPPTFSPALLVVTEGDNATFTCSFSNTSESFVLNWY<br>RMSPSNQTDKLAAFPEDRSQPGQDCRFRVTQLPNGRD<br>FHMSVVRARRNDSGTYLCGAISLAPKAQIKESLRAELR<br>VTERRAEVPTAHPSPGSGARASPGSAASPRLREGPELSP<br>DDPAGLLDLRQGMFAQLVAQNVLLIDGPLSWYSDPGL<br>AGVSLTGGLSYKEDTKELVVAKAGVYYVFFQLELRRV<br>VAGEGSGSVSLALHLQPLRSAAGAAALALTVDLPPASS<br>EARNSAFGFQGRLLHLSAGQRLGVHLHTEARARHAW<br>QLTQGATVLGLFRVTPEIPAGLPSPRSE<br>(SEQ ID NO: 49) | PD1 SEQ ID NO:<br>19 (128 aa),<br>glycine linker, 4-<br>1BBL SEQ ID<br>NO: 25 (199<br>amino acids) | Deletion of the 10AA<br>from the N-ter of PD1 +<br>12AA from the C-ter of<br>PD1 + Deletion of 6<br>amino acids from the N-<br>terminal of 4-1BBL | |

| Variant | Sequence | description | |
|---|---|---|---|
| DSP105_var10 | PWNPPTFSPALLVVTEGDNATFTCSFSNTSESFVLNWY RMSPSNQTDKLAAFPEDRSQPGQDCRFRVTQLPNGRD FHMSVVRARRNDSGTYLCGAISLAPKAQIKESLRAELR VTERRAEVPTAHPSPGsAASPRLREGPELSPDDPAGLLD LRQGMFAQLVAQNVLLIDGPLSWYSDPGLAGVSLTGG LSYKEDTKELVVAKAGVYYVFFQLELRRVVAGEGSGS VSLALHLQPLRSAAGAAALALTVDLPPASSEARNSAFG FQGRLLHLSAGQRLGVHLHTEARARHAWQLTQGATV LGLFRVTPEIPAGLPSPRSE (SEQ ID NO: 50) | PD1 SEQ ID NO: 19 (128 aa), glycine linker, 4-1BBL SEQ ID NO: 22 (191 amino acids) | Deletion of the 10AA from the N-ter of PD1 + 12AA from the C-ter of PD1 + Deletion of 14 amino acids from the N-terminal of 4-1BBL |
| DSP105_var11 | PWNPPTFSPALLVVTEGDNATFTCSFSNTSESFVLNWY RMSPSNQTDKLAAFPEDRSQPGQDCRFRVTQLPNGRD FHMSVVRARRNDSGTYLCGAISLAPKAQIKESLRAELR VTERRAEVPTAHPSPGARASPGSAASPRLREGPELSPD DPAGLLDLRQGMFAQLVAQNVLLIDGPLSWYSDPGLA GVSLTGGLSYKEDTKELVVAKAGVYYVFFQLELRRVV AGEGSGSVSLALHLQPLRSAAGAAALALTVDLPPASSE ARNSAFGFQGRLLHLSAGQRLGVHLHTEARARHAWQ LTQGATVLGLFRVTPEIPAGLPSPRSE (SEQ ID NO: 51) | PD1 SEQ ID NO: 19 (128 aa), glycine linker, 4-1BBL SEQ ID NO: 23 (197 amino acids) | Deletion of the 10AA from the N-ter of PD1 + 12AA from the C-ter of PD1 + Deletion of 8 amino acids from the N-terminal of 4-1BBL |
| DSP105_var12 | PWNPPTFSPALLVVTEGDNATFTCSFSNTSESFVLNWY RMSPSNQTDKLAAFPEDRSQPGQDCRFRVTQLPNGRD FHMSVVRARRNDSGTYLCGAISLAPKAQIKESLRAELR VTERRAEVPTAHPSPGLREGPELSPDDPAGLLDLRQGM FAQLVAQNVLLIDGPLSWYSDPGLAGVSLTGGLSYKE DTKELVVAKAGVYYVFFQLELRRVVAGEGSGSVSLAL HLQPLRSAAGAAALALTVDLPPASSEARNSAFGFQGR LLHLSAGQRLGVHLHTEARARHAWQLTQGATVLGLF RVTPEIPAGLPSPRSE (SEQ ID NO: 52) | PD1 SEQ ID NO: 19 (128 aa), glycine linker, 4-1BBL SEQ ID NO: 24 (185 amino acids) | Deletion of the 10AA from the N-ter of PD1 + 12AA from the C-ter of PD1 +20AA from the N-ter of 4-1BBL (keeping the Gly linker) |
| DSP105_var13 | PWNPPTFSPALLVVTEGDNATFTCSFSNTSESFVLNWY RMSPSNQTDKLAAFPEDRSQPGQDCRFRVTQLPNGRD FHMSVVRARRNDSGTYLCGAISLAPKAQIKESLRAELR VTERRAEVPTAHPSPSPRPAGQGSGARASPGSAASPRL REGPELSPDDPAGLLDLRQGMFAQLVAQNVLLIDGPLS WYSDPGLAGVSLTGGLSYKEDTKELVVAKAGVYYVF FQLELRRVVAGEGSGSVSLALHLQPLRSAAGAAALAL TVDLPPASSEARNSAFGFQGRLLHLSAGQRLGVHLHTE ARARHAWQLTQGATVLGLFRVTPEIPAGLPSPRSE (SEQ ID NO: 53) | PD1 SEQ ID NO: 20 (135 amino acids), glycine linker, 4-1BBL SEQ ID NO: 25 (199 amino acids) | Deletion of the 10AA from the N-ter of PD1 + 5AA from the C-ter of PD1 + Deletion of 6 amino acids from the N-terminal of 4-1BBL |
| DSP105_var14 | PWNPPTFSPALLVVTEGDNATFTCSFSNTSESFVLNWY RMSPSNQTDKLAAFPEDRSQPGQDCRFRVTQLPNGRD FHMSVVRARRNDSGTYLCGAISLAPKAQIKESLRAELR VTERRAEVPTAHPSPSPRPAGQGSAASPRLREGPELSPD DPAGLLDLRQGMFAQLVAQNVLLIDGPLSWYSDPGLA GVSLTGGLSYKEDTKELVVAKAGVYYVFFQLELRRVV AGEGSGSVSLALHLQPLRSAAGAAALALTVDLPPASSE ARNSAFGFQGRLLHLSAGQRLGVHLHTEARARHAWQ LTQGATVLGLFRVTPEIPAGLPSPRSE (SEQ ID NO: 54) | PD1 SEQ ID NO: 20 (135 amino acids), glycine linker, 4-1BBL SEQ ID NO: 22 (191 amino acids) | Deletion of the 10AA from the N-ter of PD1 + 5AA from the C-ter of PD1 + Deletion of 14 amino acids from the N-terminal of 4-1BBL |
| DSP105_var15 | PWNPPTFSPALLVVTEGDNATFTCSFSNTSESFVLNWY RMSPSNQTDKLAAFPEDRSQPGQDCRFRVTQLPNGRD FHMSVVRARRNDSGTYLCGAISLAPKAQIKESLRAELR VTERRAEVPTAHPSPSPRPAGQGARASPGSAASPRLRE GPELSPDDPAGLLDLRQGMFAQLVAQNVLLIDGPLSW YSDPGLAGVSLTGGLSYKEDTKELVVAKAGVYYVFFQ LELRRVVAGEGSGSVSLALHLQPLRSAAGAAALALTV DLPPASSEARNSAFGFQGRLLHLSAGQRLGVHLHTEAR ARHAWQLTQGATVLGLFRVTPEIPAGLPSPRSE (SEQ ID NO: 55) | PD1 SEQ ID NO: 20 (135 amino acids), glycine linker, 4-1BBL SEQ ID NO: 23 (197 amino acids) | Deletion of the 10AA from the N-ter of PD1 + 5AA from the C-ter of PD1 + Deletion of 8 amino acids from the N-terminal of 4-1BBL |
| DSP105_var16 | PWNPPTFSPALLVVTEGDNATFTCSFSNTSESFVLNWY RMSPSNQTDKLAAFPEDRSQPGQDCRFRVTQLPNGRD FHMSVVRARRNDSGTYLCGAISLAPKAQIKESLRAELR VTERRAEVPTAHPSPSPRPAGQGLREGPELSPDDPAGL LDLRQGMFAQLVAQNVLLIDGPLSWYSDPGLAGVSLT GGLSYKEDTKELVVAKAGVYYVFFQLELRRVVAGEG SGSVSLALHLQPLRSAAGAAALALTVDLPPASSEARNS AFGFQGRLLHLSAGQRLGVHLHTEARARHAWQLTQG ATVLGLFRVTPEIPAGLPSPRSE (SEQ ID NO: 56) | PD1 SEQ ID NO: 20 (135 amino acids), glycine linker, 4-1BBL SEQ ID NO: 24 (185 amino acids) | Deletion of the 10AA from the N-ter of PD1 + 5AA from the C-ter of PD1 + 20AA from the N-ter of 4-1BBL (keeping the Gly linker) |
| DSP105_var17 | DSPDRPWNPPTFSPALLVVTEGDNATFTCSFSNTSESFV LNWYRMSPSNQTDKLAAFPEDRSQPGQDSRFRVTQLP NGRDFHMSVVRARRNDSGTYLCGAISLAPKAQIKESL RAELRVTERRAEVPTAHPSPSPRPAGQGSAASPRLREG | PD1 SEQ ID NO: 75 (140 amino acids), glycine linker, 4-1BBL | Deletion of the 5AA from the N-ter of PD1 + 5AA from the C-ter of PD1 + Mutation of C73 |

| Variant | Sequence | | description |
|---|---|---|---|
| | PELSPDDPAGLLDLRQGMFAQLVAQNVLLIDGPLSWY SDPGLAGVSLTGGLSYKEDTKELVVAKAGVYYVFFQL ELRRVVAGEGSGSVSLALHLQPLRSAAGAAAALALTVD LPPASSEARNSAFGFQGRLLHLSAGQRLGVHLHTEARA RHAWQLTQGATVLGLFRVTPEIPAGLPSPRSE (SEQ ID NO: 97) | SEQ ID NO: 22 (191 amino acids) | corresponding to SEQ ID NO: 2 to S + Deletion of the N-ter segment from 4-1BBL 14AA |
| DSP105_var18 | WNPPTFSPALLVVTEGDNATFTCSFSNTSESFVLNWYR MSPSNQTDKLAAFPEDRSQPGQDSRFRVTQLPNGRDF HMSVVRARRNDSGTYLCGAISLAPKAQIKESLRAELRV TERRAEVPTAHPSPGSAASPRLREGPELSPDDPAGLLDL RQGMFAQLVAQNVLLIDGPLSWYSDPGLAGVSLTGGL SYKEDTKELVVAKAGVYYVFFQLELRRVVAGEGSGSV SLALHLQPLRSAAGAAAALALTVDLPPASSEARNSAFGF QGRLLHLSAGQRLGVHLHTEARARHAWQLTQGATVL GLFRVTPEIPAGLPSPRSE (SEQ ID NO: 101) | PD1 SEQ ID NO: 87 (127 amino acids), glycine linker, 4-1BBL SEQ ID NO: 22 (191 amino acids) | Deletion of the 11AA from the N-ter of PD1 + 12AA from the C-ter of PD1 + Mutation of C73 corresponding to SEQ ID NO: 2 to S + Deletion of the N-ter segment from 4-1BBL 14AA |
| DSP105_var19 | WNPPTFSPALLVVTEGDNATFTCSFSNTSESFVLNWYR MSPSNQTDKLAAFPEDRSQPGQDSRFRVTQLPNGRDF HMSVVRARRNDSGTYLCGAISLAPKAQIKESLRAELRV TERRAEVPTAHPSPSPRPAGQGSAASPRLREGPELSPDD PAGLLDLRQGMFAQLVAQNVLLIDGPLSWYSDPGLAG VSLTGGLSYKEDTKELVVAKAGVYYVFFQLELRRVVA GEGSGSVSLALHLQPLRSAAGAAAALALTVDLPPASSEA RNSAFGFQGRLLHLSAGQRLGVHLHTEARARHAWQL TQGATVLGLFRVTPEIPAGLPSPRSE (SEQ ID NO: 103) | PD1 SEQ ID NO: 91 (134 amino acids), glycine linker, 4-1BBL SEQ ID NO: 22 (191 amino acids) | Deletion of the 11AA from the N-ter of PD1 + 5AA from the C-ter of PD1 + Mutation of C73 corresponding to SEQ ID NO: 2 to S + Deletion of the N-ter segment from 4-1BBL 14AA |
| DSP105_var20 | DSPDRPWNPPTFSPALLVVTEGDNATFTCSFSNTSESFV LNWYRMSPSNQTDKLAAFPEDRSQPGQDSRFRVTQLP NGRDFHMSVVRARRNDSGTYLCGAISLAPKAQIKESL RAELRVTERRAEVPTAHPSPGSAASPRLREGPELSPDDP AGLLDLRQGMFAQLVAQNVLLIDGPLSWYSDPGLAG VSLTGGLSYKEDTKELVVAKAGVYYVFFQLELRRVVA GEGSGSVSLALHLQPLRSAAGAAAALALTVDLPPASSEA RNSAFGFQGRLLHLSAGQRLGVHLHTEARARHAWQL TQGATVLGLFRVTPEIPAGLPSPRSE (SEQ ID NO: 105) | PD1 SEQ ID NO: 83 (133 amino acids), glycine linker, 4-1BBL SEQ ID NO: 22 (191 amino acids) | Deletion of the 5AA from the N-ter of PD1 + 12AA from the C-ter of PD1 + Mutation of C73 corresponding to SEQ ID NO: 2 to S + Deletion of the N-ter segment from 4-1BBL 14AA |
| DSP105_var21 | DSPDRPWNPPTFSPALLVVTEGDNATFTCSFSNTSESFV LNWYRMSPSNQTDKLAAFPEDRSQPGQDSRFRVTQLP NGRDFHMSVVRARRNDSGTYLCGAISLAPKAQIKESL RAELRVTERRAEVPTAHPSPSPRPAGSAASPRLREGPEL SPDDPAGLLDLRQGMFAQLVAQNVLLIDGPLSWYSDP GLAGVSLTGGLSYKEDTKELVVAKAGVYYVFFQLELR RVVAGEGSGSVSLALHLQPLRSAAGAAAALALTVDLPP ASSEARNSAFGFQGRLLHLSAGQRLGVHLHTEARARH AWQLTQGATVLGLFRVTPEIPAGLPSPRSE (SEQ ID NO: 107) | PD1 SEQ ID NO: 95 (138 amino acids), glycine linker, 4-1BBL SEQ ID NO: 22 (191 amino acids) | Deletion of the 5AA from the N-ter of PD1 + 7AA from the C-ter of PD1 + Mutation of C73 corresponding to SEQ ID NO: 2 to S + Deletion of the N-ter segment from 4-1BBL 14AA |
| DSP105_var22 | PGWFLDSPDRPWNPPTFSPALLVVTEGDNATFTCSFSN TSESFVLNWYRMSPSNQTDKLAAFPEDRSQPGQDSRF RVTQLPNGRDFHMSVVRARRNDSGTYLCGAISLAPKA QIKESLRAELRVTERRAEVPTAHPSPSPRPAGQFQTLVG ACPWAVSGARASPGSAASPRLREGPELSPDDPAGLLDL RQGMFAQLVAQNVLLIDGPLSWYSDPGLAGVSLTGGL SYKEDTKELVVAKAGVYYVFFQLELRRVVAGEGSGSV SLALHLQPLRSAAGAAAALALTVDLPPASSEARNSAFGF QGRLLHLSAGQRLGVHLHTEARARHAWQLTQGATVL GLFR VTPEIPAGLPSPRSE (SEQ ID NO: 111) | PD1 SEQ ID NO: 73 (156 amino acids), glycine linker, 4-1BBL SEQ ID SEQ ID NO: 3 (205 amino acids) | Mutation of C73 corresponding to SEQ ID NO: 2 to S |
| DSP105_var23 | DSPDRPWNPPTFSPALLVVTEGDNATFTCSFSNTSESFV LNWYRMSPSNQTDKLAAFPEDRSQPGQDCRFRVTQLP NGRDFHMSVVRARRNDSGTYLCGAISLAPKAQIKESL RAELRVTERRAEVPTAHPSPSPRPAGSAASPRLREGPEL SPDDPAGLLDLRQGMFAQLVAQNVLLIDGPLSWYSDP GLAGVSLTGGLSYKEDTKELVVAKAGVYYVFFQLELR RVVAGEGSGSVSLALHLQPLRSAAGAAAALALTVDLPP ASSEARNSAFGFQGRLLHLSAGQRLGVHLHTEARARH AWQLTQGATVLGLFRVTPEIPAGLPSPRSE (SEQ ID NO: 113) | PD1 SEQ ID NO: 93 (138 amino acids), glycine linker, 4-1BBL SEQ ID NO: 22 (191 amino acids) | Deletion of the 5AA from the N-ter of PD1 + 7AA from the C-ter of PD1 Deletion of the N-ter segment from 4-1BBL 14AA |
| DSP105_var24 | DSPDRPWNPPTFSPALLVVTEGDNATFTCSFSNTSESFV LNWYRMSPSNQTDKLAAFPEDRSQPGQDCRFRVTQLP NGRDFHMSVVRARRNDSGTYLCGAISLAPKAQIKESL RAELRVTERRAEVPTAHPSPSPRGREGPELSPDDPAGL LDLRQGMFAQLVAQNVLLIDGPLSWYSDPGLAGVSLT GGLSYKEDTKELVVAKAGVYYVFFQLELRRVVAGEG SGSVSLALHLQPLRSAAGAAAALALTVDLPPASSEARNS | PD1 SEQ ID NO: 115 (136 amino acids), glycine linker, 4-1BBL SEQ ID NO: 123 (184 amino acids) | Deletion of the 5AA from the N-ter of PD1 + 9AA from the C-ter of PD1. Deletion of 21AA From the N-ter segment of 4-1BBL |

| Variant | Sequence | | description |
|---|---|---|---|
| | AFGFQGRLLHLSAGQRLGVHLHTEARARHAWQLTQG<br>ATVLGLFRVTPEIPAGLPSPRSE (SEQ ID NO: 133) | | |
| DSP105_<br>var25 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPSPRRGGPELSPDDPAGLLD<br>LRQGMFAQLVAQNVLLIDGPLSWYSDPGLAGVSLTGG<br>LSYKEDTKELVVAKAGVYYVFFQLELRRVVAGEGSGS<br>VSLALHLQPLRSAAGAAALALTVDLPPASSEARNSAFG<br>FQGRLLHLSAGQRLGVHLHTEARARHAWQLTQGATV<br>LGLFRVTPEIPAGLPSPRSE (SEQ ID NO: 135) | PD1 SEQ ID NO:<br>115 (136 amino<br>acids), glycine<br>linker, 4-1BBL<br>SEQ ID NO: 125<br>(182 amino acids) | Deletion of the 5AA<br>from the N-ter of PD1 +<br>9AA from the C-ter of<br>PD1.<br>Deletion of 23AA<br>From the N-ter segment<br>of 4-1BBL |
| DSP105_<br>var26 | PGWFLDSPDRPWNPPTFSPALLVVTEGDNATFTCSFSN<br>TSESFVLNWYRMSPSNQTDKLAAFPEDRSQPGQDCRF<br>RVTQLPNGRDFHMSVVRARRNDSGTYLCGAISLAPKA<br>QIKESLRAELRVTERRAEVPTAHPSPSPRPAGQGSAASP<br>RLREGPELSPDDPAGLLDLRQGMFAQLVAQNVLLIDG<br>PLSWYSDPGLAGVSLTGGLSYKEDTKELVVAKAGVY<br>YVFFQLELRRVVAGEGSGSVSLALHLQPLRSAAGAAA<br>LALTVDLPPASSEARNSAFGFQGRLLHLSAGQRLGVHL<br>HTEARARHAWQLTQGATVLGLFRVTPEIPA (SEQ ID<br>NO: 137) | PD1 SEQ ID NO:<br>117 (145 amino<br>acids), glycine<br>linker, 4-1BBL<br>SEQ ID NO: 127<br>(183 amino acids) | Deletion of the 5AA<br>from the C-ter of PD1.<br>Deletion of 14 AA<br>from the N-ter segment<br>of 4-1BBL and 8 AA<br>from the C-ter of<br>4-1BBL |
| DSP105_<br>var27 | PGWFLDSPDRPWNPPTFSPALLVVTEGDNATFTCSFSN<br>TSESFVLNWYRMSPSNQTDKLAAFPEDRSQPGQDCRF<br>RVTQLPNGRDFHMSVVRARRNDSGTYLCGAISLAPKA<br>QIKESLRAELRVTERRAEVPTAHPSPSPRPAGREGPELS<br>PDDPAGLLDLRQGMFAQLVAQNVLLIDGPLSWYSDPG<br>LAGVSLTGGLSYKEDTKELVVAKAGVYYVFFQLELRR<br>VVAGEGSGSVSLALHLQPLRSAAGAAALALTVDLPPA<br>SSEARNSAFGFQGRLLHLSAGQRLGVHLHTEARARHA<br>WQLTQGATVLGLFRVTPEIPA (SEQ ID NO: 139) | PD1 SEQ ID NO:<br>119 (143 amino<br>acids), glycine<br>linker, 4-1BBL<br>SEQ ID NO: 129<br>(176 amino acids) | Deletion of the 7AA<br>from the C-ter of PD1.<br>Deletion of 21 AA<br>from the N-ter segment<br>of 4-1BBL and 8 AA<br>from the C-ter of<br>4-1BBL |
| DSP105_<br>var28 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPSPRPAGQGACPWAVSGA<br>RASPGSAASPRLREGPELSPDDPAGLLDLRQGMFAQLV<br>AQNVLLIDGPLSWYSDPGLAGVSLTGGLSYKEDTKEL<br>VVAKAGVYYVFFQLELRRVVAGEGSGSVSLALHLQPL<br>RSAAGAAALALTVDLPPASSEARNSAFGFQGRLLHLSA<br>GQRLGVHLHTEARARHAWQLTQGATVLGLFRVTPEIP<br>AGLPSPRSE (SEQ ID NO: 141) | PD1 SEQ ID NO:<br>18 (140 amino<br>acids), glycine<br>linker, 4-1BBL<br>SEQ ID NO: 3<br>(205 amino acids) | Deletion of the 5AA<br>from the N-ter of PD1 +<br>5AA from the C-ter of<br>PD1 |
| DSP105_<br>var29 | PGWFLDSPDRPWNPPTFSPALLVVTEGDNATFTCSFSN<br>TSESFVLNWYRMSPSNQTDKLAAFPEDRSQPGQDCRF<br>RVTQLPNGRDFHMSVVRARRNDSGTYLCGAISLAPKA<br>QIKESLRAELRVTERRAEVPTAHPSPSPRPAGQFQTLVG<br>SGARASPGSAASPRLREGPELSPDDPAGLLDLRQGMFA<br>QLVAQNVLLIDGPLSWYSDPGLAGVSLTGGLSYKEDT<br>KELVVAKAGVYYVFFQLELRRVVAGEGSGSVSLALHL<br>QPLRSAAGAAALALTVDLPPASSEARNSAFGFQGRLLH<br>LSAGQRLGVHLHTEARARHAWQLTQGATVLGLFRVT<br>PEIPAGLPSPRSE (SEQ ID NO: 143) | PD1 SEQ ID NO:<br>2 (150 amino<br>acids), glycine<br>linker, 4-1BBL<br>SEQ ID NO: 25<br>(109 amino acids) | Deletion of 6 AA<br>from the N-ter segment<br>of 4-1BBL |
| DSP105_<br>var30 | PGWFLDSPDRPWNPPTFSPALLVVTEGDNATFTCSFSN<br>TSESFVLNWYRMSPSNQTDKLAAFPEDRSQPGQDCRF<br>RVTQLPNGRDFHMSVVRARRNDSGTYLCGAISLAPKA<br>QIKESLRAELRVTERRAEVPTAHPSPSPRPAGQFQTLVG<br>GGGSGGGGSACPWAVSGARASPGSAASPRLREGPELS<br>PDDPAGLLDLRQGMFAQLVAQNVLLIDGPLSWYSDPG<br>LAGVSLTGGLSYKEDTKELVVAKAGVYYVFFQLELRR<br>VVAGEGSGSVSLALHLQPLRSAAGAAALALTVDLPPA<br>SSEARNSAFGFQGRLLHLSAGQRLGVHLHTEARARHA<br>WQLTQGATVLGLFRVTPEIPAGLPSPRSE (SEQ ID<br>NO: 145) | PD1 SEQ ID NO:<br>2 (150 amino<br>acids),<br>(GGGGS)x2 (SEQ<br>ID NO: 149)<br>linker 4-1BBL<br>SEQ ID NO: 3<br>(205 amino acids) | WT PD1 and 4-1BBL<br>linked by (GGGGS)x2 |
| DSP105_<br>var31 | DSPDRPWNPPTFSPALLVVTEGDNATFTCSFSNTSESFV<br>LNWYRMSPSNQTDKLAAFPEDRSQPGQDCRFRVTQLP<br>NGRDFHMSVVRARRNDSGTYLCGAISLAPKAQIKESL<br>RAELRVTERRAEVPTAHPSPSPRPAGQGGGGSGGGGS<br>AASPRLREGPELSPDDPAGLLDLRQGMFAQLVAQNVL<br>LIDGPLSWYSDPGLAGVSLTGGLSYKEDTKELVVAKA<br>GVYYVFFQLELRRVVAGEGSGSVSLALHLQPLRSAAG<br>AAALALTVDLPPASSEARNSAFGFQGRLLHLSAGQRL<br>GVHLHTEARARHAWQLTQGATVLGLFRVTPEIPAGLP | PD1 SEQ ID NO:<br>18 (140 amino<br>acids), GGGGSGG<br>GG (SEQ ID NO:<br>122) as a linker,<br>sc3x41BBL [SEQ<br>ID NO 131 (601<br>aa): 3 times SEQ<br>ID NO: 22) | Deletion of the 5AA<br>from the N-ter of PD1 +<br>5AA from the C-ter of<br>PD1.<br>Single chain containing<br>three 4-1BBL with 14<br>AA deletion at the N-<br>ter<br>segment. |

-continued

| Variant | Sequence | description | |
|---|---|---|---|
| | SPRSEGGGGSGGGGSGGGGSAASPRLREGPELSPDDPA GLLDLRQGMFAQLVAQNVLLIDGPLSWYSDPGLAGVS LTGGLSYKEDTKELVVAKAGVYYVFFQLELRRVVAGE GSGSVSLALHLQPLRSAAGAAALALTVDLPPASSEARN SAFGFQGRLLHLSAGQRLGVHLHTEARARHAWQLTQ GATVLGLFRVTPEIPAGLPSPRSEGGGGSGGGGSGGGG SAASPRLREGPELSPDDPAGLLDLRQGMFAQLVAQNV LLIDGPLSWYSDPGLAGVSLTGGLSYKEDTKELVVAK AGVYYVFFQLELRRVVAGEGSGSVSLALHLQPLRSAA GAAALALTVDLPPASSEARNSAFGFQGRLLHLSAGQR LGVHLHTEARARHAWQLTQGATVLGLFRVTPEIPAGL PSPRSE (SEQ ID NO: 147) | separated by GGGGSGGGGSG GGG linker (SEQ ID NO: 121)] | |
| DSP105_var32 | SAASPRLREGPELSPDDPAGLLDLRQGMFAQLVAQNV LLIDGPLSWYSDPGLAGVSLTGGLSYKEDTKELVVAK AGVYYVFFQLELRRVVAGEGSGSVSLALHLQPLRSAA GAAALALTVDLPPASSEARNSAFGFQGRLLHLSAGQR LGVHLHTEARARHAWQLTQGATVLGLFRVTPEIPAGL PSPRSEGDSPDRPWNPPTFSPALLVVTEGDNATFTCSFS NTSESFVLNWYRMSPSNQTDKLAAFPEDRSQPGQDCR FRVTQLPNGRDFHMSVVRARRNDSGTYLCGAISLAPK AQIKESLRAELRVTERRAEVPTAHPSPSPRPAGQ (SEQ ID NO: 168) | 4-1BBL SEQ ID NO: 22 (191 amino acids), glycine linker, PD1 SEQ ID NO: 18 (140 amino acids) | Deletion of 14AA from the N-ter of 4-1BBL + the 5AA from the N-ter of PD1 + 5AA from the C-ter of PD1 (keeping the Gly linker) |

| Variant | comment |
|---|---|
| DSP105 | |
| DSP105_var1 | Removing small hydrophobic flanking segments (predicted to be less structured) from both terminals of PD1, in addition to removal of the first 14 N-ter AA of 4-1BBL due to the long unstructured and hydrophobic segments preceding the structured domain of 4-1BBL |
| DSP105_var2 | Removing small hydrophobic flanking segments (predicted to be less structured) from both terminals of PD1, in addition to removal of the first 8 N-ter AA of 4-1BBL which are predicted to be unstructured and are the core hydrophobic segment preceding the structured domain of 4-1BBL |
| DSP105_var3 | Removing small hydrophobic flanking segments (predicted to be less structured) from both terminals of PD1, in addition to removal of the first 20 N-ter AA of 4-1BBL due to the long unstructured and hydrophobic segments preceding the structured domain of 4-1BBL |
| DSP105_var4 | Removing small hydrophobic flanking segments (predicted to be less structured) from both terminals of PD1, and Removing core hydrophobic segment of 4-1BBL |
| DSP105_var5 | Removing a small hydrophobic segment from N-ter of PD1 and a larger flanking segment (predicted to be less structured) from the C-ter of PD1 (based on crystalized constructs), in addition to removing core hydrophobic segment of 4-1BBL |
| DSP105_var6 | Removing a small hydrophobic segment from N-ter of PD1 and a larger flanking segment (predicted to be less structured) from the C-ter of PD1 (based on crystalized constructs), in addition to removing flanking (predicted to be less structured) and hydrophobic segment of 4-1BBL |

-continued

| Variant Sequence | description |
|---|---|
| DSP105_var7 | Removing a small hydrophobic segment from N-ter of PD1 and a larger flanking segment (predicted to be less structured) from the C-ter of PD1 (based on crystalized constructs), in addition to removal of the first 8 N-ter AA of 4-1BBL which are predicted to be unstructured and are the core hydrophobic segment preceding the structured domain of 4-1BBL |
| DSP105_var8 | Removing a small hydrophobic segment from N-ter of PD1 and a larger flanking segment (predicted to be less structured) from the C-ter of PD1 (based on crystalized constructs), in addition to removal of the first 20 N-ter AA of 4-1BBL due to the long unstructured and hydrophobic segments preceding the structured domain of 4-1BBL |
| DSP105_var9 | Removing larger flanking segments (predicted to be less structured) from both terminals of PD1 (based on crystalized constructs), in addition to removing core hydrophobic segment of 4-1BBL |
| DSP105_var10 | Removing larger flanking segments (predicted to be less structured) from both terminals of PD1 (based on crystalized constructs), in addition to in addition to removing flanking (predicted to be less structured) and hydrophobic segment of 4-1BBL |
| DSP105_var11 | Removing larger flanking segments (predicted to be less structured) from both terminals of PD1 (based on crystalized constructs), in addition to removal of the first 8 N-ter AA of 4-1BBL which are predicted to be unstructured and are the core hydrophobic segment preceding the structured domain of 4-1BBL |
| DSP105_var12 | Removing larger flanking segments (predicted to be less structured) from both terminals of PD1 (based on crystalized constructs), in addition to removal of the first 20 N-ter AA of 4-1BBL due to the long unstructured and hydrophobic segments preceding the structured domain of 4-1BBL |
| DSP105_var13 | Removing larger flanking segment (predicted to be less structured) from N-ter and smaller hydrophobic segment from C-ter of PD1 (based on crystalized constructs), in addition to removing core hydrophobic segment of 4-1BBL |
| DSP105_var14 | Removing larger flanking segment (predicted to be less structured) from N-ter and smaller hydrophobic segment from C-ter of PD1 (based on crystalized constructs), in addition to removing flanking (predicted to be less structured) and hydrophobic segment of 4-1BBL |
| DSP105_var15 | Removing a larger flanking segment (predicted to be less structured) from N-ter and a smaller hydrophobic segment from C-ter of PD1 (based on |

-continued

| Variant Sequence | description |
|---|---|
| | crystalized constructs), in addition to removal of the first 8 N-ter AA of 4-1BBL which are predicted to be unstructured and are the core hydrophobic segment preceding the structured domain of 4-1BBL |
| DSP105_var16 | Removing a larger flanking segment (predicted to be less structured) from N-ter and a smaller hydrophobic segment from C-ter of PD1 (based on crystalized constructs), in addition to removal of the first 20 N-ter AA of 4-1BBL due to the long unstructured and hydrophobic segments preceding the structured domain of 4-1BBL |
| DSP105_var17 | Removing a small hydrophobic segment from N-ter of PD1 and a larger flanking segment (predicted to be less structured) from the C-ter of PD1 (based on crystalized constructs); a mutation of C to S in PD1 to prevent un desired S-S bridges; and removing a flanking (predicted to be less structured) and hydrophobic segment of 4-1BBL |
| DSP105_var18 | Removing a larger flanking segment (predicted to be less structured) from N-ter and a large hydrophobic segment from C-ter of PD1 (based on crystalized constructs); a mutation of C to S in PD1 to prevent un desired S-S bridges; and removing a flanking (predicted to be less structured) and hydrophobic segment of 4-1BBL |
| DSP105_var19 | Removing a larger flanking segment (predicted to be less structured) from N-ter and a small hydrophobic segment from C-ter of PD1 (based on crystalized constructs), a mutation of C to S in PD1 to prevent un desired S-S bridges; and removing flanking (predicted to be less structured) and hydrophobic segment of 4-1BBL |
| DSP105 var20 | Removing a small flanking segment (predicted to be less structured) from N-ter and a large hydrophobic segment from C-ter of PD1 (based on crystalized constructs); a mutation of C to S in PD1 to prevent un desired S-S bridges; and removing a flanking (predicted to be less structured) and hydrophobic segment of 4-1BBL |
| DSP105_var21 | Removing a larger flanking segment (predicted to be less structured) from N-ter and a small hydrophobic segment from C-ter of PD1 (based on crystalized constructs); a mutation of C to S in PD1 to prevent un desired S-S bridges; and removing flanking (predicted to be less structured) and hydrophobic segment of 4-1BBL |
| DSP105_var22 | A mutation of C to S in PD1 to prevent un desired S-S bridges |
| DSP105_var23 | Removing a larger flanking segment (predicted to be less structured) from N-ter and a small hydrophobic segment from C-ter of PD1 (based on crystalized constructs) and removing flanking (predicted to be less structured) and hydrophobic segment of 4-1BBL |

| Variant | Sequence | description |
|---|---|---|
| DSP105_var24 | | shortening the relatively long linker (from both PD1 C-ter side and 41BBL N-ter side) keeping maximal positive charged residues to complement for the negatively charged N-ter of 4-1BBL |
| DSP105_var25 | | Larger shortening of the relatively long linker (from both PD1 C-ter side and 41BBL N-ter side), keeping maximal positive charged residues to complement for the negatively charged N-ter of 41BBL |
| DSP105_var26 | | No deletion of N-ter of PD1 (the N-ter is at the PDL1 interaction side, therefore, there is a posisbility that deletion at this area may affect the proteins interaction). Removing hydrophobic segment from C-ter of PD1 (based on crystalized constructs) and removing flanking (predicted to be less structured) and hydrophobic segment of 4-1BBL and the C-ter side of 41BBL seq (possible interaction of this segment with the linker) |
| DSP105_var27 | | Shortening the relatively long linker (from both PD1 C-ter side and 41BBL N-ter side) and the C-ter side of 41BBL seq (possible interaction of this segment with the linker) |
| DSP105_var28 | | Removing a small flanking segment (predicted to be less structured) from N-ter and a small hydrophobic segment from C-ter of PD1 (based on crystalized constructs). Living relatively long linker between the PD1 and 4-1BBL to allow long distance between the PD1 domains after trimerization of the 4-1BBL |
| DSP105_var29 | | A long native sequence without defined structure which may serve as a long linker between the PD1 and 4-1BBL to allow long distance between the PD1 domains after trimerization of the 4-1BBL. Removing core hydrophobic segment from the 4-1BBL. |
| DSP105_var30 | | Extension of the linker between the PD1 and 4-1BBL to allow long distance between the PD1 domains after trimerization of the 4-1BBL |
| DSP105_var31 | | Removing a small flanking segment (predicted to be less structured) from N-ter and a small hydrophobic segment from C-ter of PD1 (based on crystalized constructs). Avoiding the need for trimerization by combining three domains of 4-1BBL (without the 14 AA of the N-ter which predicted to be less structured and hydrophobic) |
| DSP105_var32 | | Removing the first 14 N-ter AA of 4-1BBL due to the long unstructured and hydrophobic segments preceding the structured domain of 4-1BBL; and removing small hydrophobic flanking segments (predicted to be less structured) from both terminals of PD1 |

Example 2

Manufacturing OF PD1-4-1BBL Variants

For comparative functional analysis and production evaluation, several PD1-4-1BBL fusion proteins were produced, namely: a PD1-4-1BBL fusion protein referred to herein as "DSP105" (SEQ ID NO: 5) and nine DSP105 variants referred to herein as "DSP105_V1", "DSP105_V2", "DSP105_V3", "DSP105_V17". "DSP105_V18", "DSP105_V19". "DSP105_V20", "DSP105_V21", "DSP105_V22", "DSP_V23", "DSP105_V24", "DSP105_V25", "DSP105_V26", "DSP105_V27", "DSP105_V28", "DSP105_V29", "DSP105_V30" and "DSP105_V31" (SEQ ID NO: 12, 14, 16, 97, 101, 103, 105,107, 111 113, 133, 135, 137, 139, 141, 143, 145 and 147) respectively.

Production was effected in ExpiCHO, Expi293F or CHO-3E7 cells were transfected by a pcDNA3.4 or pTT5 expression vector cloned with coding sequence for DSP105 and its variants. The sequences were cloned into the vector using EcoRI and HindIII restriction enzymes, with addition of Kozak sequence, artificial signal peptide (MEAPAQLL-FLLLLWLPDTTG, SEQ ID NO: 4) with or without 6 His-tag in the N or C terminus and a stop codon in the C terminus. The proteins were collected from the supernatant of cell culture, The supernatants were purified by one-step purification by HisTrap™ FF Crude column.

The production of the tagged fusion proteins was verified by SDS-PAGE and Western blot analysis using specific antibodies against His tag or one of the domains of the molecule (i.e. the extracellular domain each of PD1 or 4-1BBL), see e.g. FIGS. 8A-E.

For examples, western blot analysis of variants His-tagged-DSP105_V17, DSP105-V18, DSP105_V19, DSP105_V20 and DSP105_V23 separated on an SDS-PAGE gel under reducing conditions followed by immunoblotting with an anti-PD1 antibody or anti His-tag antibody demonstrated that the variants were expressed in CHO-3E7 cells.

Optionally, the produced fusion proteins are further purified by size exclusion chromatography to collect the fraction of a purified trimer. To this end, the proteins are loaded on Superdex column with PBS as mobile phase and at a flow rate of 1 ml/min. The major peak corresponding to protein trimers is collected.

Yield is assessed using BCA or Bradford protein concentration determination, or by optical density measurement by Nanodrop, at 280 nm, divided by the protein extinction coefficient. Proteins stability is evaluated under storage and accelerated conditions.

Example 3

Determination of the Oligomeric State of the PD1-4-1BBL Variants

Materials-N-terminal his-tagged DSP105 (SEQ ID NO: 1) produced in Expi293 cells [referred to herein as "DSP105 (HEK-NH)"] as described in Example 2 hereinabove, N-terminal his-tagged DSP105 (SEQ ID NO: 1) produced in ExpiCHO cells [referred to herein as "DSP105 (CHO-NH)"], N-terminal his-tagged DSP105 variants DSP105_V1 (SEQ ID NO: 13), DSP105_V2 (SEQ ID NO: 15) and DSP105_V3 (SEQ ID NO: 17) produced in ExpiCHO cells [referred to herein as "DSP105 (CHO-NH)-V1", "DSP105 (CHO-NH)-V2" and "DSP105 (CHO-NH)-V3"], N-terminal His-tagged DSP105 variants DSP105_V17 (SEQ ID NO: 99) and DSP105_V22 (SEQ ID NO: 109) produced in CHO-3E7 or ExpiCHO cells and DSP105 variants DSP107_V17 (SEQ ID NO: 97), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced in CHO-3E7 cells or ExpiCHO cells, as described in Example 2 hereinabove.

Spectra BR Protein molecular weight marker (Thermo Fisher Scientific, cat #26634), 4-20% polyacrylamide gel (BioRad, cat #556-8094), e-Stain peds (GenScript, cat #L02011), Laemmeli Loading buffer (BioRad, cat #161-0747). Superdex 200 Increase column (GE Healthcare), SEC-MALS system: AKTA Explorer (GE)+MiniDawn TREOS+OPTILAB T-reX (WYATT).

Methods—

SDS-PAGE analysis—Two µg protein or 35 µl supernatant from each sample was mixed with loading buffer with or without β-mercaptoethanol (reduced and non-reduced conditions, respectively), heated for 5 minutes at 95° C. and separated on 4-20% gradient polyacrylamide gel electrophoresis SDS-PAGE. Proteins migration on the gel is visualized by Coomassie blue staining with e-Stain peds and washing using the e-Stain machinery (GenScript), according to manufacturer instructions.

SEC-MALS analysis-Proteins are loaded on a Superdex 200 Increase column (GE Healthcare) and run at a flow rate of 0.8 ml/min with 10 mM KPO4 pH 8.0+150 mM NaCl as mobile phase. Detection is performed by UV, MALS and RI using AKTA Explorer (GE)+MiniDawn TREOS+OPTILAB T-rex (WYATT).

Results—

As demonstrated in FIG. 7, a high proportion of high molecular weight forms (HMW, aggregates) was observed in N-terminal His-tagged DSP105 (SEQ ID NO: 1) under non-reducing conditions but not in reducing conditions. On the other hand, only a minor level of aggregates was detected in N-terminal His-tagged DSP105_V17 (SEQ ID NO: 99), indicating that aggregation of DSP105 due to incorrect disulfide bonds formation was prevented in DSP105_V17. A low level of aggregates was observed in other PD1-4-1BBL variants [namely, DSP105_V18 (SEQ ID NO: 101), DSP105_V19 (SEQ ID NO: 103), DSP105_V20 (SEQ ID NO: 105) and DSP105_V23 (SEQ ID NO: 113], as demonstrated in FIGS. 8A-E.

As shown in FIGS. 9A-B, when separated on an SDS-PAGE under non-reducing conditions N-terminal his-tagged DSP105 (WT; SEQ ID NO: 1) His N-terminal His-tagged DSP105 variants DSP105_V17 (SEQ ID NO: 99), DSP105_V17 (SEQ ID NO: 97), DSP105_V20 (SEQ ID NO: 105), DSP_V22 (SEQ ID NO: 111), DSP105_V23 (SEQ ID NO: 113), DSP105_V24 (SEQ ID NO: 133), DSP105_V25 (SEQ ID NO: 135), and DSP105_V31 (SEQ ID NO: 147), variants of PD1-4-1BBL were detected at the same molecular weight as under reducing conditions. Additional bands of higher molecular weight were detected in his-tagged DSP105 (WT; SEQ ID NO: 1, designated as "DSP105WT" in FIGS. 9A-B), which were stronger under the non-reducing conditions compared to the reducing conditions. This might suggest the formation of multimers, probably mediated by S—S bridges. Interestingly this main "high molecular weight" band that appeared in non-reduced DSP105WT was not seen in DSP105_V22 (SEQ ID NO: 111) containing the CYS73>Ser substitution, emphasizing that this high molecular band is probably mediated by the CYS73.

Example 4

The PD1-4-1BBL Variants Contain Both Domains

Materials-DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP_V17 (SEQ ID NO: 97), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced as described in Example 2 hereinabove.

For the Western blot analysis: Spectra BR protein marker (Thermo Fisher Scientific, cat #26634), Laemmeli Loading buffer (BioRad, cat #161-0747), 4-20% polyacrylamide gel (BioRad, cat #556-8094), anti 4-1BBL (BioVision, 5369-100), anti PD1 (Cell Signaling, cat #86163), anti-His (GenScript, Cat.No. A00186), secondary Goat Anti Rabbit IgG (H+L)-HRP Conjugate (R&D, cat #170-6515), ECL Plus Western Blotting substrate (Pierce, cat #32132).

For the sandwich ELISA: Anti 4-1BBL antibody (capture antibody from a matched pair; Abnova #H00008744-AP41), anti PD1-biotinylated antibody, Streptavidin Protein, HRP (#21126, Thermo Scientific), TMB substrate (1-Step™ Ultra TMB-ELISA Substrate Solution, Thermo Scientific #34028).

Methods—

Western blot analysis—Proteins (50-500 ng per lane) were treated at reducing or non-reducing conditions (in loading buffer containing β-mercaptoethanol and boiled for 5 minutes at 95° C., or, in sample buffer without β-mercaptoethanol without heating, respectively) and separated on a 4-20% gradient SDS-PAGE gel. Following, proteins were transferred onto a PVDF membrane and incubated with primary antibodies overnight, anti 4-1BBL, anti-PD1 or anti-His, followed by 1 hour incubation with an HRP-conjugated secondary antibody. Signals were detected following ECL development.

Sandwich ELISA—Plates are coated with anti 4-1BBL capture antibody (2.5 ug/ml in PBS) and blocked in blocking solution (PBS, 1% BSA, 0.005% Tween). The produced PD1-4-1BBL fusion proteins, serially diluted in blocking solution, are applied and incubated in coated plates for 2 hours, followed by incubation with detecting anti-PD1 biotinylated antibody, and subsequent detection with streptavidin-HRP and TMB substrate, according to manufacturer recommendation. Plates are analyzed using Plate reader (Thermo Scientific, Multiscan FC) at 450 nm, with reference at 620 nm.

Example 5

The PD1-4-1BBL Variants Bind PDL1 and 4-1BB
Binding Analysis of the PD1 Moiety of PD1-4-1BBL Protein to PDL1

The binding of the PD1 domain of PD1-4-1BBL to human PDL1 was determined using DLD1-PDL1 cell line overexpressing PDL1. DLD1-WT cells served as a negative control. Cells were incubated with different concentrations of the produced PD1-4-1BBL fusion proteins, followed by immuno-staining with a secondary anti 4-1BBL antibody. Binding was analyzed by flow cytometry.

Materials—DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP105_V17 (SEQ ID NO: 97), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced as described in Example 2 hereinabove.

DLD1-WT and DLD1-PDL1 cell lines (Hendriks et al 2016), True stain FCX (Biolegend, cat #422302), anti 4-1BBL (Biolegend, cat #311506), isotype IgG1, k (Biolegend, cat #400122), anti PDL1 (Bioledgend, cat #329708), isotype IgG2b, (Biolegend, cat #400322).

Methods—Cells were incubated for 30 minutes on ice with different concentrations (0.05-50 μg/ml) of the produced PD1-4-1BBL fusion proteins, followed by immuno-staining with antibodies against 4-1BBL and analysis by flow cytometry.

Binding Analysis of the 4-1BBL Moiety of PD1-4-1BBL Protein to 4-1BB

The binding of the 4-1BBL domain of PD1-4-1BBL to human 4-1BB was determined using HT1080-4-1BB cell line overexpressing 4-1BB. HT1080 WT cells served as a negative control. Cells were incubated with different dilutions of the produced PD1-4-1BBL fusion proteins, followed by immuno-staining with a secondary anti PD1 antibody. Binding was analyzed by flow cytometry.

Materials—DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP105_V17 (SEQ ID NO: 97), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced as described in Example 2 hereinabove.

HT1080 WT and HT1080-4-1BB cells (Wyzgol et al, 2009), Fixable Viability Dye (BD Biosciences, cat #562247), True stain FCX (Biolegend, cat #422302), anti PD1 (Bioledgend cat #329908), anti 41BB (Bioledgend cat #309801) isotype IgG1, K (Bioledgend, cat #400122).

Methods—Cells were incubated for 30 minutes on ice with different dilutions (1:8-1:1024) of the produced PD1-4-1BBL fusion proteins, followed by immuno-staining with antibodies against PD1 and analysis by flow cytometry.

Results—As shown in FIG. 10A, DLD1-PD1 and HT1080-4-1BB cells express the relevant receptors, PD1 and 41BB, respectively. Binding assays showed that the His-tagged DSP105_V17 (SEQ ID NO: 97), binds to DLD1-PDL1 cells and to HT1080-41BB cells in a dose dependent anner (FIG. 10B). Different dilutions of the supernatant control (from non-transfected cells) did not bind to HT1080-41BB cells (FIG. 10B). Following. GMFI values were used to create a binding curve graph with a GraphPad Prism software (FIG. 10C). Taken together, both sides of the His-tagged DSP105_V17 (SEQ ID NO: 97), fusion protein, bind their relevant counterparts overexpressed on the surface of cells.

Binding of PD1-4-1BBL to Human, Mouse and Cynomolgus Monkey PDL1 and 4-1BB Counterparts The binding of PD1-4-1BBL proteins to PDL1 and 4-1BB counterparts is determined by Surface Plasmon Resonance (SPR) assays.

Materials—DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP105_V17 (SEQ ID NO: 97), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced as described in Example 2 hereinabove.

Series S sensor chip CM5 (GE, cat. #BR100530), Ab capture kit, human hCD47 (negative control), human PDL1, mouse PDL1, cynomolgus PDL1, human 4-1BB, mouse 4-1BB, cynomolgus 4-1BB.

Methods—SPR assays are performed using Biacore T100 biosensor (GE Healthcare). Antibody from the capture kit is coupled to all four flow-channels of the chip (Fc1-4), using standard amine coupling protocol as recommended by the manufacturer. PD1-4-1BBL counterpart proteins (PDL1 and 4-1BB) binding to the chip is performed in HBS-EP+ running buffer (10 mM HEPES pH7.3, 150 mM NaCl, 3 mM EDTA, 0.05% Tween20): Human CD47 (negative control) is loaded onto the reference channel Fc1, while Fc2-4 are loaded with the human, mouse and cynomolgus PDL1 proteins. Following automated regeneration of the chip, the chip is re-loaded with the human CD47 on channel Fc1, and with the human, mouse and cynomolgus 4-1BB proteins on channels Fc2-4. Following counterparts binding, the PD1-4-1BBL analytes are passed over all four channels. This process is iteratively repeated with various concentrations of PD1-4-1BBL analytes at flow rate of 50 µl/min. 3M MgCl2 solution is injected (45 sec at 20 µl/min) at the end of each cycle, to regenerate the active surface by dislodging the captured molecules. The binding parameters are evaluated using Kinetic 1:1 Binding model in BiaEvaluation software v. 3.0.2 (GE Healthcare).

Example 6

Dual Side Binding—Potency Assay

The binding of both sides of the molecule to their counterparts, i.e. the binding of PD1 to PDL1 and the binding of 4-1BBL to 4-1BB, is tested by a sandwich ELISA based potency assay. This assay is also used to compare the functional properties of the different production batches.

Materials—DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP105_V17 (SEQ ID NO: 97), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced as described in Example 2 hereinabove. Human recombinant PDL1 (ACRO Biosystem, A001-214), human recombinant protein 4-1BB-Biotin (cat #41B-H82E3, ACRO Biosystem), Streptavidin Protein-HRP (cat #21126, Thermoscientific), 1-Step™ Ultra TMB-ELISA Substrate Solution (cat #34028, Thermoscientific).

Methods—PDL1 is bound on the surface of a plastic plate, PD1-4-1BBL is added and allowed to bind to the immobilized PDL1. Following washing, biotinylated 4-1BB is added and allowed to bind to the 4-1BBL arm of the molecule. Following, the plates are washed and streptavidin HRP is added. Detection is effected with a TMB substrate according to standard ELISA protocol using a Plate reader (Thermo Scientific, Multiscan FC) at 450 nm, with reference at 540 nm.

Example 7

Activation of 4-1BB by the PD1-4-1BBL Variants

The activation effect of the 4-1BB receptor by the produced PD1-4-1BBL fusion proteins was determined using HT1080 cells or another cell line that are overexpressing the 4-1BB receptor. Specifically, the HT1080-4-1BB cell line is overexpressing 4-1BB and is known to secrete IL8 upon binding of 4-1BBL (Wyzgol et al., 2009, The Journal of Immunology). Upon binding of 4-1BBL to the 4-1BB receptor on the surface of these cells, a signaling pathway is activated resulting in secretion of IL8. To this end, the cells were incubated in the presence of different concentrations of the produced PD1-4-1BBL with or without PDL1 expressing cells, and IL8 secretion to the culture media was determined by ELISA.

Materials—DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP105_V17 (SEQ ID NO: 99), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27

(SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced as described in Example 2 hereinabove.

HT1080-4-1BB cells, IL-8 ELISA kit (R&D, cat #D8000C), DMEM (Biological industries, cat #01-055-1A), FBS (Rhenium, cat #10270106), anti 4-1BB (Biolegend, cat #359810), isotype IgG1, k (Biolegend, cat #400122).

Methods—HT1080-4-1BB cells (10000 per well) were incubated for 24 hours in medium with different concentrations of the produced PD1-4-1BBL fusion proteins. Following incubation, IL8 concentration in the supernatant was determined by an IL8 ELISA kit according to the manufacturer's protocol. Plates were analyzed using a Plate reader (Thermo Scientific, Multiscan FC) at 450 nm, with reference at 540 nm Results—As shown in FIG. 11, HT1080-4-1BB cells express the relevant receptor 4-1BB. All DSP105 variant proteins tested (N-terminal His-tagged DSP105_V17 (SEQ ID NO: 99), His-tagged DSP105_V22 (SEQ ID NO: 109), DSP105_V17 (SEQ ID NO: 99), and DSP105_V23 (SEQ ID NO: 13) were able to trigger the 4-1BB signaling as determined by IL8 secretion from the HT1080-4-1BB cells, in a dose dependent manner in medium containing FBS (FIG. 12).

Example 8

The Effect of the PD1-4-1BBL Variants on Blocking PDL1 Binding

The PD1 part of PD1-4-1BBL is designed to block the interaction of endogenous PD1 expressed on T cells with PDL1 expressed on tumor cells. To this end, effectiveness of the produced PD1-4-1BBL variants as blockers of this interaction is evaluated.

Materials—DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP105_V17 (SEQ ID NO: 99), DSP105_V18 (SEQ ID NO: 101), DSP105_V19 (SEQ ID NO: 103), DSP105_V20 (SEQ ID NO: 105) DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced as described in Example 2 hereinabove.

PD-1: PDL1 Inhibitor Screening ELISA Assay Pair (Acro Biosystems, cat. #EP101), including the following: recombinant human PDL1, anti hPD1 neutralizing antibody, Biotinylated hPD1.

Methods—ELISA plates are coated overnight with recombinant human PDL1. Plates are washed and incubated for 1 hour with different concentrations of the produced PD1-4-1BBL fusion proteins or the positive control anti PD1 antibody. Biotinylated PD1 is added followed by additional 1 hour incubation. Following the incubation, the plate is washed and blotted with Streptavidin-HRP and TMB substrate according to standard ELISA protocol.

Plates are analyzed using a Plate reader (Thermo Scientific, Multiscan FC) at 450 nm, with reference at 620 nm.

Example 9

Activation of PBMCs or T Cells by the PD1-4-1BBL Variants

The activation of a T cell requires two signals: ligation of the T-Cell Receptor (TCR) with the Major Histocompatibility Complex (MHC)/peptide complex on the Antigen Presenting Cell (APC) and cross-linking of co-stimulatory receptors on the T cell with the corresponding ligands on the APC. 4-1BB is a T cell co-stimulatory receptor which upon ligation to 4-1BBL promotes expansion, survival, differentiation and cytokine expression of both CD8+ and CD4+ T cells.

Numerous methods are known in the art to determine activation of T cells, including but not limited to:

Expression of activation markers on the surface of the T cells (for example: CD25, CD69, CD62L, CD137, CD107a, PD1 etc.). Expression of activation markers is tested by staining the cells with specific antibodies and flow cytometry analysis (FACS).

Secretion of inflammatory cytokines (for example: IL2, IL6, IL8, INF gamma etc.). Secretion of inflammatory cytokine is tested by ELISA.

Proliferation, measured by pre-staining of T cells with CFSE (carboxyfluorescein succinimidyl ester) or other cell proliferation dyes and determining deviation of cells by CFSE dilution that is determined by FACS. Proliferation is also determined using an Incucyte machine taking photos overtime and analyzing the photos with a specific software.

Killing of a target cell e.g. cancer cell that is measured by pre-labeling the cancer cells using Calcine-AM reagent and measuring Calcine release into the culture medium using luminescence plate reader. Killing is also determined by an Incucyte machine using labeled target cells and caspase sensitive florescent substrate.

To this end, the effect of the produced PD1-4-1BBL fusion proteins on enhancing human T cells or Peripheral Blood Mononuclear Cells (PBMCs) activation is evaluated.

Materials—DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP105_V17 (SEC ID NO: 97), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147), produced as described in Example 2 hereinabove. Ficoll-Paque (GE Healthcare, cat #17-1440-03), Leaf purified Anti-human CD3 (BioLegend, cat #BLG-317315), Recombinant human IL-2 (Biolegend, cat #589106), anti CD27, anti CD25, CD69, CD107a, CD137, PD1 antibodies, EasySep Direct Human T Cell Isolation Kit (Stemcell, cat #19661), αCD3/CD28 dynabeads (Thermo, cat #Dy-11131D), IFNg ELISA kit (Peprotech, cat #900-TM27), CFSE.

Methods—Human PBMCs are isolated from peripheral blood of healthy donors using Ficoll-Paque method (Grienvic et al. 2016 *Biopreserv Biobank.* 14 (5): 410-415), and T cells are further isolated by negative selection magnetic beads. Following isolation, cells are cultured with addition of different concentrations of the produced PD1-4-1BBL fusion proteins, in the presence of sub-optimal concentrations of anti-CD3 (30 ng/ml) or IL-2 (1000 U/ml) or anti-CD3 plus IL-2, or αCD3/CD28 dynabeads (1:10 bead per cell). Cells are cultured for 1-7 days with or without the presence of PDL1 expressing cells or in PDL1 coated plates. Secretion of proinflammatory cytokines such as IFNγ to the culture media is measured by ELISA. Proliferation is determined by The IncuCyte® S3 Live-Cell Analysis System (IncuCyte), or using CFSE, according to the manufacturer's protocol. Cells are further tested for activation markers CD25, CD69, CD107a, CD137 (4-1BB), PD1, surface expression at different time points, by flow cytometry. Killing is evaluated by Calcein AM release or by Incucyte machine according to the manufacturer protocol.

Example 10

The In-Vivo Anti-Tumor Effect of the PD1-4-1BBL Variants

Three different in-vivo mouse models are used for testing the efficacy of PD1-4-1BBL in treating cancer:

1. NSG mice inoculated with human stem cells or with human PBMCs or with immobilized human PBMCs and with human tumor cells. In this model, PD1-4-1BBL interacts with human PDL1 (expressed on the tumor and the immune cells) and with 4-1BB on human T cells.

2. C57BL/6—human-4-1BB knock-in mice inoculated with MC38 mouse colon carcinoma or other cancer cell line or with cancer cell line overexpressing the human PDL1. In this model, the mouse 4-1BB extracellular domain is replaced by that of a human 4-1BB, so PD1-4-1BBL can interact with the human 4-1BB expressed on mouse T cells. PD1-4-1BBL interacts with mouse and with human PDL1 expressed on the tumor cells.

3. Syngeneic mouse tumor models that express mouse PDL1. In these models, PD1-4-1BBL interacts with mouse PDL1 on the tumor cells.

Methods—In all three models, mice are inoculated with tumor cells intravenously (IV), intraperitoneally (IP), subcutaneously (SC) or orthotopically. Once the tumor is palpable (~80 mm$^3$), mice are treated IV, IP, SC or orthotopically, with different doses and different regimens of the produced PD1-4-1BBL fusion proteins e.g. DSP105 (HEK-NH) (SEQ ID NO: 1), DSP105 (CHO-NH) (SEQ ID NO: 1), DSP105 (CHO-NH)-V1 (SEQ ID NO: 13), DSP105 (CHO-NH)-V2 (SEQ ID NO: 15), DSP105 (CHO-NH)-V3 (SEQ ID NO: 17), N-terminal His-tagged DSP105_V17 (SEQ ID NO: 99), His-tagged DSP105_V22 (SEQ ID NO: 109), DSP105_V17 (SEQ ID NO: 99), DSP105_V18 (SEQ ID NO: 101), DSP105_V19 (SEQ ID NO: 103), DSP105_V20 (SEQ ID NO: 105), DSP105_V21 (SEQ ID NO: 107), DSP_V22 (SEQ ID NO: 111), DSP105_V23 (SEQ ID NO: 113), DSP105_V24 (SEQ ID NO: 133), DSP105_V25 (SEQ ID NO: 135), DSP105_V26 (SEQ ID NO: 137), DSP105_V27 (SEQ ID NO: 139), DSP105_V28 (SEQ ID NO: 141), DSP105_V29 (SEQ ID NO: 143), DSP105_V30 (SEQ ID NO: 145) and DSP105_V31 (SEQ ID NO: 147).

Mice are followed for weights and clinical signs. Tumors are measured few times a week by a caliper; and tumor volume is calculated according to the following equation: $V=\text{length}\times\text{width}^2/2$. Mice Weight is measured routinely. Tumor growth and survival are monitored through the whole experiment.

Infiltration and sub-typing of immune cells in the tumor is tested by resecting the tumor or draining lymph nodes, digestion and immune phenotyping using specific antibodies staining and flow cytometry analysis. Additionally or alternatively, infiltration of immune cells or necrotic grade of tumors is determined by resecting the tumors, paraffin embedding and sectioning for immunohistochemistry staining with specific antibodies.

At sacrificing, mice organs are harvested and embedded into paraffin blocks for H&E and IHC staining.

Blood samples are taken from mice at different time points, according to common procedures, for the following tests: PK analysis, cytokines measurements in plasma, FACS profiling of blood cells sub-populations in circulation, hematology testing, serum chemistry testing, anti-drug-antibody (ADA) analysis and neutralizing antibodies analysis (NAB).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

In addition, any priority document(s) of this application is/are hereby incorporated herein by reference in its/their entirety

What is claimed is:

1. A PD1-4-1BBL fusion protein comprising a PD1 amino acid sequence and a 4-1BBL amino acid sequence, wherein
   (a) said PD1 amino acid sequence consists of SEQ ID NO: 75, 83, 87, 91 or 93 and said 4-1BBL amino acid sequence consists of SEQ ID NO: 22; or
   (b) said PD1 amino acid sequence consists of SEQ ID NO: 115 and said 4-1BBL amino acid sequence consists of SEQ ID NO: 123 or 125;

and wherein said fusion protein is capable of at least one of:
   (i) binding PDL1 and 4-1BB;
   (ii) activating said 4-1BB signaling pathway in a cell expressing said 4-1BB; and/or
   (iii) co-stimulating immune cells expressing said 4-1BB.

2. The PD1-4-1BBL fusion protein of claim 1, wherein production yield of said fusion protein is at least 1.5 fold higher than the production yield of SEQ ID NO: 5 under the same production conditions, said production conditions comprise expression in a mammalian cell and culturing at 32-37° C., 5-10% $CO_2$ for 5-13 days.

3. The PD1-4-1BBL fusion protein of claim 1, wherein the amount of aggregates of said fusion protein is at least 20% lower than the amount of aggregates of SEQ ID NO: 5 under the same production conditions, said aggregates are of at least 300 kDa in molecular weight and said production conditions comprise expression in a mammalian cell and culturing at 32-37° C., 5-10% $CO_2$ for 5-13 days.

4. The PD1-4-1BBL fusion protein of claim 1, wherein said PD1-4-1BBL fusion protein amino acid sequence consists of an amino acid sequence selected from the group consisting of SEQ ID NO: 97, 101, 103, 105, 113, 133 and 135.

5. The PD1-4-1BBL fusion protein of claim 1, wherein said fusion protein being characterized by a single glycine linker between said PD1 and said 4-1BBL.

6. A polynucleotide encoding the PD1-4-1BBL fusion protein of claim 1.

7. A nucleic acid construct comprising the polynucleotide of claim 6, and a regulatory element for directing expression of said polynucleotide in a host cell.

8. A host cell comprising the PD1-4-1BBL fusion protein of claim 1.

9. A method of producing a PD1-4-1BBL fusion protein, the method comprising expressing in a host cell the polynucleotide of claim 6.

10. The method of claim 9, comprising isolating the fusion protein.

11. A method of treating a disease that can benefit from activating immune cells comprising administering to a subject in need thereof the PD1-4-1BBL fusion protein of claim 1.

12. An article of manufacture comprising a packaging material packaging a therapeutic agent for treating a disease that can benefit from activating immune cells; and the PD1-4-1BBL fusion protein of claim 1.

13. A method of activating immune cells, the method comprising in-vitro activating immune cells in the presence of the PD1-4-1BBL fusion protein of claim 1.

* * * * *